(12) United States Patent
Alanine et al.

(10) Patent No.: US 11,066,443 B2
(45) Date of Patent: Jul. 20, 2021

(54) ANTI-BACTERIAL PEPTIDE MACROCYCLES AND USE THEREOF

(71) Applicant: Hoffmann-La Roche Inc., Little Falls, NJ (US)

(72) Inventors: Alexander Alanine, Cambridge (GB); Kurt Amrein, Basel (CH); Konrad Bleicher, Basel (CH); Bernhard Fasching, Basel (CH); Hans Hilpert, Basel (CH); Sabine Kolczewski, Basel (CH); Carsten Kroll, Basel (CH); Adrian Schaeublin, Basel (CH); Claudia Zampaloni, Basel (CH)

(73) Assignee: Hoffmann-La Roche Inc., Little Falls, NJ (US)

( * ) Notice: Subject to any disclaimer, the term of this patent is extended or adjusted under 35 U.S.C. 154(b) by 0 days.

(21) Appl. No.: 16/485,200

(22) PCT Filed: Apr. 9, 2018

(86) PCT No.: PCT/EP2018/058957
§ 371 (c)(1),
(2) Date: Aug. 12, 2019

(87) PCT Pub. No.: WO2018/189065
PCT Pub. Date: Oct. 18, 2018

(65) Prior Publication Data
US 2020/0040031 A1 Feb. 6, 2020

(30) Foreign Application Priority Data

Apr. 10, 2017 (EP) .................................... 17165651

(51) Int. Cl.
*A61K 38/00* (2006.01)
*C07K 5/02* (2006.01)
*C07K 5/09* (2006.01)
*C07K 5/093* (2006.01)

(52) U.S. Cl.
CPC .......... *C07K 5/0202* (2013.01); *C07K 5/0815* (2013.01); *C07K 5/0819* (2013.01); *A61K 38/00* (2013.01)

(58) Field of Classification Search
CPC .. C07K 5/0202; C07K 5/0815; C07K 5/0819; C07K 5/02; A61K 38/00; A61P 31/04
See application file for complete search history.

(56) References Cited

U.S. PATENT DOCUMENTS

| | | | |
|---|---|---|---|
| 7,521,420 B2 | 4/2009 | Fraser et al. | |
| 7,727,960 B2 | 6/2010 | Hummel et al. | |
| 2005/0256037 A1 | 11/2005 | Lampe et al. | |
| 2006/0025566 A1 | 2/2006 | Hoveyda et al. | |
| 2007/0021331 A1 | 1/2007 | Fraser et al. | |
| 2007/0129288 A1 | 6/2007 | Lampe et al. | |
| 2008/0161232 A1 | 7/2008 | Hummel et al. | |
| 2017/0233437 A1* | 8/2017 | Alanine | C07K 5/0821 514/2.8 |

FOREIGN PATENT DOCUMENTS

| | | |
|---|---|---|
| CN | 103387601 A | 11/2013 |
| EP | 3388444 A1 | 10/2018 |
| WO | 0114346 A1 | 3/2001 |
| WO | 2004111077 A1 | 12/2004 |
| WO | 2005012331 A1 | 2/2005 |
| WO | 2005012332 A1 | 2/2005 |
| WO | 2005090388 A1 | 9/2005 |
| WO | 2005118613 A2 | 12/2005 |
| WO | 2006009645 A1 | 1/2006 |
| WO | 2006009674 A1 | 1/2006 |
| WO | 2007131966 A1 | 11/2007 |
| WO | 2008095999 A1 | 8/2008 |
| WO | 2009099677 A2 | 8/2009 |
| WO | 2010022249 A2 | 2/2010 |
| WO | 2011050270 A2 | 4/2011 |
| WO | 2011050276 A1 | 4/2011 |
| WO | 2011053821 A1 | 5/2011 |

(Continued)

OTHER PUBLICATIONS

The International Search Report and Written Opinion, dated May 28, 2018, in the corresponding PCT Appl. No. PCT/EP2018/058957.
V. Balraju et al., "Synthesis of Cyclic Peptides Constrained with Biarylamine Linkers Using Buchwald-Hartwig C—N Coupling#" The Journal of Organic Chemistry 71(23):8954-56 (Nov. 1, 2006).
Webster et al: "Synthesis of biaryl-linked cyclic peptoids", Tetrahedron Letters, Elsevier, Amsterdam, NL, vol. 58, No. 10, Jan. 28, 2017 (Jan. 28, 2017), pp. 1010-1014, XP029915742.

(Continued)

*Primary Examiner* — Sudhakar Katakam

(57) ABSTRACT

The present invention relates to compounds of formula (I)

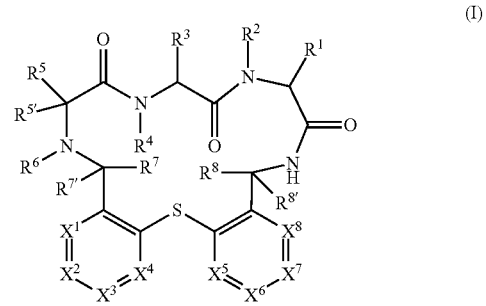

wherein $X^1$ to $X^8$ and $R^1$ to $R^8$ are as described herein, as well as pharmaceutically acceptable salts thereof for the use in the treatment or prevention of infections and resulting diseases caused by *Pseudomonas aeruginosa*.

5 Claims, No Drawings

(56) References Cited

FOREIGN PATENT DOCUMENTS

| WO | 2012021874 A1 | 2/2012 |
| WO | 2013033645 A1 | 3/2013 |
| WO | 2013123266 A1 | 8/2013 |
| WO | 2014081886 A1 | 5/2014 |
| WO | 2014110420 A1 | 7/2014 |

OTHER PUBLICATIONS

U.S. Office Actions, dated Apr. 11, 2019, Jul. 11, 2019, Feb. 5, 2020 and Jun. 16, 2020, in the related U.S. Appl. No. 16/006,564.
U.S. Office Actions, dated Dec. 6, 2017 and Mar. 12, 2018, in the related U.S. Appl. No. 15/336,128.
International Search Report & Written Opinion for PCT/EP2019/057489, dated May 17, 2019.
International Search Report & Written Opinion of the International Searching Authority for PCT/EP2019/060272, dated Jul. 9, 2019.
International Search Report & Written Opinion of the International Searching Authority for PCT/EP2016/075499, dated Jan. 5, 2017.
Ballatore et al., "Carboxylic Acid (Bio)Isosteres in Drug Design," ChemMedChem 8(3):385-395 (2013).
Hiroki Azuma et al., "A publication of reliable methods for the preparation of organic compounds" Organic Syntheses. pp. 152-161. 2011.
Marsault et al., "Efficient parallel synthesis of macrocyclic peptidomimetics" Bioorg Med Chem Lett 18:4731-4735 ( 2008).

* cited by examiner

ANTI-BACTERIAL PEPTIDE MACROCYCLES AND USE THEREOF

CROSS-REFERENCE TO RELATED APPLICATIONS

This application is a National Stage Application of PCT/EP2018/058957 filed Apr. 9, 2018, which claims priority from European Patent Application No. 17165651.5, filed on Apr. 10, 2017. The priority of both said PCT and European Patent Application are claimed. Each of prior mentioned applications is hereby incorporated by reference herein in its entirety.

The present invention relates to compounds of formula (I)

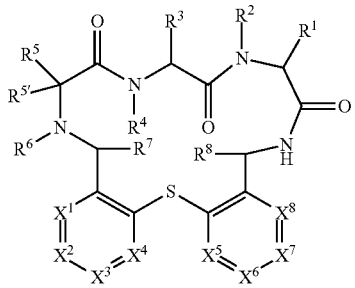

wherein $X^1$ to $X^8$ and $R^1$ to $R^8$ are as described hereinafter, as well as pharmaceutically acceptable salts thereof for the use in the treatment or prevention of infections and resulting diseases caused by Pseudomonas aeruginosa.

BACKGROUND

P. aeruginosa is considered to be a serious threat by the US Centers for Disease Control and Prevention and belongs to the so called 'ESKAPE' pathogens (Enterococcus faecium, Staphylococcus aureus, Klebsiella pneumoniae, Acinetobacter baumannii, Pseudomonas aeruginosa and Enterobacter species & E. coli) that currently cause the majority of nosocomial infections and effectively "escape" the activity of antimicrobial agents.

Pseudomonas aeruginosa (P. aeruginosa) is an opportunistic pathogen that rarely causes disease in healthy people, but is a significant problem for critically ill or immunocompromised individuals. Infection is a major problem in individuals who have cystic fibrosis (CF), where P. aeorginosa is a causative agent in the progressive loss of lung function resulting from recurrent and chronic respiratory tract infections with the bacterium. Others at risk from Pseudomonas aeruginosa infection include patients on mechanical ventilators, neutropenic cancer patients, and burn patients. P. aeruginosa is often resistant to most antibiotics and new treatment approaches are greatly needed.

P. aeruginosa has been defined and still remains "a prime example of a mismatch between unmet medical needs and the current antimicrobial research and development pipeline" according to the Antimicrobial Availability Task Force (AATF) of the Infectious Diseases Society of America (IDSA). Thus, there is a high demand and need to identify compounds suitable for the treatment of diseases and infections caused by P. aeruginosa.

DETAILED DESCRIPTION OF THE INVENTION

Unless otherwise defined, all technical and scientific terms used herein have the same meaning as commonly understood by one of ordinary skill in the art to which this invention belongs. Although methods and materials similar or equivalent to those described herein can be used in the practice or testing of the invention, suitable methods and materials are described below.

All publications, patent applications, patents, and other references mentioned herein are incorporated by reference in their entirety.

The nomenclature used in this Application is based on IUPAC systematic nomenclature, unless indicated otherwise.

AutoNom 2000 (Automatic Nomenclature) for ISIS/Draw was employed to generate IUPAC chemical names.

Any open valency appearing on a carbon, oxygen, sulfur or nitrogen atom in the structures herein indicates the presence of a hydrogen, unless indicated otherwise.

The term "moiety" refers to an atom or group of chemically bonded atoms that is attached to another atom or molecule by one or more chemical bonds thereby forming part of a molecule.

For example, the variables $R^1$, $R^2$ and $R^3$ of formula (I) refer to moieties that are attached to the core structure of formula (I) by a covalent bond.

When indicating the number of substituents, the term "one or more" refers to the range from one substituent to the highest possible number of substitution, i.e. replacement of one hydrogen up to replacement of all hydrogens by substituents.

The term "optional" or "optionally" denotes that a subsequently described event or circumstance can but need not occur, and that the description includes instances where the event or circumstance occurs and instances in which it does not.

The term "substituent" denotes an atom or a group of atoms replacing a hydrogen atom on the parent molecule.

The term "substituted" denotes that a specified group bears one or more substituents. Where any group can carry multiple substituents and a variety of possible substituents is provided, the substituents are independently selected and need not to be the same. The term "unsubstituted" means that the specified group bears no substituents. The term "optionally substituted" means that the specified group is unsubstituted or substituted by one or more substituents, independently chosen from the group of possible substituents. When indicating the number of substituents, the term "one or more" means from one substituent to the highest possible number of substitution, i.e. replacement of one hydrogen up to replacement of all hydrogens by substituents.

The term "compound(s) of this invention" and "compound(s) of the present invention" refers to compounds as disclosed herein and stereoisomers, tautomers, solvates, and salts (e.g., pharmaceutically acceptable salts) thereof.

When the compounds of the invention are solids, it is understood by those skilled in the art that these compounds, and their solvates and salts, may exist in different solid forms, particularly different crystal forms, all of which are intended to be within the scope of the present invention and specified formulas.

The term, "structurally related substances" denotes substances that share a common or core structure of the substance that has biological activity, such as a common pharmacophore or olfactophore. Such structurally related substances can differ from each other, however, in their substituent groups.

The term "pharmaceutically acceptable esters" denotes derivatives of the compounds of present invention, in which a carboxy group has been converted to an ester, wherein carboxy group means —C(O)O—. Methyl-, ethyl-, methoxymethyl-, methylthiomethyl-, and pivaloyloxymethylesters are examples of such suitable esters. The term "pharmaceutically acceptable esters" furthermore embraces derivatives of the compounds of present invention in which hydroxy groups have been converted to the corresponding esters with inorganic or organic acids such as nitric acid, sulfuric acid, phosphoric acid, citric acid, formic acid, maleic acid, acetic acid, succinic acid, tartaric acid, methanesulfonic acid, or p-toluenesulfonic acid, and which are non toxic to living organisms.

The term "pharmaceutically acceptable salts" denotes salts which are not biologically or otherwise undesirable. Pharmaceutically acceptable salts include both acid and base addition salts.

The term "pharmaceutically acceptable acid addition salt" denotes those pharmaceutically acceptable salts formed with inorganic acids such as hydrochloric acid, hydrobromic acid, sulfuric acid, nitric acid, carbonic acid, phosphoric acid, and organic acids selected from aliphatic, cycloaliphatic, aromatic, araliphatic, heterocyclic, carboxylic, and sulfonic classes of organic acids such as formic acid, acetic acid, propionic acid, glycolic acid, gluconic acid, lactic acid, pyruvic acid, oxalic acid, malic acid, maleic acid, maloneic acid, succinic acid, fumaric acid, tartaric acid, citric acid, aspartic acid, ascorbic acid, glutamic acid, anthranilic acid, benzoic acid, cinnamic acid, mandelic acid, embonic acid, phenylacetic acid, methanesulfonic acid, ethanesulfonic acid, p-toluenesulfonic acid, and salicyclic acid.

The term "pharmaceutically acceptable base addition salt" denotes those pharmaceutically acceptable salts formed with an organic or inorganic base. Examples of acceptable inorganic bases include sodium, potassium, ammonium, calcium, magnesium, iron, zinc, copper, manganese, and aluminum salts. Salts derived from pharmaceutically acceptable organic nontoxic bases includes salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-diethylaminoethanol, trimethamine, dicyclohexylamine, lysine, arginine, histidine, caffeine, procaine, hydrabamine, choline, betaine, ethylenediamine, glucosamine, methylglucamine, theobromine, purines, piperizine, piperidine, N-ethylpiperidine, and polyamine resins.

Stereochemical definitions and conventions used herein generally follow S. P. Parker, Ed., McGraw-Hill Dictionary of Chemical Terms (1984) McGraw-Hill Book Company, New York; and Eliel, E. and Wilen, S., "Stereochemistry of Organic Compounds", John Wiley & Sons, Inc., New York, 1994. In describing an optically active compound, the prefixes D and L, or R and S, are used to denote the absolute configuration of the molecule about its chiral center(s). The substituents attached to the chiral center under consideration are ranked in accordance with the Sequence Rule of Cahn, Ingold and Prelog. (Cahn et al. Angew. Chem. Inter. Edit. 1966, 5, 385; errata 511). The prefixes D and L or (+) and (−) are employed to designate the sign of rotation of plane-polarized light by the compound, with (−) or L designating that the compound is levorotatory. A compound prefixed with (+) or D is dextrorotatory.

The term "halo", "halogen", and "halide" are used interchangeably herein and denote fluoro, chloro, bromo, or iodo. Particular examples of halo are fluoro and chloro.

The term "alkyl" denotes a monovalent linear or branched saturated hydrocarbon group of 1 to 12 carbon atoms. In particular embodiments, alkyl has 1 to 7 carbon atoms, and in more particular embodiments 1 to 4 carbon atoms. Examples of alkyl include methyl, ethyl, propyl, isopropyl, n-butyl, iso-butyl, sec-butyl, or tert-butyl. Particular examples of alkyl are methyl, ethyl, isopropyl, n-butyl, sec-butyl and tert-butyl, most particularly methyl and ethyl.

The term "alkoxy" denotes a group of the formula —O—R', wherein R' is an alkyl group. Examples of alkoxy moieties include methoxy, ethoxy, isopropoxy, and tert-butoxy. Particular examples of alkoxy is methoxy.

The term "haloalkyl" denotes an alkyl group wherein at least one of the hydrogen atoms of the alkyl group has been replaced by same or different halogen atoms, particularly fluoro atoms.

Examples of haloalkyl include monofluoro-, difluoro- or trifluoro-methyl, -ethyl or -propyl, for example 3,3,3-trifluoropropyl, 2-fluoroethyl, 2,2,2-trifluoroethyl, fluoromethyl, or trifluoromethyl. The term "perhaloalkyl" denotes an alkyl group where all hydrogen atoms of the alkyl group have been replaced by the same or different halogen atoms. Particular examples of haloalkyl is trifluoromethyl.

The term "haloalkoxy" denotes an alkoxy group wherein at least one of the hydrogen atoms of the alkoxy group has been replaced by same or different halogen atoms, particularly fluoro atoms. Examples of haloalkoxyl include monofluoro-, difluoro- or trifluoro-methoxy, -ethoxy or -propoxy, for example 3,3,3-trifluoropropoxy, 2-fluoroethoxy, 2,2,2-trifluoroethoxy, fluoromethoxy, or trifluoromethoxy. The term "perhaloalkoxy" denotes an alkoxy group where all hydrogen atoms of the alkoxy group have been replaced by the same or different halogen atoms.

The term "hydroxyalkyl" denotes an alkyl group wherein at least one of the hydrogen atoms of the alkyl group has been replaced by a hydroxy group. Examples of hydroxyalky include hydroxymethyl, 2-hydroxyethyl, 2-hydroxypropyl, 3-hydroxypropyl, 1-(hydroxymethyl)-2-methylpropyl, 2-hydroxybutyl, 3-hydroxybutyl, 4-hydroxybutyl, 2,3-dihydroxypropyl, 2-hydroxy-1-hydroxymethylethyl, 2,3-dihydroxybutyl, 3,4-dihydroxybutyl or 2-(hydroxymethyl)-3-hydroxypropyl.

The term "bicyclic ring system" denotes two rings which are fused to each other via a common single or double bond (annelated bicyclic ring system), via a sequence of three or more common atoms (bridged bicyclic ring system) or via a common single atom (spiro bicyclic ring system). Bicyclic ring systems can be saturated, partially unsaturated, unsaturated or aromatic. Bicyclic ring systems can comprise heteroatoms selected from N, O and S.

The term "cycloalkyl" denotes a monovalent saturated monocyclic or bicyclic hydrocarbon group of 3 to 10 ring carbon atoms. In particular embodiments cycloalkyl denotes a monovalent saturated monocyclic hydrocarbon group of 3 to 8 ring carbon atoms. Bicyclic means consisting of two saturated carbocycles having one or more carbon atoms in common. Particular cycloalkyl groups are monocyclic. Examples for monocyclic cycloalkyl are cyclopropyl, cyclobutanyl, cyclopentyl, cyclohexyl or cycloheptyl.

Examples for bicyclic cycloalkyl are bicyclo[2.2.1]heptanyl, or bicyclo[2.2.2]octanyl. Particular cycloalkyl is cyclopropyl.

The term "heterocycloalkyl" denotes a monovalent saturated or partly unsaturated mono- or bicyclic ring system of 3 to 9 ring atoms, comprising 1, 2, or 3 ring heteroatoms selected from N, O and S, the remaining ring atoms being carbon. In particular embodiments, heterocycloalkyl is a monovalent saturated monocyclic ring system of 4 to 7 ring atoms, comprising 1, 2, or 3 ring heteroatoms selected from N, O and S, the remaining ring atoms being carbon. Examples for monocyclic saturated heterocycloalkyl are aziridinyl, oxiranyl, azetidinyl, oxetanyl, pyrrolidinyl, tetrahydrofuranyl, tetrahydro-thienyl, pyrazolidinyl, imidazolidinyl, oxazolidinyl, isoxazolidinyl, thiazolidinyl, piperidinyl, tetrahydropyranyl, tetrahydrothiopyranyl, piperazinyl, morpholinyl, thiomorpholinyl, 1,1-dioxo-thiomorpholin-4-yl, azepanyl, diazepanyl, homopiperazinyl, or oxazepanyl. Examples for bicyclic saturated heterocycloalkyl are 8-aza-bicyclo[3.2.1]octyl, quinuclidinyl, 8-oxa-3-aza-bicyclo[3.2.1]octyl, 9-aza-bicyclo[3.3.1]nonyl, 3-oxa-9-aza-bicyclo[3.3.1]nonyl, or 3-thia-9-aza-bicyclo[3.3.1]nonyl. Examples for partly unsaturated heterocycloalkyl are dihydrofuryl, imidazolinyl, dihydro-oxazolyl, tetrahydro-pyridinyl, or dihydropyranyl. Particular examples of heterocycloalkyl are pyrrolidinyl, piperidinyl, piperazinyl, morpholinyl, 2-oxa-5-aza-bicyclo[2.2.1]heptyl and dihydropyranyl. Particular examples of saturated heterocycloalkyl are pyrrolidinyl, piperidinyl, piperazinyl, morpholinyl and 2-oxa-5-aza-bicyclo[2.2.1]heptyl. Particular examples of partly unsaturated heterocycloalkyl are dihydropyranyl and dihydroindolyl.

The term "aromatic" denotes the conventional idea of aromaticity as defined in the literature, in particular in IUPAC—Compendium of Chemical Terminology, 2nd, A. D. McNaught & A. Wilkinson (Eds). Blackwell Scientific Publications, Oxford (1997).

The term "aryl" denotes a monovalent aromatic carbocyclic mono- or bicyclic ring system comprising 6 to 10 carbon ring atoms. Examples of aryl moieties include phenyl and naphthyl, most particularly phenyl. Particular aryl substituted by aryl is biphenyl.

The term "heteroaryl" denotes a monovalent aromatic heterocyclic mono- or bicyclic ring system of 5 to 12 ring atoms, comprising 1, 2, 3 or 4 heteroatoms selected from N, O and S, the remaining ring atoms being carbon. Examples of heteroaryl moieties include pyrrolyl, furanyl, thienyl, imidazolyl, oxazolyl, thiazolyl, triazolyl, oxadiazolyl, thiadiazolyl, tetrazolyl, pyridinyl, pyrazinyl, pyrazolyl, pyridazinyl, pyrimidinyl, triazinyl, azepinyl, diazepinyl, isoxazolyl, benzofuranyl, isothiazolyl, benzothienyl, indolyl, isoindolyl, isobenzofuranyl, benzimidazolyl, benzoxazolyl, benzoisoxazolyl, benzothiazolyl, benzoisothiazolyl, benzooxadiazolyl, benzothiadiazolyl, benzotriazolyl, purinyl, quinolinyl, isoquinolinyl, quinazolinyl, or quinoxalinyl. Particular examples of heteroaryl are imidazolyl, pyrazolyl, pyrrolyl, isoxazolyl, pyridinyl, pyrazinyl, pyridazinyl, pyrimidinyl, indolyl and quinolyl. Most particular examples of heteroaryl are pyridinyl and indolyl.

The term "protecting group" denotes the group which selectively blocks a reactive site in a multifunctional compound such that a chemical reaction can be carried out selectively at another unprotected reactive site in the meaning conventionally associated with it in synthetic chemistry. Protecting groups can be removed at the appropriate point. Exemplary protecting groups are amino-protecting groups, carboxy-protecting groups or hydroxy-protecting groups.

The term "amino-protecting group" denotes groups intended to protect an amino group and includes benzyl, benzyloxycarbonyl (carbobenzyloxy, CBZ), Fmoc (9-Fluorenylmethyloxycarbonyl), p-methoxybenzyloxycarbonyl, p-nitrobenzyloxycarbonyl, tert-butoxycarbonyl (BOC), and trifluoroacetyl. Further examples of these groups are found in T. W. Greene and P. G. M. Wuts, "Protective Groups in Organic Synthesis", 2nd ed., John Wiley & Sons, Inc., New York, N.Y., 1991, chapter 7; E. Haslam, "Protective Groups in Organic Chemistry", J. G. W. McOmie, Ed., Plenum Press, New York, N.Y., 1973, Chapter 5, and T. W. Greene, "Protective Groups in Organic Synthesis", John Wiley and Sons, New York, N.Y., 1981. The term "protected amino group" refers to an amino group substituted by an amino-protecting groups.

The term "carboxy-protecting group" denotes groups intended to protect a carboxy group and includes ester groups and heterocycloalkyl groups. Examples of such ester groups include substituted arylalkyl esters, including esters with substituted benzyls, such as 4-nitrobenzyl, 4-methoxybenzyl, 3,4-dimethoxybenzyl, 2,4-dimethoxybenzyl, 2,4,6-trimethoxybenzyl, 2,4,6-trimethylbenzyl, pentamethylbenzyl, 3,4-methylenedioxybenzyl, benzhydryl, 4,4'-dimethoxybenzhydryl, 2,2',4,4'-tetramethoxybenzhydryl, esters with alkyl or substituted alkyl such as methyl, ethyl, t-butyl allyl or t-amyl, triphenylmethyl (trityl), 4-methoxytrityl, 4,4'-dimethoxytrityl, 4,4',4"-trimethoxytrityl, 2-phenylprop-2-yl, thioesters such as t-butyl thioester, silyl esters such as trimethylsilyl, t-butyldimethylsilyl esters, phenacyl, 2,2,2-trichloroethyl, beta-(trimethylsilyl)ethyl, beta-(di(n-butyl)methylsilyl)ethyl, p-toluenesulfonylethyl, 4-nitrobenzylsulfonylethyl, allyl, cinnamyl, and 1-(trimethylsilylmethyl)prop-1-en-3-yl. Another example of carboxy-protecting groups are heterocycloalkyl groups such as 1,3-oxazolinyl. Further examples of these groups are found in T. W. Greene and P. G. M. Wuts, "Protective Groups in Organic Synthesis", 2nd ed., John Wiley & Sons, Inc., New York, N.Y., 1991, chapter 5; E. Haslam, "Protective Groups in Organic Chemistry", J. G. W. McOmie, Ed., Plenum Press, New York, N.Y., 1973, Chapter 5, and T. W. Greene, "Protective Groups in Organic Synthesis", John Wiley and Sons, New York, N.Y., 1981, Chapter 5. The term "protected carboxy group" denotes a carboxy group substituted by a carboxy-protecting group.

The term "hydroxy-protecting group" denotes groups intended to protect a hydroxy group and include ester- and ether-forming groups, in particular tetrahydropyranyloxy, benzoyl, acetoxy, carbamoyloxy, benzyl, and silylethers (e.g. TBS, TBDPS) groups. Further examples of these groups are found in T. W. Greene and P. G. M. Wuts, "Protective Groups in Organic Synthesis", 2nd ed., John Wiley & Sons, Inc., New York, N.Y., 1991, chapters 2-3; E. Haslam, "Protective Groups in Organic Chemistry", J. G. W. McOmie, Ed., Plenum Press, New York, N.Y., 1973, Chapter 5, and T. W. Greene, "Protective Groups in Organic Synthesis", John Wiley and Sons, New York, N.Y., 1981. The term "protected hydroxy group" refers to a hydroxy group substituted by a hydroxy-protecting group.

The term "deprotection" or "deprotecting" denotes the process by which a protective group is removed after the selective reaction is completed. Deprotecting reagents include acids, bases or hydrogen, in particular potassium or sodium carbonates, lithium hydroxide in alcoholic solutions, zinc in methanol, acetic acid, trifluoroacetic acid, palladium catalysts, or boron tribromide.

The term "active pharmaceutical ingredient" (or "API") denotes the compound or molecule in a pharmaceutical composition that has a particular biological activity.

The terms "pharmaceutical composition" and "pharmaceutical formulation" (or "formulation") are used interchangeably and denote a mixture or solution comprising a therapeutically effective amount of an active pharmaceutical ingredient together with pharmaceutically acceptable excipients to be administered to a mammal, e.g., a human in need thereof.

The term "pharmaceutically acceptable" denotes an attribute of a material which is useful in preparing a pharmaceutical composition that is generally safe, non-toxic, and neither biologically nor otherwise undesirable and is acceptable for veterinary as well as human pharmaceutical use.

The terms "pharmaceutically acceptable excipient", "pharmaceutically acceptable carrier" and "therapeutically inert excipient" can be used interchangeably and denote any pharmaceutically acceptable ingredient in a pharmaceutical composition having no therapeutic activity and being non-toxic to the subject administered, such as disintegrators, binders, fillers, solvents, buffers, tonicity agents, stabilizers, antioxidants, surfactants, carriers, diluents or lubricants used in formulating pharmaceutical products.

The term "therapeutically effective amount" denotes an amount of a compound or molecule of the present invention that, when administered to a subject, (i) treats or prevents the particular disease, condition or disorder, (ii) attenuates, ameliorates or eliminates one or more symptoms of the particular disease, condition, or disorder, or (iii) prevents or delays the onset of one or more symptoms of the particular disease, condition or disorder described herein. The therapeutically effective amount will vary depending on the compound, the disease state being treated, the severity of the disease treated, the age and relative health of the subject, the route and form of administration, the judgement of the attending medical or veterinary practitioner, and other factors.

The term "treating" or "treatment" of a disease state includes inhibiting the disease state, i.e., arresting the development of the disease state or its clinical symptoms, or relieving the disease state, i.e., causing temporary or permanent regression of the disease state or its clinical symptoms.

The term "preventing" or "prevention" of a disease state denotes causing the clinical symptoms of the disease state not to develop in a subject that can be exposed to or predisposed to the disease state, but does not yet experience or display symptoms of the disease state.

The term "amino acid" as used herein denotes an organic molecule possessing an amino moiety located at a-position to a carboxylic group. Examples of amino acids include: arginine, glycine, ornithine, lysine, histidine, glutamic acid, asparagic acid, isoleucine, leucine, alanine, phenylalanine, tyrosine, tryptophane, methionine, serine, proline. The amino acid employed is optionally in each case the L-form.

In detail, the present invention relates to a compound of formula (I)

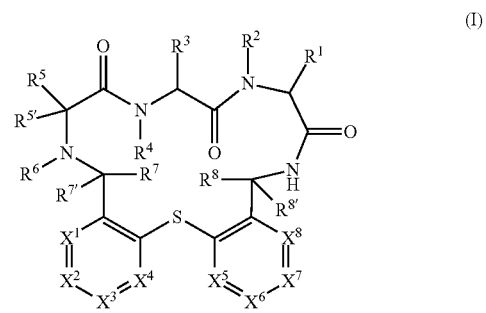

(I)

wherein:

$X^1$ is C—$R^{11}$ or N;

$X^2$ is C—$R^{12}$ or N;

$X^3$ is C—$R^{13}$ or N;

$X^4$ is C—$R^{14}$ or N, with the proviso that not more than three of $X^1$, $X^2$, $X^3$ and $X^4$ are N;

$X^5$ is C—$R^{15}$ or N;

$X^6$ is C—$R^{16}$ or N;

$X^7$ is C—$R^{17}$ or N;

$X^8$ is C—$R^{18}$ or N, with the proviso that not more than three of $X^5$, $X^6$, $X^7$ and $X^8$ are N;

$R^1$ is —$(CH_2)_m$-heteroaryl optionally substituted with one or more halo or $C_{1-7}$-alkyl;

$R^2$, $R^4$ and $R^6$ are each individually selected from hydrogen or $C_{1-7}$-alkyl;

$R^3$ and $R^5$ are each independently selected from hydrogen, —$C_{1-7}$-alkyl, hydroxy-$C_{1-7}$-alkyl, —$(CH_2)_m$—$NR^{20}R^{21}$, —$(CH_2)_m$—C(O)$NR^{20}R^{21}$, —$(CH_2)_m$—$CF_2$—$(CH_2)_m$—$NR^{20}R^{21}$, —$(CH_2)_m$—NH—C(O)—$(CH_2)_m$—$NR^{20}R^{21}$ or —$(CH_2)_m$—O—$(CH_2)_n$—$NR^{20}R^{21}$, —$(CH_2)_m$—NH—C(NH)—$NR^{20}R^{21}$, —$(CH_2)_m$—NH—C(O)—$OR^{21}$, —$(CH_2)_o$, —$C_{3-7}$-cycloalkyl, —$(CH_2)_o$-heterocycloalkyl, —$(CH_2)_o$-heteroaryl, —$(CH_2)_o$-aryl, wherein cycloalkyl, heterocycloalkyl, heteroaryl and aryl are optionally substituted by halo, cyano, $C_{1-7}$-alkyl, $C_{1-7}$-haloalkyl, $C_{1-7}$-hydroxyalkyl, $C_{1-7}$-alkoxy or aryl;

$R^{5'}$ is hydrogen or $C_{1-7}$-alkyl;

$R^7$, $R^{7'}$ and $R^8$, $R^{8'}$ are each individually selected from hydrogen or $C_{1-7}$-alkyl;

$R^{11}$, $R^{12}$, $R^{13}$, $R^{14}$, $R^{15}$, $R^{16}$, $R^{17}$ and $R^{18}$ are each individually selected from hydrogen, halogen, $C_{1-7}$-alkyl, $C_{1-7}$-haloalkyl, hydroxy, $C_{1-7}$-hydroxyalkyl, $C_{1-7}$-alkoxy, $C_{1-7}$-haloalkoxy, —$NR^{24}R^{25}$, $C_{1-7}$-alkyl-$NR^{24}R^{25}$, aryl-$C_{1-7}$-alkyl-O—$C_{1-7}$-alkinyl-, aryl and heteroaryl, wherein aryl and heteroaryl are optionally substituted with one, two or three substituents selected from the list of halogen, cyano, $C_{1-7}$-alkyl, $C_{1-7}$-haloalkyl, hydroxy, $C_{1-7}$-alkoxy, —$NR^{24}R^{25}$, $C_{1-7}$-alkyl-$NR^{24}R^{25}$, —CO—NH—$(CH_2)_n$—$NR^{24}R^{25}$, —CO—NH—$(CH_2)_r$—OH, —CO—NH—$(CH_2)_o$-heterocycloalkyl, —CO—OH, —O—$C_{1-7}$-hydroxyalkyl, —O—$(CH_2)_r$—CO—OH, —$SO_2$—$C_{1-7}$-alkyl, —$SO_2$—$NR^{24}R^{25}$, heterocycloalkyl, —O— heterocycloalkyl and heterocycloalkyl substituted with $C_{1-7}$-alkyl or oxo;

$R^{20}$ and $R^{22}$ are each individually selected from hydrogen, $C_{1-7}$-alkyl and benzyl;

$R^{21}$ and $R^{23}$ are each individually selected from hydrogen and $C_{1-7}$-alkyl;

$R^{24}$ and $R^{25}$ are each individually selected from hydrogen, $C_{1-7}$-alkyl, $C_{1-7}$-haloalkyl, $C_{1-7}$-hydroxyalkyl, and $C_{3-7}$-cycloalkyl;

m is 1, 2, 3, 4, 5 or 6;

n is 2, 3, 4, 5 or 6;

o is 0, 1, 2, 3, 4, 5, 6, 7 or 8;

or a pharmaceutically acceptable salt thereof, for the use in the treatment or prevention of infections and resulting diseases caused by *Pseudomonas aeruginosa*.

In a particular embodiment, the present invention relates to a compound of formula (I) described in the foregoing paragraphs, wherein:

$X^1$ is $CR^{11}$ or N;

$X^2$ is $CR^{12}$ or N;

$X^3$ is $CR^{13}$ or N;

$X^4$ is $CR^{14}$ or N, with the proviso that not more than two of $X^1$, $X^2$, $X^3$ and $X^4$ are N;

$X^5$ is $CR^{15}$ or N;

$X^6$ is $CR^{16}$ or N;

$X^7$ is $CR^{17}$ or N;

$X^8$ is $CR^{18}$ or N, with the proviso that not more than two of $X^5$, $X^6$, $X^7$ and $X^8$ are N;

$R^1$ is —$(CH_2)_m$-heteroaryl optionally substituted with one or more halo or $C_{1-7}$-alkyl;

$R^2$, $R^4$ and $R^6$ are each individually selected from hydrogen or $C_{1-7}$-alkyl;

$R^3$ is —$(CH_2)_m$—$NR^{20}R^{21}$;

$R^5$ is —$(CH_2)_m$—$NR^{22}R^{23}$ or —$(CH_2)_o$-heterocycloalkyl, wherein heterocycloalkyl is optionally substituted by halo or $C_{1-7}$-alkyl;

$R^7$, $R^{7'}$ and $R^8$, $R^{8'}$ are hydrogen;

$R^{11}$, $R^{12}$, $R^{13}$, $R^{14}$, $R^{15}$, $R^{16}$, $R^{17}$ and $R^{18}$ are each individually selected from hydrogen, halogen, $C_{1-7}$-alkyl, $C_{1-7}$-haloalkyl, hydroxy, $C_{1-7}$-hydroxyalkyl, $C_{1-7}$-alkoxy, $C_{1-7}$-haloalkoxy, —$NR^{24}R^{25}$, $C_{1-7}$-alkyl-$NR^{24}R^{25}$, aryl-$C_{1-7}$-alkyl-O—$C_{1-7}$-alkinyl-, aryl and heteroaryl, wherein aryl and heteroaryl are optionally substituted with one, two or three substituents selected from the list of halogen, cyano, $C_{1-7}$-alkyl $C_{1-7}$-haloalkyl, hydroxy, $C_{1-7}$-alkoxy, —$NR^{24}R^{25}$, $C_{1-7}$-alkyl-$NR^{24}R^{25}$, —CO—NH—$(CH_2)_n$—$NR^{24}R^{25}$, —CO—NH—$(CH_2)_r$—OH, —CO—NH—$(CH_2)_o$-heterocycloalkyl, —CO—OH, —O—$C_{1-7}$-hydroxyalkyl, —O—$(CH_2)_o$—CO—OH, —$SO_2$—$C_{1-7}$-alkyl, —$SO_2$—$NR^{24}R^{25}$, heterocycloalkyl, —O— heterocycloalkyl and heterocycloalkyl substituted with $C_{1-7}$-alkyl or oxo;

$R^{20}$, $R^{21}$, $R^{22}$ and $R^{23}$ are hydrogen;

$R^{24}$ and $R^{25}$ are each individually selected from hydrogen and $C_{1-7}$-alkyl;

m, n, o, p, q and r are each individually selected from 1, 2, 3 and 4;

or a pharmaceutically acceptable salt thereof, for the use in the treatment or prevention of infections and resulting diseases caused by *Pseudomonas aeruginosa*.

In another particular embodiment, the present invention relates to a compound of formula (Ia)

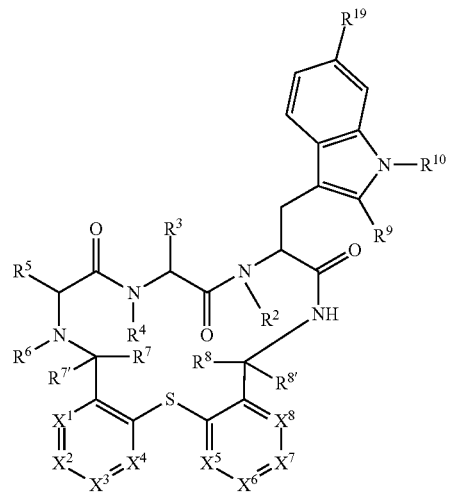

(Ia)

wherein:

$X^1$ is $CR^{11}$ or N;

$X^2$ is $CR^{12}$ or N;

$X^3$ is $CR^{13}$ or N;

$X^4$ is $CR^{14}$ or N, with the proviso that not more than two of $X^1$, $X^2$, $X^3$ and $X^4$ are N;

$X^5$ is $CR^{15}$ or N;

$X^6$ is $CR^{16}$ or N;

$X^7$ is $CR^{17}$ or N;

$X^8$ is $CR^{18}$ or N, with the proviso that not more than two of $X^5$, $X^6$, $X^7$ and $X^8$ are N;

$R^2$, $R^4$ and $R^6$ are each individually selected from hydrogen or $C_{1-7}$-alkyl;

$R^3$ is —$(CH_2)_m$—$NR^{20}R^{21}$;

$R^5$ is —$(CH_2)_m$—$NR^{22}R^{23}$ or —$(CH_2)_o$-heterocycloalkyl, wherein heterocycloalkyl is optionally substituted by halo or $C_{1-7}$-alkyl;

$R^7$, $R^{7'}$ and $R^8$, $R^{8'}$ are hydrogen;

$R^9$ is hydrogen, halo or $C_{1-7}$-alkyl;

$R^{10}$ is hydrogen or $C_{1-7}$-alkyl;

$R^{11}$, $R^{12}$, $R^{13}$, $R^{14}$, $R^{15}$, $R^{16}$, $R^{17}$ and $R^{18}$ are each individually selected from hydrogen, halogen, $C_{1-7}$-alkyl, $C_{1-7}$-haloalkyl, hydroxy, $C_{1-7}$-hydroxyalkyl, $C_{1-7}$-alkoxy, $C_{1-7}$-haloalkoxy, —$NR^{24}R^{25}$, $C_{1-7}$-alkyl-$NR^{24}R^{25}$, aryl-$C_{1-7}$-alkyl-O—$C_{1-7}$-alkinyl-, aryl and heteroaryl, wherein aryl and heteroaryl are optionally substituted with one, two or three substituents selected from the list of halogen, cyano, $C_{1-7}$-alkyl $C_{1-7}$-haloalkyl, hydroxy, $C_{1-7}$-alkoxy, —$NR^{24}R^{25}$, $C_{1-7}$-alkyl-$NR^{24}R^{25}$, —CO—NH—$(CH_2)_n$—$NR^{24}R^{25}$, —CO—NH—$(CH_2)_o$—OH, —CO—NH—$(CH_2)_o$-heterocycloalkyl, —CO—OH, —O—$C_{1-7}$-hydroxyalkyl, —O—$(CH_2)_o$—CO—OH, —$SO_2$—$C_{1-7}$-alkyl, —$SO_2$—$NR^{24}R^{25}$, heterocycloalkyl, —O— heterocycloalkyl and heterocycloalkyl substituted with $C_{1-7}$-alkyl or oxo;

$R^{19}$ is hydrogen, halo, $C_{1-7}$-alkyl;

$R^{20}$, $R^{21}$, $R^{22}$ and $R^{23}$ are hydrogen;

$R^{24}$ and $R^{25}$ are each individually selected from hydrogen and $C_{1-7}$-alkyl;

or a pharmaceutically acceptable salt thereof, for the use in the treatment or prevention of infections and resulting diseases caused by *Pseudomonas aeruginosa*.

In yet another particular embodiment, the present invention relates to a compound of formula (Ib)

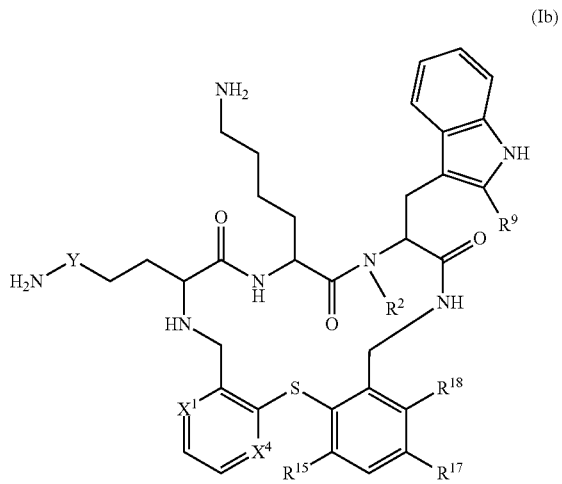

(Ib)

wherein:
$X^1$ is $CR^{11}$ or N;
$X^4$ is $CR^{14}$ or N;
$R^2$ is selected from hydrogen and $C_{1-7}$-alkyl;
$R^9$ is hydrogen, halo or $C_{1-7}$-alkyl;
$R^{15}$ is hydrogen, halogen, $C_{1-7}$-alkyl, $C_{1-7}$-haloalkyl, —$NR^{24}R^{25}$, $C_{1-7}$-alkyl-$NR^{24}R^{25}$, hydroxy, $C_{1-7}$-alkoxy, halo$C_{1-7}$-alkoxy, benzyloxy-propynyl (—C≡C—$CH_2$—O-benzyl), heterocycloalkyl, aryl and heteroaryl, wherein aryl is optionally substituted with one —$NR^{20}R^{21}$ or heterocycloalkyl substituted with $C_{1-7}$-alkyl;
$R^{17}$ is hydrogen, halogen, $C_{1-7}$-alkyl, $C_{1-7}$-haloalkyl, —$NR^{24}R^{25}$, $C_{1-7}$-alkyl-$NR^{24}R^{25}$, hydroxy, $C_{1-7}$-alkoxy, halo$C_{1-7}$-alkoxy, benzyloxy-prop-1-ynyl, heterocycloalkyl, aryl and heteroaryl, wherein heterocycloalkyl is optionally substituted with one —$NR^{24}R^{25}$, wherein aryl and heteroaryl are optionally substituted with one, two or three substituents selected from the list of halogen, $C_{1-7}$-alkyl, $C_{1-7}$-haloalkyl, $C_{1-7}$-hydroxyalkyl, hydroxy, $C_{1-7}$-alkoxy, —$NR^{24}R^{25}$, —$SO_2$—$C_{1-7}$-alkyl, —$SO_2$—$NR^{24}R^{25}$, heterocycloalkyl and heterocycloalkyl substituted with $C_{1-7}$-alkyl;
$R^{18}$ is hydrogen, halogen, $C_{1-7}$-alkyl, $C_{1-7}$-haloalkyl, hydroxy, $C_{1-7}$-hydroxyalkyl, $C_{1-7}$-alkoxy, $C_{1-7}$-haloalkoxy, —$NR^{24}R^{25}$, $C_{1-7}$-alkyl-$NR^{24}R^{25}$, aryl and heteroaryl, wherein aryl and heteroaryl are optionally substituted with one, two or three substituents selected from the list of halogen, cyano, $C_{1-7}$-alkyl $C_{1-7}$-haloalkyl, hydroxy, $C_{1-7}$-alkoxy, —$NR^{24}R^{25}$, $C_{1-7}$-alkyl-$NR^{24}R^{25}$, —CO—NH—$(CH_2)_o$—$NR^{24}R^{25}$, —CO—NH—$(CH_2)_r$—OH, —CO—NH—$(CH_2)_o$-heterocycloalkyl, —CO—OH, —O—$C_{1-7}$-hydroxyalkyl, —O—$(CH_2)_r$—CO—OH, —$SO_2$—$C_{1-7}$-alkyl, —$SO_2$—$NR^{24}R^{25}$, heterocycloalkyl, —O-heterocycloalkyl and heterocycloalkyl substituted with $C_{1-7}$-alkyl or oxo;
$R^{19}$ is hydrogen, halo, $C_{1-7}$-alkyl;
$R^{20}$, $R^{21}$, $R^{22}$ and $R^{23}$ are hydrogen;
$R^{24}$ and $R^{25}$ are each individually selected from hydrogen and $C_{1-7}$-alkyl; Y is —$CH_2$— or —CO—;
or a pharmaceutically acceptable salt thereof,
for the use in the treatment or prevention of infections and resulting diseases caused by Pseudomonas aeruginosa.

Particular compounds of formula (I) of the present invention are those selected from the group consisting of:
(12S,15S,18S)-15-(4-Amino-butyl)-18-(3-amino-propyl)-6-chloro-12-(1H-indol-3-ylmethyl)-13-methyl-2-thia-10,13,16,19-tetraaza-tricyclo[19.4.0.0*3,8*]pentacosa-1(21),3,5,7,22,24-hexaene-11,14,17-trione;
(12S,15S,18S)-15-(4-Amino-butyl)-18-(3-amino-propyl)-5-chloro-12-(1H-indol-3-ylmethyl)-13-methyl-2-thia-10,13,16,19-tetraaza-tricyclo[19.4.0.0*3,8*]pentacosa-1(21),3,5,7,22,24-hexaene-11,14,17-trione;
(12S,15S,18S)-15-(4-Amino-butyl)-18-(3-amino-propyl)-4-chloro-12-(1H-indol-3-ylmethyl)-13-methyl-2-thia-10,13,16,19-tetraaza-tricyclo[19.4.0.0*3,8*]pentacosa-1(21),3,5,7,22,24-hexaene-11,14,17-trione;
(12S,15S,18S)-15-(4-Amino-butyl)-18-(3-amino-propyl)-12-(1H-indol-3-ylmethyl)-13-methyl-5-trifluoromethyl-2-thia-10,13,16,19-tetraaza-tricyclo[19.4.0.0*3,8*]pentacosa-1(21),3,5,7,22,24-hexaene-11,14,17-trione;
(12S,15S,18S)-15-(4-Amino-butyl)-18-(3-amino-propyl)-12-(6-chloro-1H-indol-3-ylmethyl)-13-methyl-2-thia-10,13,16,19-tetraaza-tricyclo[19.4.0.0*3,8*]pentacosa-1(21),3,5,7,22,24-hexaene-11,14,17-trione;
(12S,15S,18S)-15-(4-Amino-butyl)-18-(3-amino-propyl)-6-chloro-13-methyl-12-(1-methyl-1H-indol-3-ylmethyl)-2-thia-10,13,16,19-tetraaza-tricyclo[19.4.0.0*3,8*]pentacosa-1(21),3,5,7,22,24-hexaene-11,14,17-trione;
(12S,15S,18S)-15-(4-Amino-butyl)-18-(3-amino-propyl)-6-chloro-12-(6-chloro-1H-indol-3-ylmethyl)-13-methyl-2-thia-10,13,16,19-tetraaza-tricyclo[19.4.0.0*3,8*]pentacosa-1(21),3,5,7,22,24-hexaene-11,14,17-trione;
(12S,15S,18S)-15-(4-Amino-butyl)-18-(3-amino-propyl)-6-chloro-12-(6-chloro-1-methyl-1H-indol-3-ylmethyl)-13-methyl-2-thia-10,13,16,19-tetraaza-tricyclo[19.4.0.0*3,8*]pentacosa-1(21),3,5,7,22,24-hexaene-11,14,17-trione;
(12S,15S,18S)-15-(4-Amino-butyl)-18-(3-amino-propyl)-6,7-dichloro-12-(1H-indol-3-ylmethyl)-13-methyl-2-thia-10,13,16,19-tetraaza-tricyclo[19.4.0.0*3,8*]pentacosa-1(25),3,5,7,21,23-hexaene-11,14,17-trione;
(12S,15S,18S)-15-(4-Amino-butyl)-18-(3-amino-propyl)-4-chloro-12-(1H-indol-3-ylmethyl)-13-methyl-7-trifluoromethyl-2-thia-10,13,16,19-tetraaza-tricyclo[19.4.0.0*3,8*]pentacosa-1(25),3,5,7,21,23-hexaene-11,14,17-trione;
(12S,15S,18S)-15-(4-Amino-butyl)-18-(3-amino-propyl)-4-chloro-12-(1H-indol-3-ylmethyl)-13-methyl-6-trifluoromethyl-2-thia-10,13,16,19-tetraaza-tricyclo[19.4.0.0*3,8*]pentacosa-1(25),3,5,7,21,23-hexaene-11,14,17-trione;
(12S,15S,18S)-15-(4-Amino-butyl)-18-(3-amino-propyl)-4,6-dichloro-23-fluoro-12-(1H-indol-3-ylmethyl)-13-methyl-2-thia-10,13,16,19-tetraaza-tricyclo[19.4.0.0*3,8*]pentacosa-1(25),3,5,7,21,23-hexaene-11,14,17-trione;
(12S,15S,18S)-15-(4-Amino-butyl)-18-(3-amino-propyl)-6-chloro-12-(1H-indol-3-ylmethyl)-13-methyl-4-trifluoromethyl-2-thia-10,13,16,19-tetraaza-tricyclo[19.4.0.0*3,8*]pentacosa-1(25),3,5,7,21,23-hexaene-11,14,17-trione;
(12S,15S,18S)-15-(4-Amino-butyl)-18-(3-amino-propyl)-6-chloro-12-(1H-indol-3-ylmethyl)-4,13-dimethyl-2-thia-10,13,16,19-tetraaza-tricyclo[19.4.0.0*3,8*]pentacosa-1(25),3,5,7,21,23-hexaene-11,14,17-trione;
(12S,15S,18S)-15-(4-Amino-butyl)-18-(3-amino-propyl)-6-chloro-13-methyl-12-(2-methyl-1H-indol-3-ylmethyl)-2-thia-10,13,16,19-tetraaza-tricyclo[19.4.0.0*3,8*]pentacosa-1(21),3,5,7,22,24-hexaene-11,14,17-trione;
(12S,15S,18S)-15-(4-Amino-butyl)-18-(3-amino-propyl)-4,13-dimethyl-12-(2-methyl-1H-indol-3-ylmethyl)-2-thia-10,13,16,19-tetraaza-tricyclo[19.4.0.0*3,8*]pentacosa-1(21),3,5,7,22,24-hexaene-11,14,17-trione;
(12S,15S,18S)-15-(4-Amino-butyl)-18-(3-amino-propyl)-4,6-dichloro-13-methyl-12-(2-methyl-1H-indol-3-ylmethyl)-2-thia-10,13,16,19-tetraaza-tricyclo[19.4.0.0*3, 8*]pentacosa-1(21),3,5,7,22,24-hexaene-11,14,17-trione;
(12S,15S,18S)-15-(4-Amino-butyl)-18-(3-amino-propyl)-6-ethyl-12-(1H-indol-3-ylmethyl)-13-methyl-2-thia-10,13, 16,19-tetraaza-tricyclo[19.4.0.0*3,8*]pentacosa-1(25),3, 5,7,21,23-hexaene-11,14,17-trione;
(12S,15S,18S)-15-(4-Amino-butyl)-18-(3-amino-propyl)-12-(1H-indol-3-ylmethyl)-13-methyl-6-phenyl-2-thia-10, 13,16,19-tetraaza-tricyclo[19.4.0.0*3,8*]pentacosa-1 (25),3,5,7,21,23-hexaene-11,14,17-trione;
(12S,15S,18S)-15-(4-Amino-butyl)-18-(3-amino-propyl)-6-tert-butyl-12-(1H-indol-3-ylmethyl)-13-methyl-2-thia-10,13,16,19-tetraaza-tricyclo[19.4.0.0*3,8*]pentacosa-1 (25),3,5,7,21,23-hexaene-11,14,17-trione;
(12S,15S,18S)-15-(4-Amino-butyl)-18-(3-amino-propyl)-12-(1H-indol-3-ylmethyl)-6-isopropyl-13-methyl-2-thia-10,13,16,19-tetraaza-tricyclo[19.4.0.0*3,8*]pentacosa-1 (25),3,5,7,21,23-hexaene-11,14,17-trione;
(11S,14S,17S)-14-(4-Amino-butyl)-11-(3-amino-propyl)-17-(1H-indol-3-ylmethyl)-16-methyl-23-phenyl-25-trifluoromethyl-2-thia-4,10,13,16,19-pentaaza-tricyclo [19.4.0.0*3,8*]pentacosa-1(25),3,5,7,21,23-hexaene-12, 15,18-trione;
(11S,14S,17S)-14-(4-Amino-butyl)-1-(3-amino-propyl)-17-(1H-indol-3-ylmethyl)-16-methyl-23,25-bis-trifluoromethyl-2-thia-4,10,13,16,19-pentaaza-tricyclo[19.4.0.0*3, 8*]pentacosa-1(25),3,5,7,21,23-hexaene-12,15,18-trione;
(11S,14S,17S)-14-(4-Amino-butyl)-11-(3-amino-propyl)-25-chloro-17-(1H-indol-3-ylmethyl)-16-methyl-23-trifluoromethyl-2-thia-7,10,13,16,19-pentaaza-tricyclo [19.4.0.0*3,8*]pentacosa-1(25),3,5,7,21,23-hexaene-12, 15,18-trione;
(11R,14S,17S)-14-(4-Amino-butyl)-11-(3-amino-propyl)-25-chloro-17-(1H-indol-3-ylmethyl)-24-phenyl-2-thia-4, 10,13,16,19-pentaaza-tricyclo[19.4.0.0*3,8*]pentacosa-1 (25),3,5,7,21,23-hexaene-12,15,18-trione;
(11S,14S,17S)-14-(4-Amino-butyl)-11-(3-amino-propyl)-25-chloro-17-(1H-indol-3-ylmethyl)-24-phenyl-2-thia-4, 10,13,16,19-pentaaza-tricyclo[19.4.0.0*3,8*]pentacosa-1 (25),3,5,7,21,23-hexaene-12,15,18-trione;
(11R,14S,17S)-14-(4-Amino-butyl)-11-(3-amino-propyl)-25-chloro-17-(1H-indol-3-ylmethyl)-16-methyl-24-phenyl-2-thia-4,10,13,16,19-pentaaza-tricyclo[19.4.0.0*3, 8*]pentacosa-1(25),3,5,7,21,23-hexaene-12,15,18-trione;
(12S,15S,18S)-15-(4-Amino-butyl)-18-(3-amino-propyl)-12-(1H-indol-3-ylmethyl)-13-methyl-6-phenyl-4-trifluoromethyl-2-thia-10,13,16,19-tetraaza-tricyclo [19.4.0.0*3,8*]pentacosa-1(25),3,5,7,21,23-hexaene-11, 14,17-trione;
(11S,14S,17S)-14-(4-Amino-butyl)-11-(3-amino-propyl)-25-chloro-17-(1H-indol-3-ylmethyl)-16-methyl-22-phenyl-2-thia-4,10,13,16,19-pentaaza-tricyclo[19.4.0.0*3, 8*]pentacosa-1(25),3(8),4,6,21,23-hexaene-12,15,18-trione;
(12S,15S,18S)-15,18-Bis-(3-amino-propyl)-4,6-dichloro-12-(1H-indol-3-ylmethyl)-13-methyl-2-thia-10,13,16,19-tetraaza-tricyclo[19.4.0.0*3,8*]pentacosa-1(25),3,5,7,21, 23-hexaene-11,14,17-trione;
(11S,14S,17S)-14-(4-Amino-butyl)-11-(3-amino-propyl)-25-chloro-17-(5-chloro-1H-indol-3-ylmethyl)-16-methyl-22-trifluoromethyl-2-thia-4,10,13,16,19-pentaaza-tricyclo[19.4.0.0*3,8*]pentacosa-1(25),3,5,7,21, 23-hexaene-12,15,18-trione;
(12S,15S,18S)-15-(4-Amino-butyl)-18-(3-amino-propyl)-4-chloro-12-(1H-indol-3-ylmethyl)-13-methyl-6-phenyl-2-thia-10,13,16,19-tetraaza-tricyclo[19.4.0.0*3,8*]pentacosa-1(25),3,5,7,21,23-hexaene-11,14,17-trione;
(12S,15S,18S)-15-(4-Amino-butyl)-18-(3-amino-propyl)-4-chloro-6-(2-chloro-phenyl)-12-(1H-indol-3-ylmethyl)-13-methyl-2-thia-10,13,16,19-tetraaza-tricyclo [19.4.0.0*3,8*]pentacosa-1(25),3,5,7,21,23-hexaene-11, 14,17-trione;
(12S,15S,18S)-15-(4-Amino-butyl)-18-(3-amino-propyl)-4-chloro-12-(1H-indol-3-ylmethyl)-13-methyl-6-pyridin-3-yl-2-thia-10,13,16,19-tetraaza-tricyclo[19.4.0.0*3,8*] pentacosa-1(25),3,5,7,21,23-hexaene-11,14,17-trione;
11-(3-amino-propyl)-25-chloro-17-(1H-indol-3-ylmethyl)-16-methyl-23-phenyl-2-thia-4,10,13,16,19-pentaaza-tricyclo[19.4.0.0*3,8*]pentacosa-1(25),3(8),4,6,21,23-hexaene-12,15,18-trione;
(12S,15S,18S)-15-(4-Amino-butyl)-18-(3-amino-propyl)-6-bromo-4-chloro-12-(1H-indol-3-ylmethyl)-13-methyl-2-thia-10,13,16,19-tetraaza-tricyclo[19.4.0.0*3,8*]pentacosa-1(25),3,5,7,21,23-hexaene-11,14,17-trione;
(12S,15S,18S)-15-(4-Amino-butyl)-18-(3-amino-propyl)-4-chloro-12-(1H-indol-3-ylmethyl)-13-methyl-6-(1-methyl-1H-imidazol-4-yl)-2-thia-10,13,16,19-tetraaza-tricyclo[19.4.0.0*3,8*]pentacosa-1(25),3,5,7,21,23-hexaene-11,14,17-trione;
3-[(11S,14S,17S)-14-(4-Amino-butyl)-17-(1H-indol-3-ylmethyl)-16-methyl-12,15,18-trioxo-23-phenyl-25-trifluoromethyl-2-thia-10,13,16,19-tetraaza-tricyclo [19.4.0.0*3,8*]pentacosa-1(25),3,5,7,21,23-hexaen-11-yl]-propionamide;
3-[(11S,14S,17S)-11-(3-Amino-propyl)-17-(1H-indol-3-ylmethyl)-16-methyl-12,15,18-trioxo-23-phenyl-25-trifluoromethyl-2-thia-10,13,16,19-tetraaza-tricyclo [19.4.0.0*3,8*]pentacosa-1(25),3,5,7,21,23-hexaen-14-yl]-propionamide;
(11S,14S,17S)-14-(4-Amino-butyl)-11-(3-amino-propyl)-25-chloro-23-(2-chloro-pyridin-4-yl)-17-(1H-indol-3-ylmethyl)-16-methyl-2-thia-4,10,13,16,19-pentaaza-tricyclo[19.4.0.0*3,8*]pentacosa-1(21),3,5,7,22,24-hexaene-12,15,18-trione;
(12S,15S,18S)-15-(4-Amino-butyl)-18-(3-amino-propyl)-5-bromo-4-chloro-12-(1H-indol-3-ylmethyl)-13-methyl-2-thia-10,13,16,19-tetraaza-tricyclo[19.4.0.0*3,8*]pentacosa-1(25),3,5,7,21,23-hexaene-11,14,17-trione;
(12S,15S,18S)-15-(4-Amino-butyl)-18-(3-amino-propyl)-4-chloro-12-(1H-indol-3-ylmethyl)-13-methyl-5-phenyl-2-thia-10,13,16,19-tetraaza-tricyclo[19.4.0.0*3,8*]pentacosa-1(25),3,5,7,21,23-hexaene-11,14,17-trione;
(8S,11S,14S)-8-((1H-Indol-3-yl)methyl)-11-(4-aminobutyl)-14-(3-aminopropyl)-3-chloro-9-methyl-5,6,8,9, 11,12,15,16-octahydrobenzo[b]pyrido[3,2-p][1,5,8,11, 14]thiatetraazacycloheptadecine-7,10,13(14H)-trione;
(11S,14S,17S)-14-(4-Amino-butyl)-11-(3-amino-propyl)-25-chloro-23-(2-chloro-pyridin-4-yl)-16-methyl-17-(2-methyl-1H-indol-3-ylmethyl)-2-thia-4,10,13,16,19-pentaaza-tricyclo[19.4.0.0*3,8*]pentacosa-1(25),3(8),4,6,21, 23-hexaene-12,15,18-trione;
(11S,14S,17S)-14-(4-Amino-butyl)-11-(3-amino-propyl)-23-(3-benzyloxy-prop-1-ynyl)-25-chloro-17-(1H-indol-3-ylmethyl)-16-methyl-2-thia-4,10,13,16,19-pentaaza-tricyclo[19.4.0.0*3,8*]pentacosa-1(25),3(8),4,6,21,23-hexaene-12,15,18-trione;
(8S,11S,14S)-8-((1H-Indol-3-yl)methyl)-11-(4-aminobutyl)-14-(3-aminopropyl)-9-methyl-2-morpholino-5, 6,8,9,11,12,15,16-octahydrobenzo[b]pyrido[3,2-p][1,5,8, 11,14]thiatetraazacycloheptadecine-7,10,13(14H)-trione;
(11S,14S,17S)-14-(4-Amino-butyl)-11-(3-amino-propyl)-25-chloro-16-methyl-17-(2-methyl-1H-indol-3-ylmethyl)-22-pyridin-4-yl-2-thia-4,10,13,16,19-pentaaza-tricyclo[19.4.0.0*3,8*]pentacosa-1(25),3(8),4,6,21,23-hexaene-12,15,18-trione;

(12S,15S,18S)-15-(4-Amino-butyl)-18-(3-amino-propyl)-23-bromo-4-chloro-12-(1H-indol-3-ylmethyl)-13-methyl-2-thia-10,13,16,19-tetraaza-tricyclo[19.4.0.0*3,8*]pentacosa-1(25),3,5,7,21,23-hexaene-11,14,17-trione;

(12S,15S,18S)-15-(4-Amino-butyl)-18-(3-amino-propyl)-4-chloro-12-(1H-indol-3-ylmethyl)-13-methyl-23-phenyl-2-thia-10,13,16,19-tetraaza-tricyclo[19.4.0.0*3,8*]pentacosa-1(25),3,5,7,21,23-hexaene-11,14,17-trione;

(12S,15S,18S)-15-(4-Amino-butyl)-23-(4-aminomethyl-phenyl)-18-(3-amino-propyl)-4-chloro-12-(1H-indol-3-ylmethyl)-13-methyl-2-thia-10,13,16,19-tetraaza-tricyclo[19.4.0.0*3,8*]pentacosa-1(25),3,5,7,21,23-hexaene-11,14,17-trione;

(12S,15S,18S)-15-(4-Amino-butyl)-18-(3-amino-propyl)-24-bromo-4-chloro-12-(1H-indol-3-ylmethyl)-13-methyl-2-thia-10,13,16,19-tetraaza-tricyclo[19.4.0.0*3,8*]pentacosa-1(25),3,5,7,21,23-hexaene-11,14,17-trione;

(12S,15S,18S)-15-(4-Amino-butyl)-18-(3-amino-propyl)-4-chloro-12-(1H-indol-3-ylmethyl)-13-methyl-24-phenyl-2-thia-10,13,16,19-tetraaza-tricyclo[19.4.0.0*3,8*]pentacosa-1(25),3,5,7,21,23-hexaene-11,14,17-trione;

4-[(11S,14S,17S)-14-(4-Amino-butyl)-11-(3-amino-propyl)-25-chloro-16-methyl-17-(2-methyl-1H-indol-3-ylmethyl)-12,15,18-trioxo-2-thia-4,10,13,16,19-pentaaza-tricyclo[19.4.0.0*3,8*]pentacosa-1(25),3(8),4,6,21,23-hexaen-23-yl]-benzenesulfonamide;

(11S,14S,17S)-14-(4-Amino-butyl)-22-[3-(2-amino-ethyl)-phenyl]-11-(3-amino-propyl)-25-chloro-17-(1H-indol-3-ylmethyl)-16-methyl-2-thia-4,10,13,16,19-pentaaza-tricyclo[19.4.0.0*3,8*]pentacosa-1(25),3(8),4,6,21,23-hexaene-12,15,18-trione;

(11S,14S,17S)-14-(4-Amino-butyl)-11-(3-amino-propyl)-25-chloro-17-(1H-indol-3-ylmethyl)-16-methyl-22-(4-piperazin-1-yl-phenyl)-2-thia-4,10,13,16,19-pentaaza-tricyclo[19.4.0.0*3,8*]pentacosa-1(25),3(8),4,6,21,2-hexaene-12,15,18-trione; and
pharmaceutically acceptable salts thereof.

Manufacturing Processes

Compounds of formula (I), (I'), (Ia), (Ib) or (Ic) and pharmaceutically acceptable salts thereof as defined above can be prepared following standard methods known in the art.

1. General Synthesis of the Tether

The tether intermediate of formula (III) can be prepared following standard methods known in the art, particularly according to methods as described in the examples (e.g. PG=Fmoc).

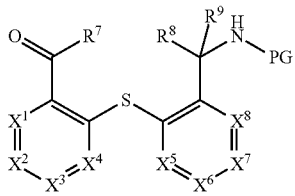

(III)

2. General Synthesis of the Tripeptide

The tripeptide of formula (IV) can be prepared following standard methods known in the art.

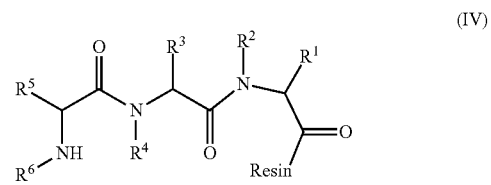

(IV)

The tripeptide sequence can for example be synthesized via state-of-the-art solid-phase peptide synthesis (SPPS) protocols (e.g. Fmoc-chemistry) as follows:
a) A resin (e.g. 2-Cl-Trityl resin) as solid support is loaded with the first N-protected amino acid and Hünig's base (N,N-Diisopropylethylamine or DIPEA) followed by cleavage of the protecting group.
b) A second N-protected amino acid is coupled with a coupling reagent and Hünig's base followed by cleavage of the protecting group (e.g. Fmoc).
c) A third N-protected amino acid is coupled with a coupling reagent and Hünig's base followed by cleavage of the protecting group.

In case N-methylated amino acids are present in the compound of formula (IV), the alkylation may be performed on the solid phase. After the appropriate step of the SPPS, the terminal amine is protected in a first step e.g. by swelling the resin in tetrahydrofurane (THF) and addition of Hünig's base and 2-nitrobenzene-1-1sulfonylchloride (Nbs). In the second step, methyl-4-nitrobenzenesulfonate together with 7-methyl-1,5,7-triazabicyclo[4.4.0]dec-5-ene can be added to the resin in dimethylfurane (DMF). For removal of the 2-nitrobenzene-1-isulfonamide protecting group, 1,8-diazabicyclo[5.4.0]undec-7-ene (DBU) can be added to the resin in DMF followed by addition of mercaptoethanol.

In a particular embodiment, the solid support is a 2-Chlortritylchloride resin.

In a particular embodiment, the N-protected amino acids are protected with 9-fluorenylmethyloxycarbonyl (Fmoc).

In a particular embodiment, the resin is loaded in step a) with 0.1-1.0 eq of the first amino acid and excess Hünig's base in dichloromethane (DCM).

In a particular embodiment, the resin is thoroughly washed after the coupling reaction in step a) with dimethylformamide (DMF) and dichloromethane (DCM).

In a particular embodiment, the Fmoc protecting group is cleaved off in step a) with a mixture of 50% Piperidine in DCM/DMF (1:1).

In a particular embodiment, the resin is thoroughly washed after the deprotection in step a) with DMF, DCM and Methanol (MeOH) followed by drying under vacuum and weighing.

In a particular embodiment, the coupling reagent in step b) is Mukaiyama's reagent (2-chloro-1-methylpyridinium iodide).

In a particular embodiment, the second amino acid in step b) is coupled with 4 eq of Mukaiyama's reagent as coupling reagent and 6 eq of Hünig's base in DMF/DCM (1:1).

In a particular embodiment, the resin is thoroughly washed after the coupling reaction in step b) with dimethylformamide (DMF) and dichloromethane (DCM).

In a particular embodiment, the Fmoc protecting group is cleaved off in step b) with a mixture of 50% Piperidine in DCM/DMF (1:1).

In a particular embodiment, the resin is thoroughly washed after the deprotection in step b) with DMF and DCM followed by drying under vacuum and weighing.

In a particular embodiment, the coupling reagent in step c) is HATU (1-[bis(dimethyl-amino)methylene]-1H-1,2,3-triazolo[4,5-b]pyridinium 3-oxid hexafluorophosphate).

In a particular embodiment, the third amino acid in step c) is coupled with 4 eq of HATU as coupling reagent and 6 eq of Hünig's base in DMF/DCM (1:1).

In a particular embodiment, the resin is thoroughly washed after the coupling reaction in step c) with dimethylformamide (DMF) and dichloromethane (DCM).

In a particular embodiment, the Fmoc protecting group is cleaved off in step c) with a mixture of 20% Piperidine in DMF.

In a particular embodiment, the resin is thoroughly washed after the deprotection in step c) with DMF and DCM followed by drying under vacuum and weighing.

3. General Synthesis for the Coupling of the Tripeptide to the Tether

The compound of formula (I) can be obtained starting from the compounds of formula (III) and of formula (IV) according to Scheme 1.

Scheme 1.

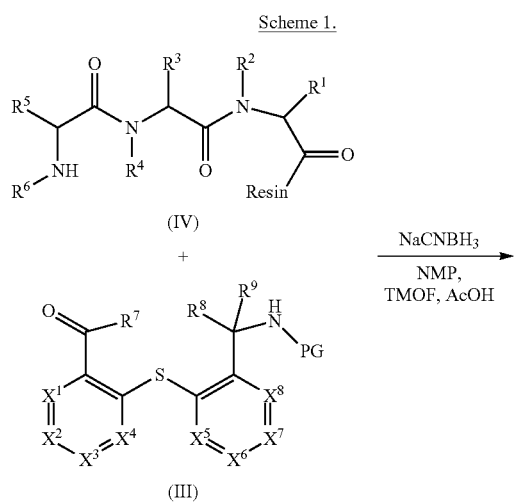

(IV)

+

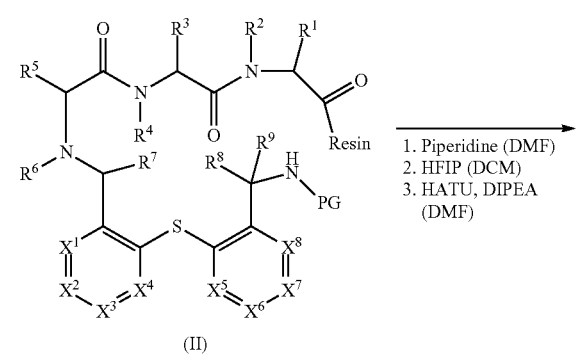

(III)

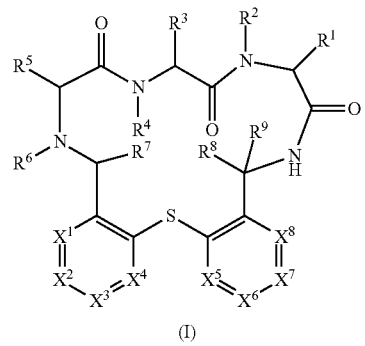

(I)

The tether aldehyde or ketone of formula (III) is dissolved in a mixture of N-methyl-2-pyrrolidone (NMP), trimethyl orthoformate (TMOF) and acetic acid (AcOH) and the resin comprising the tripeptide of formula (IV) is added to the solution. After agitation of the mixture, sodium cyanoborohydride (NaCNBH₃) is added to provide a compound of formula (II).

After the Borch reaction, the protecting group (PG) on the tether is cleaved off, e.g. with a mixture of 20% Piperidine in DMF. The resin on the tripeptide can be cleaved e.g. by addition of 20% hexafluoroisopropanol (HFIP) in DCM and filtered off. The compound of formula (I) is finally obtained through cyclisation of the cleaved compound of formula (II) using HATU and Hünig's base followed by global deprotection of remaining protected amine groups.

A particular embodiment of the invention relates to a process for the manufacture of a compound of formula (I) comprising the steps of:

a) reacting a compound of formula (III) with a compound of formula (IV) using sodium cyanoborohydride (NaCNBH₃) to provide a compound of formula (II);

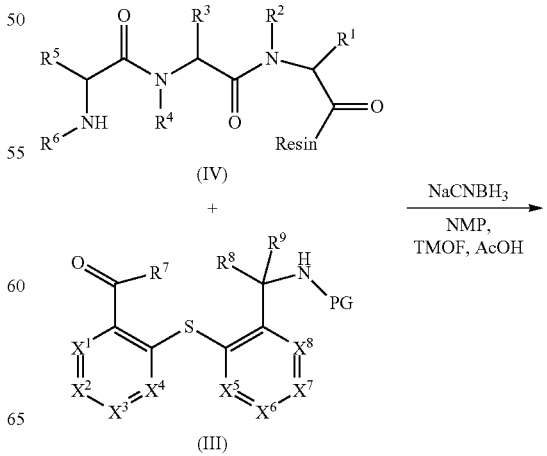

-continued

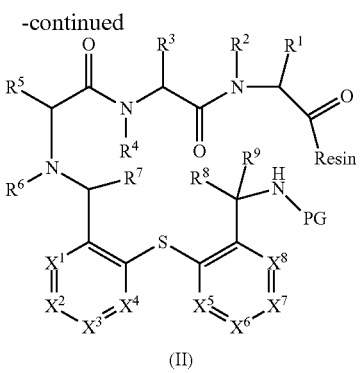

(II)

b) cleaving off the protecting group (PG) and the resin from the compound of formula (II);

c)

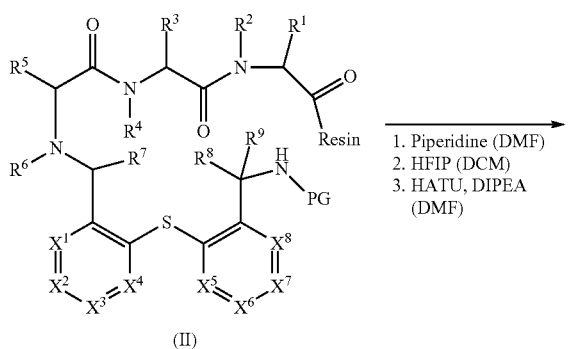

1. Piperidine (DMF)
2. HFIP (DCM)
3. HATU, DIPEA (DMF)

followed by cyclisation of the cleaved compound of formula (II) using HATU and Hünig's base.

In particular embodiment, the tripeptide of formula (IV) is washed with DCM prior to adding it to the tether aldehyde or ketone of formula (III).

In a particular embodiment, the solvent of the tether aldehyde of formula (III) consists of a mixture of N-methyl-2-pyrrolidone (NMP), trimethyl orthoformate (TMOF) and acetic acid (AcOH).

In a particular embodiment, the reaction mixture is washed after the Borch reaction with DMF, DCM, MeOH/DCM and/or DMF.

In a particular embodiment, the cyclization of the deprotected and cleaved compound of formula (II) takes place using HATU and DIPEA in DMF.

In a particular embodiment, the global BOC-deprotection is achieved by treatment with TFA in a solvent, particularly DCM, at RT.

Pharmaceutical Compositions

Another embodiment provides pharmaceutical compositions or medicaments comprising the compounds of the invention and a therapeutically inert carrier, diluent or pharmaceutically acceptable excipient, as well as methods of using the compounds of the invention to prepare such compositions and medicaments.

Compositions are formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners.

The compounds of the invention may be administered by any suitable means, including oral, topical (including buccal and sublingual), rectal, vaginal, transdermal, parenteral, subcutaneous, intraperitoneal, intrapulmonary, intradermal, intrathecal and epidural and intranasal, and, if desired for local treatment, intralesional administration. Parenteral infusions include intramuscular, intravenous, intraarterial, intraperitoneal, or subcutaneous administration.

The compounds of the present invention may be administered in any convenient administrative form, e.g., tablets, powders, capsules, solutions, dispersions, suspensions, syrups, sprays, suppositories, gels, emulsions, patches, etc. Such compositions may comprise components conventional in pharmaceutical preparations, e.g., diluents, carriers, pH modifiers, preservatives, solubilizers, stabilizers, wetting agents, emulsifiers, sweeteners, colorants, flavorants, salts for varying the osmotic pressure, buffers, masking agents, antioxidants, and further active agents. They can also comprise still other therapeutically valuable substances.

A typical formulation is prepared by mixing a compound of the present invention and a carrier or excipient. Suitable carriers and excipients are well known to those skilled in the art and are described in detail in, e.g., Ansel H. C. et al., *Ansel's Pharmaceutical Dosage Forms and Drug Delivery Systems* (2004) Lippincott, Williams & Wilkins, Philadelphia; Gennaro A. R. et al., *Remington: The Science and Practice of Pharmacy* (2000) Lippincott, Williams & Wilkins, Philadelphia; and Rowe R. C, *Handbook of Pharmaceutical Excipients* (2005) Pharmaceutical Press, Chicago. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents, diluents and other known additives to provide an elegant presentation of the drug (i.e., a compound of the present invention or pharmaceutical composition thereof) or aid in the manufacturing of the pharmaceutical product (i.e., medicament).

The dosage at which compounds of the invention can be administered can vary within wide limits and will, of course, be fitted to the individual requirements in each particular case. In general, in the case of oral administration a daily dosage of about 0.01 to 1000 mg per person of a compound of general formula (I) should be appropriate, although the above upper limit can also be exceeded when necessary.

An example of a suitable oral dosage form is a tablet comprising about 100 mg to 500 mg of the compound of the invention compounded with about 30 to 90 mg anhydrous lactose, about 5 to 40 mg sodium croscarmellose, about 5 to 30 mg polyvinylpyrrolidone (PVP) K30, and about 1 to 10 mg magnesium stearate. The powdered ingredients are first mixed together and then mixed with a solution of the PVP.

The resulting composition can be dried, granulated, mixed with the magnesium stearate and compressed to tablet form using conventional equipment.

An example of an aerosol formulation can be prepared by dissolving the compound, for example 10 to 100 mg, of the invention in a suitable buffer solution, e.g. a phosphate buffer, adding a tonicifier, e.g. a salt such as sodium chloride, if desired. The solution may be filtered, e.g., using a 0.2 μm filter, to remove impurities and contaminants.

Uses

As described above, the compounds of formula (I), (Ia) and (Ib) and their pharmaceutically acceptable salts possess valuable pharmacological properties for the treatment or prevention of infections and resulting diseases, particularly bacteremia, pneumonia, meningitis, urinary tract infection, and wound infection, caused by pathogens, particularly by bacteria, more particularly by *Pseudomonas* species, most particularly by *Pseudomonas aeruginosa*.

The compounds of formula (I), (Ia) and (Ib) and their pharmaceutically acceptable salts exhibit activity as antibiotics, particularly as antibiotics against *Pseudomonas* species, more particularly as antibiotics against *Pseudomonas aeruginosa*, most particularly as pathogen-specific antibiotics against *Pseudomonas aeruginosa*.

The compounds of formula (I), (Ia) and (Ib) and their pharmaceutically acceptable salts can be used as antibiotics, i.e. as antibacterial pharmaceutical ingredients suitable in the treatment and prevention of bacterial infections, particularly in the treatment and prevention of bacterial infections caused by *Pseudomonas* species, more particularly in the treatment and prevention of bacterial infections caused by *Pseudomonas aeruginosa*.

The compounds of the present invention can be used, either alone or in combination with other drugs, for the treatment or prevention of infections and resulting diseases, particularly bacteremia, pneumonia, meningitis, urinary tract infection, and wound infection, caused by pathogens, particularly by bacteria, more particularly caused by *Pseudomonas* species, most particularly by *Pseudomonas aeruginosa*.

A particular embodiment of the present invention relates to pharmaceutical compositions comprising compounds of formula (I), (Ia) and (Ib) as defined above or their pharmaceutically acceptable salts as defined above and one or more pharmaceutically acceptable excipients.

A particular embodiment of the present invention relates to pharmaceutical compositions comprising compounds of formula (I), (Ia) and (Ib) or their pharmaceutically acceptable salts as defined above and one or more pharmaceutically acceptable excipients for the treatment or prevention of infections and resulting diseases, particularly bacteremia, pneumonia, meningitis, urinary tract infection, and wound infection, caused by pathogens, particularly by bacteria, more particularly caused by *Pseudomonas* species, most particularly by *Pseudomonas aeruginosa*.

A particular embodiment of the present invention relates to compounds of formula (I), (Ia) and (Ib) or their pharmaceutically acceptable salts as defined above for use as therapeutically active substances, especially for use as therapeutically active substances for the treatment or prevention of infections and resulting diseases, particularly bacteremia, pneumonia, meningitis, urinary tract infection, and wound infection, caused by pathogens, particularly by bacteria, more particularly caused by *Pseudomonas* species, most particularly by *Pseudomonas aeruginosa*.

A particular embodiment of the present invention relates to compounds of formula (I), (Ia) and (Ib) or their pharmaceutically acceptable salts as defined above for the use in the treatment or prevention of infections and resulting diseases, particularly bacteremia, pneumonia, meningitis, urinary tract infection, and wound infection, caused by pathogens, particularly by bacteria, more particularly caused by *Pseudomonas* species, most particularly by *Pseudomonas aeruginosa*.

A particular embodiment of the present invention relates to a method for the treatment or prevention of infections and resulting diseases, particularly bacteremia, pneumonia, meningitis, urinary tract infection, and wound infection, caused by pathogens, particularly by bacteria, more particularly caused by *Pseudomonas* species, most particularly by *Pseudomonas aeruginosa*, which method comprises administering compounds of formula (I), (Ia) and (Ib) or their pharmaceutically acceptable salts as defined above to a subject.

A particular embodiment of the present invention relates to the use of compounds of formula (I), (Ia) and (Ib) or their pharmaceutically acceptable salts as defined above for the treatment or prevention of infections and resulting diseases, particularly bacteremia, pneumonia, meningitis, urinary tract infection, and wound infection, caused by pathogens, particularly by bacteria, more particularly caused by *Pseudomonas* species, most particularly by *Pseudomonas aeruginosa*.

A particular embodiment of the present invention relates to the use of compounds of formula (I), (Ia) and (Ib) or their pharmaceutically acceptable salts as defined above for the preparation of medicaments for the treatment or prevention of infections and resulting diseases, particularly bacteremia, pneumonia, meningitis, urinary tract infection, and wound infection, caused by pathogens, particularly by bacteria, more particularly caused by *Pseudomonas* species, most particularly by *Pseudomonas aeruginosa*. Such medicaments comprise compounds of formula (I), (Ia) and (Ib) or their pharmaceutically acceptable salts as defined above.

EXAMPLES

The invention will be more fully understood by reference to the following examples. They should however not be construed as limiting the scope of the invention.

ABBREVIATIONS USED

Agp: 2-amino-3-guanidino-propionic acid
Boc: tert. Butyloxycarbonyl
DCM: Dichlormethane
DIPEA: N,N-Diisopropylamine
DMF: N,N-Dimethylformamide
EA: Ethyl acetate
EtOAc: Ethyl acetate
EtOH: Ethanol
Fmoc: 9-Fluorenylmethoxycarbonyl
Fmoc-OSu: N-(9-Fluorenylmethoxycarbonyloxy)succinimide
HATU: O-(7-Azabenzotriazol-1-yl)-N,N,N',N'-tetramethyluronium-hexafluorophosphate
HHFIP: Hexafluoroisopropanol
HOBt: Hydroxy-benzotriazole
LAH: Lithium aluminium hydride
Lys: Lysine
MeCN: Acetonitrile
Mukaiyama's reagent: 2-Chloro-1-methyl-pyridinium iodide
MTBD: 7-Methyl-1,5,7-triazabicyclo[4.4.0]dec-5-ene NMP: N-Methylprolidone
Orn: Ornithine
Pd$_2$(dba)$_3$: Tris(dibenzylideneacetone)dipalladium(0)
THF: tetrahydrofurane
TLC: Thin layer chromatography
TMOF: Trimethyl-orthoformiate
Trp: Tryptophane
p-TSA: p-Toluenesulfonic acid or tosylic acid
HMPA: Hexamethylphosphoramide Intermediate 1

9H-fluoren-9-ylmethyl N-[[3-chloro-2-(2-formylphenyl)sulfanyl-phenyl]methyl]carbamate

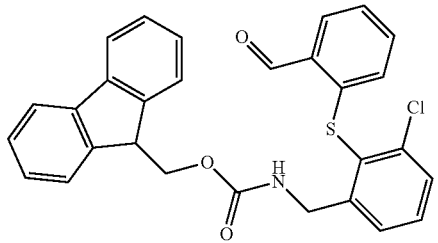 [SMILES: O=Cc1ccccc1Sc1c(Cl)cccc1CNC(=O)OCC1c2ccccc2-c2ccccc21]

To a suspension of 3-Chloro-2-fluoro-benzaldehyde (2.8 g, 16.64 mmol) and K$_2$CO$_3$ (4.5 g, 33.29 mmol) in DMF (15 mL) was added 2-Mercapto-benzoic acid methyl ester (7.9 g, 49.93 mmol) and the reaction mixture was stirred for 2 h at room temperature. Progress of the reaction was monitored by TLC. After completion, the reaction mixture was diluted with water (100 mL) and extracted with (3×100 mL) ethyl acetate. Combined organic layer was dried over sodium sulphate and concentrated under reduced pressure to get the crude compound which was purified by silica gel column chromatography (20% ethyl acetate and hexane) to afford methyl 2-(2-chloro-6-formyl-phenyl)sulfanylbenzoate (4.4 g, 86.17%) as white solid. LC-MS: 307.2 [M+H]$^+$.

To a solution of methyl 2-(2-chloro-6-formyl-phenyl)sulfanylbenzoate (4.4 g, 14.37 mmol) and tert-butyl sulphinamide (2.61 g, 21.56 mmol) in THF (50 mL) was added titanium tetra ethoxide (4.92 g, 21.56 mmol) and the reaction mixture was heated to 80° C. for 3 h. Progress of the reaction was monitored by TLC. After completion, the reaction mixture was diluted with water (100 mL) and extracted with ethyl acetate (3×100 mL). Combined organic layers were dried over sodium sulphate and concentrated under reduced pressure to get the crude compound which was purified by silica gel column chromatography (20% ethyl acetate and hexane) to afford methyl 2-[2-[(E)-tert-butylsulfinyliminomethyl]-6-chloro-phenyl]sulfanylbenzoate (4.2 g, 71.25%) as brown solid. LC-MS: =409.8 [M+H]$^+$.

To an ice cooled solution of methyl 2-[2-[(E)-tert-butylsulfinyliminomethyl]-6-chloro-phenyl]sulfanylbenzoate (4.2 g, 10.26 mmol) in THF (50 mL) was added LAH (1.1 g, 37.95 mmol) portion wise and the reaction mixture was stirred for 1 h at the same temperature. Progress of the reaction was monitored by TLC. After completion, the reaction mixture was diluted with aq. sodium sulphate solution (50 mL) and extracted with ethyl acetate (3×100 mL). Combined organic layers were dried over sodium sulphate and concentrated under reduced pressure to get crude compound which was purified by triturating with hexane followed by pentane to get N-[[3-chloro-2-[2-(hydroxymethyl)phenyl]sulfanyl-phenyl]methyl]-2-methyl-propane-2-sulfinamide (3.7 g, 94.06%) as brown solid. LC-MS: 383.8 [M+H].

To a solution of N-[[3-chloro-2-[2-(hydroxymethyl)phenyl]sulfanyl-phenyl]methyl]-2-methyl-propane-2-sulfinamide (3.7 g, 9.64 mmol) in DCM (100 mL) was added Dess-Martin periodinane (1,1,1-Triacetoxy-1,1-dihydro-1,2-benziodoxol-3(1H)-one) (12.26 g, 28.90 mmol) and the reaction mixture was stirred at room temperature for 4 h. Progress of the reaction was monitored by TLC. After completion, the reaction mixture was diluted with water (100 mL) and extracted with DCM (3×100 mL). Combined organic layer was dried over sodium sulphate and concentrated under reduced pressure to get the crude compound. The crude compound was purified by silica gel column chromatography (ethyl acetate) to get N-[[3-chloro-2-(2-formylphenyl)sulfanyl-phenyl]methyl]-2-methyl-propane-2-sulfinamide (0.7 g, 19.02%) as white solid. LC-MS: 381.8 [M+H]$^+$.

To an ice cooled solution of N-[[3-chloro-2-(2-formylphenyl)sulfanyl-phenyl]methyl]-2-methyl-propane-2-sulfinamide (0.800 g, 2.09 mmol) in dioxane (10 mL) was added 4M HCl in dioxane (0.9 mL) and the resulting reaction mixture was stirred at room temperature for 2 h. Progress of the reaction was monitored by TLC. Volatiles were removed under reduced pressure to obtain 2-[2-(aminomethyl)-6-chloro-phenyl]sulfanylbenzaldehyde (0.660 g, quantitative) as off white solid. LC-MS: 278.0 [M+H]$^+$.

To a solution of 2-[2-(aminomethyl)-6-chloro-phenyl]sulfanylbenzaldehyde (0.660 g, 2.09 mmol) in 5% aqueous NaHCO$_3$ (6 mL) was added Fmoc-OSu (0.754 g, 2.24 mmol) in CH$_3$CN (20 mL) and the reaction mixture was stirred at room temperature for 3 h. Progress of the reaction mixture was monitored by TLC. After completion, the reaction mixture was diluted with ethyl acetate and washed with water followed by brine. Organic layer was dried over sodium sulfate and evaporated under reduced pressure to get the crude compound which was purified by flash-chromatography (5-7% ethyl acetate in hexane) to afford 9H-fluoren-9-ylmethyl N-[[3-chloro-2-(2-formylphenyl)sulfanyl-phenyl]methyl]carbamate (0.460 g, 44%) as off white solid. LC-MS: 500.3 [M+H]

$^1$H-NMR: (400 MHz, DMSO-d6): δ 4.22-4.19 (1H, m), 4.33-4.29 (4H, m), 6.47 (1H, d, J=8.00 Hz), 7.37-7.28 (4H, m), 7.47-7.40 (3H, m), 7.57 (1H, t, J=7.8 Hz), 7.64 (1H, d, J=7.6 Hz), 7.68 (2H, d, J=7.4 Hz), 7.90-7.81 (3H, m), 8.00 (1H, d, J=7.5 Hz), 10.20 (1H, s).

Intermediate 2

9H-fluoren-9-ylmethyl N-[[4-chloro-2-(2-formylphenyl)sulfanyl-phenyl]methyl]carbamate

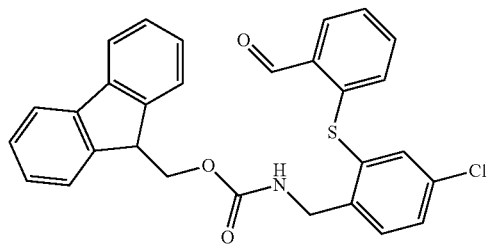 [SMILES: O=Cc1ccccc1Sc1cc(Cl)ccc1CNC(=O)OCC1c2ccccc2-c2ccccc21]

Intermediate 2 was generated in analogy to Intermediate 1 starting from the accordingly substituted benzaldehyde.

¹H-NMR: (400 MHz, DMSO-d6) δ 4.20-4.22 (m; 3H); 4.32 (2H; d; J=6.8 Hz); 7.6 (1H; d; J=7.6 Hz); 7.31-7.36 (m; 4H); 7.40 (3H; t; J=7.4 Hz); 7.46 (1H; br s); 7.54 (2H; t; J=8.4 Hz); 7.69 (2H; d; J=7.6 Hz); 7.82-7.84 (m; 1H); 7.90 (2H; d; J=7.2 Hz); 7.99 (1H; d; J=7.2 Hz); 10.21 (1H; s).

Intermediate 3

9H-fluoren-9-ylmethyl N-[[5-chloro-2-(2-formylphenyl)sulfanyl-phenyl]methyl]carbamate

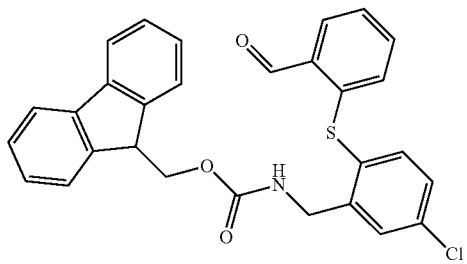 [SMILES: O=Cc1ccccc1Sc1ccc(Cl)cc1CNC(=O)OCC1c2ccccc2-c2ccccc21]

Intermediate 3 was generated in analogy to Intermediate 1 starting from the accordingly substituted benzaldehyde.

1H-NMR: (400 MHz, DMSO-d6) δ 4.23-4.25 (m; 3H); 4.32 (2H; d; J=6.8 Hz); 6.7 (1H; d; J=8.0 Hz); 7.31 (2H; t; J=7.4 Hz); 7.39-7.43 (4H; m); 7.44-7.54 (2H; m); 7.70 (2H; d; J=7.6 Hz); 7.82-7.84 (m; 2H); 7.98 (2H; d; J=7.2 Hz); 10.20 (1H; s).

Intermediate 4

9H-fluoren-9-ylmethyl N-[[2-(2-formylphenyl)sulfanylphenyl]methyl]carbamate

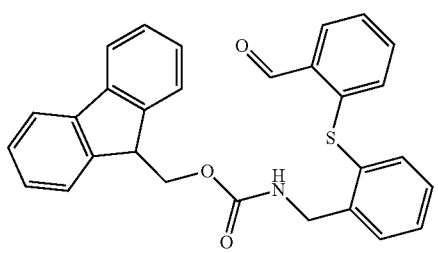 [SMILES: O=Cc1ccccc1Sc1ccccc1CNC(=O)OCC1c2ccccc2-c2ccccc21]

Intermediate 4 was generated accordingly from commercially available [2-[2-(aminomethyl)phenyl]sulfanylphenyl] methanol.

1H NMR (600 MHz, CHCl3-d6) δ ppm 4.15-4.22 (m, 1H) 4.38 (d, J=6.9 Hz, 2H) 4.48 (d, J=6.3 Hz, 2H) 5.12-5.20 (m, 1H) 6.77 (d, J=7.8 Hz, 1H) 7.17-7.25 (m, 1H) 7.27-7.58 (m, 12H) 7.76 (d, J=7.6 Hz, 2H) 7.86 (d, J=7.6 Hz, 1H) 10.13-10.40 (m, 1H).

Intermediate 5

9H-fluoren-9-ylmethyl N-[[2-(2-formylphenyl)sulfanyl-3-methyl-phenyl]methyl]carbamate

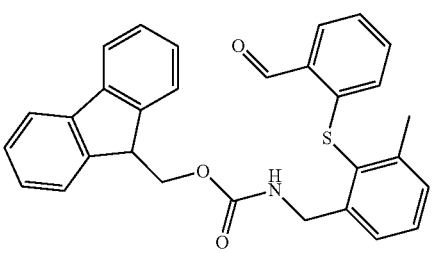 [SMILES: Cc1cccc(CNC(=O)OCC2c3ccccc3-c3ccccc32)c1Sc1ccccc1C=O]

A suspension of Na₂S. 9H₂O (4.79 g, 61.41 mmol) and MgSO₄ (10.87 g, 90.31 mmol) in NMP (100 mL) was stirred at 80° C. for a period of 30 min under argon atmosphere. To the resulting reaction mixture was added a solution of 2-Fluoro-3-methyl benzaldehyde (5 g, 36.12 mmol) in NMP (25 mL) drop-wise at 80° C. and stirring was continued for 30 min at 80° C. Then the reaction mixture was cooled in an ice-bath. To the resulting reaction mixture was added acetic anhydride (6 mL) drop wise and the reaction mixture was stirred for 30 min. Progress of the reaction was monitored by TLC. Reaction mixture was then partitioned between water and ethyl acetate; organic layer was separated off, dried over anhydrous sodium sulfate and concentrated under reduced pressure to get the crude compound. The crude compound was purified by flash-chromatography (25% ethyl acetate in hexane) to afford S-(2-formyl-6-methyl-phenyl) ethanethioate (3.2 g, 45.64%) as brown color solid. LC-MS: 194.25 (M+H).

To a solution of S-(2-formyl-6-methyl-phenyl) ethanethioate (3.2 g, 16.47 mmol) in anhydrous THF (100 mL) were added 2-methylpropane-2-sulfinamide (1.99 g, 16.47 mmol) and titanium tetra ethoxide (3.76 g, 16.474 mmol) sequentially. The resultant reaction mixture was stirred for a period of 2 h under argon atmosphere at 60° C. Then the reaction mixture was cooled to ambient temperature, poured onto ice-water and filtered through a short pad of celite. Filtrate was extracted with ethyl acetate (100 mL×2) and the combined organic layer was washed with brine (100 mL×2), dried over anhydrous sodium sulfate and concentrated under reduced pressure to get the crude compound which was purified by flash-chromatography (10-20% ethyl acetate in hexane) to afford S-[2-[(E)-tert-butylsulfinyliminomethyl]-6-methyl-phenyl]ethanethioate (2.9 g, 59.30%) as viscous oil. LC-MS: 297.44 (M+H).

A solution of S-[2-[(E)-tert-butylsulfinyliminomethyl]-6-methyl-phenyl] ethanethioate (2.7 g, 9.091 mmol) in THF-Ethanol (4:1; 75 mL) was degassed with Argon for 15 min and then sodium borohydride (2.75 g, 72.727 mmol) was added portion wise at 0° C. The resulting reaction mixture was stirred for 30 min at 0° C. and 30 min at room temperature. Then the reaction mixture was quenched with acetone/ethanol (1:1; 30 mL) (degassed with argon) and stirred for 1 hour at 0° C. Volatiles were evaporated under reduced pressure and released under argon to afford 2-methyl-N-[(3-methyl-2-sulfanyl-phenyl)methyl]propane-2-sulfinamide (crude) as yellow solid. This compound was used as such in next step without further purification. LC-MS: 257.41 (M+H).

To a solution of 2-methyl-N-[(3-methyl-2-sulfanyl-phenyl)methyl]propane-2-sulfinamide (2.31 g, 8.98 mmol) in DMF (80 mL) (degassed with argon prior to addition for 10 min) were added potassium carbonate (2.48 g, 17.947 mmol) and 2-Fluorobenzaldehyde (3.34 g, 26.92 mmol) and the reaction mixture was heated to 70° C. for 5 h. Then the reaction mixture was diluted with ethyl acetate (50 mL), washed with water (50 mL) followed by brine (50 mL×2), dried over sodium sulfate and concentrated under reduced pressure to get the crude compound. The crude compound thus obtained was purified by silica gel (100-200 mesh) column chromatography (3% methanol in DCM) to get N-[[2-(2-formylphenyl)sulfanyl-3-methyl-phenyl]methyl]-2-methyl-propane-2-sulfinamide (1.0 g, 25% over two steps) as brown color viscous oil. LC-MS: 361.53 (M+H).

To an ice cooled solution of N-[[2-(2-formylphenyl)sulfanyl-3-methyl-phenyl]methyl]-2-methyl-propane-2-sulfinamide (0.950 g, 2.63 mmol) in dioxane (10 mL) was added 4M HCl in dioxane (0.95 mL) and the resultant reaction mixture was stirred at room temperature for 2 h. Progress of the reaction was monitored by TLC. Volatiles were evaporated under reduced pressure to obtain crude compound which was washed with diethyl ether and dried to get 2-[2-(aminomethyl)-6-methyl-phenyl]sulfanylbenzaldehyde (0.670 g, 87.10%) as white solid. This compound was used as such in next step without further purification. LC-MS: 257.36 (M+H).

To a stirred suspension of 2-[2-(aminomethyl)-6-methyl-phenyl]sulfanylbenzaldehyde (0.670 g, 2.607 mmol) in 5% sodium bicarbonate (5 mL) was added a solution of Fmoc-OSU (0.879 g, 2.607 mmol) in acetonitrile (10 mL) and the reaction mixture was stirred at room temperature for 3 h. The reaction mixture was then diluted with ethyl acetate (50 mL) and washed with brine (50 mL), dried over anhydrous sodium sulfate and concentrated under reduced pressure to get the crude compound. The crude thus obtained was purified by flash-chromatography (25% ethyl acetate in hexane) to afford 9H-fluoren-9-ylmethyl N-[[2-(2-formylphenyl)sulfanyl-3-methyl-phenyl]methyl]carbamate (0.48 g, 44.12%) as white solid. LC-MS: 479.60 (M+H).

¹H-NMR: (400 MHz, DMSO-d6): δ 2.29 (3H, s), 4.20 (1H, t, J=6.7 Hz), 4.26 (2H, d, J=6.00 Hz), 4.30 (2H, t, J=6.8 Hz), 6.45 (1H, d, J=8.00 Hz), 7.21 (1H, d, J=7.56 Hz), 7.35-7.29 (4H, m), 7.48-7.38 (4H, m), 7.69 (2H, d, J=7.52 Hz), 7.78 (1H, t, J=6.00 Hz), 7.89 (2H, d, J=7.5 Hz), 7.97 (1H, d, J=6.2 Hz), 10.22 (1H, s).

Intermediate 6

9H-fluoren-9-ylmethyl N-[[2-(2-formylphenyl)sulfanyl-4-(trifluoromethyl)phenyl]methyl]carbamate

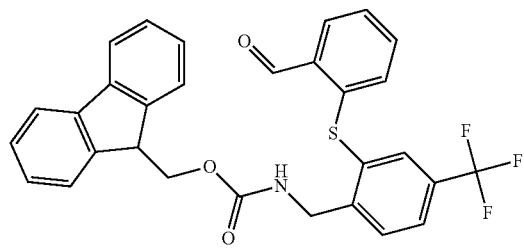 [SMILES: O=Cc1ccccc1Sc1cc(C(F)(F)F)ccc1CNC(=O)OCC1c2ccccc2-c2ccccc21]

To a solution of 2-Fluoro-4-trifluoromethyl-benzaldehyde (2.0 g, 10.41 mmol) in DMF (4 mL) was added K₂CO₃ (2.8 g, 20.82 mmol) followed by 2-Mercapto-benzoic acid methyl ester (2.62 g, 15.61 mmol) and the reaction mixture was stirred for 6 h at room temperature. Progress of the reaction was monitored by TLC. After completion, the reaction mixture was diluted with water (30 mL) and extracted with ethyl acetate (70 mL). Organic layer was dried over sodium sulphate and concentrated under reduced pressure to obtain methyl 2-[2-formyl-5-(trifluoromethyl)phenyl]sulfanylbenzoate (3.0 g, 84.67%) as off white solid. LC-MS: 341.1 (M+H).

To a solution of methyl 2-[2-formyl-5-(trifluoromethyl)phenyl]sulfanylbenzoate (3 g, 8.81 mmol) in anhydrous THF (50 mL) was added tert butylsulphinamide (1.6 g, 13.22 mmol) followed by titanium (IV) ethoxide (2.77 g, 13.22 mmol) and the reaction mixture was heated to 80° C. for 1 h under argon atmosphere. Progress of the reaction was monitored by TLC. After completion, the reaction mixture was diluted with water (30 mL) and extracted with ethyl acetate (70 mL). Organic layer was dried over anhydrous sodium sulphate and concentrated under reduced pressure to get methyl 2-[2-[(E)-tert-butylsulfinyliminomethyl]-5-(trifluoromethyl)phenyl]sulfanylbenzoate (3.8 g, 97.19%) as pale yellow viscous oil. LC-MS: 443.9 (M+H).

To an ice cooled suspension of LAH (0.977 g, 25.73 mmol) in THF (30 mL) was added methyl 2-[2-[(E)-tert-butylsulfinyliminomethyl]-5-(trifluoromethyl)phenyl]sulfanylbenzoate (3.8 g, 8.57 mmol) in THF (30 mL) and the reaction mixture was stirred for 2 h at 0° C. Progress of the reaction was monitored by TLC. After completion, the reaction mixture was quenched with saturated sodium sulphate solution (3 mL) and filtered through celite. Residue was washed with ethyl acetate (80 mL) and filtrate was concentrated to get N-[[2-[2-(hydroxymethyl)phenyl]sulfanyl-4-(trifluoromethyl)phenyl]methyl]-2-methyl-propane-2-sulfinamide (3.5 g, 99%) as yellow oil. LC-MS: 418.1 (M+H).

To an ice cooled solution of N-[[2-[2-(hydroxymethyl)phenyl]sulfanyl-4-(trifluoromethyl)phenyl]methyl]-2-methyl-propane-2-sulfinamide (3.5 g, 8.39 mmol) in DCM (100 mL) was added Dess-Martin periodinane (10.67 g, 25.18 mmol) and the reaction mixture was stirred at room temperature for 1 h. Progress of the reaction was monitored by TLC. After completion, the reaction mixture was poured onto saturated sodium bicarbonate solution and extracted with DCM (3×100 mL). Combined organic layer was washed with sodium thiosulphate, dried over sodium sulphate and concentrated under reduced pressure to get the crude compound. The crude compound was purified by using combiflash (ethyl acetate) to afford N-[[2-(2-formylphenyl)sulfanyl-4-(trifluoromethyl)phenyl]methyl]-2-methyl-propane-2-sulfinamide (1.7 g, 48.75%) as yellow viscous oil. LC-MS: 415.9 (M+H).

To an ice cooled solution of N-[[2-(2-formylphenyl)sulfanyl-4-(trifluoromethyl)phenyl]methyl]-2-methyl-propane-2-sulfinamide (1.7 g, 4.091 mmol) in dioxane (17 mL) was added 4M HCl in dioxane (1.7 mL) and the reaction mixture was stirred at room temperature for 1 h. Progress of the reaction was monitored by TLC. After completion, volatiles were evaporated under reduced pressure to obtain 2-[2-(aminomethyl)-5-(trifluoromethyl)phenyl]sulfanylbenzaldehyde (1.1 g, 86%) as off white solid. LC-MS: 311.9 (M+H).

To an ice cooled suspension of 2-[2-(aminomethyl)-5-(trifluoromethyl)phenyl]sulfanylbenzaldehyde (1.1 g, 3.53 mmol) in acetonitrile (15 mL) and 5% aqueous NaHCO₃ solution (8 mL) was added a solution of Fmoc-OSu (1.19 g, 3.53 mmol) in CH₃CN (15 mL) and the reaction mixture was stirred at room temperature for 3 h. Progress of the reaction was monitored by TLC. After completion, the reaction mixture was diluted with ethyl acetate (50 mL) and organic layer was separated off. Organic layer was washed with water followed by brine, dried over anhydrous sodium sulfate and evaporated under reduced pressure to get the crude compound. The crude compound was purified by flash-chromatography (5-7% EtOAc in hexane) to afford 9H-fluoren-9-ylmethyl N-[[2-(2-formylphenyl)sulfanyl-4-methyl-phenyl]methyl]carbamate (0.530 g, 31%) as off white solid. LC-MS: 534.2 (M+H).

$^1$H-NMR: (400 MHz, DMSO-d6): δ 4.22 (1H, t, J=6.7 Hz), 4.29 (2H, d, J=5.7 Hz), 4.35 (2H, d, J=6.7 Hz), 6.76 (1H, d, J=7.9 Hz), 7.35-7.31 (2H, m), 7.46-7.40 (3H, m), 7.52 (1H, d, J=7.2 Hz), 7.56 (1H, d, J=7.8 Hz), 7.69 (2H, d, J=7.4 Hz), 7.91-7.85 (3H, m), 7.73 (1H, s), 7.94 (1H, t, J=8.00 Hz), 8.00 (1H, d, J=7.4 Hz), 10.22 (1H, s).

Intermediate 7

9H-fluoren-9-ylmethyl N-[[2,3-dichloro-6-(2-formylphenyl)sulfanyl-phenyl]methyl]carbamate

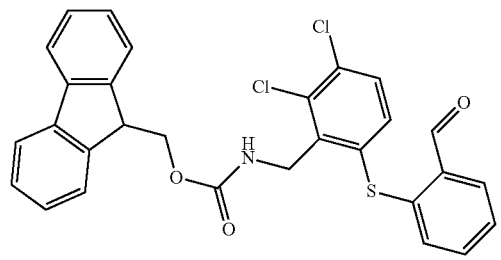 [SMILES: O=Cc1ccccc1Sc1ccc(Cl)c(Cl)c1CNC(=O)OCC1c2ccccc2-c2ccccc21]

To an ice-cooled suspension of 2,3-Dichloro-6-fluoro-benzaldehyde (3 g, 15.54 mmol) and K$_2$CO$_3$ (4.29 g, 31.08 mmol) in DMF (10 mL) was added 2-Mercapto-benzoic acid methyl ester (2.12 mL, 15.54 mmol) and the reaction mixture was stirred for 1 h. Progress of the reaction was monitored by TLC. After completion, the reaction mixture was poured onto water and extracted with ethyl acetate (50 mL×3). Combined organic layer was washed with brine, dried over sodium sulphate and evaporated under reduced pressure to get crude compound which was purified by flash column chromatography (10% EtOAc in hexane) to get methyl 2-(3,4-dichloro-2-formyl-phenyl)sulfanylbenzoate (3 g, 57%) as an off-white solid.

To a solution of methyl 2-(3,4-dichloro-2-formyl-phenyl)sulfanylbenzoate (3 g, 8.79 mmol) in anhydrous THF (100 mL) were added tert-butyl sulphinamide (1.60 g, 13.19 mmol) and titanium (IV) ethoxide (3 mL, 13.19 mmol) sequentially and the resulting reaction mixture was heated to 60° C. for 1 h under argon atmosphere. Progress of the reaction was monitored by TLC. After completion, the reaction mixture was poured onto water (100 mL) filtered through celite and celite bed was washed with ethyl acetate. Organic layer was separated off and washed with brine. Organic layer was dried over anhydrous sodium sulphate and concentrated under reduced pressure to get the crude compound which was triturated with hexane to get methyl 2-[2-[(E)-tert-butylsulfinyliminomethyl]-3,4-dichloro-phenyl]sulfanylbenzoate (3.8 g, 92%) as an off-white solid.

To an ice-cooled suspension of LAH (0.97 g, 25.67 mmol) in THF (40 mL) was added methyl 2-[2-[(E)-tert-butylsulfinyliminomethyl]-3,4-dichloro-phenyl]sulfanylbenzoate (3.8 g, 8.56 mmol) in THF (30 mL) and the reaction mixture was stirred for 30 min. Then the reaction mixture was quenched with saturated sodium sulphate (5 mL) solution, filtered through celite and celite bed was washed with ethyl acetate (3×50 mL). Filtrate was concentrated and the crude compound thus obtained was triturated with hexane to get N-[[2,3-dichloro-6-[2-(hydroxymethyl)phenyl]sulfanyl-phenyl]methyl]-2-methyl-propane-2-sulfinamide (2.5 g, 70%) as an off-white solid. LC-MS: 417.8 (M+H).

To an ice-cooled solution of N-[[2,3-dichloro-6-[2-(hydroxymethyl)phenyl]sulfanyl-phenyl]methyl]-2-methyl-propane-2-sulfinamide (2.5 g, 5.98 mmol) in DCM (100 mL) was added Dess-Martin periodinane (3.80 g, 8.97 mmol) and the resulting reaction mixture was stirred at ambient temperature for 1 h. After completion, the reaction mixture was poured onto saturated sodium bicarbonate solution and extracted with DCM (100 mL×3). Combined organic layer was washed with sodium thiosulphate solution and dried over anhydrous sodium sulphate. Organic layer was concentrated under reduced pressure and the crude compound thus obtained was purified by flash column chromatography (10% EtOAc in hexane) to get N-[[2,3-dichloro-6-(2-formylphenyl)sulfanyl-phenyl]methyl]-2-methyl-propane-2-sulfinamide (1.7 g, 69%) as an off-white solid. LC-MS: 416.0 (M+H).

To an ice-cooled solution of N-[[2,3-dichloro-6-(2-formylphenyl)sulfanyl-phenyl]methyl]-2-methyl-propane-2-sulfinamide (1.7 g, 4.08 mmol) in dioxane (25 mL) was added 4M HCl in dioxane (10 mL) and the resultant reaction mixture was allowed to stir at ambient temperature for 6 h. Volatiles were evaporated under reduced pressure to obtain crude compound which was triturated with diethyl ether to get 2-[2-(aminomethyl)-3,4-dichloro-phenyl]sulfanylbenzaldehyde (1.27 g, 99%) as white solid. LC-MS: 311.9 (M+H).

To an ice-cooled suspension of 2-[2-(aminomethyl)-3,4-dichloro-phenyl]sulfanylbenzaldehyde (1.3 g, 4.16 mmol) in acetonitrile (40 mL) was added 5% aqueous NaHCO$_3$ solution (10 mL) followed by a solution of Fmoc-OSu (1.40 g, 4.16 mmol) in CH$_3$CN (15 mL) and the reaction mixture was stirred at ambient temperature for 3 h. Then the reaction mixture was diluted with ethyl acetate (100 mL) and water (100 mL). Organic layer was separated off and washed with brine. Organic layer was dried over anhydrous sodium sulfate and evaporated under reduced pressure to get the crude compound. The crude compound thus obtained was purified by flash column chromatography (20% EtOAc in hexane) to afford 9H-fluoren-9-ylmethyl N-[[2,3-dichloro-6-(2-formylphenyl)sulfanyl-phenyl]methyl]carbamate (0.610 g, 28%) as white solid. LC-MS: 534.1 (M+H).

$^1$H-NMR: (400 MHz, CDCl$_3$): δ 4.17-4.15 (1H, m), 4.22-4.21 (2H, m), 4.50 (2H, d, J=4.4 Hz), 6.89 (1H, d, J=7.8 Hz), 7.30 (2H, t, J=7.4 Hz), 7.42-7.38 (4H, m), 7.51 (2H, t, J=7.5 Hz), 7.70-7.64 (3H, m), 7.88 (2H, d, J=7.6 Hz), 7.97 (1H, d, J=7.8 Hz), 10.19 (1H, s).

Intermediate 8

9H-fluoren-9-ylmethyl N-[[3-chloro-2-(2-formylphenyl)sulfanyl-6-(trifluoromethyl)-phenyl]methyl] carbamate

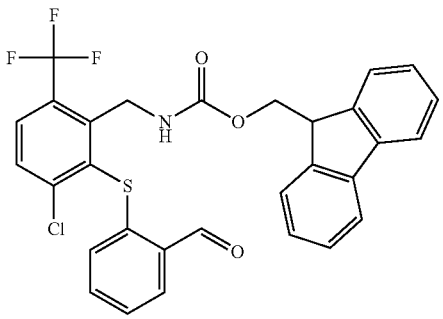 [SMILES: O=Cc1ccccc1Sc1c(Cl)ccc(C(F)(F)F)c1CNC(=O)OCC1c2ccccc2-c2ccccc21]

To a stirred solution of methyl 2-mercapto-benzoic acid methyl ester (2 g, 11.89 mmol) and 2,3-dichloro-6-(trifluoromethyl)benzaldehyde (2.89 g, 11.889 mmol) in DMF (20 mL) was added K$_2$CO$_3$ (1.64 g, 11.89 mmol) and reaction mass was stirred at 25° C. for 30 min. Reaction mixture was diluted with ethyl acetate and washed with water. The separated organic layer was washed with brine solution, dried over anhydrous sodium sulfate and evaporated under reduced pressure. The crude thus obtained was purified by normal silica column using 0-5% ethyl acetate in hexane to get methyl 2-[6-chloro-2-formyl-3-(trifluoromethyl)phenyl]sulfanylbenzoate (2.3 g, 51%) as a white solid. MS found: 375 (M+H).

To a stirred solution of methyl 2-[6-chloro-2-formyl-3-(trifluoromethyl)phenyl]sulfanyl-benzoate (4.5 g, 12.007 mmol) in THF (50 mL) was added 2-methylpropane-2-sulfinamide (1.45 g, 12.0 mmol), Ti(OEt)$_4$ (12.68 mL, 60.04 mmol) and reaction mass was heated to 70° C. for 16h. The reaction mass was quenched with saturated sodium chloride solution, solid obtained was filtered through celite pad, washed with ethyl acetate. The separated organic layer was dried over anhydrous sodium sulfate and evaporated under reduced pressure to get ethyl 2-[2-[(E)-tert-butylsulfinyliminomethyl]-6-chloro-3-(trifluoromethyl)phenyl]sulfanylbenzoate (5.8 g crude) which was directly used for next step without further purification. MS found: 491.8 (M+H).

To a stirred solution of ethyl 2-[2-[(E)-tert-butylsulfinyliminomethyl]-6-chloro-3-(trifluoromethyl)phenyl]sulfanylbenzoate (5.8 g, 15.185 mmol) in THF (60 mL) was added LiBH$_4$ (3.2 g, 151.85 mmol) and reaction mass was heated to 50° C. for 4h. Reaction mixture was quenched with saturated ammonium chloride solution and extracted with ethyl acetate. The separated organic layer was washed with water, brine solution, dried over anhydrous sodium sulfate and evaporated under reduced pressure. The crude thus obtained was purified by normal silica column using 5-40% ethyl acetate in hexane to get N-[[3-chloro-2-[2-(hydroxymethyl)phenyl]sulfanyl-6-(trifluoromethyl)phenyl]methyl]-2-methyl-propane-2-sulfinamide (3.7 g, 69%, 2 steps) as a off white solid. MS found: 452.2 (M+H).

To a stirred solution of N-[[3-chloro-2-[2-(hydroxymethyl)phenyl]sulfanyl-6-(trifluoromethyl)phenyl]methyl]-2-methyl-propane-2-sulfinamide (3.7 g, 8.18 mmol) in MeOH (40 mL), was added 4M HCl in dioxane (20 mL) at 0° C. and reaction mixture was stirred at 25° C. for 1 h. After completion of reaction, reaction mixture was concentrated under reduced pressure to get [2-[2-(aminomethyl)-6-chloro-3-(trifluoromethyl)phenyl]sulfanylphenyl]methanol (3.6 g, crude) which was directly used for next step without further purification. MS found: 347.8 (M+H).

To a stirred suspension of [2-[2-(aminomethyl)-6-chloro-3-(trifluoromethyl)phenyl]sulfanylphenyl]methanol (3.6 g, 9.368 mmol) in 5% NaHCO$_3$(35 mL) was added Fmoc OSU (3.1 g, 9.368 mmol) in CH$_3$CN (35 mL) at 25° C. and reaction mixture was stirred at 25° C. for 2h. Then reaction mass was diluted with water and extracted with ethyl acetate. The separated organic layer was washed with brine solution, dried over anhydrous sodium sulfate and evaporated under reduced pressure. The crude thus obtained was purified by normal silica column using 5-30% ethyl acetate in hexane to get 9H-fluoren-9-ylmethyl N-[[3-chloro-2-[2-(hydroxymethyl)phenyl]sulfanyl-6-(trifluoromethyl)phenyl]methyl]carbamate (2.96 g, 63%, 2 steps) as a off white solid. MS found: 569.9 (M+H).

To a stirred solution of get 9H-fluoren-9-ylmethyl N-[[3-chloro-2-[2-(hydroxymethyl)phenyl]sulfanyl-6-(trifluoromethyl)phenyl]methyl]carbamate (2.9 g, 5.087 mmol) in DCM/THF (1:1, 60 mL) was added MnO$_2$(8.84 g, 101.749 mmol) and reaction mixture was stirred at 25° C. for 2h. The reaction mass was filtered through celite pad, filtrate was evaporated under reduced pressure. The crude thus obtained was purified by normal silica column using 5-20% ethyl acetate in hexane to get 9H-fluoren-9-ylmethyl N-[[3-chloro-2-(2-formylphenyl)sulfanyl-6-(trifluoromethyl)phenyl]methyl]carbamate (2 g, 69%) as a off white solid. MS found: 567.9 (M+H).

$^1$H-NMR: (400 MHz, DMSO-d6) δ 4.01-4.03 (1H; m); 4.22-4.28 (2H; m); 4.41 (2H; d; J=5.6 Hz); 6.53 (1H; d; J=7.76 Hz); 7.30 (2H; t; J=7.4 Hz); 7.42 (3H; t; J=7.4 Hz); 7.49-7.51 (1H; m); 7.67 (2H; d; J=7.36 Hz); 7.74 (1H; br s); 7.89 (2H; d; J=7.8 Hz); 7.99-8.03 (2H; m); 8.07 (1H; s); 10.20 (1H; s).

Intermediate 9

9H-fluoren-9-ylmethyl N-[[5-chloro-2-(2-formylphenyl)sulfanyl-3-(trifluoromethyl)phenyl]methyl] carbamate

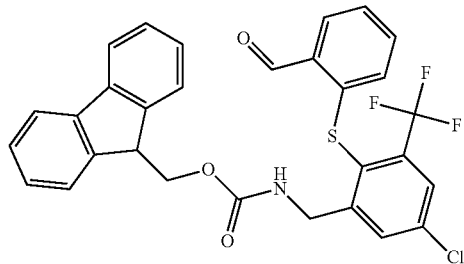 [SMILES: O=Cc1ccccc1Sc1c(CNC(=O)OCC2c3ccccc3-c3ccccc32)cc(Cl)cc1C(F)(F)F]

To a suspension of 5-Chloro-2-fluoro-3-trifluoromethyl-benzaldehyde (1.5 g, 6.62 mmol) and K$_2$CO$_3$ (1.8 g, 13.24 mmol) in DMF (15 mL) was added 2-Mercapto-benzoic acid methyl ester (1.1 g, 6.62 mmol) added and the reaction mixture was stirred for 2 h at room temperature. Progress of the reaction was monitored by TLC. After completion, the reaction mixture was diluted with water (100 mL) and extracted with (3×250 mL) ethyl acetate. Combined organic layer was dried over sodium sulphate and concentrated under reduced pressure to get crude compound which was purified by silica gel (100-200 mesh) column chromatography (20% ethyl acetate and hexane) to get methyl 2-[4-chloro-2-formyl-6-(trifluoromethyl)phenyl]sulfanylbenzoate (2.3 g, 93%) as brown solid.

To a solution of methyl 2-[4-chloro-2-formyl-6-(trifluoromethyl)phenyl]sulfanylbenzoate (2.6 g, 6.95 mmol) and tert-butyl sulphinamide (1.8 g, 15.29 mmol) in THF (50 mL) was added titanium tetraethoxide (3.48 g, 15.29 mmol) and the reaction mixture was heated to 60° C. for 3h. Progress of the reaction was monitored by TLC. After completion, the reaction mixture was diluted with water (100 mL) and extracted with ethyl acetate (3×100 mL). Combined organic layer was dried over sodium sulphate and concentrated to get crude compound which was purified by silica gel (100-200 mesh) column chromatography (30% ethyl acetate and hexane) to get methyl 2-[2-[(E)-tert-butylsulfinyliminomethyl]-4-chloro-6-(trifluoromethyl)phenyl]sulfanylbenzoate (1.9 g, 57%) as brown solid. LC-MS: 477.9 (M+H).

To an ice cooled suspension LAH (0.45 g, 11.95 mmol) in THF (20 mL) was added a solution of methyl 2-[2-[(E)-tert-butylsulfinyliminomethyl]-4-chloro-6-(trifluoromethyl)phenyl]sulfanylbenzoate (1.9 g, 3.98 mmol) in THF (30 mL) and the reaction mixture was stirred for 1 h. Progress of the reaction was monitored by TLC. After completion, the reaction mixture was quenched with aq. sodium sulphate solution (50 mL) and extracted with ethyl acetate (3×100 mL). Combined organic layer was dried over sodium sulphate and concentrated under reduced pressure to get crude compound which was washed with hexane followed by pentane to get N-[[5-chloro-2-[2-(hydroxymethyl)phenyl]sulfanyl-3-(trifluoromethyl)phenyl]methyl]-2-methyl-propane-2-sulfinamide (1.6 g, 89%) as off white solid. LC-MS: 452.0 (M+H).

To a suspension of N-[[5-chloro-2-[2-(hydroxymethyl)phenyl]sulfanyl-3-(trifluoromethyl)phenyl]methyl]-2-methyl-propane-2-sulfinamide (1.6 g, 3.54 mmol) in DCM (50 mL) was added Dess-Martin periodinane (3.7 g, 8.86 mmol) and the reaction mixture was stirred at RT for 2 h. Progress the reaction mass was monitored by TLC. After completion, the reaction mixture was diluted with water (100 mL) and extracted with DCM (3×100 mL). Combined organic layer was dried over sodium sulphate and concentrated under reduced pressure to get crude compound. The crude compound thus obtained was purified by silica gel (100-200 mesh) column chromatography (ethyl acetate) and concentrated under reduced pressure to get N-[[5-chloro-2-(2-formylphenyl)sulfanyl-3-(trifluoromethyl)phenyl]methyl]-2-methyl-propane-2-sulfinamide (0.900 g, 56%) as white solid. LC-MS: 449.7 (M+H).

To an ice cooled solution of N-[[5-chloro-2-(2-formylphenyl)sulfanyl-3-(trifluoromethyl)phenyl]methyl]-2-methyl-propane-2-sulfinamide (0.9 g, 0.0020 mol) in 1,4 dioxane (20 mL) was added 4M HCl in dioxane (4 mL) and the reaction mixture was stirred at ambient temperature for 2 h. Volatiles were removed under reduced pressure to obtain 2-[2-(aminomethyl)-4-chloro-6-(trifluoromethyl)phenyl]sulfanylbenzaldehyde (0.65 g, 94%) as off white solid. LC-MS: 346.0 (M+H).

To a solution of N-[[5-chloro-2-(2-formylphenyl)sulfanyl-3-(trifluoromethyl)phenyl]methyl]-2-methyl-propane-2-sulfinamide (0.9 g, 0.0020 mol) in 5% aqueous NaHCO$_3$ solution (12 mL) was added Fmoc-OSu (0.558 g, 0.0020 mol) in CH$_3$CN (50 mL) and the reaction mixture was stirred at room temperature for 3 h. Then the reaction mixture was diluted with ethyl acetate and washed with water followed by brine. Organic layer was separated off, dried over sodium sulfate and evaporated under reduced pressure to get the crude compound which was purified by flash-chromatography to get 9H-fluoren-9-ylmethyl N-[[5-chloro-2-(2-formylphenyl)sulfanyl-3-(trifluoromethyl)phenyl]methyl]carbamate (0.435 g, 32%) as off white solid. LC-MS: 568.0 (M+H).

$^1$H-NMR: (400 MHz, DMSO-d6): δ 4.23-4.20 (3H, m), 4.32-4.30 (2H, m), 6.43 (1H, d, J=8.0 Hz), 7.34-7.30 (2H, m), 7.44-7.37 (4H, m), 7.67 (2H, d, J=7.4 Hz), 7.70 (1H, br s), 7.89 (3H, d, J=7.5 Hz), 8.03-8.00 (2H, m), 10.15 (1H, s).

Intermediate 10

9H-fluoren-9-ylmethyl N-[[3-chloro-2-(2-formylphenyl)sulfanyl-5-(trifluoromethyl)phenyl]methyl] carbamate

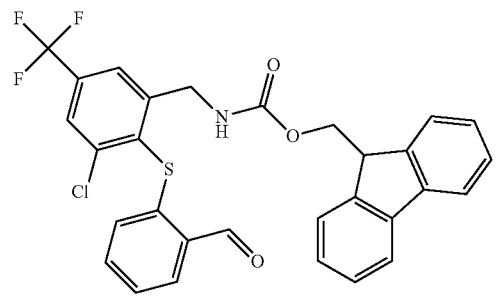 [SMILES: O=Cc1ccccc1Sc1c(Cl)cc(C(F)(F)F)cc1CNC(=O)OCC1c2ccccc2-c2ccccc21]

A suspension of 3-Chloro-2-fluoro-5-trifluoromethyl-benzaldehyde (2.5 g, 11.06 mmol) and K$_2$CO$_3$ (3.0 g, 22.12 mmol) in DMF (15 mL) was added 2-Mercapto-benzoic acid methyl ester (1.8 g, 11.06 mmol) and the reaction mixture was stirred for 2 h at room temperature. Progress of the reaction was monitored by TLC. After completion, the reaction mixture was diluted with water (100 mL) and extracted with ethyl acetate (3×250 mL). Combined organic layer was dried over sodium sulphate and concentrated under reduced pressure to get crude compound. The crude compound thus obtained was purified by silica gel column chromatography (100-200 mesh) using 20% ethyl acetate and hexane as eluent to get methyl 2-[2-chloro-6-formyl-4-(trifluoromethyl)phenyl]sulfanylbenzoate (3.5 g, 85%) as brown solid.

To a suspension of methyl 2-[2-chloro-6-formyl-4-(trifluoromethyl)phenyl]sulfanylbenzoate (3.5 g, 9.36 mmol) and tert-butyl sulphinamide (1.6 g, 14.03 mmol) in THF (50 mL) was added titanium tetraethoxide (3.2 g, 14.03 mmol) and the reaction mixture was heated to 60° C. for 3 h. Progress of the reaction was monitored by TLC. After completion, the reaction mixture was diluted water (100 mL) and extracted with ethyl acetate (3×100 mL). Combined organic layer was dried over sodium sulphate and concentrated under reduced pressure to get crude compound. The crude compound thus obtained was purified by silica gel (100-200 mesh) column chromatography (30% ethyl acetate and hexane) to get methyl 2-[2-[(E)-tert-butylsulfinyliminomethyl]-6-chloro-4-(trifluoromethyl)phenyl]sulfanylbenzoate (4 g, 89%) as brown solid. LC-MS: 477.9 (M+H).

To an ice cooled suspension of LAH (0.955 g, 25.15 mmol) in THF (25 mL) was added a solution of 2-[2-[(E)-tert-butylsulfinyliminomethyl]-6-chloro-4-(trifluoromethyl)phenyl]sulfanylbenzoate (4 g, 8.38 mmol) in THF (25 mL) and the reaction mixture was stirred for 1 h. Progress of the reaction was monitored by TLC. After completion, the reaction mixture was diluted with aq. sodium sulphate solution (100 mL) and extracted with ethyl acetate (3×250 ml). Combined organic layer was dried over sodium sulphate and concentrated under reduced pressure to get crude compound which was purified by washing with hexane followed by pentane to get N-[[3-chloro-2-[2-(hydroxymethyl)phenyl]sulfanyl-5-(trifluoromethyl)phenyl]methyl]-2-methyl-propane-2-sulfinamide (3.9 g, 95%) as brown solid. LC-MS: 452.1 (M+H).

To a solution of N-[[3-chloro-2-[2-(hydroxymethyl)phenyl]sulfanyl-5-(trifluoromethyl)phenyl]methyl]-2-methyl-propane-2-sulfinamide (3.9 g, 8.64 mmol) in DCM (100 mL) was added Dess-Martin periodinane (9.17 g, 21.62 mmol) and the reaction mixture was stirred at RT for 3 h. Progress of the reaction was monitored by TLC. After completion, the reaction mixture was diluted with NaHCO$_3$ solution (100 mL) and extracted with DCM (3×100 mL). Combined organic layer was dried over sodium sulphate and concentrated under reduced pressure to get crude compound. The crude compound thus obtained was purified by silica gel (100-200 mesh) column chromatography (ethyl acetate) to get N-[[3-chloro-2-(2-formylphenyl)sulfanyl-5-(trifluoromethyl)phenyl]methyl]-2-methyl-propane-2-sulfinamide (2 g, 51%) as white solid. LC-MS: 449.7 (M+H).

To an ice cooled solution of N-[[3-chloro-2-(2-formylphenyl)sulfanyl-5-(trifluoromethyl)phenyl]methyl]-2-methyl-propane-2-sulfinamide (2 g, 4.45 mmol) in 1, 4 dioxane (50 mL) was added 4M HCl in dioxane (4 mL) and the resultant reaction mixture was stirred at ambient temperature for 2 h. Volatiles were evaporated under reduced pressure to obtain 2-[2-(aminomethyl)-6-chloro-4-(trifluoromethyl)phenyl]sulfanylbenzaldehyde (1.5 g, 98%) as off white solid. LC-MS: 346.1 (M+H).

To a solution of 2-[2-(aminomethyl)-6-chloro-4-(trifluoromethyl)phenyl]sulfanylbenzaldehyde (2 g, 5.24 mmol) in 5% aqueous NaHCO$_3$ solution (12 mL) was added Fmoc-OSu (1.42 g, 4.19 mmol) in CH$_3$CN (50 mL) and the reaction mixture was stirred at ambient temperature for 3 h. Progress of the reaction was monitored by TLC. After completion, the reaction mixture was diluted with ethyl acetate and washed with water followed by brine. Combined organic layer was dried over sodium sulfate and evaporated under reduced pressure to get crude compound which was purified by flash-chromatography to get 9H-fluoren-9-ylmethyl N-[[3-chloro-2-(2-formylphenyl)sulfanyl-5-(trifluoromethyl)phenyl]methyl]carbamate (0.700 g, 34%) as off white solid. LC-MS: 568.1 (M+H).

$^1$H-NMR: (400 MHz, CDCl$_3$): δ 4.15 (1H, t, J=6.9 Hz), 4.37 (2H, d, J=6.9 Hz), 4.55 (2H, d, J=6.4 Hz), 5.29-5.26 (1H, br), 6.52 (1H, d, J=7.0 Hz), 7.29-7.27 (2H, m), 7.34-7.30 (2H, m), 7.41-7.36 (2H, m), 7.51 (2H, d, J=7.4 Hz), 7.76-7.73 (4H, m), 7.87-7.85 (1H, m), 10.25 (1H, s).

Intermediate 11

9H-fluoren-9-ylmethyl N-[[3,5-dichloro-2-(4-fluoro-2-formyl-phenyl)sulfanyl-phenyl]methyl]carbamate

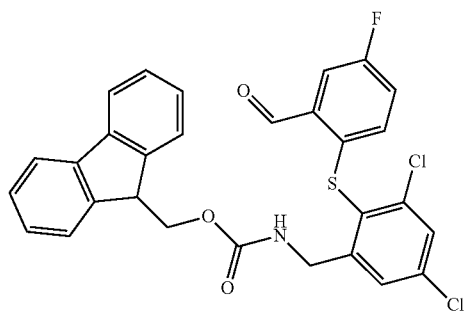 [SMILES: O=Cc1cc(F)ccc1Sc1c(Cl)cc(Cl)cc1CNC(=O)OCC1c2ccccc2-c2ccccc21]

To a stirred solution of 5-Fluoro-2-mercapto-benzoic acid (1 g, 5.808 mmol) in THF (20 mL), was added 2,2,2-Trichloro-acetimidic acid tert-butyl ester (3.6 mL, 20.328 mmol) followed by slow addition of BF$_3$.OEt$_2$ (0.615 mL, 5.808 mmol) at 0° C. and stirred at 25° C. for 2 h. After completion of reaction, reaction mixture was quenched with water and extracted with ethyl acetate. The combined organic layer was washed with brine, dried over anhydrous sodium sulfate and concentrated under reduced pressure to get crude which was purified by normal silica column using 2% ethyl acetate in hexane to afford tert-butyl 5-fluoro-2-sulfanyl-benzoate (620 mg, 47%) as a colourless liquid.

To a stirred solution tert-butyl 5-fluoro-2-sulfanyl-benzoate (600 mg, 2.628 mmol) in DMF (10 mL) were added 2,3,5-Trichloro-benzaldehyde (660 mg, 3.154 mmol), Cs$_2$CO$_3$ (2.13 g, 6.571 mmol) and reaction mixture was heated 60° C. for 3 h. After completion of reaction, reaction mixture was quenched with water and extracted with ethyl acetate. The combined organic layer was washed with brine, dried over anhydrous sodium sulfate and concentrated under reduced pressure to get crude which was purified by normal silica column using 2% ethyl acetate in hexane to afford tert-butyl 2-(2,4-dichloro-6-formyl-phenyl)sulfanyl-5-fluoro-benzoate (660 mg, 62%) as a colorless liquid.

To a stirred solution of 2-(2,4-dichloro-6-formyl-phenyl)sulfanyl-5-fluoro-benzoate (900 mg, 2.243 mmol) in THF (20 mL) were added 2-methyl 2-propane sulfonamide (271 mg, 2.243 mmol) and Ti(OEt)$_4$ (2.3 mL, 11.214 mmol) and heated to 70° C. for 16h. Reaction mixture was quenched with brine solution and extracted with ethyl acetate. The separated organic layer was dried over anhydrous sodium sulfate and concentrated under vacuum to afford tert-butyl 2-[2-[(E)-tert-butylsulfinyliminomethyl]-4,6-dichloro-phenyl]sulfanyl-5-fluoro-benzoate (1 g, crude) as a yellow liquid. MS found: 504.1 (M+H).

To a stirred solution of tert-butyl 2-[2-[(E)-tert-butylsulfinyliminomethyl]-4,6-dichloro-phenyl]sulfanyl-5-fluoro-benzoate (1 g, 1.982 mmol) in THF (20 mL) was added LiBH$_4$(215 mg, 9.911 mmol) and reaction mass was heated to 50° C. for 4h. Reaction mass was quenched with saturated ammonium chloride and extracted with ethyl acetate. The separated organic layer washed with brine solution, dried over anhydrous sodium sulfate and evaporated under reduced pressure to get N-[[3,5-dichloro-2-[4-fluoro-2-(hydroxymethyl)phenyl]sulfanyl-phenyl]methyl]-2-methyl-propane-2-sulfinamide (1.2 g, crude) as a off white solid. MS found: 435.7 (M+H).

To a stirred solution of N-[[3,5-dichloro-2-[4-fluoro-2-(hydroxymethyl)phenyl]sulfanyl-phenyl]methyl]-2-methyl-propane-2-sulfinamide (1.2 g, 2.75 mmol) in MeOH (20 mL), was added 4M HCl/dioxane (10 mL) at 0° C. and reaction mixture was stirred at 25° C. for 1 h. After completion of reaction, reaction mixture was concentrated under reduced pressure to get [2-[2-(aminomethyl)-4,6-dichloro-phenyl]sulfanyl-5-fluoro-phenyl]methanol (1 g, crude) as a off white solid. MS found: 332 (M+H).

To a stirred suspension of [2-[2-(aminomethyl)-4,6-di-chloro-phenyl]sulfanyl-5-fluoro-phenyl]methanol (1 g, 2.712 mmol) in 5% NaHCO$_3$ (20 mL) was added Fmoc OSU (914 mg, 2.712 mmol) in CH$_3$CN (20 mL) at 25° C. and reaction was stirred at 25° C. for 2h. Then reaction mass was diluted with water and extracted with ethyl acetate. The separated organic layer was washed with brine solution, dried over sodium sulfate and evaporated under reduced pressure. The crude thus obtained was purified by normal silica column using 5-30% ethyl acetate in hexane to get 9H-fluoren-9-ylmethyl N-[[3,5-dichloro-2-[4-fluoro-2-(hydroxymethyl)phenyl]sulfanyl-phenyl]methyl]carbamate (800 mg, 64%, 4 steps) as a off white solid. MS found: 554 (M+H).

To a stirred solution of 9H-fluoren-9-ylmethyl N-[[3,5-dichloro-2-[4-fluoro-2-(hydroxymethyl)phenyl]sulfanyl-phenyl]methyl]carbamate (800 mg, 1.661 mmol) in DCM/THF (1:1, 20 mL) was added MnO$_2$ (2.88 g, 33.221 mmol) and reaction mixture was stirred at 25° C. for 2h. The reaction mixture was filtered through celite pad; filtrate was evaporated under reduced pressure. The crude thus obtained was purified by normal silica column using 5-20% ethyl acetate in hexane to get 9H-fluoren-9-ylmethyl N-[[3,5-dichloro-2-(4-fluoro-2-formyl-phenyl)sulfanyl-phenyl]methyl]carbamate (700 mg, 76%) as an off white solid. MS found: 552.3 (M+H).

$^1$H-NMR: (400 MHz, DMSO-d6): δ 4.17-4.12 (3H, m), 4.35 (2H, d, J=5.1 Hz), 7.45-7.28 (6H, m), 7.67-7.60 (4H, m), 7.88 (2H, d, J=7.5 Hz), 8.35 (1H, dd, J=7.6, 1.8 Hz), 8.41 (1H, dd, J=4.8, 1.8 Hz), 10.19 (1H, s).

Intermediate 12

9H-fluoren-9-ylmethyl N-[[3-chloro-2-[(3-formyl-2-pyridyl)sulfanyl]-6-(trifluoromethyl)phenyl]methyl] carbamate

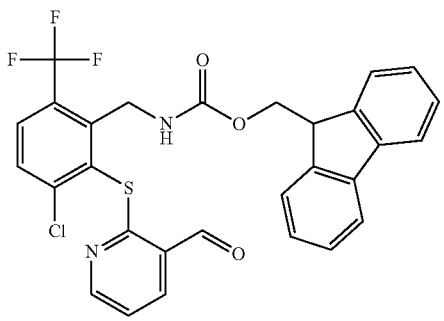 [SMILES: O=Cc1cccnc1Sc1c(Cl)ccc(C(F)(F)F)c1CNC(=O)OCC1c2ccccc2-c2ccccc21]

To an ice-cooled solution of NaH (1.13 g, 27.80 mmol) in DMF (10 mL) was added 2-thionicotinic acid (2.15 g, 13.90 mmol) in DMF (10 mL) and the reaction mixture was stirred for 15 min. To the resulting reaction mixture was added a solution of 3-Chloro-2-fluoro-6-methyl-benzaldehyde (2.1 g, 9.26 mmol) in DMF (10 mL) and the reaction mixture was stirred at room temperature for 9h. Then the reaction mixture was cooled to 0° C. and K$_2$CO$_3$ (3.84 g, 27.80 mmol) followed by methyl iodide (3.10 mL, 27.80 mmol) were added. The resulting reaction mixture was stirred at room temperature for 16h. Then the reaction mixture was quenched by saturated NH$_4$Cl solution (20 mL) and extracted with ethyl acetate (60 mL). Organic layer was separated off, washed with water (2×30 mL) followed by brine (2×30 mL) and dried over anhydrous sodium sulfate. Organic layer was concentrated under reduced pressure and the crude compound was purified by flash-chromatography to afford methyl 2-[6-chloro-2-formyl-3-(trifluoromethyl)phenyl]sulfanylpyridine-3-carboxylate (1.3 g, 37%) as an off-white solid. LC-MS: 375.7 (M+H).

To a degassed solution of methyl 2-[6-chloro-2-formyl-3-(trifluoromethyl)phenyl]sulfanylpyridine-3-carboxylate (1.4 g, 3.72 mmol) in THF (30 mL) was added titanium (IV) ethoxide (8.49 g, 37.25 mmol) followed by tert-butyl sulphinamide (4.50 g, 37.25 mmol) and the resulting reaction mixture was heated to 60° C. for 2 h. Then the reaction mixture was diluted with water (30 mL) and extracted with EtOAc (70 mL). Organic layer was dried over anhydrous sodium sulfate and concentrated under reduced pressure to afford methyl 2-[2-[(E)-tert-butylsulfinyliminomethyl]-6-chloro-3-(trifluoromethyl)phenyl]sulfanylpyridine-3-carboxylate (1.25 g, 70%) as an off-white solid. It's a mixture of ethyl and methyl ester. MS found: 478.7 (M+H).

To an ice-cooled solution of LAH (0.297 g, 7.83 mmol) in THF (10 mL) was added methyl 2-[2-[(E)-tert-butylsulfinyliminomethyl]-6-chloro-3-(trifluoromethyl)phenyl]sulfanylpyridine-3-carboxylate (1.25 g, 2.61 mmol) in THF (15 mL) and the reaction mixture was stirred for 0.5h at same temperature. Then the reaction mixture was quenched by saturated sodium sulfate solution (2 mL) and EtOAc (80 mL). The reaction mixture was filtered through celite and filtrate was concentrated under reduced pressure to afford N-[[3-chloro-2-[[3-(hydroxymethyl)-2-pyridyl]sulfanyl]-6-(trifluoromethyl)phenyl]methyl]-2-methyl-propane-2-sulfinamide (1.1 g, 93%) as an off-white solid. MS found: 452.8 (M+H).

To an ice-cooled solution of N-[[3-chloro-2-[[3-(hydroxymethyl)-2-pyridyl]sulfanyl]-6-(trifluoromethyl)phenyl]methyl]-2-methyl-propane-2-sulfinamide (1.1 g, 2.42 mmol) in DCM (30 mL) was added Dess-Martin periodinane (2.06 g, 4.85 mmol) and the reaction mixture was allowed to stir at ambient temperature for 1 h. Progress of the reaction was monitored by TLC. After completion, the reaction mixture was poured onto saturated sodium bicarbonate solution and extracted with DCM (3×50 mL). Combined organic layer was washed with sodium thiosulphate, dried over sodium sulfate and concentrated under reduced pressure to afford N-[[3-chloro-2-[(3-formyl-2-pyridyl)sulfanyl]-6-(trifluoromethyl)phenyl]methyl]-2-methyl-propane-2-sulfinamide (1.0 g, 91%) as an off-white solid. MS found: 450.8 (M+H).

To an ice-cooled solution of N-[[3-chloro-2-[(3-formyl-2-pyridyl)sulfanyl]-6-(trifluoromethyl)phenyl]methyl]-2-methyl-propane-2-sulfinamide (1.2 g, 2.66 mmol) in dioxane (20 mL) was added 4 M HCl in dioxane (15 mL) and the reaction mixture was allowed to stir at ambient temperature for 1 h. TLC showed consumption of starting material. Volatiles were evaporated under reduced pressure to obtain 2-[2-(aminomethyl)-6-chloro-3-(trifluoromethyl)phenyl]sulfanylpyridine-3-carbaldehyde (0.91 g, 99%) as an off-white solid.

To an ice-cooled suspension of 2-[2-(aminomethyl)-6-chloro-3-(trifluoromethyl)phenyl]sulfanylpyridine-3-carbaldehyde (0.91 g, 2.62 mmol) in acetonitrile (15 mL) were added 5% aqueous NaHCO₃ solution (12 mL) and Fmoc-OSu (0.708 g, 2.09 mmol) in CH₃CN (15 mL) and the reaction mixture was stirred at ambient temperature for 4h. It was then diluted with ethyl acetate (80 mL) and water (30 mL). Organic layer was separated off, washed with water, brine and dried over anhydrous sodium sulfate. Organic layer was concentrated under reduced pressure to get the crude compound which was purified by flash-chromatography to afford 9H-fluoren-9-ylmethyl N-[[3-chloro-2-[(3-formyl-2-pyridyl)sulfanyl]-6-(trifluoromethyl)phenyl]methyl]carbamate (0.590 g, 40%) as an off-white solid. LC-MS: 569.0 (M+H).

¹H-NMR: (400 MHz, CDCl₃): δ 4.21-4.16 (3H, m), 4.43 (2H, br s), 7.33-7.29 (2H, m), 7.43-7.36 (3H, m), 7.56 (1H, br s), 7.66 (2H, m), 7.94-7.84 (4H, m), 8.38 (1H, d, J=7.4 Hz), 8.43 (1H, d, J=3.8 Hz), 10.19 (1H, s).

Intermediate 13

9H-fluoren-9-ylmethyl N-[[3,5-dichloro-2-(2-formylphenyl)sulfanyl-phenyl]methyl]carbamate

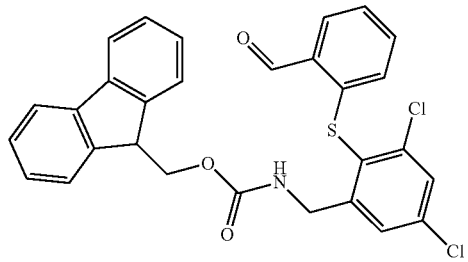 [SMILES: O=Cc1ccccc1Sc1c(Cl)cc(Cl)cc1CNC(=O)OCC1c2ccccc2-c2ccccc21]

To an ice cooled solution of 3,5-Dichloro-2-fluoro-benzaldehyde (2.78 g, 16.57 mmol) in DMF (20 mL, purged with argon for 10 min) under argon atmosphere were added 2-Mercapto-benzoic acid methyl ester (4.0 g, 20.72 mmol) and potassium carbonate (8.59 g, 62.17 mmol) slowly and the reaction mixture was stirred at 0° C. for 30 min. Then the reaction mixture was diluted with water (100 mL) and the aq. phase was extracted with ethyl acetate (50 mL×3). Combined organic layer was washed with brine, dried over sodium sulfate and concentrated under reduced pressure to get crude compound. The crude compound thus obtained was purified by flash-chromatography (5% ethyl acetate in hexane) to afford methyl 2-(2,4-dichloro-6-formyl-phenyl)sulfanylbenzoate (1.6 g, 23%) as off white solid. LC-MS: 339.8 (M+H).

To a stirred solution of methyl 2-(2,4-dichloro-6-formyl-phenyl)sulfanylbenzoate (1.6 g, 4.69 mmol) in dry THF (50 mL) under argon atmosphere was added titanium (IV) ethoxide (2.14 g, 9.38 mmol) followed by tert-butyl sulphinamide (1.137 g, 9.38 mmol). The resulting reaction mixture was stirred at room temperature for 1 h and heated to 60° C. for 4h. Then the reaction mixture was cooled to room temperature, poured onto water (100 mL) and filtered through celite bed. Celite bed was washed with ethyl acetate. Organic layer was separated off and the aqueous layer was extracted with ethyl acetate (50 mL×3). Combined organic layer was dried over sodium sulfate and concentrated under reduced pressure to get the crude compound. The crude compound thus obtained was purified by combiflash (25% ethyl acetate in hexane) to afford methyl 2-[2-[(E)-tert-butylsulfinyliminomethyl]-4,6-dichloro-phenyl]sulfanylbenzoate (2.0 g, 95%) as viscous oil. LC-MS: 443.9 (M+H).

To an ice cooled solution of methyl 2-[2-[(E)-tert-butylsulfinyliminomethyl]-4,6-dichloro-phenyl]sulfanylbenzoate (2.0 g, 4.5 mmol) in THF (50 mL) under argon atmosphere was added LAH (0.512 g, 13.50 mmol) portion wise and the reaction mixture was stirred at 0° C. for 1 h. Progress of the reaction was monitored by TLC. After completion, the reaction mixture was quenched with ethyl acetate and saturated sodium sulfate solution. Then the reaction mixture was filtered through celite and washed with EtOAc. Filtrate was concentrated to get N-[[3,5-dichloro-2-[2-(hydroxymethyl)phenyl]sulfanyl-phenyl]methyl]-2-methyl-propane-2-sulfinamide (1.8 g, 95%) as off white solid. LC-MS: 417.7 (M+H).

To an ice cooled solution of N-[[3,5-dichloro-2-[2-(hydroxymethyl)phenyl]sulfanyl-phenyl]methyl]-2-methyl-propane-2-sulfinamide (1.8 g, 4.30 mmol) in DCM (50 mL) was added Dess-Martin periodinane (2.24 g, 6.45 mmol) portion-wise and the reaction mixture was stirred at room temperature for 2h under argon atmosphere. Progress of the reaction was monitored by TLC. After completion, the reaction mixture was diluted with DCM (50 mL) and saturated solution of sodium bicarbonate (50 mL). Organic layer was separated off and the aqueous layer was extracted with DCM (50 mL×2). Combined organic layer was washed with sodium thiosulphate solution followed by brine. Volatiles were removed under reduced pressure to get N-[[3,5-dichloro-2-(2-formylphenyl)sulfanyl-phenyl]methyl]-2-methyl-propane-2-sulfinamide (2.0 g, crude) as viscous oil which was used as such in next step without further purification. LC-MS: 416.0 (M+H).

To an ice cooled solution of N-[[3,5-dichloro-2-(2-formylphenyl)sulfanyl-phenyl]methyl]-2-methyl-propane-2-sulfinamide (2.0 g, crude) in dioxane (20 mL) was added 4M HCl in dioxane (30 mL) and the reaction mixture was stirred at room temperature for a period of 2 h. Progress of the reaction was monitored by LCMS. Volatiles were removed under reduced pressure to get the crude compound which was washed with diethyl ether (30 mL×2) and dried well to get 2-[2-(aminomethyl)-4,6-dichloro-phenyl]sulfanylbenzaldehyde (1.2 g, crude) as yellow solid. LC-MS: 312.1 (M+H)

To a stirred suspension of 2-[2-(aminomethyl)-4,6-dichloro-phenyl]sulfanylbenzaldehyde (1.2 g, crude) in 5% sodium bicarbonate solution and acetonitrile (30 mL, 1:1) was added a solution of Fmoc-OSu (1.047 g, 3.10 mmol) in acetonitrile (15 mL) and the reaction mixture was stirred at room temperature for 3 h. Progress of the reaction was monitored by TLC. After completion, volatiles were removed under reduced pressure and the crude reaction mixture was diluted with water (50 mL). The aq. phase was extracted with ethyl acetate (50 mL×3). Combined organic layer was washed with brine (50 mL×1), dried over anhydrous sodium sulfate and evaporated under reduced pressure to get crude compound. The crude compound thus obtained was purified by flash-chromatography (20% ethyl acetate in hexane) to afford desired compound which was further washed with n-pentane (5 mL) and dried to get 9H-fluoren-9-ylmethyl N-[[3,5-dichloro-2-(2-formylphenyl)sulfanyl-phenyl]methyl]carbamate (0.75 g, 33% over three steps) as white solid. LC-MS: 533.7 (M+H).

¹H-NMR: (400 MHz, DMSO-d6): δ 4.22-4.19 (2H, m), 4.31-4.29 (3H, m), 6.51 (1H, d, J=7.9 Hz), 7.37-7.31 (3H, m), 7.47-7.38 (4H, m), 7.68 (2H, d, J=7.4 Hz), 7.85 (1H, d,

J=2.0 Hz), 7.89 (2H, d, J=7.5 Hz), 7.94 (1H, t, J=5.9 Hz), 8.01 (1H, d, J=7.4 Hz), 10.18 (1H, s).

Intermediate 14

9H-fluoren-9-ylmethyl N-[[5-chloro-2-(2-formylphenyl)sulfanyl-3-methyl-phenyl]methyl]carbamate

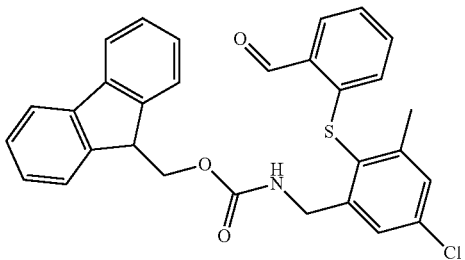 [SMILES: Cc1cc(Cl)cc(CNC(=O)OCC2c3ccccc3-c3ccccc32)c1Sc1ccccc1C=O]

To a stirred solution of 5-chloro-2-fluoro-3-methylbenzoic acid (2.0 g, 10.605 mmol) in THF (20 mL) was added LiAlH4 (21.0 ml, 21.0 mmol) drop-wise in ice cold condition and stirred at 25° C. for 30 min. It was then quenched with saturated Na$_2$SO$_4$ solution and extracted with ethyl acetate, washed with brine and dried over Na$_2$SO$_4$ and concentrated under vacuum to get (5-chloro-2-fluoro-3-methyl-phenyl)methanol (1.8 g, crude) as a light yellow liquid. To a stirred solution of (5-chloro-2-fluoro-3-methyl-phenyl)methanol (1.8 g, 10.345 mmol) in DCM/THF (1:1.40 mL) was added MnO$_2$(8.993 g, 103.448 mmol) and reaction mass was stirred at 25° C. for 2h. The reaction mass was filtered through celite pad, filtrate was evaporated under reduced pressure The crude thus obtained was purified by normal silica column using 2% ethyl acetate in hexane to afford 5-chloro-2-fluoro-3-methyl-benzaldehyde (1.2 g, 64.86%, 2 steps) as yellow liquid.

To a solution of 5-chloro-2-fluoro-3-methyl-benzaldehyde (1.0 g, 5.814 mmol) in DMF (15.0 ml) were added Cs$_2$CO$_3$ (4.727 g, 14.535 mmol) and methyl 2-sulfanylbenzoate (0.978 g, 5.814 mmol) and stirred at 60° C. for 2.5 h. Reaction mixture was diluted with water and extracted with EtOAc. The combined organic layer was washed with brine, dried over anhydrous sodium sulfate and concentrated under vacuum to get the compound which was purified by normal silica column using 0-2% ethyl acetate in hexane to methyl 2-(4-chloro-2-formyl-6-methyl-phenyl)sulfanylbenzoate (1.5 g, 80.43%) as a yellow solid. MS found: 321.2 (M+H).

To a stirred solution of methyl 2-(4-chloro-2-formyl-6-methyl-phenyl)sulfanylbenzoate (1.5 g, 4.688 mmol) in THF (25 mL) was added 2-methylpropane-2-sulfinamide (568 mg, 4.688 mmol), Ti(OEt)$_4$ (4.914 ml, 23.438 mmol) and reaction mass was heated to 70° C. for 16h. The reaction mass was quenched with saturated sodium chloride solution, solid obtained was filtered through celite pad, washed with ethyl acetate. The separated organic layer was dried over anhydrous sodium sulfate and evaporated under reduced pressure to get ethyl 2-[2-[(Z)-tert-butylsulfinyliminomethyl]-4-chloro-6-methyl-phenyl]sulfanylbenzoate (2.0 g, crude) which was directly used for next step without further purification. MS found: 438.2 (M+H).

To a stirred solution of ethyl 2-[2-[(Z)-tert-butylsulfinyliminomethyl]-4-chloro-6-methyl-phenyl]sulfanylbenzoate (2.0 g, 4.577 mmol) in THF (25 mL) was added LiBH$_4$ (0.997 g, 45.767 mmol) at 0° C. and reaction mass was heated to 50° C. for 4h. The solvent was evaporated and the reaction mass was quenched with NH$_4$Cl and extracted with ethyl acetate. The separated organic layer was washed with brine solution, dried over sodium sulfate and evaporated under reduced pressure to get N-[[5-chloro-2-[2-(hydroxymethyl)phenyl]sulfanyl-3-methyl-phenyl]methyl]-2-methyl-propane-2-sulfinamide (1.8 g crude) which was directly used for next step without further purification. MS found: 398.1 (M+H).

To a stirred solution of N-[[5-chloro-2-[2-(hydroxymethyl)phenyl]sulfanyl-3-methyl-phenyl]methyl]-2-methyl-propane-2-sulfinamide (1.8 g, 4.534 mmol) in MeOH (40 mL), was added 4M HCl in dioxane (20 mL) at 0° C. and reaction mixture was stirred at 25° C. for 1 h. After completion of reaction, reaction mixture was concentrated under reduced pressure to get [2-[2-(aminomethyl)-4-chloro-6-methyl-phenyl]sulfanylphenyl]methanol (1.6 g, crude) which was directly used for next step without further purification. MS found: 293.8 (M+H).

To a stirred suspension of [2-[2-(aminomethyl)-4-chloro-6-methyl-phenyl]sulfanylphenyl]methanol (1.6 g, 5.461 mmol) in 5% NaHCO$_3$(20 mL) was added Fmoc OSU (1.841 g, 5.461 mmol) in CH$_3$CN (20 mL) at 25° C. and reaction mixture was stirred at 25° C. for 2h. Then reaction mass was diluted with water and extracted with ethyl acetate. The separated organic layer was washed with brine solution, dried over anhydrous sodium sulfate and evaporated under reduced pressure. The crude thus obtained was purified by normal silica column using 5-30% ethyl acetate in hexane to 9H-fluoren-9-ylmethyl N-[[5-chloro-2-[2-(hydroxymethyl)phenyl]sulfanyl-3-methyl-phenyl]methyl]carbamate (1.4 g, 72%, 4 steps) as a off white solid. MS found: 516.2 (M+H).

To a stirred solution of 9H-fluoren-9-ylmethyl N-[[5-chloro-2-[2-(hydroxymethyl)phenyl]sulfanyl-3-methyl-phenyl]methyl]carbamate (1.6 g, 3.107 mmol) in DCM/THF (1:1, 50 mL) was added MnO$_2$(5.401 g, 62.136 mmol) and reaction mixture was stirred at 25° C. for 2h. The reaction mass was filtered through celite pad, filtrate was evaporated under reduced pressure. The crude thus obtained was purified by normal silica column using 5-20% ethyl acetate in hexane to 9H-fluoren-9-ylmethyl N-[[5-chloro-2-(2-formylphenyl)sulfanyl-3-methyl-phenyl]methyl]carbamate (1.1 g, 68%) as a off white solid. MS found: 514.4 (M+H).

$^1$H-NMR: (400 MHz, DMSO-d6) δ 2.32 (3H; s); 4.19-4.29 (5H; m); 6.47 (1H; d; J=7.8 Hz); 6.29-6.37 (4H; m); 7.37-7.44 (3H; m); 7.51 (1H; br s); 7.69 (2H; d; J=7.36 Hz); 7.87 (1H; m); 7.96 (2H; d; J=7.4 Hz); 7.99 (1H; d; J=7.6 Hz); 10.20 (1H; s)

Intermediate 15

9H-fluoren-9-ylmethyl N-[[3,5-dichloro-2-[(3-formyl-2-pyridyl)sulfanyl]phenyl]methyl]carbamate

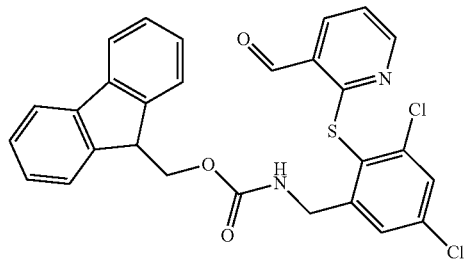 [SMILES: O=Cc1cccnc1Sc1c(Cl)cc(Cl)cc1CNC(=O)OCC1c2ccccc2-c2ccccc21]

To a stirred solution of 2-mercapto-nicotinic acid (2.44 g, 15.755 mmol), in DMF (30 mL) was added KOtBu (3.2 g, 28.645 mmol) and reaction mixture was stirred at 25° C. for 30 min. Then 2,3,5-trichloro-benzaldehyde (3 g, 14.323 mmol) was added to the reaction mass and it was heated to 80° C. for 4h. Then K$_2$CO$_3$(5.93 g, 42.968 mmol) was added followed by addition of MeI (2.67 mL, 42.968 mmmol) and reaction mass was stirred at 25° C. for 16h. The reaction mixture was quenched with water and extracted with ethyl acetate. The separated organic layer was washed with brine solution, dried over anhydrous sodium sulfate and evaporated under reduced pressure. The crude thus obtained was purified by normal silica column using 5-15% ethyl acetate in hexane to get methyl 2-(2,4-dichloro-6-formyl-phenyl) sulfanylpyridine-3-carboxylate (2.3 g, 46%) as a yellow solid. MS found: 341.8 (M+H).

To a stirred solution of methyl 2-(2,4-dichloro-6-formyl-phenyl)sulfanylpyridine-3-carboxylate (2.3 g, 6.721 mmol) in THF (20 mL) were added 2-methylpropane-2-sulfinamide (815 mg, 6.721 mmol) and Ti(OEt)$_4$ (7.09 mL, 33.606 mmol) and reaction mass heated to 70° C. for 1 h. Reaction mixture was quenched with brine solution and extracted with ethyl acetate. The separated organic layer was dried over anhydrous sodium sulfate and concentrated under reduced pressure to afford ethyl 2-[2-[(Z)-tert-butylsulfinyliminomethyl]-4,6-dichloro-phenyl]sulfanylpyridine-3-carboxylate (2.6 g, crude) which was directly used for next step without further purification. MS found: 458.7 (M+H).

To a stirred solution of methyl 2-[2-[(Z)-tert-butylsulfinyliminomethyl]-4,6-dichloro-phenyl]sulfanylpyridine-3-carboxylate (2.6 g, 5.659 mmol) in THF (25 mL) was added LAH (1M in THF, 11.31 mL, 11.31 mmol) at 0° C. and reaction mass was stirred at 25° C. for 2h. Reaction mixture was quenched with saturated sodium sulfate solution and extracted with ethyl acetate. The separated organic layer was washed with water, brine solution, dried over anhydrous sodium sulfate and evaporated under reduced pressure. The crude thus obtained was purified by normal silica column using 10-60% ethyl acetate in hexane to get N-[[3,5-dichloro-2-[[3-(hydroxymethyl)-2-pyridyl]sulfanyl]phenyl]methyl]-2-methyl-propane-2-sulfinamide (1.5 g, 53%, 2 steps) as off white solid. MS found: 418.8 (M+H).

To a stirred solution of N-[[3,5-dichloro-2-[[3-(hydroxymethyl)-2-pyridyl]sulfanyl]phenyl]methyl]-2-methyl-propane-2-sulfinamide (1.9 g, 11.429 mmol) in MeOH (20 mL), was added 4M HCl in dioxane (12 mL) at 0° C. and reaction mixture was stirred at 25° C. for 1 h. After completion of reaction, the mixture was concentrated under reduced pressure to get [2-[2-(aminomethyl)-4,6-dichloro-phenyl] sulfanyl-3-pyridyl]methanol (1.9 g, crude) as off white solid which was directly used for next step. MS found: 315.1 (M+H).

To a stirred suspension of [2-[2-(aminomethyl)-4,6-dichloro-phenyl]sulfanyl-3-pyridyl]methanol (1.9 g, 6.051 mmol) in 5% NaHCO$_3$(25 mL) was added Fmoc OSU (2.04 g, 6.051 mmol) in CH$_3$CN (25 mL) at 25° C. and reaction mass was stirred at 25° C. for 3h. Then reaction mass was diluted with water and extracted with ethyl acetate. The separated organic layer was washed with brine solution, dried over sodium sulfate and evaporated under reduced pressure to get 9H-fluoren-9-ylmethyl N-[[3,5-dichloro-2-[[3-(hydroxymethyl)-2-pyridyl]sulfanyl]phenyl]methyl]carbamate (2.5 g, crude) which was directly used for next step. MS found: 537.0 (M+H).

To a stirred solution of 9H-fluoren-9-ylmethyl N-[[3,5-dichloro-2-[[3-(hydroxymethyl)-2-pyridyl]sulfanyl]phenyl] methyl]carbamate (2.5 g, 4.664 mmol) in DCM/THF (1:1, 70 mL) was added MnO$_2$(4.055 g, 46.642 mmol) and reaction mass was stirred at 25° C. for 3h. The reaction mass was filtered through celite pad, filtrate was evaporated under reduced pressure to get the crude which was purified by silica chromatography using 5-40% ethyl acetate in hexane to afford 9H-fluoren-9-ylmethyl N-[[3,5-dichloro-2-[(3-formyl-2-pyridyl)sulfanyl]phenyl]methyl]carbamate as off-white solid (1.7 g, 69%, 3 steps).

$^1$H-NMR: (400 MHz, DMSO-d6) δ 4.21-4.30 (5H; m); 7.25-7.43 (6H; m); 7.67 (2H; d; J=7.26 Hz); 7.79 (1H; s); 7.90 (2H; br d; J=7.16 Hz); 8.36 (1; br d; J=7.36 Hz); 8.40 (1H; br s); 10.18 (1H; s)

Intermediate 16

9H-fluoren-9-ylmethyl N-[[5-ethyl-2-(2-formylphenyl)sulfanyl-phenyl]methyl]carbamate

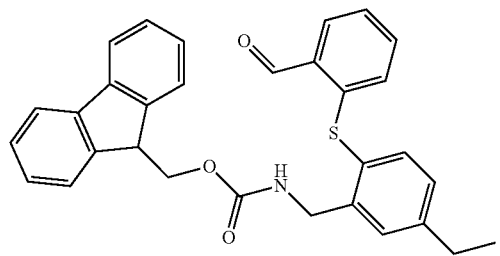 [SMILES: CCc1ccc(Sc2ccccc2C=O)c(CNC(=O)OCC2c3ccccc3-c3ccccc32)c1]

To a solution of 2-Fluoro-5-iodo-benzaldehyde (2.0 g, 8 mmol) in dioxane: water (30 mL) were added vinyl boronic acid pinacol ester (1.6 mL, 9.6 mmol) and Cs$_2$CO$_3$ (3.9 g, 12 mmol) sequentially. Then the reaction mixture was degassed with argon and Pd(PPh$_3$)$_4$(0.184 g, 0.16 mmol) was added. The resulting reaction mixture was heated to 70° C. for 2h. Progress of the reaction was monitored by TLC. After completion, the reaction mixture was extracted with EtOAc (3×50 mL). Combined organic layer was washed with water followed by brine and dried over anhydrous sodium sulfate. Solvent was evaporated under reduced pressure to get crude compound which was further purified by flash-chromatography (hexane) to get 2-fluoro-5-vinyl-benzaldehyde (0.83 g, 69%) as colorless oil.

To a degassed solution of 2-fluoro-5-vinyl-benzaldehyde (0.83 g, 5.5 mmol) in dry DMF (4 mL) were added K$_2$CO$_3$ (1.2 g, 13.8 mmol) and methyl thiosalicylate (0.91 mL, 0.66 mmol). Then the reaction mixture was stirred for 1 h. Progress of the reaction was monitored by TLC. After completion the reaction mixture was diluted with water (30 mL) and extracted with EtOAc (3×20 mL). Combined organic layer was washed with water followed by brine and dried over Na$_2$SO$_4$. Solvent was evaporated under reduced pressure to get crude compound which was purified by combiflash (20% ethyl acetate in hexane) to afford methyl 2-(2-formyl-4-vinyl-phenyl)sulfanylbenzoate (1.4 g, 85%) as yellow oil. MS found: 299.2 (M+H).

To a degassed solution of methyl 2-(2-formyl-4-vinyl-phenyl)sulfanylbenzoate (1.4 g, 4.6 mmol) in ethyl acetate (25 mL) was added PtO$_2$ (0.05 g) and the reaction mixture was stirred under hydrogen atmosphere for 3h. Progress of the reaction was monitored by TLC. After completion, the reaction mixture was filtered through celite and the filtrate was concentrated under reduced pressure to get methyl 2-(4-ethyl-2-formyl-phenyl)sulfanylbenzoate (1.4 g, 99%) as white solid. MS found: 301.0 (M+H).

To a solution of methyl 2-(4-ethyl-2-formyl-phenyl)sulfanylbenzoate (1.4 g, 4.6 mmol) in THF (30 mL) was added 2-methylpropane-2-sulfinamide (1.4 g, 11.66 mmol) followed by titanium ethoxide (2.4 mL, 11.66 mmol) and the reaction mixture was heated at 55° C. for 2 h. Progress of the reaction was monitored by TLC. After completion the reaction mixture was diluted with water (30 mL) and filtered through celite. Organic layer was separated off, dried over sodium sulphate and concentrated under reduced pressure to get methyl 2-[2-[(Z)-tert-butylsulfinyliminomethyl]-4-ethyl-phenyl]sulfanylbenzoate (1.6 g, 85%) as colorless oil. MS found: 404.3 (M+H).

To an ice-cooled solution of LAH (0.471 g, 12.40 mmol) in dry THF (10 mL) was added a solution of methyl 2-[2-[(Z)-tert-butylsulfinyliminomethyl]-4-ethyl-phenyl] sulfanylbenzoate (2.5 g, 6.20 mmol) in THF (20 mL) and the resulting reaction mixture was stirred for 0.5h. Progress of the reaction was monitored by TLC. After completion, the reaction was quenched with saturated sodium sulphate solution (5 mL) and ethyl acetate. Then the reaction mixture was filtered through celite and washed with ethyl acetate (50 mL). The filtrate was concentrated under reduced pressure to get N-[[5-ethyl-2-[2-(hydroxymethyl)phenyl]methyl]-2-methyl-propane-2-sulfinamide (2.0 g, 93%) which was used as such in next step. MS found: 378.1 (M+H).

To an ice cold solution of N-[[5-ethyl-2-[2-(hydroxymethyl)phenyl]sulfanyl-phenyl]methyl]-2-methyl-propane-2-sulfinamide (1.2 g, 4.23 mmol) in acetonitrile (20 mL) was added 5% sodium bicarbonate solution (12 mL) followed by a solution of Fmoc-Osu (1.4 g, 4.29 mmol) in acetonitrile (10 mL) and the reaction mixture was stirred at ambient temperature for 4h. Progress of the reaction was monitored by TLC. After completion, the reaction mixture was diluted with water (50 mL) and ethyl acetate (80 mL). Organic layer was separated from which volatiles were removed under reduced pressure to get crude compound which was then purified by flash-chromatography (20% ethyl acetate in hexane) to 9H-fluoren-9-ylmethyl N-[[5-ethyl-2-(2-formylphenyl)sulfanyl-phenyl]methyl]carbamate (0.670 g, 35%) as white solid. LC-MS: 494.0 (M+H).

¹H-NMR: (400 MHz, DMSO-d6): δ 1.20 (3H, t, J=7.6 Hz), 2.65 (2H, q, J=7.6 Hz), 4.30-4.23 (5H, m), 6.66 (1H, d, J=8.0 Hz), 7.36-7.23 (5H, m), 7.48-7.38 (4H, m), 7.70 (2H, d, J=7.4 Hz), 7.83 (1H, t, J=5.9 Hz), 7.89 (2H, d, J=7.5 Hz), 7.95 (1H, d, J=7.6 Hz), 10.21 (1H, s).

Intermediate 17

9H-fluoren-9-ylmethyl N-[[2-(2-formylphenyl)sulfanyl-5-phenyl-phenyl]methyl]carbamate

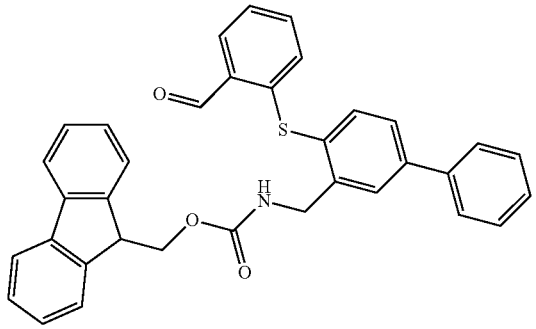 [SMILES: O=Cc1ccccc1Sc1ccc(-c2ccccc2)cc1CNC(=O)OCC1c2ccccc2-c2ccccc21]

A solution of 4-Fluoro-biphenyl (2 g, 11.61 mmol) and PMDTA (3 mL) in THF (50 mL) was cooled to −78° C. and 1.6 M nBuLi (10.88 mL, 17.42 mmol) was added drop wise. The resultant reaction mixture was stirred for 40 min at −60° C. The reaction mixture was cooled to −78° C. again and DMF (2.12 mL, 29.03 mmol) was added. Then the reaction mixture was stirred at −78° C. for 30 min before allowing the mixture to warm up to room temperature. The reaction mixture was quenched with aqueous NH₄Cl and the whole mixture was extracted with diethyl ether (30 mL). Combined organic layer was washed with brine (30 mL) and concentrated under reduced pressure to afford crude compound which was purified by flash-chromatography (10% ethylacetate in hexane) to get 2-fluoro-5-phenyl-benzaldehyde (1.8 g, 77%) as viscous oil.

To a solution of 2-fluoro-5-phenyl-benzaldehyde (2.5 g, 10 mmol) in dioxane-water (1:1) (30 mL) was added phenyl boronic ester (1.45 g, 12 mmol) and Cs₂CO₃ (4.87 g, 15 mmol) sequentially. The solution was then degassed with argon for 30 min. To this solution was added Pd(PPh₃)₄ (0.23 g, 0.2 mmol) and heated to 70° C. for 2h. Then the reaction mixture was filtered, filtrate was concentrated and diluted with water (50 mL). The aq. layer was extracted with ethyl acetate (100 mL×2). Combined organic layer was washed with brine (50 mL) and dried over anhydrous sodium sulphate. Organic layer was concentrated to get the crude compound which was purified by flash-chromatography (10% ethyl acetate in hexane) to afford 2-fluoro-5-phenyl-benzaldehyde (1.7 g, 85%) as viscous oil.

To a solution of 2-fluoro-5-phenyl-benzaldehyde (1.7 g, 8.5 mmol) and methyl thiosalicylate (1.43 g, 8.5 mmol) in DMF (20 mL) was added K₂CO₃ (2.35 g, 17 mmol) and the reaction mixture was heated to 60° C. for 16h. Then the reaction mixture was diluted with water and extracted with ethyl acetate (100 mL×2). Combined organic layer was washed with brine (40 mL×2), dried over sodium sulphate and concentrated to afford crude compound which was further purified by combiflash (30% ethyl acetate in hexane) to afford methyl 2-(2-formyl-4-phenyl-phenyl)sulfanylbenzoate (1.8 g, 60%) as an off-white solid. LCMS: 349.1 (M+H).

To a stirred solution of methyl 2-(2-formyl-4-phenyl-phenyl)sulfanylbenzoate (1.7 g, 4.88 mmol) in anhydrous THF (50 mL) were added 2-methylpropane-2-sulfinamide (1.18 g, 9.77 mmol) and titanium tetraethoxide (2.23 g, 9.77 mmol) sequentially and the resultant reaction mixture was heated at 60° C. for 5h. Then the reaction mixture was poured onto ice-water and filtered through a short pad of celite. Filtrate was extracted with ethyl acetate (100 mL×2), washed with brine (100 mL×2), dried over anhydrous sodium sulfate and concentrated under reduced pressure to get the crude compound which was purified by flash-chromatography column (10-20% ethyl acetate in hexane) to afford methyl 2-[2-[(Z)-tert-butylsulfinyliminomethyl]-4-phenyl-phenyl]sulfanylbenzoate (1.8 g, crude) as sticky mass. MS found: 452.1 (M+H).

To an ice-cooled suspension of LAH (0.279 g, 7.54 mmol) in THF (50 mL) was added a solution of methyl 2-[2-[(Z)-tert-butylsulfinyliminomethyl]-4-phenyl-phenyl]sulfanyl-benzoate (1.7 g, crude) in THF (50 mL) and the reaction mixture was stirred at 0° C. for 30 min. Progress of the reaction was monitored by TLC. After completion, the reaction mixture was quenched with saturated sodium sulphate solution (5 mL) and diluted with ethyl acetate (20 mL). The reaction mixture was filtered through celite and filtrate was concentrated to get N-[[2-[2-(hydroxymethyl)

phenyl]sulfanyl-5-phenyl-phenyl]methyl]-2-methyl-propane-2-sulfinamide (1.4 g, crude) as white solid. MS found: 426.1 (M+H).

To an ice-cooled solution of N-[[2-[2-(hydroxymethyl) phenyl]sulfanyl-5-phenyl-phenyl]methyl]-2-methyl-propane-2-sulfinamide (2 g, crude) in DCM (50 mL) was added Dess-Martin periodinane (2.59 g, 6.12 mmol) portion wise and the reaction mixture was stirred at room temperature for 2h under argon atmosphere. Progress of the reaction was monitored by TLC. After completion, the reaction mixture was diluted with DCM (50 mL) and saturated sodium bicarbonate solution (50 mL). Organic layer was separated off and the aqueous layer was extracted with DCM (50 mL×2). Combined organic layer was washed with sodium thiosulphate solution followed by brine. Volatiles were removed under reduced pressure to get N-[[2-(2-formylphenyl)sulfanyl-5-phenyl-phenyl]methyl]-2-methyl-propane-2-sulfinamide (0.8 g, 40% over four steps) as viscous oil. MS found: 423.9 (M+H).

To an ice-cooled solution of N-[[2-(2-formylphenyl)sulfanyl-5-phenyl-phenyl]methyl]-2-methyl-propane-2-sulfinamide (1.5 g, 3.5 mmol) in dioxane (20 mL) was added 4M HCl in dioxane and the reaction mixture was stirred at same temperature for 1 h. Volatiles were removed under reduced pressure to get the crude compound which was triturated with diethyl ether to get 2-[2-(aminomethyl)-4-phenyl-phenyl]sulfanylbenzaldehyde (0.9 g, 79%) as white solid. MS found: 320.0 (M+H).

To a stirred suspension of 2-[2-(aminomethyl)-4-phenyl-phenyl]sulfanylbenzaldehyde (0.7 g, 1.88 mmol) in 5% sodium bicarbonate solution (12 mL) was added a solution of Fmoc-OSu (0.443 g, 1.314 mmol) in acetonitrile (30 mL) and the reaction mixture was stirred at room temperature for 3 h. Volatiles were removed under reduced pressure and the crude reaction mixture was diluted with water (10 mL). Then the aq. phase was extracted with ethyl acetate (50 mL×3) and washed with brine (50 mL), dried over anhydrous sodium sulfate and evaporated under reduced pressure to get the crude compound which was purified by flash-chromatography (10% ethyl acetate in hexane) to 9H-fluoren-9-ylmethyl N-[[2-(2-formylphenyl)sulfanyl-5-phenyl-phenyl]methyl]carbamate (0.45 g, 44%) as white solid. LC-MS: 542.2 (M+H).

¹H-NMR: (400 MHz, DMSO-d6): δ 4.22-4.19 (1H, m), 4.28 (2H, d, J=7.0 Hz), 4.35 (2H, d, J=5.6 Hz), 6.82 (1H, d, J=7.9 Hz), 7.25 (2H, t, J=7.4 Hz), 7.44-7.36 (4H, m), 7.55-7.47 (4H, m), 7.69-7.67 (5H, m), 7.76 (1H, s), 7.87 (2H, d, J=7.4 Hz), 7.99-7.96 (2H, m), 10.24 (1H, s).

Intermediate 18

9H-fluoren-9-ylmethyl N-[[5-tert-butyl-2-(2-formylphenyl)sulfanyl-phenyl]methyl]carbamate

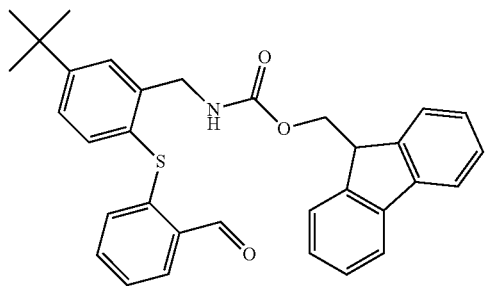 [SMILES: CC(C)(C)c1ccc(Sc2ccccc2C=O)c(CNC(=O)OCC2c3ccccc3-c3ccccc32)c1]

To a stirred solution of 1-tert-butyl-4-flurobenzene (2.0 g, 13.15 mmol) in dry THF (20 mL) was added PMDTA (3.4 mL, 19.73 mmol) and n-BuLi (1.6 M in THF, 12.3 mL, 26.31 mmol) at −78° C. and the resulting reaction mixture was stirred at the same temperature for 1 h. To the reaction mixture was added DMF (2.6 mL, 32.89 mmol) at −78° C. and stirred further at the same temperature for 1 h. Then the reaction mixture was quenched by the addition of saturated NH₄Cl (20 mL) and extracted with diethyl ether (2×25 mL). Combined organic layer was washed with water (20 mL), brine (20 mL), dried over anhydrous Na₂SO₄ and concentrated under reduced pressure. The crude compound thus obtained was purified by flash-chromatography (1% ethyl acetate in hexane) to afford 5-tert-butyl-2-fluoro-benzaldehyde (2.1 g, 88%) as a pale yellow oil.

To a stirred solution of 5-tert-butyl-2-fluoro-benzaldehyde (1.3 g, 7.22 mmol) in dry DMF (20 mL) were added methyl thiosalicylate (2.0 mL, 14.44 mmol) and KOtBu (1.6 g, 14.44 mmol) sequentially and the resulting reaction mixture was heated to 50° C. for 16 h. Then the reaction mixture was cooled to room temperature, diluted with water (30 mL) and extracted with ethyl acetate (2×25 mL). Combined organic layer was washed with water (30 mL), brine (30 mL), dried over anhydrous Na₂SO₄ and concentrated under reduced pressure. The crude compound thus obtained was purified by flash-chromatography (1.8% ethyl acetate in hexane) to afford methyl 2-(4-tert-butyl-2-formyl-phenyl)sulfanylbenzoate (0.7 g, 30%) as a pale yellow oil. MS found: 329.3 (M+H).

To a stirred solution of methyl 2-(4-tert-butyl-2-formylphenyl)sulfanylbenzoate (0.7 g, 2.13 mmol) in dry THF (20 mL) was added 2-methylpropane-2-sulfinamide (0.6 g, 5.33 mmol) followed by titanium (IV) ethoxide (1.1 mL, 5.33 mmol) and the resulting reaction mixture was heated to 70° C. for 2 h. Then the reaction mixture was cooled to room temperature, diluted with water, filtered through celite. The filtrate was extracted with ethyl acetate (2×20 mL). Combined organic layer was washed with water (10 mL) followed by brine (10 mL) and dried over anhydrous Na₂SO₄. Organic layer was concentrated under reduced pressure to get the crude compound which was purified by flash-chromatography (18% ethyl acetate in hexane) to afford methyl 2-[4-tert-butyl-2-[(E)-tert-butylsulfinyliminomethyl]phenyl]sulfanylbenzoate (0.9 g, 97%) as a pale yellow oil.

To an ice cooled solution of LAH (0.2 g, 6.26 mmol) in dry THF (20 mL) was added a solution of methyl 2-[4-tert-butyl-2-[(E)-tert-butylsulfinyliminomethyl]phenyl]sulfanylbenzoate (0.9 g, 2.08 mmol) in dry THF (20 mL) and the resulting reaction mixture was stirred at room temperature for 2 h. Then reaction mixture was quenched with ethyl acetate (30 mL), filtered through celite and concentrated under reduced pressure to afford N-[[5-tert-butyl-2-[2-(hydroxymethyl)phenyl]sulfanyl-phenyl]methyl]-2-methyl-propane-2-sulfinamide (0.7 g, 82%) as a white solid.

To an ice-cooled solution of N-[[5-tert-butyl-2-[2-(hydroxymethyl)phenyl]sulfanyl-phenyl]methyl]-2-methyl-propane-2-sulfinamide (0.7 g, 1.72 mmol) in dry DCM (10 mL) was added Dess-Martin periodinane (0.8 g, 1.90 mmol) and the resulting reaction mixture was stirred at room temperature for 2 h. The reaction mixture was quenched with saturated NaHCO₃ solution (25 mL) and extracted with DCM (2×25 mL). Combined organic layer was washed with water (15 mL), dried over anhydrous Na₂SO₄ and concentrated under reduced pressure. The crude compound thus obtained was purified by flash-chromatography (50% ethyl acetate in hexane) to afford N-[[5-tert-butyl-2-(2-formylphenyl)sulfanyl-phenyl]methyl]-2-methyl-propane-2-sulfinamide (0.55 g, 78%) as an off-white solid.

To an ice-cooled solution of N-[[5-tert-butyl-2-(2-formylphenyl)sulfanyl-phenyl]methyl]-2-methyl-propane-2-sulfinamide (0.55 g, 1.36 mmol) in dioxane (2 mL) was added 4M dioxane in HCl (2 mL) and the resulting reaction mixture was stirred at room temperature for 3 h. Volatiles were reduced under reduced pressure to afford 2-[2-(aminomethyl)-4-tert-butyl-phenyl]sulfanylbenzaldehyde (0.45 g, 100%) as a yellow solid. The crude was used as such for the next step.

To an ice-cooled solution of 2-[2-(aminomethyl)-4-tert-butyl-phenyl]sulfanylbenzaldehyde (0.45 g, 1.34 mmol) in acetonitrile (10 mL) was added 5% $NaHCO_3$ solution (3 mL) followed by Fmoc-OSu (0.3 g, 0.94 mmol) and the resulting reaction mixture was stirred at room temperature for 5h. Then the reaction mixture was diluted with water (10 mL) and extracted with ethyl acetate (2×20 mL). Combined organic layer was washed with water (10 mL) followed by brine (10 mL), dried over anhydrous $Na_2SO_4$ and concentrated under reduced pressure. The crude compound thus obtained was purified by flash-chromatography (15% ethyl acetate in hexane) to afford 9H-fluoren-9-ylmethyl N-[[5-tert-butyl-2-(2-formylphenyl)sulfanyl-phenyl]methyl]carbamate (0.45 g, 64%) as a yellow solid. LC-MS: 522.4 (M+H).
$^1$H-NMR: (400 MHz, $CDCl_3$): δ 1.34 (9H, s), 4.17 (1H, t, J=7.1 Hz), 4.34 (2H, d, J=7.1 Hz), 4.46 (2H, d, J=6.2 Hz), 5.14 (1H, br), 6.76 (1H, d, J=8.2 Hz), 7.30-7.27 (3H, m), 7.42-7.32 (5H, m), 7.55-7.51 (3H, m), 7.74 (2H, d, J=7.4 Hz), 7.84 (1H, d, J=7.9 Hz), 10.30 (1H, s).

Intermediate 19

9H-fluoren-9-ylmethyl N-[[2-(2-formylphenyl)sulfanyl-5-isopropyl-phenyl]methyl]carbamate

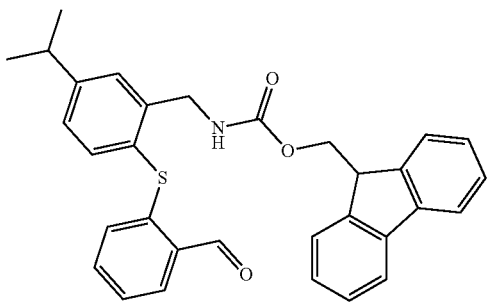 [SMILES: CC(C)c1ccc(Sc2ccccc2C=O)c(CNC(=O)OCC2c3ccccc3-c3ccccc32)c1]

To a solution of 5-Bromo-2-fluoro-benzaldehyde (2 g, 9.85 mmol) in dioxane:water (1:1) (40 mL, 1:1) was added isoprenylboronic ester (1.98 g, 11.82 mmol) and $Cs_2CO_3$ (8 g, 24.63 mmol) sequentially. The reaction mixture was then degassed with argon for 0.5 h and to it was added $Pd(PPh_3)_4$ (0.22 g, 0.19 mmol). The reaction mixture was then heated at 70° C. for 2h. Progress of the reaction was monitored by TLC. After completion, the reaction mixture was filtered. The filtrate was concentrated and diluted with ethyl acetate (100 mL). Organic layer was washed with water followed by brine and dried over anhydrous sodium sulfate. Organic layer was concentrated to get the crude compound which was purified by flash-chromatography (20% ethyl acetate in hexane) to afford 2-fluoro-5-isopropenyl-benzaldehyde (1.2 g, 74%) as viscous oil.

To an ice-cooled solution of 2-fluoro-5-isopropenyl-benzaldehyde (1.3 g, 7.92 mmol) and methyl thiosalicylate (1.59 g, 9.51 mmol) in DMF (30 mL) under argon atmosphere was added potassium carbonate (2.73 g, 19.81 mmol) and the reaction mixture was heated at 60° C. for 3 h. Then the reaction mixture was diluted with water (50 mL) and extracted with ethyl acetate (40 mL×3). The organic layer was washed with brine (40 mL×3), dried over sodium sulfate and concentrated under reduced pressure to get crude compound which was purified by flash-chromatography (30% ethyl acetate in hexane) to afford methyl 2-(2-formyl-4-isopropenyl-phenyl)sulfanylbenzoate (2.2 g, 89%) as pale yellow solid. MS found: 313.1 (M+H).

To a degassed solution of methyl 2-(2-formyl-4-isopropenyl-phenyl)sulfanylbenzoate (1.6 g, 5.12 mmol) in THF (50 mL) was added Raney Ni (0.2 g) and the reaction mixture was then stirred under hydrogen atmosphere for 16h. Then the reaction mixture was filtered through celite, washed with THF and concentrated under reduced pressure to get crude compound which was purified by flash-chromatography (60% ethyl acetate in hexane) to afford methyl 2-[2-(hydroxymethyl)-4-isopropyl-phenyl]sulfanylbenzoate (1.4 g, 87%) as viscous oil. MS found: 317.1 (M+H).

To an ice-cooled solution of methyl 2-[2-(hydroxymethyl)-4-isopropyl-phenyl]sulfanylbenzoate (1.4 g, 4.43 mmol) in DCM (50 mL) was added Dess-Martin periodinane (2.25 g, 5.31 mmol) portion wise and the reaction mixture was stirred at room temperature for 2h under argon atmosphere. Progress of the reaction was monitored by TLC. After completion, the reaction mixture was diluted with DCM (50 mL) and saturated sodium bicarbonate solution (50 mL×2). Organic layer was separated off and the aqueous layer was extracted with DCM (50 mL×2). Combined organic layer was washed with sodium thiosulphate solution followed by brine. Volatiles were removed under reduced pressure to get the crude compound which was purified by flash-chromatography (30% ethyl acetate in hexane) to afford methyl 2-(2-formyl-4-isopropyl-phenyl)sulfanylbenzoate (1.2 g, 86%) as viscous oil. MS found: 314.9 (M+H).

To a stirred solution of methyl 2-(2-formyl-4-isopropyl-phenyl)sulfanylbenzoate (1.2 g, 3.82 mmol) in anhydrous THF (50 mL) were added 2-methylpropane-2-sulfinamide (1.15 g, 9.55 mmol) and titanium tetraethoxide (2.17 g, 9.77 mmol) sequentially. The resultant reaction mixture was heated to 60° C. for 5 h under argon atmosphere. Then the reaction mixture was poured onto ice-water and filtered through celite. Filtrate was extracted with ethyl acetate (100 mL×2), washed with brine (100 mL×2), dried over anhydrous sodium sulfate and concentrated under reduced pressure to get the crude compound which was purified by flash column (10-20% ethyl acetate in hexane) to afford methyl 2-[2-[(E)-tert-butylsulfinyliminomethyl]-4-isopropyl-phenyl]sulfanylbenzoate (1.45 g, 91%) as brown solid. MS found: 418.2 (M+H).

To an ice-cooled suspension of LAH (0.25 g, 6.95 mmol) in THF (30 mL) was added a solution of afford methyl 2-[2-[(E)-tert-butylsulfinyliminomethyl]-4-isopropyl-phenyl]sulfanylbenzoate (1.45 g, 3.47 mmol) in THF (20 mL) and the reaction mixture was stirred for 30 min at 0° C. Progress of the reaction was monitored by TLC. After completion, the reaction mixture was quenched with saturated sodium sulphate solution (5 mL) and diluted with ethyl acetate (20 mL). The reaction mixture was filtered through celite. The filtrate was concentrated to afford N-[[2-[2-(hydroxymethyl)phenyl]sulfanyl-5-isopropyl-phenyl]methyl]-2-methyl-propane-2-sulfinamide (1.1 g, 81%) as white solid. MS found: 392.0 (M+H).

To an ice-cooled solution of N-[[2-[2-(hydroxymethyl)phenyl]sulfanyl-5-isopropyl-phenyl]methyl]-2-methyl-propane-2-sulfinamide (1 g, 2.55 mmol) in dioxane (20 mL) was added 4M HCl in dioxane and the resulting reaction mixture was stirred at room temperature for 1 h. Volatiles were removed under reduced pressure to get crude compound which was triturated with diethyl ether and dried to get [2-[2-(aminomethyl)-4-isopropyl-phenyl]sulfanylphenyl]methanol (0.735 g, 87%) as white solid. MS found: 287.9 (M+H).

To a stirred suspension of [2-[2-(aminomethyl)-4-isopropyl-phenyl]sulfanylphenyl]methanol (0.7 g, 2.16 mmol) in 5% sodium bicarbonate solution (12 mL) was added Fmoc-OSu (0.51 g, 1.51 mmol) in acetonitrile (30 mL) and the reaction mixture was stirred at ambient temperature for 3 h. Volatiles were concentrated under vacuum then diluted with water (50 mL) and extracted with ethyl acetate (50 mL×3) and washed with brine (50 mL), dried over anhydrous sodium sulfate and evaporated under reduced pressure to get crude compound. Crude compound was purified by flash-chromatography (20% ethyl acetate in hexane) to afford [2-(2-ethyl-4-isopropyl-phenyl)sulfanylphenyl]methanol (0.7 g, 63%) as white solid. MS found: 510.2 (M+H).

To an ice-cooled solution of [2-(2-ethyl-4-isopropyl-phenyl)sulfanylphenyl]methanol (0.7 g, 1.38 mmol) in DCM (30 mL) was added Dess-Martin periodinane (0.75 g, 1.78 mmol) portion wise and the reaction mixture was stirred at room temperature for 2h under argon atmosphere. Progress of the reaction was monitored by TLC. After completion, the reaction mixture was diluted with DCM (50 mL) and saturated sodium bicarbonate solution (50 mL×2). Organic layer was separated off and the aqueous layer was extracted with DCM (50 mL×2). Combined organic layer was washed with sodium thiosulfate solution followed by brine. Volatiles were removed under reduced pressure to get crude compound which was purified by flash-chromatography (30% ethyl acetate in hexane) to afford 9H-fluoren-9-ylmethyl N-[[2-(2-formylphenyl)sulfanyl-5-isopropyl-phenyl]methyl]carbamate (0.530 g, 76%) as white solid. LC-MS: 508.1 (M+H).

$^1$H-NMR: (400 MHz, DMSO-d6): δ 1.21 (6H, d, J=6.9 Hz), 2.92 (1H, sep, J=6.9 Hz), 4.28-4.19 (5H, m), 6.67 (1H, d, J=8.0 Hz), 7.49-7.25 (9H, m), 7.70 (2H, d, J=7.4 Hz), 7.85 (1H, t, J=5.7 Hz), 7.89 (2H, d, J=7.5 Hz), 7.96 (1H, d, J=7.3 Hz), 10.21 (1H, s).

Intermediate 20

9H-fluoren-9-ylmethyl N-({2-[(3-formylpyridin-2-yl)sulfanyl]-5-phenyl-3-(trifluoromethyl)phenyl}methyl) carbamate

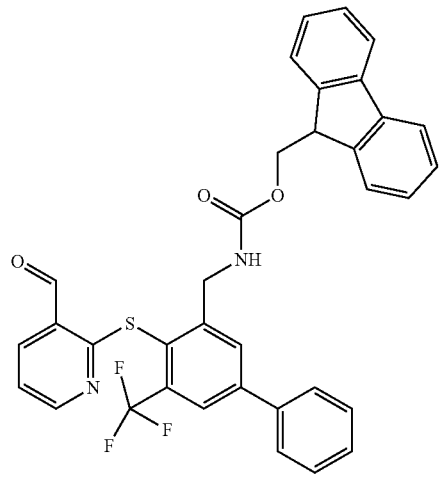 [SMILES: O=Cc1cccnc1Sc1c(CNC(=O)OCC2c3ccccc3-c3ccccc32)cc(-c2ccccc2)cc1C(F)(F)F]

To a stirred solution of 2-mercapto nicotinic acid (3.2 g, 20.3 mmol) in DMF (50 mL) was added NaH (60%, 1.47 g, 36.9 mmol) and reaction mass was stirred at 25° C. for 30 min. Then 5-bromo-2-fluoro-3-trifluoromethyl-benzaldehyde (5.0 gm, 18.5 mmol) was added and reaction mixture was stirred at 80° C. for 1 h. Then K$_2$CO$_3$ (7.6 g, 55.3 mmol) was added followed by addition of MeI (3.4 mL, 55.3 mmmol) and reaction mass was stirred at 25° C. for 2 h. Reaction mass was quenched with water and extracted with ethyl acetate. The separated organic layer was washed with brine, dried over anhydrous sodium sulfate and evaporated under reduced pressure. The crude material obtained was purified by normal silica column using 0-30% ethyl acetate in hexane to get methyl 2-{[4-bromo-2-formyl-6-(trifluoromethyl)phenyl]sulfanyl}pyridine-3-carboxylate (5 g, 64%) as a yellow solid.

To a stirred solution of methyl 2-{[4-bromo-2-formyl-6-(trifluoromethyl)phenyl]sulfanyl}pyridine-3-carboxylate (4.5 g, 10.7 mmol) in THF (100 mL) were added 2-methylpropane-2-sulfinamide (2.6 g, 21.4 mmol), Ti(OEt)$_4$ (6.7 mL, 32 μmmol) and reaction mass was heated to 70° C. for 1 h. The reaction mass was quenched with saturated sodium chloride solution, solid obtained was filtered through celite pad, washed with ethyl acetate. The separated organic layer was dried over anhydrous sodium sulfate and concentrated under reduced pressure to afford methyl 2-({4-bromo-2-[(1E)-[(2-methylpropane-2-sulfinyl)imino]methyl]-6-(trifluoromethyl)phenyl}sulfanyl) pyridine-3-carboxylate (5.5 g, crude) which was directly used for next step without further purification. LC-MS: 523.0 [M+H]$^+$ To a stirred solution of methyl 2-({4-bromo-2-[(1E)-[(2-methylpropane-2-sulfinyl)imino]methyl]-6-(trifluoromethyl)phenyl}sulfanyl)pyridine-3-carboxylate (5.5 g, 10.5 mmol) in THF (100 mL) was added LAH (2M in THF, 10.5 mL, 21 mmol) at 0° C. and reaction mass was stirred at 0° C. for 1 h. Reaction mixture was quenched with saturated sodium sulfate solution and extracted with ethyl acetate. The separated organic layer was washed with water, brine, dried over anhydrous sodium sulfate and evaporated under reduced pressure to get N-[(5-bromo-2-{[3-(hydroxymethyl)pyridin-2-yl]sulfanyl}-3-(trifluoromethyl)phenyl)methyl]-2-methylpropane-2-sulfinamide (5.0 g, crude) which was directly used for next step without further purification. LC-MS: 496.7 [M+H]+

To a stirred solution of N-[(5-bromo-2-{[3-(hydroxymethyl)pyridin-2-yl]sulfanyl}-3-(trifluoromethyl)phenyl)methyl]-2-methylpropane-2-sulfinamide (3.6 g, 7.2 mmol) in DCM (50 mL) were added imidazole (1.5 g, 21.7 mmol) and TBDMSCl (1.6 gm, 10.9 mmol) at 0° C. and stirred at 25° C. for 2h. Reaction mass was quenched with aq NaHCO₃ solution and extracted with ethyl acetate. The separated organic layer was washed with water, brine solution, dried over sodium sulfate and evaporated under reduced pressure. The crude thus obtained was purified by combiflash column chromatography using 20% ethyl acetate in hexane to get N-({5-bromo-2-[(3-{[(tert-butyldimethylsilyl)oxy]methyl}pyridin-2-yl)sulfanyl]-3-(trifluoromethyl)phenyl}methyl)-2-methylpropane-2-sulfinamide (3.1 g, 70%, 3 steps) as off white solid. LC-MS: 611.1 [M+H]+

To a stirred solution of compound N-({5-bromo-2-[(3-{[(tert-butyldimethylsilyl)oxy]methyl}pyridin-2-yl)sulfanyl]-3-(trifluoromethyl)phenyl}methyl)-2-methylpropane-2-sulfinamide (250 mg, 0.4 mmol) in toluene (8 mL) were added phenyl boronic acid (140.5 mg, 0.7 mmol), Na₂CO₃ (129.9 mg, 1.2 mmol), water (2.0 ml) and degassed for 10 min in argon atmosphere. Then to it was added Pd(PPh₃)₄ (47.23 mg, 0.04 mmol) and again degassed for 5 min. The reaction mass was heated to 100° C. for 12 h. Reaction mixture was then cooled to 25° C., filtered through celite pad and washed with EtOAc. The separated organic layer was washed with brine, dried over sodium sulfate and concentrated under vacuum to get the crude material which was purified by combiflash column chromatography using 0-25% ethyl acetate in hexane to get N-({2-[(3-{[(tert-butyldimethylsilyl)oxy]methyl}pyridin-2-yl)sulfanyl]-5-phenyl-3-(trifluoromethyl)phenyl}methyl)-2-methylpropane-2-sulfinamide (200 mg, 80%) as colourless sticky liquid. LC-MS: 609.0 [M+H]+

To a stirred solution of N-({2-[(3-{[(tert-butyldimethylsilyl)oxy]methyl}pyridin-2-yl)sulfanyl]-5-phenyl-3-(trifluoromethyl)phenyl}methyl)-2-methylpropane-2-sulfinamide (2.2 g, 3.6 mmol) in MeOH (20 mL), was added 4M HCl in dioxane (10 mL) at 0° C. and reaction mixture was stirred at 25° C. for 1 h. Reaction mass was evaporated under reduced pressure to get (2-{[2-(aminomethyl)-4-phenyl-6-(trifluoromethyl)phenyl]sulfanyl}pyridin-3-yl)methanol HCl salt (1.2 g, crude) which was directly used for next step. LC-MS: 390.7 [M+H]+

To a stirred suspension of (2-{[2-(aminomethyl)-4-phenyl-6-(trifluoromethyl)phenyl]sulfanyl}pyridin-3-yl)methanol HCl salt (1.2 g, 3.1 mmol) in 5% NaHCO₃ (30 mL) was added Fmoc-OSU (1.13 g, 3.35 mmol) in dioxan (30 mL) at 25° C. and reaction mass was stirred at the same temperature for 3h. Then reaction mass was diluted with water and extracted with ethyl acetate. The separated organic layer was washed with brine, dried over sodium sulfate and evaporated under reduced pressure. The crude material obtained was purified by column chromatography (10%-30% ethylacetate-hexane) to get 9H-fluoren-9-ylmethyl N-[(2-{3-(hydroxymethyl)pyridin-2-yl]sulfanyl}-5-phenyl-3-(trifluoromethyl)phenyl)methyl] carbamate (1.5 g, 79%, 2 steps) as white solid.

To a stirred solution of 9H-fluoren-9-ylmethyl N-[(2-{[3-(hydroxymethyl)pyridin-2-yl]sulfanyl}-5-phenyl-3-(trifluoromethyl)phenyl)methyl]carbamate (1.5 g, 2.45 mmol) in DCM:THF (1:1, 50 mL) was added MnO₂ (3.15 g, 36.7 mmol) and reaction mass was stirred at 25° C. for 4 h. The reaction mass was filtered through celite pad and filtrate was evaporated under reduced pressure. The crude material obtained was purified by combiflash chromatography (10%-30% ethylacetate-hexane) to get 9H-fluoren-9-ylmethyl N-({2-[(3-formylpyridin-2-yl)sulfanyl]-5-phenyl-3-(trifluoromethyl)phenyl} methyl)carbamate (1.0 g, 66%) as white solid with 95.56% purity. LC-MS: 611.2 [M+H]+

1H NMR (400 MHz, DMSO-d6): δ 3.98-4.08 (1H, m), 4.21 (1H, d, J=5.9 Hz), 4.27 (3H, d, J=6.6 Hz), 7.24 (2H, t, J=6.3 Hz), 7.36-7.40 (3H, m), 7.51 (4H, dq, J=13.3, 6.8 Hz), 7.67 (2H, d, J=7.1 Hz), 7.78 (3H, d, J=7.4 Hz), 7.87 (2H, d, J=7.5 Hz), 7.89-7.97 (1H, m), 8.00 (2H, d, J=17.9 Hz), 8.37-8.47 (2H, m), 10.20 (1H, s)

Intermediate 21

9H-fluoren-9-ylmethyl N-({2-[(3-formylpyridin-2-yl)sulfanyl]-3,5-bis(trifluoromethyl)phenyl}methyl)carbamate To a stirred solution of 1-fluoro-2,4-bis(trifluoromethyl)benzene (3 g, 12.9 mmol), TMEDA (2.3 mL, 15.5 mmol) in THF (30 mL) was added nBuLi (2.2M in THF, 6.4 mL, 14.2 mmol) at −78 deg C. and reaction mass was stirred at −78° C. for 1 h. Then 1-formylpiperidine (2.2 mL, 19.4 mmol) was added to the reaction mass at −78° C. and it was stirred at −78° C. for 1 h and then at 25° C. for 1 h. Reaction mass was quenched with saturated ammonium chloride solution and extracted with pentane. The separated organic layer was washed with brine solution, dried over anhydrous sodium sulfate and evaporated under reduced pressure to get 2-fluoro-3,5-bis(trifluoromethyl) benzaldehyde (2.2 g).

To a stirred solution of 2-mercapto nicotinic acid (3.9 g, 25.4 mmol) in DMF (50 mL) was added NaH (60%, 1.8 g, 46.1 mmol) and reaction mass was stirred at 25° C. for 30 min. Then 2-fluoro-3,5-bis(trifluoromethyl)benzaldehyde (6 g, 23.1 mmol) was added and reaction mixture was stirred at 70° C. for 4h. Then K₂CO₃ (9.6 g, 69.2 mmol) was added followed by addition of MeI (4.3 mL, 69.2 mmmol) and reaction mass was stirred at 25° C. for 16h. Reaction mass was quenched with water and extracted with ethyl acetate. The separated organic layer was washed with brine solution, dried over anhydrous sodium sulfate and evaporated under reduced pressure. The crude thus obtained was purified by normal silica column using 0-8% ethyl acetate in hexane to get methyl 2-{[2-formyl-4,6-bis(trifluoromethyl)phenyl] sulfanyl}pyridine-3-carboxylate (1.4 g, 11%, 2 steps) as a yellow solid. LC-MS: 409.5

To a stirred solution of methyl 2-{[2-formyl-4,6-bis(trifluoromethyl)phenyl]sulfanyl}pyridine-3-carboxylate (1.4 g, 3.4 mmol) in THF (10 mL) were added 2-methylpropane-2-sulfinamide (415 mg, 3.4 mol), Ti(OEt)$_4$ (3.6 mL, 17.1 mmol) and reaction mass was heated to 70° C. for 1 h. The reaction mass was quenched with saturated sodium chloride solution. The solid obtained was filtered through celite pad and washed with ethyl acetate. The separated organic layer was dried over anhydrous sodium sulfate and concentrated under reduced pressure to afford ethyl 2-({2-[(1E)-[(2-methylpropane-2-sulfinyl)imino]methyl]-4,6-bis(trifluoromethyl)phenyl}sulfanyl) pyridine-3-carboxylate (1.6 g, crude) which was directly used for next step without further purification. LC-MS: 527.1 [M+H]$^+$ To a stirred solution of ethyl 2-({2-[(1E)-[(2-methylpropane-2-sulfinyl)imino]methyl]-4,6-bis(trifluoromethyl) phenyl}sulfanyl) pyridine-3-carboxylate (1.5 g, 2.8 mmol) in THF (15 mL) was added LAH (2M in THF, 2.13 mL, 4.3 mmol) at 0° C. and reaction mass was stirred at 0° C. for 2h. Reaction mixture was quenched with saturated sodium sulfate solution and extracted with ethyl acetate. The separated organic layer was washed with water, brine solution, dried over anhydrous sodium sulfate and evaporated under reduced pressure. The crude thus obtained was purified by normal silica column using 5-60% ethyl acetate in hexane to get N-[(2-{[3-(hydroxymethyl)pyridin-2-yl]sulfanyl}-3,5-bis(trifluoromethyl)phenyl)methyl]-2-methylpropane-2-sulfinamide (800 mg, 48%, 2 steps) as off-white solid. LC-MS: 486.7 [M+H]$^+$ To a stirred solution of N-[(2-{[3-(hydroxymethyl)pyridin-2-yl]sulfanyl}-3,5-bis(trifluoromethyl)phenyl)methyl]-2-methylpropane-2-sulfinamide (800 mg, 1.6 mmol) in MeOH (8 mL), was added 4M HCl in dioxan (4 mL) at 0° C. and reaction mixture was stirred at 25° C. for 1 h. Reaction mass was evaporated under reduced pressure to get (2-{[2-(aminomethyl)-4,6-bis(trifluoromethyl)phenyl] sulfanyl}pyridin-3-yl)methanol HCl salt (650 mg, crude) which was directly used for next step. LC-MS: 382.8 [M+H]$^+$ To a stirred suspension of (2-{[2-(aminomethyl)-4,6-bis (trifluoromethyl)phenyl]sulfanyl}pyridin-3-yl)methanol HCl salt (650 mg, 1.6 mmol) in 5% NaHCO$_3$ (100 mL) was added Fmoc-OSU (523 mg, 1.6 mmol) in acetonitrile (20 mL) at 25° C. and reaction mass was stirred at the same temperature for 2h. Then reaction mass was diluted with water and extracted with ethyl acetate. The separated organic layer was washed with brine, dried over sodium sulfate and evaporated under reduced pressure to get 9H-fluoren-9-ylmethyl N-[(2-{[3-(hydroxymethyl)pyridin-2-yl]sulfanyl}-3,5-bis(trifluoromethyl)phenyl)methyl]carbamate (950 mg) as off white solid. LC-MS: 605.2 [M+H]$^+$ To a stirred solution of 9H-fluoren-9-ylmethyl N-[(2-{[3-(hydroxymethyl)pyridin-2-yl]sulfanyl}-3,5-bis(trifluoromethyl)phenyl)methyl]carbamate (950 mg, 1.6 mmol) in DCM/THF (1:1, 20 mL) was added MnO$_2$ (2.7 g, 31.46 mmol) and reaction mass was stirred at 25° C. for 2 h. The reaction mass was filtered through celite pad. The filtrate was evaporated under reduced pressure. The crude material obtained was purified by normal silica column using 5-20% ethyl acetate in hexane to get 9H-fluoren-9-ylmethyl N-({2-[(3-formylpyridin-2-yl)sulfanyl]-3,5-bis(trifluoromethyl) phenyl} methyl) carbamate (600 mg) as off white solid with 95% LCMS purity. LC-MS: 602.9 [M+H]$^+$ 1H NMR (400 MHz, DMSO-d6): δ 4.22 (1H, d, J=6.8 Hz), 4.29 (4H, d, J=6.8 Hz), 7.31 (2H, t, J=7.4 Hz), 7.41 (3H, t, J=6.0 Hz), 7.67 (2H, d, J=7.5 Hz), 7.89 (2H, d, J=7.4 Hz), 7.94 (1H, s), 8.01 (1H, s), 8.12 (1H, s), 8.41 (2H, d, J=7.2 Hz), 10.18 (1H, s).

Intermediate 22

(9H-Fluoren-9-yl)methyl 3-chloro-2-((2-formylpyridin-3-yl)thio)-5-(trifluoromethyl)benzylcarbamate

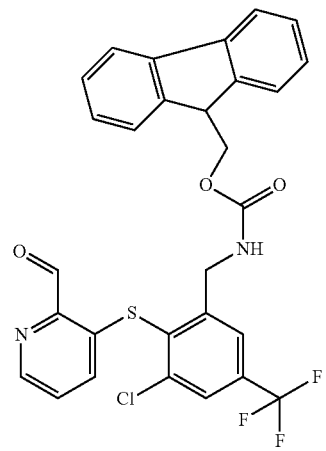 [SMILES: O=Cc1ncccc1Sc1c(Cl)cc(C(F)(F)F)cc1CNC(=O)OCC1c2ccccc2-c2ccccc21]

This material was prepared in analogy to Intermediate 63 starting from 3-chloro-2-fluoro-5-(trifluoromethyl)benzaldehyde and 3-mercaptopicolinic acid. The title compound was obtained as brown solid (183 mg). MS ESI (m/z): 569.1 [(M+H)$^+$]

Intermediate 23

9H-fluoren-9-ylmethyl N-[[3-chloro-2-[(3-formyl-2-pyridyl)sulfanyl]-4-phenyl-phenyl]methyl]carbamate

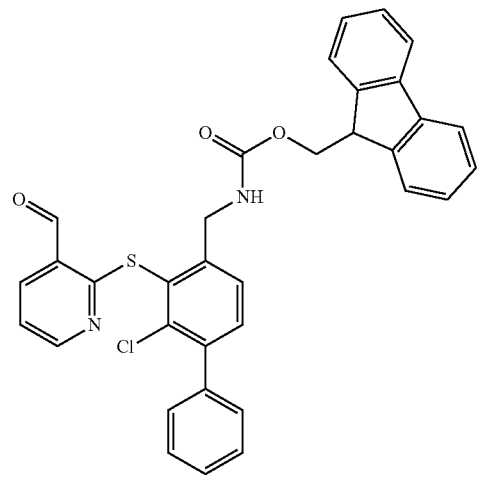 [SMILES: O=Cc1cccnc1Sc1c(CNC(=O)OCC2c3ccccc3-c3ccccc32)ccc(-c2ccccc2)c1Cl]

To a stirred solution of 1-brmo-2-chloro-3-fluoro benzene (1.0 g, 4.79 mmol) in toluene (20 mL) were added phenyl boronic acid (875 mg, 7.18 mmol), Na2CO3 (1.52 g, 14.35 mmol), water (5 mL) and degassed for 10 min in argon atmosphere. Then to it was added Pd(PPh3)4 (553 mg, 0.48 mmol) and again degassed for 5 min. The reaction was heated to 100° C. for 16 h. The reaction mixture was then cooled to 25° C., filtered through celite and washed with ethyl acetate. The separated organic layer was washed with brine solution, dried over sodium sulfate and concentrated under reduced pressure to get the crude product which was purified by combiflash column chromatography using hexane to get 2-chloro-1-fluoro-3-phenylbenzene (920 mg, 93%) as yellow, sticky liquid.

To the stirred solution of 2-chloro-1-fluoro-3-phenylbenzene (4.0 g, 19.42 mmol) in THF (25 ml) was added LDA (2M in THF, 14.4 mL) at −78° C. and reaction mass was stirred at the same condition for 1 h. Then to the reaction mixture was added DMF (5 mL) at −78° C. and stirred at room temperature for 2h. The reaction was quenched with water and extracted with ethyl acetate. The separated organic layer was washed with brine solution, dried over sodium sulfate and evaporated under reduced pressure to get the crude product which was purified by silica column chromatography using 0-10% ethyl acetate in hexane to get 3-chloro-2-fluoro-4-phenylbenzaldehyde as light yellow solid (2.5 g, 54%).

To a stirred solution of 2-mercapto nicotinic acid (3.6 g, 23.2 mmol) in DMF (30 mL) was added NaH (60%, 1.11 g, 46.4 mmol) and the reaction was stirred at 25° C. for 30 min. Then 3-chloro-2-fluoro-4-phenylbenzaldehyde (5.971 g, 25.519 mmol) was added and the reaction mixture was stirred at 90° C. for 6h. Then K2CO3 (9.62 g, 69.6 mmol) was added followed by addition of methyliodide (4.33 ml, 69.597 mmol) and the reaction was stirred at 25° C. for 16h. The Reaction was quenched with water and extracted with ethyl acetate. The separated organic layer was washed with brine solution, dried over anhydrous sodium sulfate and evaporated under reduced pressure. The crude product was purified by normal silica column using 0-20% ethyl acetate in hexane to get methyl 2-[(2-chloro-6-formyl-3-phenylphenyl)sulfanyl]pyridine-3-carboxylate (4.5 g, 50%) as a sticky solid.

LC-MS: m/z=383.9 (M+H)$^+$ for monoisotopic mass 383.04

To a stirred solution of methyl 2-[(2-chloro-6-formyl-3-phenylphenyl)sulfanyl]pyridine-3-carboxylate (4.5 g, 11.75 mmol) in THF (40 mL) were added 2-methylpropane-2-sulfinamide (1.42 g, 11.75 mmol), Ti(OEt)4 (12.317 ml, 58.747 mmol) and the reaction was heated to 70° C. for 45 min. The reaction was quenched with saturated sodium chloride solution, the obtained solid was filtered through celite, washed with ethyl acetate. The separated organic layer was dried over anhydrous sodium sulfate and concentrated under reduced pressure to afford methyl 2-({2-chloro-6-[(1Z)-[(2-methylpropane-2-sulfinyl)imino]methyl]-3-phenylphenyl}sulfanyl)pyridine-3-carboxylate (4.8 g, crude) which was directly used for next step without further purification.

LC-MS: m/z=486.8 (M+H)$^+$ for monoisotopic mass 486.08

To a stirred solution of methyl 2-({2-chloro-6-[(1Z)-[(2-methylpropane-2-sulfinyl)imino]methyl]-3-phenylphenyl}sulfanyl)pyridine-3-carboxylate (4.8 g, 9.88 mmol) in THF (40 mL) was added LAH (2M in THF, 7.4 mL, 14.81 mmol) at 0° C. and the reaction was stirred at 0° C. for 1 h. The reaction mixture was quenched with saturated sodium sulfate solution and extracted with ethyl acetate. The separated organic layer was washed with water, brine solution, dried over anhydrous sodium sulfate and evaporated under reduced pressure. The crude obtained product was purified by normal silica column using 50-90% ethyl acetate in hexane to get N-[(3-chloro-2-{[3-(hydroxymethyl)pyridin-2-yl]sulfanyl}-4-phenylphenyl)methyl]-2-methylpropane-2-sulfinamide (4.0 g, 74% 2 steps) as off-white solid.

LC-MS: m/z=460.8 (M+H)$^+$ for monoisotopic mass 460.10

To a stirred solution of N-[(3-chloro-2-{[3-(hydroxymethyl)pyridin-2-yl]sulfanyl}-4-phenylphenyl)methyl]-2-methylpropane-2-sulfinamide (4.0 g, 8.7 mmol) in MeOH (40 mL), was added 4M HCl in dioxane (20 mL) at 0° C. and the reaction mixture was stirred at 25° C. for 3h. The solvent was evaporated under reduced pressure to yield (2-{[6-(aminomethyl)-2-chloro-3-phenylphenyl]sulfanyl}pyridin-3-yl)methanol HCl salt (3.5 g, crude) which was directly used for next step.

LC-MS: m/z=356.9 (M+H)$^+$ for monoisotopic mass 356.08

To a stirred suspension of (2-{[6-(aminomethyl)-2-chloro-3-phenylphenyl]sulfanyl}pyridin-3-yl)methanol HCl salt (3.5 g, 9.831 mmol) in 5% NaHCO$_3$ (25 mL) was added Fmoc OSU (3.32 g, 9.83 mmol) in CH3CN (25 mL) at 25° C. and the reaction was stirred at the same temperature for 16h. Then the reaction was diluted with water and extracted with ethyl acetate. The separated organic layer was washed with brine solution, dried over sodium sulfate and evaporated under reduced pressure to get 9H-fluoren-9-ylmethyl N-[(3-chloro-2-{[3-(hydroxymethyl)pyridin-2-yl]sulfanyl}-4-phenylphenyl)methyl]carbamate (3.7 g, crude) which was directly used for next step.

LC-MS: m/z=579.1 (M+H)$^+$ for monoisotopic mass 578.14

To a stirred solution of 9H-fluoren-9-ylmethyl N-[(3-chloro-2-{[3-(hydroxymethyl)pyridin-2-yl]sulfanyl}-4-phenylphenyl)methyl]carbamate (3.7 g, 6.40 mmol) in DCM/THF (1:1, 60 mL) was added MnO2 (5.57 g, 64.01 mmol) and the reaction was stirred at 25° C. for 1 h. The reaction was filtered through a pad of celite; the filtrate was evaporated under reduced pressure. The crude product was purified by normal silica column using 10-30% ethyl acetate in hexane to get 9H-fluoren-9-ylmethyl N-({3-chloro-2-[(3-formylpyridin-2-yl)sulfanyl]-4-phenylphenyl}methyl)carbamate (3.5 g, 70%) as a off white solid.

LC-MS: m/z=577.0 (M+H)$^+$ for monoisotopic mass 576.13

1H NMR (400 MHz, DMSO-d$_6$) δ 10.20 (s, 1H), 8.47 (d, 1H), 8.36 (d, 1H), 7.89 (d, 2H), 7.69 (d, 2H), 7.51-7.31 (m, 12H), 4.33-4.29 (m, 4H), 4.22 (m, 1H)

Intermediate 24

9H-fluoren-9-ylmethyl N-[[2-(2-formylphenyl)sulfanyl-5-phenyl-3-(trifluoromethyl)phenyl]methyl]carbamate

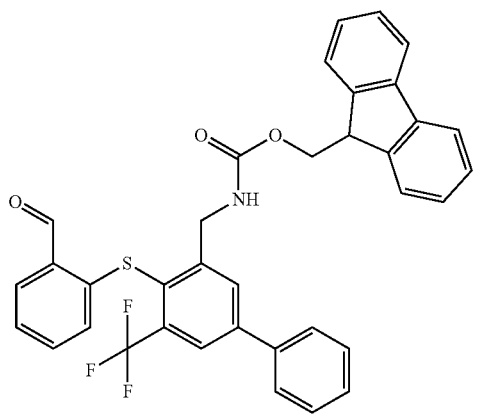 [SMILES: O=Cc1ccccc1Sc1c(CNC(=O)OCC2c3ccccc3-c3ccccc32)cc(-c2ccccc2)cc1C(F)(F)F]

To a stirred solution of 5-bromo-2-fluoro-3-trifluoromethylbenzaldehyde (4.63 g, 21.4 mmol) and methyl 2-sulfanylbenzoate (3.0 g, 17.9 mmol) in DMF (30 mL) was added K2CO3 (4.93 g, 35.7 mmol) and the reaction was stirred at 25° C. for 1 h. Reaction mixture was diluted with ethyl acetate and washed with water. The separated organic layer was washed with sat. NaCl solution, dried over anhydrous sodium sulfate and evaporated under reduced pressure. The obtained crude product was purified by combiflash column chromatography using 10% EA/Hexane to get methyl 2-{[4-bromo-2-formyl-6-(trifluoromethyl)phenyl]sulfanyl}benzoate (6 g, 80%) as off white solid.

To a stirred solution of methyl 2-{[4-bromo-2-formyl-6-(trifluoromethyl) phenyl] sulfanyl}benzoate (0.5 g, 1.19 mmol) in THF (5 mL) were added 2-methylpropane-2-sulfinamide (288.6 mg, 2.38 mol), Ti(OEt)4 (0.75 mL, 3.57 mmol) and reaction mass was heated to 70° C. for 2h. The reaction was quenched with saturated sodium chloride solution, the obtained solid was filtered through celite, washed with ethyl acetate. The separated organic layer was dried over anhydrous sodium sulfate and concentrated under reduced pressure to afford ethyl 2-({4-bromo-2-[(1Z)-[(2-methylpropane-2-sulfinyl)imino]methyl]-6-(trifluoromethyl) phenyl}sulfanyl)benzoate (0.6 g, crude) which was directly used for next step without further purification.

LC-MS: mixture of methyl- and ethyl-ester, ratio ca. 3:1; m/z=522.2 (M+H)+ for methyl ester (MW 520.99 for monoisotopic mass) and 536.2 (M+H)+ for ethyl ester (MW 535.01 for monoisotopic mass)

To a stirred solution of ethyl 2-({4-bromo-2-[(1Z)-[(2-methylpropane-2-sulfinyl)imino]methyl]-6-(trifluoromethyl) phenyl}sulfanyl)benzoate (0.9 g, 1.724 mmol) in THF (20 mL) was added LiAlH4(2M in THF, 1.7 mL, 3.44 mmol) at 0° C. and the reaction was stirred at 0° C. for 1 h. Reaction mixture was quenched with saturated sodium sulfate solution and extracted with ethyl acetate. The separated organic layer was washed with water, brine solution, dried over anhydrous sodium sulfate and evaporated under reduced pressure to get N-[[5-bromo-2-[2-(hydroxymethyl)phenyl]sulfanyl-3-(trifluoromethyl)phenyl]methyl]-2-methyl-propane-2-sulfinamide (0.8 g, crude) which was directly used for next step without further purification.

LC-MS: m/z=495.9 (M+H)+ for monoisotopic mass 495.01

To a stirred solution of N-[[5-bromo-2-[2-(hydroxymethyl)phenyl]sulfanyl-3-(trifluoromethyl)phenyl]methyl]-2-methyl-propane-2-sulfinamide (1 g, 2 mmol) in DCM (30 mL) were added imidazole (0.41 g, 6 mmol) and TBDMSCl (0.455 g, 3. mmol) at 0° C. and stirred at 25° C. for 1 h. Reaction mass was quenched with aq NaHCO3 solution and extracted with ethyl acetate. The separated organic layer was washed with water, brine solution, dried over sodium sulfate and evaporated under reduced pressure. The crude product was purified by normal silica gel column chromatography using 10% ethyl acetate in hexane to get N-({5-bromo-2-[(2-{[(tert-butyldimethylsilyl)oxy]methyl}phenyl)sulfanyl]-3-(trifluoromethyl) phenyl}methyl)-2-methylpropane-2-sulfinamide (0.95 g, 77%) as colorless sticky liquid.

LC-MS: m/z=611.8 (M+H)+ for monoisotopic mass 609.10

To a stirred solution of N-({5-bromo-2-[(2-{[(tert-butyldimethylsilyl)oxy]methyl}phenyl)sulfanyl]-3-(trifluoromethyl) phenyl}methyl)-2-methylpropane-2-sulfinamide (5.5 g, 9.55 mmol) in toluene (88 mL) were added phenyl boronic acid (1.75 g, 14.3 mmol), Na2CO3 (3.03 g, 28.6 mmol),water (22 mL), the mixture was degassed for 10 min under argon atmosphere. Then to it was added Pd(PPh3)4 (1.1 g, 0.955 mmol) and again degassed for 5 min. The reaction mass was heated to 110° C. for 16h. Reaction mixture was then cooled to 25° C., filtered through celite, washed with ethyl acetate. The separated organic layer was washed with brine solution, dried over sodium sulfate and concentrated under reduced pressure. Crude product was purified by normal silica gel column chromatography, eluted with 50% ethylacetate in hexane to get N-({2-[(2-{[(tert-butyldimethylsilyl) oxy] methyl} phenyl) sulfanyl]-5-phenyl-3-(trifluoromethyl) phenyl} methyl)-2-methylpropane-2-sulfinamide (4.7 g, 81%) as yellow solid.

To a stirred solution of N-({2-[(2-{[(tert-butyldimethylsilyl)oxy]methyl}phenyl)sulfanyl]-5-phenyl-3-(trifluoromethyl) phenyl} methyl)-2-methylpropane-2-sulfinamide (1.5 g, 2.47 mmol) in MeOH (20 mL), was added 4M HCl in dioxane (6 mL) at 0° C. and reaction mixture was stirred at 25° C. for 2h. The solvent was evaporated under reduced pressure to get (2-{[2-(aminomethyl)-4-phenyl-6-(trifluoromethyl) phenyl] sulfanyl} phenyl) methanol hydrochloride (1.1 g, crude) which was directly used for next step.

LC-MS: m/z=390.2 (M+H)+ for monoisotopic mass 389.11

To a stirred suspension of (2-{[2-(aminomethyl)-4-phenyl-6-(trifluoromethyl) phenyl]sulfanyl}phenyl) methanol hydrochloride (3.5 g, 9 mmol) in 5% NaHCO3(250 mL) was added Fmoc N-hydroxysuccinimide ester (3.03 g, 9 mmol) in CH3CN (70 mL) at 25° C. and reaction was stirred at the same temperature for 16h. Then the reaction was diluted with water and extracted with ethyl acetate. The separated organic layer was washed with brine solution, dried over sodium sulfate and evaporated under reduced pressure to yield 9H-fluoren-9-ylmethyl N-[[2-[2-(hydroxymethyl)phenyl]sulfanyl-5-phenyl-3-(trifluoromethyl)phenyl]methyl] carbamate (3.7 g, crude) which was directly used for next step.

LC-MS: m/z=594.3 (M+H−H2O)+ for monoisotopic mass 611.17

To a stirred solution of 9H-fluoren-9-ylmethyl N-[(2-{[2-(hydroxymethyl) phenyl]sulfanyl}-5-phenyl-3-(trifluoromethyl) phenyl) methyl] carbamate (3.5 g, 5.7 mmol) in DCM/THF (1:1, 160 mL) was added MnO2 (7.47 g, 85.9 mmol) and the reaction was stirred at 25° C. for 1 h. The reaction mixture was filtered through celite; filtrate was evaporated under reduced pressure. The crude product was purified by normal silica column using 10% ethyl acetate in hexane to get 9H-fluoren-9-ylmethyl N-({2-[(2-formylphenyl)sulfanyl]-5-phenyl-3-(trifluoromethyl) phenyl}methyl) carbamate (3.2 g, 91%) as off white solid.

LC-MS: m/z=592.4 (M+H−H2O)⁺ for monoisotopic mass 609.16

1H NMR (400 MHz, DMSO-d₆) δ 10.19 (s, 1H), 8.11 (s, 1H), 8.03-7.93 (m, 3H), 7.86 (d, 2H), 7.78 (d, 2H), 7.66 (d, 2H), 7.56-7.43 (m, 4H), 7.38 (t, 3H), 7.23 (t, 2H), 6.50 (d, 1H), 4.33-4.26 (m, 4H), 4.20 (m, 1H)

Intermediate 25

9H-fluoren-9-ylmethyl N-({3-chloro-2-[(3-formylpyridin-2-yl)sulfanyl]-6-phenylphenyl} methyl) carbamate

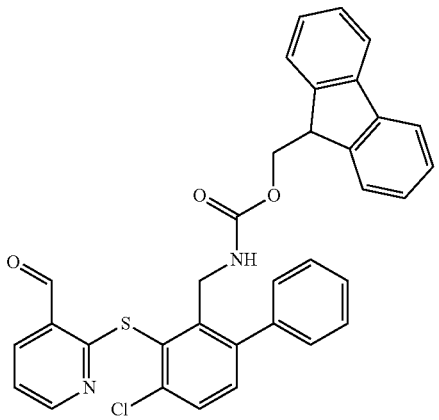 [SMILES: O=Cc1cccnc1Sc1c(Cl)ccc(-c2ccccc2)c1CNC(=O)OCC1c2ccccc2-c2ccccc21]

To a stirred solution of N-[(6-bromo-3-chloro-2-{[3-(hydroxymethyl)pyridin-2-yl]sulfanyl}phenyl)methyl]-2-methylpropane-2-sulfinamide (8.9 g, 19.2 mmol) in DCM (50 mL) were added imidazole (3.9 g, 57.6 mmol) and TBDMSCl (4.33 g, 28.8 mmol) at 0° C. and stirred at 25° C. for 2h. Reaction mass was quenched with aq NaHCO₃ solution and extracted with ethyl acetate. The separated organic layer was washed with water, brine, dried over sodium sulfate and evaporated under reduced pressure. The crude thus obtained was purified by combiflash column chromatography using 0-20% ethyl acetate in hexane to get N-({6-bromo-2-[(3-{[(tert-butyldimethylsilyl)oxy]methyl}pyridin-2-yl)sulfanyl]-3-chlorophenyl}methyl)-2-methylpropane-2-sulfinamide (9 g) as off white solid. LC-MS: 578.6 [M+H]⁺

To a stirred solution of compound N-({6-bromo-2-[(3-{[(tert-butyldimethylsilyl)oxy]methyl}pyridin-2-yl)sulfanyl]-3-chlorophenyl}methyl)-2-methylpropane-2-sulfinamide (1.5 g, 2.6 mmol) in dioxan (10 mL) were added phenyl boronic acid (411 mg, 3.4 mmol), Na₂CO₃ (825 mg, 7.8 mmol), water (5 mL) and degassed for 10 min in argon atmosphere. Then to it was added Pd(PPh₃)₄(150 mg, 0.13 mmol) and again degassed for 5 min. The reaction mass was heated to 120° C. for 16 h. Reaction mixture was then cooled to 25° C., filtered through celite pad, washed with EtOAc. The separated organic layer was washed with brine solution, dried over sodium sulfate and concentrated under reduced pressure to get N-({2-[(3-{[(tert-butyldimethylsilyl)oxy]methyl}pyridin-2-yl)sulfanyl]-3-chloro-6-phenylphenyl}methyl)-2-methylpropane-2-sulfinamide (1.3 g) as yellow solid. LC-MS: 575.0 [M+H]⁺

To a stirred solution of N N-({2-[(3-{[(tert-butyldimethylsilyl)oxy]methyl}pyridin-2-yl)sulfanyl]-3-chloro-6-phenylphenyl}methyl)-2-methylpropane-2-sulfinamide (1.3 g, 2.26 mmol) in MeOH (20 mL), was added 4M HCl in dioxan (10 mL) at 0° C. and reaction mixture was stirred at 25° C. for 2h. Reaction mass was evaporated under reduced pressure to get (2-{[2-(aminomethyl)-6-chloro-3-phenylphenyl]sulfanyl}pyridin-3-yl)methanol HCl salt (890 mg, crude) which was directly used for next step.

To a stirred suspension of (2-{[2-(aminomethyl)-6-chloro-3-phenylphenyl]sulfanyl}pyridin-3-yl)methanol HCl salt (890 mg, 2.3 mmol) in 5% NaHCO₃ (10 mL) was added Fmoc OSU (762 mg, 2.3 mmol) in acetonitrile (20 mL) at 25° C. and reaction mass was stirred at the same temperature for 2h. Then reaction mass was diluted with water and extracted with ethyl acetate. The separated organic layer was washed with brine solution, dried over sodium sulfate and evaporated under reduced pressure to get 9H-fluoren-9-ylmethyl N-[(3-chloro-2-{[3-(hydroxymethyl)pyridin-2-yl]sulfanyl}-6-phenylphenyl) methyl]carbamate (1.2 g) as off white solid. LC-MS: 578.8 [M+H]⁺

To a stirred solution of 9H-fluoren-9-ylmethyl N-[(3-chloro-2-{[3-(hydroxymethyl)pyridin-2-yl]sulfanyl}-6-phenylphenyl) methyl]carbamate (1.2 g, 2.1 mmol) in DCM/THF (1:1, 40 mL) was added MnO₂ (3.6 g, 41.4 mmol) and reaction mass was stirred at 25° C. for 2 h. The reaction mass was filtered through celite, filtrate was evaporated under reduced pressure to get crude mass that was purified by normal silica column using 10-40% ethyl acetate in hexane to get 9H-fluoren-9-ylmethyl N-({3-chloro-2-[(3-formylpyridin-2-yl)sulfanyl]-6-phenylphenyl} methyl) carbamate (710 mg) as off white solid with 98% purity. LC-MS: 576.8 [M+H]⁺

1H NMR (400 MHz, DMSO-d6): δ 4.08-4.15 (5H, m), 7.34 (4H, q, J=7.3, 6.2 Hz), 7.42 (7H, d, J=8.1 Hz), 7.58 (1H, s), 7.64-7.71 (3H, m), 7.89 (2H, d, J=7.5 Hz), 8.33 (1H, d, J=7.7 Hz), 8.48 (1H, d, J=3.2 Hz), 10.21 (1H, s).

Intermediate 26

9H-fluoren-9-ylmethyl N-({3-chloro-2-[(3-formylpyridin-2-yl)sulfanyl]-5-phenyl phenyl}methyl) carbamate

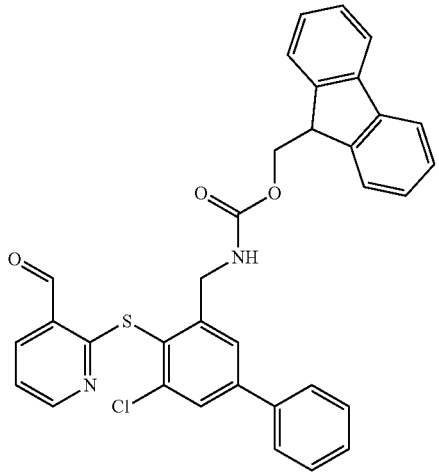 [SMILES: O=Cc1cccnc1Sc1c(Cl)cc(-c2ccccc2)cc1CNC(=O)OCC1c2ccccc2-c2ccccc21]

To a stirred solution of compound N-({5-bromo-2-[(3-{[(tert-butyldimethylsilyl)oxy]methyl}pyridin-2-yl)sulfanyl]-3-chlorophenyl} methyl)-2-methylpropane-2-sulfinamide (1.2 g, 1.9 mmol) in toluene (10 mL) were added phenyl boronic acid (311 mg, 2.5 mmol), Na₂CO₃ (625 mg, 5.9 mmol),water (5 mL) and degassed for 15 min in argon atmosphere. Then to it was added Pd(PPh₃)₄(114 mg, 0.1 mmol) and again degassed for 5 min. The reaction mass was heated to 110° C. for 16 h. Reaction mixture was then cooled to 25° C., filtered through celite pad, washed with ethyl acetate. The separated organic layer was washed with brine solution, dried over sodium sulfate and concentrated under reduced pressure to get N-({2-[(3-{[(tert-butyldimethylsilyl)oxy] methyl}pyridin-2-yl)sulfanyl]-3-chloro-5-phenylphenyl}methyl)-2-methylpropane-2-sulfinamide (1.2 g) as colourless sticky liquid. LC-MS: 575.3 [M+H]⁺

To a stirred solution of N-({2-[(3-{[(tert-butyldimethylsilyl)oxy]methyl}pyridin-2-yl)sulfanyl]-3-chloro-5-phenylphenyl}methyl)-2-methylpropane-2-sulfinamide (1.2 g, 2.1 mmol) in MeOH (10 mL), was added 4M HCl in dioxan (5 mL) at 0° C. and reaction mixture was stirred at 25° C. for 2h. Reaction mass was evaporated under reduced pressure to get (2-{[2-(aminomethyl)-6-chloro-4-phenylphenyl]sulfanyl}pyridin-3-yl)methanol HCl salt (800 mg) which was directly used for next step. LC-MS: 356.9 [M+H]⁺

To a stirred suspension of (2-{[2-(aminomethyl)-6-chloro-4-phenylphenyl]sulfanyl}pyridin-3-yl)methanol HCl salt (800 mg, 2.0 mmol) in 5% NaHCO₃ (20 mL) was added Fmoc-OSU (685 mg, 2.0 mmol) in acetonitrile (40 mL) at 25° C. and reaction mass was stirred at the same temperature for 2h. Then reaction mass was diluted with water and extracted with ethyl acetate. The separated organic layer was washed with brine solution, dried over sodium sulfate and evaporated under reduced pressure to get 9H-fluoren-9-ylmethyl N-[(3-chloro-2-{[3-(hydroxymethyl)pyridin-2-yl]sulfanyl}-5-phenylphenyl)methyl]carbamate (1.1 g) as off white solid. LC-MS: 579.3 [M+H]⁺

To a stirred solution of 9H-fluoren-9-ylmethyl N-[(3-chloro-2-{[3-(hydroxymethyl)pyridin-2-yl]sulfanyl}-5-phenylphenyl)methyl]carbamate (1.1 g, 1.9 mmol) in DCM:THF (1:1, 40 mL) was added MnO₂ (3.3 g, 38 mmol) and reaction mass was stirred at 25° C. for 2 h. The reaction mass was filtered through celite pad and the filtrate was evaporated under reduced pressure. The crude thus obtained was purified by normal silica column using 0-20% ethyl acetate in hexane to get 9H-fluoren-9-ylmethyl N-({3-chloro-2-[(3-formylpyridin-2-yl)sulfanyl]-5-phenylphenyl}methyl) carbamate (800 mg) as off white solid with 96% LCMS purity. LC-MS: 577.0 [M+H]⁺

1H NMR (400 MHz, DMSO-d6): δ 4.16-4.24 (1H, m), 4.27 (2H, d, J=7.0 Hz), 4.36 (2H, d, J=5.6 Hz), 7.25 (2H, t, J=7.5 Hz), 7.36-7.42 (3H, m), 7.49 (3H, dt, J=15.5, 7.1 Hz), 7.70 (5H, dd, J=23.8, 7.0 Hz), 7.83-7.89 (3H, m), 7.92 (1H, t, J=6.1 Hz), 8.38 (1H, d, J=6.1 Hz), 8.45 (1H, d, J=4.6 Hz), 10.22 (1H, s).

Intermediate 27

9H-Fluoren-9-ylmethyl N-{[3-chloro-5-(2-chloropyridin-4-yl)-2-[(3-formylpyridin-2-yl) sulfanyl] phenyl] methyl} carbamate

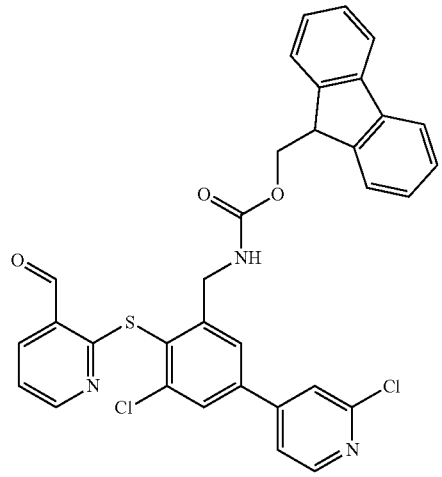 [SMILES: O=Cc1cccnc1Sc1c(Cl)cc(-c2ccnc(Cl)c2)cc1CNC(=O)OCC1c2ccccc2-c2ccccc21]

To a stirred solution of N-({5-bromo-2-[(3-{[(tert-butyldimethylsilyl)oxy]methyl}pyridin-2-yl)sulfanyl]-3-chlorophenyl} methyl)-2-methylpropane-2-sulfinamide (2.5 g, 4.3 mmol) in dioxan (20 mL) were added (2-chloropyridin-4-yl)boronic acid (818 mg, 5.2 mmol), Na₂CO₃ (1.4 g, 13 mmol), water (10 mL) and degassed for 10 min in argon atmosphere. To this was added Pd(PPh₃)₄(501 mg, 0.43 mmol) and again degassed for 5 min. The reaction mass was heated to 120° C. for 16 h. Reaction mixture was cooled to 25° C., filtered through celite pad and washed with EtOAc. The separated organic layer was washed with brine solution, dried over anhydrous sodium sulfate and concentrated under reduced pressure. The crude thus obtained was purified by silica column chromatography (SiO₂; 100-200 mesh; 50-90% EtOAC/Hexanes) to get N-({2-[(3-{[(tert-butyldimethylsilyl)oxy]methyl}pyridin-2-yl)sulfanyl]-3-chloro-5-(2-chloropyridin-4-yl)phenyl}methyl)-2-methylpropane-2-sulfinamide (2.8 g) as off white solid. LC-MS: 609.8 [M+H]⁺

To a stirred solution of N-({2-[(3-{[(tert-butyldimethylsilyl)oxy]methyl}pyridin-2-yl)sulfanyl]-3-chloro-5-(2-chloropyridin-4-yl)phenyl}methyl)-2-methylpropane-2-sulfinamide (2.8 g, 4.6 mmol) in MeOH (30 mL), was added 4M HCl in dioxan (15 mL) at 0° C. and reaction mixture was stirred at 25° C. for 2h. Reaction mass was evaporated under reduced pressure to get (2-{[2-(aminomethyl)-6-chloro-4-(2-chloropyridin-4-yl) phenyl] sulfanyl}pyridin-3-yl) methanol hydrochloride (1.5 g) as off white sticky solid, which was directly used for next step without further purification. LC-MS: 392.2 [M+H]⁺

To a stirred suspension of (2-{[2-(aminomethyl)-6-chloro-4-(2-chloropyridin-4-yl)phenyl]sulfanyl}pyridin-3-yl)methanol hydrochloride (1.5 g, 3.8 mmol) in 5% NaHCO₃ (20 mL) was added Fmoc-OSU (1.3 g, 3.8 mmol) in dioxan (20 mL) at 25° C. and reaction mass was stirred at the same temperature for 16h. Then reaction mass was diluted with water and extracted with EtOAc. The separated organic layer was washed with brine, dried over sulfate and evaporated under reduced pressure to get 9H-fluoren-9-ylmethyl N-{[3-chloro-5-(2-chloropyridin-4-yl)-2-{[3-(hydroxymethyl)pyridin-2-yl]sulfanyl}phenyl]methyl}carbamate (2.7 g) as off white solid; which was used for next step without further purification. LC-MS: 614.3 [M+H]+

To a stirred solution 9H-fluoren-9-ylmethyl N-{[3-chloro-5-(2-chloropyridin-4-yl)-2-{[3-(hydroxymethyl)pyridin-2-yl]sulfanyl}phenyl]methyl}carbamate in DCM:THF (1:1, 40 mL) was added MnO$_2$ (7.66 g, 88.1 mmol) and reaction mass was stirred at 25° C. for 2 h. The reaction mass was filtered through celite pad and the filtrate was evaporated under reduced pressure. The crude thus obtained was purified by column chromatography (SiO$_2$; 100-200 mesh; 40-80% EtOAc/Hexanes) to 9H-fluoren-9-ylmethyl N-{[3-chloro-5-(2-chloropyridin-4-yl)-2-[(3-formylpyridin-2-yl)sulfanyl]phenyl]methyl}carbamate (1.5 g) as off-white solid with 96.46% purity. LC-MS: 612.2 [M+H]+

1H NMR (400 MHz, DMSO-d6): δ 4.19-4.37 (5H, m), 7.27 (2H, t, J=7.36 Hz), 7.36-7.39 (3H, m), 7.67 (2H, d, J=7.2 Hz), 7.81 (3H, m), 7.88 (2H, d, J=7.21 Hz), 7.94 (1H, m), 8.37 (1H, d, J=7.31 Hz), 8.34 (1H, m), 8.54 (1H, d, J=5.12 Hz), 10.21 (1H, s)

Intermediate 28

9H-fluoren-9-ylmethyl N-({5-[3-(benzyloxy)prop-1-yn-1-yl]-3-chloro-2-[(3-formylpyridin-2-yl) sulfanyl]phenyl}methyl)carbamate

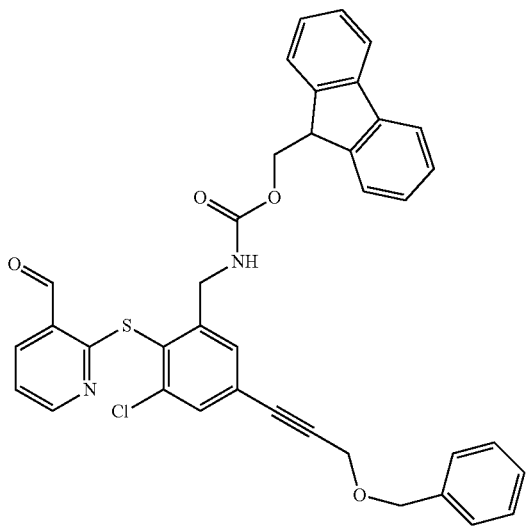 [SMILES: O=Cc1cccnc1Sc1c(Cl)cc(C#CCOCc2ccccc2)cc1CNC(=O)OCC1c2ccccc2-c2ccccc21]

To a stirred and degassed suspension of N-({5-bromo-2-[(3-{[(tert-butyldimethylsilyl) oxy]methyl} pyridin-2-yl)sulfanyl]-3-chlorophenyl} methyl)-2-methylpropane-2-sulfinamide (2 g, 3.46 mmol), [(prop-2-yn-1-yloxy)methyl]benzene (1 mL, 6.9 mmol) in triethylamine (8 mL) were added CuI (13 mg, 0.07 mmol), palladium acetate (8 mg, 0.04 mmol), PPh$_3$ (18 mg, 0.07 mmol) and reaction mass was heated to 80° C. for 6h. Reaction mass was evaporated under reduced pressure and the crude material obtained was purified by normal silica column using 0-30% ethyl acetate in hexane to get N-({5-[3-(benzyloxy)prop-1-yn-1-yl]-2-[(3-{[(tert-butyldimethylsilyl)oxy]methyl}pyridin-2-yl)sulfanyl]-3-chlorophenyl}methyl)-2-methylpropane-2-sulfinamide (1 g, 45%) as colourless sticky liquid. LC-MS: 643.2 [M+H]+

To a stirred solution of N-({5-[3-(benzyloxy)prop-1-yn-1-yl]-2-[(3-{[(tert-butyldimethylsilyl)oxy] methyl}pyridin-2-yl) sulfanyl]-3-chlorophenyl} methyl)-2-methylpropane-2-sulfinamide (1 g, 1.5 mmol) in MeOH (8 mL), was added 4M HCl in dioxan (4 mL) at 0° C. and reaction mixture was stirred at 25° C. for 2h. Reaction mass was evaporated under reduced pressure to get (2-{[2-(aminomethyl)-4-[3-(benzyloxy)prop-1-yn-1-yl]-6-chlorophenyl]sulfanyl}pyridin-3-yl)methanol HCl salt (700 mg) which was directly used for next step. LC-MS: 425.1 [M+H]+

To a stirred suspension of (2-{[2-(aminomethyl)-4-[3-(benzyloxy)prop-1-yn-1-yl]-6-chlorophenyl]sulfanyl}pyridin-3-yl)methanol HCl salt (700 mg, 1.5 mmol) in 5% NaHCO$_3$ (20 mL) was added Fmoc-OSU (511 mg, 1.5 mmol) in dioxan (40 mL) at 25° C. and reaction mass was stirred at the same temperature for 2h. Then the reaction mass was diluted with water and extracted with ethyl acetate. The separated organic layer was washed with brine solution, dried over sodium sulfate and evaporated under reduced pressure to get 9H-fluoren-9-ylmethyl N-({5-[3-(benzyloxy)prop-1-yn-1-yl]-3-chloro-2-{[3-(hydroxymethyl)pyridin-2-yl] sulfanyl} phenyl}methyl) carbamate (850 mg) as off white solid which was used for next step without further purification. LC-MS: 647.0 [M+H]+

To a stirred solution of 9H-fluoren-9-ylmethyl N-({5-[3-(benzyloxy)prop-1-yn-1-yl]-3-chloro-2-{[3-(hydroxymethyl)pyridin-2-yl] sulfanyl} phenyl} methyl) carbamate (850 mg, 1.3 mmol) in DCM:THF (1:1, 40 mL) was added MnO$_2$ (2.28 g, 26.3 mmol) and reaction mass was stirred at 25° C. for 2 h. The reaction mass was filtered through celite pad and the filtrate was evaporated under reduced pressure. The crude material obtained was purified by normal silica column using 10%-50% ethylacetate in hexane to get 9H-fluoren-9-ylmethyl N-({5-[3-(benzyloxy)prop-1-yn-1-yl]-3-chloro-2-[(3-formylpyridin-2-yl) sulfanyl]phenyl}methyl)carbamate (500 mg) as off white solid with 91% purity. LC-MS: 645.3 [M+H]+

1H NMR (400 MHz, DMSO-d6): δ 4.26-4.30 (5H, m), 4.49 (2H, s), 4.62 (2H, s), 7.30-7.42 (11H, m), 7.68 (3H, d, J=7.0 Hz), 7.88 (3H, d, J=7.1 Hz), 8.38 (1H, d, J=7.6 Hz), 8.42 (1H, d, J=4.6 Hz), 10.19 (1H, s).

Intermediate 29

9H-fluoren-9-ylmethyl N-({3-chloro-2-[(3-formylpyridin-2-yl)sulfanyl]-6-(pyridin-4-yl)phenyl} methyl) carbamate

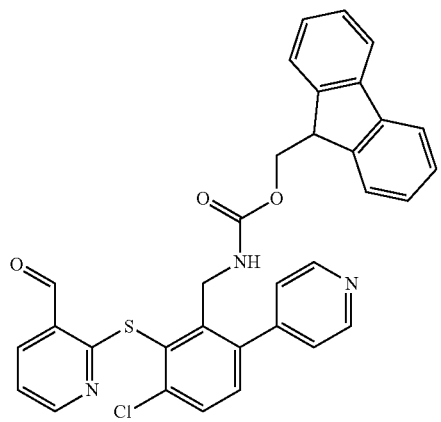 [SMILES: O=Cc1cccnc1Sc1c(Cl)ccc(-c2ccncc2)c1CNC(=O)OCC1c2ccccc2-c2ccccc21]

To a stirred solution of compound N-({6-bromo-2-[(3-{[(tert-butyldimethylsilyl)oxy]methyl}pyridin-2-yl)sulfanyl]-3-chlorophenyl}methyl)-2-methylpropane-2-sulfinamide (4 g, 6.93 mmol) in dioxan (30 mL) were added pyridine-4-boronic acid (1.1 g, 9.01 mmol), Na$_2$CO$_3$ (2.2 g, 20.79 mmol), water (15 mL) and degassed for 10 min in argon atmosphere. Then to it was added Pd(PPh$_3$)$_4$(0.8 g, 0.69 mmol) and again degassed for 5 min. The reaction mass was heated to 120° C. for 16 h. Reaction mixture was then cooled to 25° C., filtered through celite pad, washed with EtOAc. The separated organic layer was washed with brine solution, dried over sodium sulfate and concentrated under vacuum to get the crude which was purified by normal silica column using 5-80% ethyl acetate in hexane to get N-({2-[(3-{[(tert-butyldimethylsilyl)oxy]methyl}pyridin-2-yl)sulfanyl]-3-chloro-6-(pyridin-4-yl)phenyl}methyl)-2-methylpropane-2-sulfinamide (2.2 g, 55%) as off white solid. LC-MS: 575.8 [M+H]$^+$ To a stirred solution of N-({2-[(3-{[(tert-butyldimethylsilyl)oxy]methyl}pyridin-2-yl)sulfanyl]-3-chloro-6-(pyridin-4-yl)phenyl}methyl)-2-methylpropane-2-sulfinamide (2.2 g, 3.82 mmol) in MeOH (20 mL), was added 4M HCl in dioxan (10 mL) at 0° C. and reaction mixture was stirred at 25° C. for 2h. Reaction mass was evaporated under reduced pressure to get (2-{[2-(aminomethyl)-6-chloro-3-(pyridin-4-yl)phenyl]sulfanyl}pyridin-3-yl)methanol HCl salt (1.3 g) which was directly used for next step. LC-MS: 358.2 [M+H]$^+$ To a stirred suspension of (2-{[2-(aminomethyl)-6-chloro-3-(pyridin-4-yl)phenyl]sulfanyl}pyridin-3-yl)methanol HCl salt (1.3 g, 3.64 mmol) in 5% NaHCO$_3$ (20 mL) was added Fmoc-OSU (1.22 g, 3.64 mmol) in dioxan (20 mL) at 25° C. and reaction mass was stirred at the same temperature for 16h. Then reaction mass was diluted with water and extracted with ethyl acetate. The separated organic layer was washed with brine solution, dried over sodium sulfate and evaporated under reduced pressure to get 9H-fluoren-9-ylmethyl N-[(3-chloro-2-{[3-(hydroxymethyl)pyridin-2-yl]sulfanyl}-6-(pyridin-4-yl) phenyl)methyl]carbamate (2 g) which was directly used for next step. LC-MS: 580.2 [M+H]$^+$ To a stirred solution of 9H-fluoren-9-ylmethyl N-[(3-chloro-2-{[3-(hydroxymethyl)pyridin-2-yl]sulfanyl}-6-(pyridin-4-yl) phenyl)methyl]carbamate (2.0 g, 3.45 mmol) in DCM:THF (1:1, 40 mL) was added MnO$_2$ (6.0 g, 69 mmol) and reaction mass was stirred at 25° C. for 2 h. The reaction mass was filtered through celite pad; filtrate was evaporated under reduced pressure. The crude thus obtained was purified by normal silica column using 40-80% ethyl acetate in hexane to get 9H-fluoren-9-ylmethyl N-({3-chloro-2-[(3-formylpyridin-2-yl)sulfanyl]-6-(pyridin-4-yl) phenyl} methyl) carbamate (650 mg) as off white solid with 90% LCMS purity. LC-MS: 577.9 [M+H]$^+$ 1H NMR (400 MHz, DMSO-d6): δ 4.10-4.14 (5H, m), 7.33-7.46 (8H, m), 7.58 (1H, s), 7.65 (2H, d, J=7.3 Hz), 7.73 (1H, d, J=8.3 Hz), 7.89 (2H, d, J=7.4 Hz), 8.35 (1H, d, J=7.7 Hz), 8.48 (1H, d, J=3.1 Hz), 8.59 (2H, d, J=5.5 Hz), 10.21 (1H, s).

Intermediate 30

9H-fluoren-9-ylmethyl N-({3-chloro-2-[(3-formylpyridin-2-yl)sulfanyl]-5-(4-sulfamoylphenyl)phenyl}methyl)carbamate

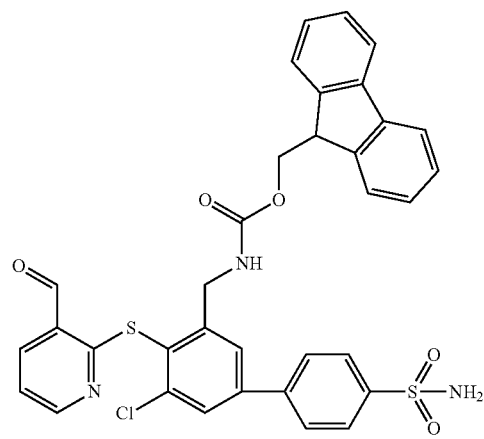 [SMILES: NS(=O)(=O)c1ccc(-c2cc(Cl)c(Sc3ncccc3C=O)c(CNC(=O)OCC3c4ccccc4-c4ccccc43)c2)cc1]

To a stirred solution of compound N-({5-bromo-2-[(3-{[(tert-butyldimethylsilyl)oxy]methyl}pyridin-2-yl)sulfanyl]-3-chlorophenyl} methyl)-2-methylpropane-2-sulfinamide (3 g, 5.19 mmol) in dioxan (30 mL) were added (4-sulfamoylphenyl)boronic acid (1.35 g, 6.7 mmol), Na$_2$CO$_3$ (1.65 g, 15.5 mmol), water (15 mL) and degassed for 10 min in argon atmosphere. Then to it was added Pd(PPh$_3$)$_4$(300 mg, 0.26 mmol) and again degassed for 5 min. The reaction mass was heated to 120° C. for 16 h. Reaction mixture was then cooled to 25° C., filtered through celite pad and washed with EtOAc. The separated organic layer was washed with brine solution, dried over sodium sulfate and concentrated under reduced pressure to get 4-{4-[(3-{[(tert-butyldimethylsilyl)oxy]methyl}pyridin-2-yl)sulfanyl]-3-chloro-5-{[(2-methylpropane-2-sulfinyl)amino] methyl}phenyl}benzene-1-sulfonamide (3 g) as colourless sticky liquid. LC-MS: 654.0 [M+H]$^+$ To a stirred solution of 4-{4-[(3-{[(tert-butyldimethylsilyl)oxy]methyl}pyridin-2-yl)sulfanyl]-3-chloro-5-{[(2-methylpropane-2-sulfinyl)amino] methyl}phenyl}benzene-1-sulfonamide (3 g, 4.58 mmol) in MeOH (12 mL), was added 4M HCl in dioxan (6 mL) at 0° C. and reaction mixture was stirred at 25° C. for 2h. Reaction mass was evaporated under reduced pressure to get 4-[3-(aminomethyl)-5-chloro-4-{[3-(hydroxymethyl)pyridin-2-yl]sulfanyl}phenyl]benzene-1-sulfonamide hydrochloride (2.2 g) which was directly used for next step. LC-MS: 435.7 [M+H]$^+$ To a stirred suspension of 4-[3-(aminomethyl)-5-chloro-4-{[3-(hydroxymethyl)pyridin-2-yl]sulfanyl}phenyl]benzene-1-sulfonamide hydrochloride (2 g, 4.23 mmol) in 5% NaHCO$_3$ (20 mL) was added Fmoc-OSU (1.43 g, 4.23 mmol) in dioxan (40 mL) at 25° C. and reaction mass was stirred at the same temperature for 2h. Then reaction mass was diluted with water and extracted with 10% methanol in dichloromethane. The separated organic layer was washed with brine solution, dried over sodium sulfate and evaporated under reduced pressure to get 9H-fluoren-9-ylmethyl N-[(3-chloro-2-{[3-(hydroxymethyl)pyridin-2-yl]sulfanyl}-5-(4-sulfamoylphenyl) phenyl)methyl]carbamate (2.5 g) as off white solid. LC-MS: 657.9 [M+H]$^+$ To a stirred solution of 9H-fluoren-9-ylmethyl N-[(3-chloro-2-{[3-(hydroxymethyl)pyridin-2-yl]sulfanyl}-5-(4-sulfamoylphenyl) phenyl)methyl]carbamate (2.5 g, 3.8 mmol) in DCM/THF (1:1, 60 mL) was added MnO$_2$ (6.6 g, 75.9 mmol) and reaction mass was stirred at 25° C. for 2 h. The reaction mass was filtered through celite pad and filtrate was evaporated under reduced pressure. The crude material obtained was purified by silica column (SiO$_2$; 100-200 mesh; 10-50% ethyl acetate in hexane) to give 9H-fluoren-9-ylmethyl N-({3-chloro-2-[(3-formylpyridin-2-yl)sulfanyl]-5-(4-sulfamoylphenyl)phenyl}methyl)carbamate (520 mg) as off white solid with 95% LCMS purity. LC-MS: 654.2 [M+H]$^+$ 1H NMR (400 MHz, DMSO-d6): δ 4.21 (1H, d, J=6.5 Hz), 4.28 (2H, d, J=6.8 Hz), 4.37 (2H, d, J=5.7 Hz), 7.25 (2H, t, J=7.4 Hz), 7.39 (4H, q, J=7.4 Hz), 7.48 (2H, s), 7.67 (2H, d, J=7.5 Hz), 7.72 (1H, s), 7.89 (4H, dd, J=12.8, 7.0 Hz), 7.93-8.02 (1H, m), 8.38 (1H, d, J=6.3 Hz), 8.45 (1H, d, J=3.4 Hz), 10.22 (1H, s).

Intermediate 31

3-[(12S,15S,18S)-15-(4-tert-Butoxycarbonylamino-butyl)-18-(3-tert-butoxycarbonylamino-propyl)-6-bromo-4-chloro-13-methyl-11,14,17-trioxo-2-thia-10,13,16,19-tetraaza-tricyclo[19.4.0.0*3,8*]pentacosa-1(25),3(8),4,6,21,23-hexaen-12-ylmethyl]-indole-1-carboxylic acid tert-butyl ester

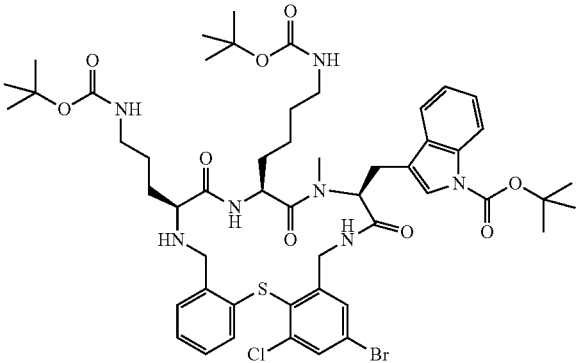 [SMILES: CN1C(=O)[C@H](CCCCNC(=O)OC(C)(C)C)NC(=O)[C@H](CCCNC(=O)OC(C)(C)C)NCc2ccccc2Sc2c(Cl)cc(Br)cc2CNC(=O)[C@@H]1Cc1cn(C(=O)OC(C)(C)C)c2ccccc12]

Intermediate 135 was prepared according to the General Procedure for Peptide Macrocycle Synthesis, but BOC-protecting groups were kept intact (no TFA deprotection) using the following starting materials:
Amino acids:
1. Fmoc-L-Trp(BOC)-OH,
2. Fmoc-L-Lys(BOC)-OH,
3. Fmoc-L-Orn(BOC)-OH.
Tether: Intermediate 89
MS (M+H)$^+$: expected 1082.37; observed 1082.5

Intermediate 32

3-[(12S,15S,18S)-15-(4-tert-Butoxycarbonylamino-butyl)-18-(3-tert-butoxycarbonylamino-propyl)-5-bromo-4-chloro-13-methyl-11,14,17-trioxo-2-thia-10,13,16,19-tetraaza-tricyclo[19.4.0.0*3,8*]pentacosa-1(25),3(8),4,6,21,23-hexaen-12-ylmethyl]-indole-1-carboxylic acid tert-butyl ester

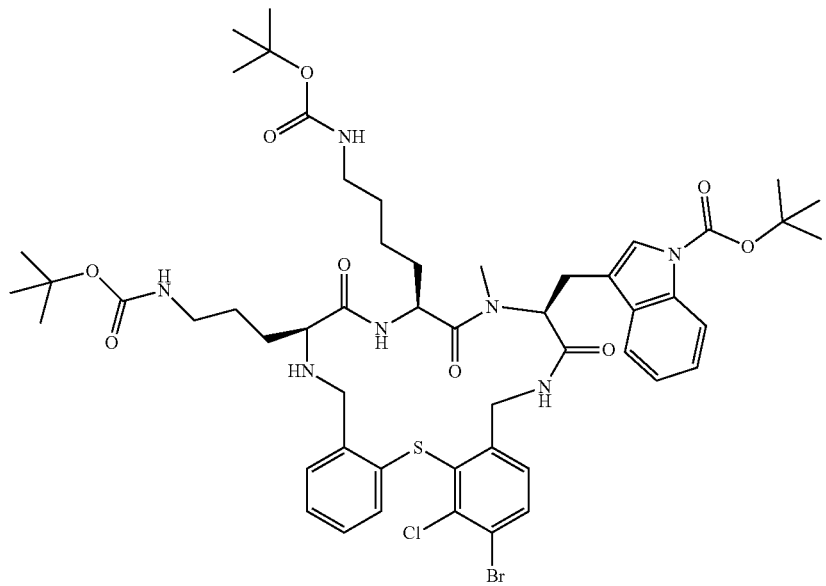 [SMILES: CN1C(=O)[C@H](CCCCNC(=O)OC(C)(C)C)NC(=O)[C@H](CCCNC(=O)OC(C)(C)C)NCc2ccccc2Sc2c(ccc(Br)c2Cl)CNC(=O)[C@@H]1Cc1cn(C(=O)OC(C)(C)C)c2ccccc12]

Intermediate 136 was prepared according to the General Procedure for Peptide Macrocycle Synthesis, but BOC-protecting groups were kept intact (no TFA deprotection) using the following starting materials:

Amino acids:
1. Fmoc-L-Trp(BOC)-OH,
2. Fmoc-L-Lys(BOC)-OH,
3. Fmoc-L-Orn(BOC)-OH.

Tether: Intermediate 100

MS (M+H)$^+$: expected 1082.37; observed 1082.5

Intermediate 33

3-[(12S,15S,18S)-15-(4-tert-Butoxycarbonylamino-butyl)-18-(3-tert-butoxycarbonylamino-propyl)-23-bromo-4-chloro-13-methyl-11,14,17-trioxo-2-thia-10,13,16,19-tetraaza-tricyclo[19.4.0.0*3,8*]pentacosa-1(25),3(8),4,6,21,23-hexaen-2-ylmethyl]-indole-1-carboxylic acid tert-butyl ester

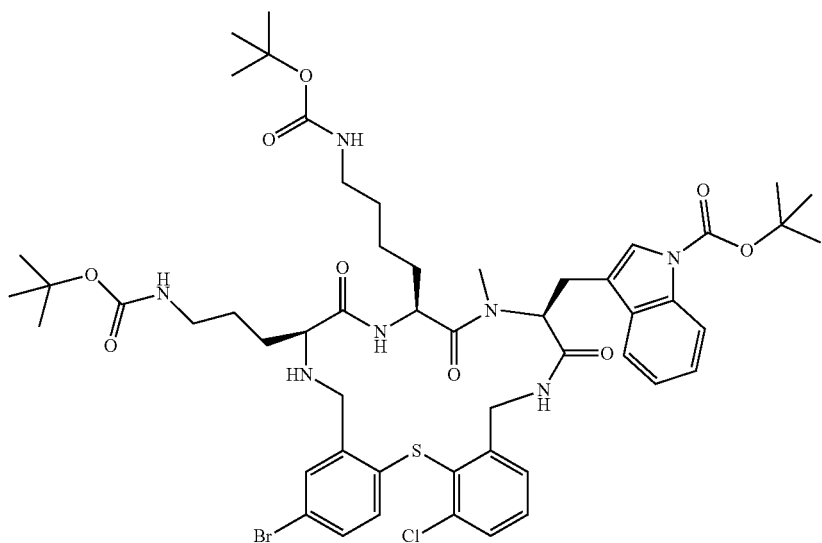 [SMILES: CN1C(=O)[C@H](CCCCNC(=O)OC(C)(C)C)NC(=O)[C@H](CCCNC(=O)OC(C)(C)C)NCc2cc(Br)ccc2Sc2c(Cl)cccc2CNC(=O)[C@@H]1Cc1cn(C(=O)OC(C)(C)C)c2ccccc12]

Intermediate 137 was prepared according to the General Procedure for Peptide Macrocycle Synthesis, but BOC-protecting groups were kept intact (no TFA deprotection) using the following starting materials:

Amino acids:
1. Fmoc-L-Trp(BOC)-OH,
2. Fmoc-L-Lys(BOC)-OH,
3. Fmoc-L-Orn(BOC)-OH.

Tether: Intermediate 115
MS (M+H)$^+$: expected 1082.37; observed 1082.5

Intermediate 34

3-[(12S,15S,18S)-15-(4-tert-Butoxycarbonylamino-butyl)-18-(3-tert-butoxycarbonylamino-propyl)-24-bromo-4-chloro-13-methyl-11,14,17-trioxo-2-thia-10,13,16,19-tetraaza-tricyclo[19.4.0.0*3,8*]pentacosa-1(25),3(8),4,6,21,23-hexaen-2-ylmethyl]-indole-1-carboxylic acid tert-butyl ester

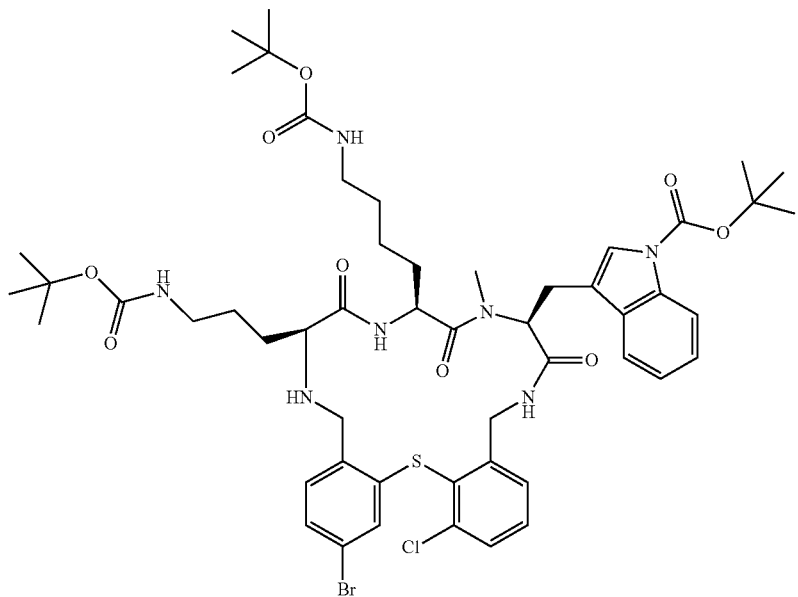 [SMILES: CN1C(=O)[C@H](CCCCNC(=O)OC(C)(C)C)NC(=O)[C@H](CCCNC(=O)OC(C)(C)C)NCc2ccc(Br)cc2Sc2c(Cl)cccc2CNC(=O)[C@@H]1Cc1cn(C(=O)OC(C)(C)C)c2ccccc12]

Intermediate 138 was prepared according to the General Procedure for Peptide Macrocycle Synthesis, but BOC-protecting groups were kept intact (no TFA deprotection) using the following starting materials:
Amino acids:
1. Fmoc-L-Trp(BOC)-OH,
2. Fmoc-L-Lys(BOC)-OH,
3. Fmoc-L-Orn(BOC)-OH.
Tether: Intermediate 120
MS (M+H)⁺: expected 1082.37; observed 1082.6

Intermediate 35

1H-indole-1-carboxylic acid, 3-[[(7S,10S,13S)-17-bromo-20-chloro-10-[4-[[(1,1-dimethylethoxy)carbonyl]amino]butyl]-7-[3-[[(1,1-dimethylethoxy)carbonyl]amino]propyl]-5,6,7,8,9,10,12,13,14,15,66-dodecahydro-12-methyl-8,11,14-trioxopyrido[2,3-b][1,5,8,11,14]benzothiatetraazacycloheptadecin-13-yl]methyl]-,1,1-dimethylethyl ester

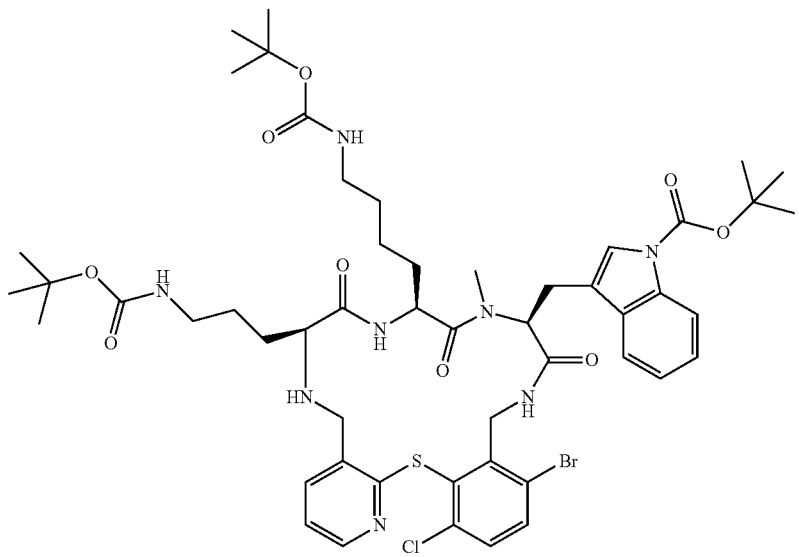 [SMILES: CN1C(=O)[C@H](CCCCNC(=O)OC(C)(C)C)NC(=O)[C@H](CCCNC(=O)OC(C)(C)C)NCc2cccnc2Sc2c(Cl)ccc(Br)c2CNC(=O)[C@@H]1Cc1cn(C(=O)OC(C)(C)C)c2ccccc12]

Intermediate 140 was prepared according to the General Procedure for Peptide Macrocycle Synthesis, but BOC-protecting groups were kept intact (no TFA deprotection) using the following starting materials:
Amino acids:
1. Fmoc-L-Trp(BOC)-OH,
2. Fmoc-L-Lys(BOC)-OH,
3. Fmoc-L-Orn(BOC)-OH.
Tether: Intermediate 59
MS (M+H)⁺: expected 1083.3; observed 1084.5

The title compound was prepared according to the following scheme:

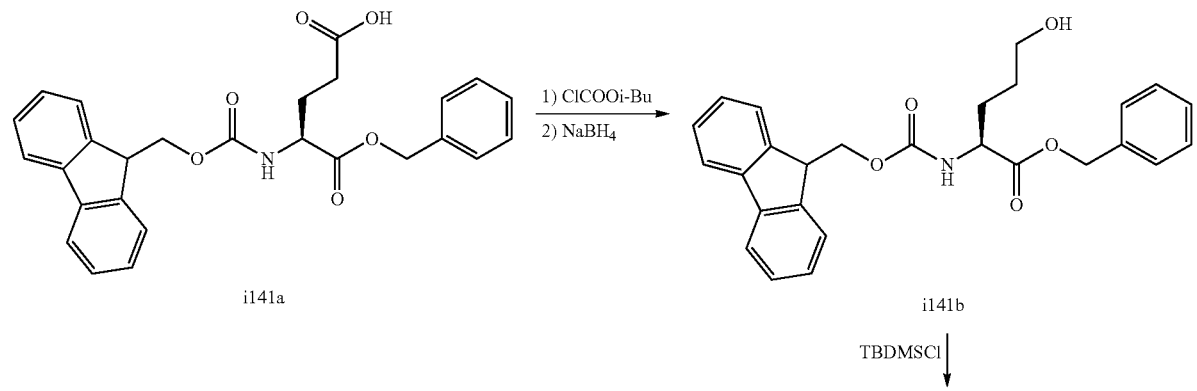

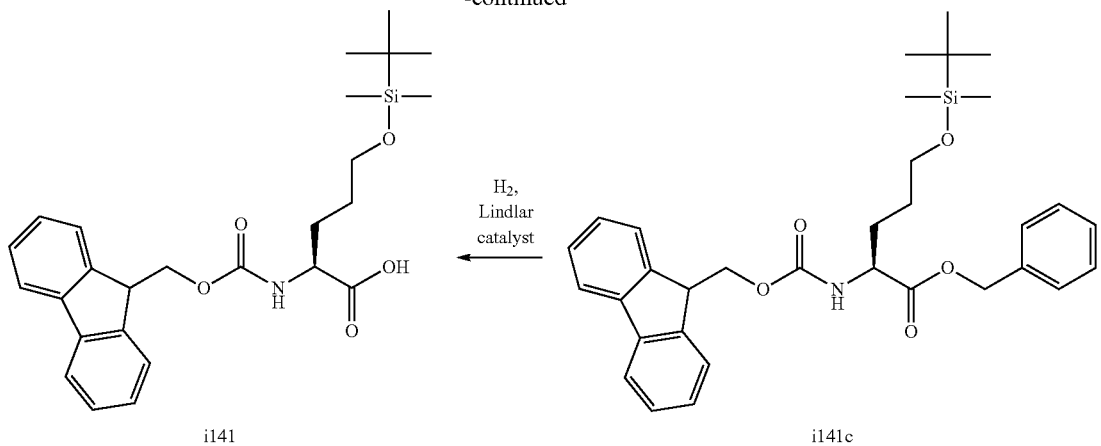

Step 1: preparation of benzyl (2S)-2-(9H-fluoren-9-ylmethoxycarbonylamino)-5-hydroxy-pentanoate (compound i141b)

To a mixture of (4S)-5-benzyloxy-4-(9H-fluoren-9-ylmethoxycarbonylamino)-5-oxo-pentanoic acid (i141a, 1.84 g, 4 mmol) and 4-methylmorpholine (607 mg, 0.66 mL, 6 mmol) in dry THF (20 ml) at −10° C. was added dropwise isobutyl carbonochloridate (660 mg, 4.8 mmol). The resulting reaction mixture was stirred at −10° C. for 2 hours, then poured into a mixture of NaBH$_4$ (460 mg, 12 mmol) and ice (10 g) and stirred for further 30 minutes. The reaction mixture was diluted with ice-cooled water, and extracted with EA twice. The combined organic phase was dried and concentrated. The residue was purified by silica gel column to give compound i141b (1.34 g). MS (M+H$^+$): 446.

Step 2: preparation of benzyl (2S)-5-[tert-butyl(dimethyl)silyl]oxy-2-(9H-fluoren-9-ylmethoxycarbonylamino)pentanoate (compound i141c)

To a mixture of benzyl (2S)-2-(9H-fluoren-9-ylmethoxycarbonylamino)-5-hydroxy-pentanoate (compound i141b, 1.34 g, 3 mmol) and imidazole (610 mg, 9 mmol) in DCM (15 ml) was added a solution of tert-butylchlorodimethylsilane (540 mg, 3.6 mmol) in DCM (5 ml). The reaction mixture was stirred at room temperature for 3 hours, and then concentrated. The residue was dissolved in PE/EA=5/1, and washed with water. The organic phase was separated and concentrated. The residue was purified by silica gel column to give compound i141c (1.3 g). MS (M+H$^+$): 560.

Step 3: preparation of (2S)-5-[tert-butyl(dimethyl)silyl]oxy-2-(9H-fluoren-9-ylmethoxycarbonylamino)pentanoic acid (Intermediate i141)

To a solution of benzyl (2S)-5-[tert-butyl(dimethyl)silyl]oxy-2-(9H-fluoren-9-ylmethoxycarbonylamino)pentanoate (compound i141c, 1.3 g, 2.3 mmol) in EtOH/i-PrOH/H$_2$O=89/5/6 (15 ml) was added Lindlar catalyst (Aldrich, 390 mg). The reaction mixture was heated at 40° C. under a H$_2$ balloon for 5 hours. After cooled to room temperature, the reaction mixture was filtered. The filtrate was treated with aq. HCl solution (1 N) to pH=6 and concentrated. The residue was taken up in EA, washed with brine, dried, and concentrated to give crude compound i141 (1.0 g). MS (M+H$^+$): 470.

General Procedure for Peptide Macrocycle Synthesis

1. Solid Phase Peptide Synthesis

The tripeptide sequence was synthesized manually via state-of-the-art solid phase synthesis protocols (Fmoc-chemistry) as referenced by e.g.: Kates and Albericio, Eds., "Solid Phase Synthesis: A practical guide", Marcel Decker, New York, Basel, 2000.

As a solid support 2-Chlor-tritylchloride resin (1.6 meq/g, 100-200 mesh) was used. This resin was loaded with 0.6 eq of amino acid and 8 eq DIPEA in dry DCM overnight at RT. After extensive washing with DMF and DCM, the Fmoc-group was cleaved off with a mixture of 50% Piperidine in DCM/DMF (1:1) in DMF (freshly prepared) for 30 min at RT. After washing with DMF, DCM and MeOH the resin was dried under vacuum at RT overnight. The resin loading was determined via weight increase.

The second amino acid was coupled with 4 eq Mukaiyama-Reagent as coupling reagent, 6 eq DIPEA in DMF/DCM (1:1) overnight at RT. The resin was extensively washed with DMF and DCM and the coupling rate was controlled by a test-cleavage.

The Fmoc-group from the dipeptide was cleaved with a mixture of 50% Piperidine (25%)/DCM (25%) in DMF for maximally 5 min followed by washings with DMF and DCM. The cleavage rates were again controlled by test-cleavage.

The third amino acid was coupled using an excess of 4 eq using 4 eq HATU as coupling reagent and 6 eq DIPEA. Complete couplings were accomplished at RT for 2-4 hours with the coupling rate again controlled by a test-cleavage.

The Fmoc-group from the tripeptide was cleaved with a mixture of 20% Piperidine in DMF for 2×15-20 min at RT followed by washings with DMF and DCM (test-cleavage).

On-Bead N-Methylation:

In case the N-methylated amino acids were not commercially available they were alkylated on the solid phase as follows:

Resin was swollen in THF (ca. 10 ml/g resin). 12 eq DIPEA were added and the reaction mixture was shaken at RT for 15 min. 3 eq 2-nitrobenzene-1-1sulfonylchloride were added and the resin was shaken at RT overnight. Resin was then drained, washed with DCM and DMF. The coupling rate was controlled via a test-cleavage.

For the second step the Resin was suspended in DMF, 12 eq MTBD (7-methyl-1,5,7-triazabicyclo[4.4.0]dec-5-ene) were added and the reaction mixture was shaken at RT for 10 min. Then 3 eq Methyl-4-nitrobenzenesulfonate was added and the slurry was shaked at RT. After 30 min. The resin was drained and washed with DMF and DCM. The coupling rate was controlled via a test-cleavage.

For removal of the 2-nitrobenzene-1-1 sulfonamide protecting group, the resin was suspended in DMF, 12 eq DBU were added, the slurry shaken for 5 min, then 12 eq mercaptoethanol was added and the reaction mixture was shaken at RT for 1 h. The resin was drained and washed with DMF and DCM. The deprotection rate was controlled via a test-cleavage.

2. Reductive Amination:

Resin with tripeptide was washed with DCM, the corresponding Intermediate dissolved in a mixture of NMP/TMOF/AcOH (49.7/49.7/0.6) and the solution was added to the resin. The mixture was shaken at RT for 30 min up to 3h, then 10 eq NaCNBH$_3$ were added and the reaction mixture was shaken at RT overnight. Finally, the resin was washed with DMF, DCM, MeOH/DCM (1:1) and DMF.

The Fmoc-group on the tether was cleaved with a mixture of 20% Piperidine in DMF for 2×15-20 min at RT followed by washings with DMF and DCM (test-cleavage).

3. Cleavage:

A cleavage-cocktail of 20% HFIP in DCM was added to the resin and the mixture was stirred for 2h at RT. The resin was filtered off and the solution was evaporated to dryness. The residue was dissolved in water/acetonitrile and lyophilized.

4. Cyclisation:

The obtained crude linear compound was cyclized by dissolving the powder in DMF. 1.2 eq HATU and 5 eq DIPEA were added and the reaction mixture stirred at RT. Progress of the reaction was monitored by HPLC. After completion, the solvent was evaporated, the resulting residue taken up in water/acetonitrile (1:1) and lyophilized.

5. Purification:

Peptide macrocycles were purified using reversed phase high-performance liquid chromatography (RP-HPLC) using a Reprospher 100 C18-TDE column (250×20 mm, 5 um particle size) as a stationary phase and water/acetonitrile as eluent (Gradient 40-100% MeCN over 60 min). Fractions were collected and analyzed by LC/MS. Pure product samples were combined and lyophilized. Product identification was obtained via mass spectrometry.

6. Global Deprotection:

Final BOC-deprotection was achieved by 50% TFA (DCM) treatment for 2h at RT. The reaction solution was concentrated down and the residue freeze-dried to yield the deprotected product as TFA salt. All peptides were obtained as white powders with a purity >90%.

General Procedure for Suzuki Coupling of boronic acid derivatives to Peptide Macrocycle Intermediates In a reaction tube to a solution of protected bromide Macrocycle Intermediate (46.1 μmol, Eq: 1) in Dioxane (1.2 ml) was added at 22° C. water (400 μl) followed by sodium carbonate (115 μmol, Eq: 2.5) and the Boronic Acid Derivative (92.3 μmol, Eq: 2). The mixture was degassed by bubbling argon into the reaction mixture for 5 minutes. Then was added tetrakis(triphenylphosphine)palladium (0) (2.31 μmol, Eq: 0.05), the tube was inserted, sealed and the reaction mixture was stirred at 80° C. for 2 h or till complete conversion.

The mixture was evaporated, treated with water (2 ml) and extracted with DCM (2×2 ml). The organic layers were dried, evaporated to dryness, purified by preparative HPLC and lyophlized to give the pure product as a lyophilized solid.

Boc-Deprotection

To a solution of lyophilized solid (15 μmol) in DCM (1.6 ml) was added at 22° C. TFA (0.4 ml) (5.22 mmol=ca. 350 eq) and stirred for 2 h to give complete conversion.

After total 2 h the mixture was evaporated, the residue was dissolved in ACN and H$_2$O (containing 0.1% TFA), allowed to stand for 4 h at 22° C. and dried frozen/lyophilized to give the peptide macrocycle as white lyoph solid.

Example 1

(12S,15S,18S)-15-(4-Amino-butyl)-18-(3-aminopropyl)-6-chloro-12-(1H-indol-3-ylmethyl)-13-methyl-2-thia-10,13,16,19-tetraaza-tricyclo[19.4.0.0*3,8*]pentacosa-1(21),3,5,7,22,24-hexaene-11,14,17-trione

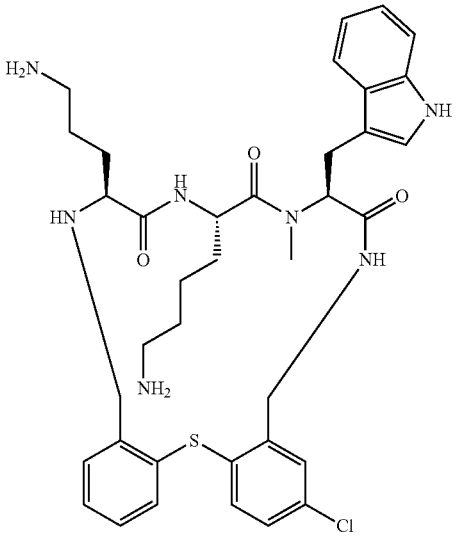 [SMILES: CN1C(=O)[C@H](CCCCN)NC(=O)[C@H](CCCN)NCc2ccccc2Sc2ccc(Cl)cc2CNC(=O)[C@@H]1Cc1c[nH]c2ccccc12]

Example 1 was prepared according to the General Procedure for Peptide Macrocycle Synthesis using the following starting materials:

Amino acids:

1. Fmoc-NMe-L-Trp(BOC)-OH,
2. Fmoc-L-Lys(BOC)-OH,
3. Fmoc-L-Orn(BOC)-OH.

Tether: Intermediate 3

MS (M+H): expected 703.3; observed 704.3

Example 2

(12S,15S,18S)-15-(4-Amino-butyl)-18-(3-amino-propyl)-5-chloro-12-(1H-indol-3-ylmethyl)-13-methyl-2-thia-10,13,16,19-tetraaza-tricyclo[19.4.0.0*3,8*]pentacosa-1(21),3,5,7,22,24-hexaene-11,14,17-trione

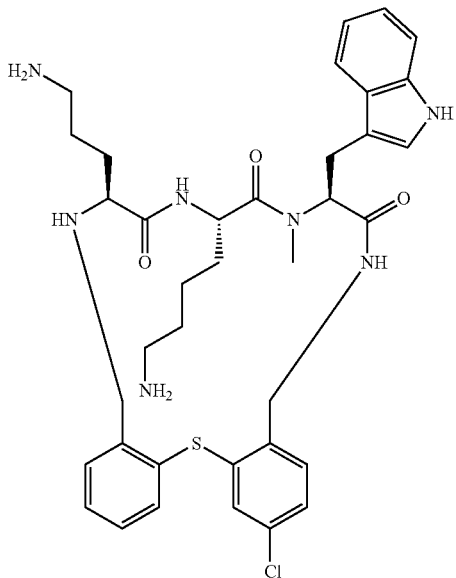 [SMILES: CN1C(=O)[C@H](CCCCN)NC(=O)[C@H](CCCN)NCc2ccccc2Sc2cc(Cl)ccc2CNC(=O)[C@@H]1Cc1c[nH]c2ccccc12]

Example 2 was prepared according to the General Procedure for Peptide Macrocycle Synthesis using the following starting materials:
Amino acids:
1. Fmoc-NMe-L-Trp(BOC)-OH,
2. Fmoc-L-Lys(BOC)-OH,
3. Fmoc-L-Orn(BOC)-OH.
Tether: Intermediate 2
MS (M+H)+: expected 703.3; observed 704.3

Example 3

(12S,15S,18S)-15-(4-Amino-butyl)-18-(3-amino-propyl)-4-chloro-12-(1H-indol-3-ylmethyl)-13-methyl-2-thia-10,13,16,19-tetraaza-tricyclo[19.4.0.0*3,8*]pentacosa-1(21),3,5,7,22,24-hexaene-11,14,17-trione

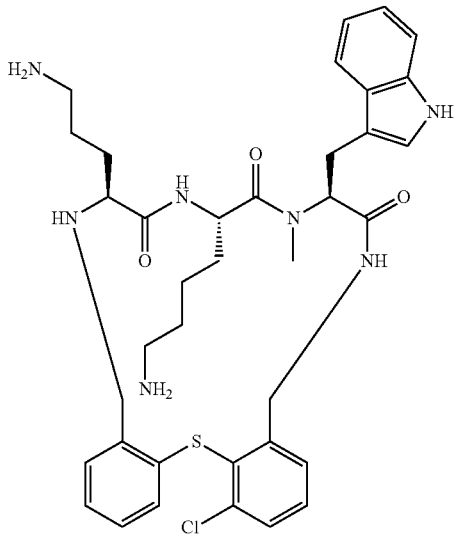 [SMILES: CN1C(=O)[C@H](CCCCN)NC(=O)[C@H](CCCN)NCc2ccccc2Sc2c(Cl)cccc2CNC(=O)[C@@H]1Cc1c[nH]c2ccccc12]

Example 3 was prepared according to the General Procedure for Peptide Macrocycle Synthesis using the following starting materials:
Amino acids:
1. Fmoc-NMe-L-Trp(BOC)-OH,
2. Fmoc-L-Lys(BOC)-OH,
3. Fmoc-L-Orn(BOC)-OH.
Tether: Intermediate 1
MS (M+H)+: expected 703.3; observed 705.2

Example 4

(12S,15S,18S)-15-(4-Amino-butyl)-18-(3-amino-propyl)-12-(1H-indol-3-ylmethyl)-13-methyl-5-trifluoromethyl-2-thia-10,13,16,19-tetraaza-tricyclo[19.4.0.0*3,8*]pentacosa-1(21),3,5,7,22,24-hexaene-11,14,17-trione

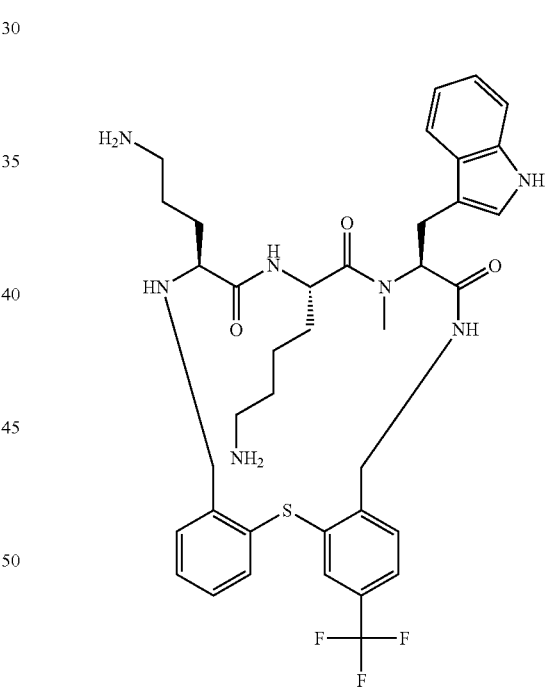

Example 4 was prepared according to the General Procedure for Peptide Macrocycle Synthesis using the following starting materials:
Amino acids:
1. Fmoc-NMe-L-Trp(BOC)-OH,
2. Fmoc-L-Lys(BOC)-OH,
3. Fmoc-L-Orn(BOC)-OH.
Tether: Intermediate 6
MS (M+H)+: expected 737.3; observed 738.4

Example 5

(12S,15S,18S)-15-(4-Amino-butyl)-18-(3-amino-propyl)-12-(6-chloro-1H-indol-3-ylmethyl)-13-methyl-2-thia-10,13,16,19-tetraaza-tricyclo[19.4.0.0*3,8*]pentacosa-1(21),3,5,7,22,24-hexaene-11,14,17-trione

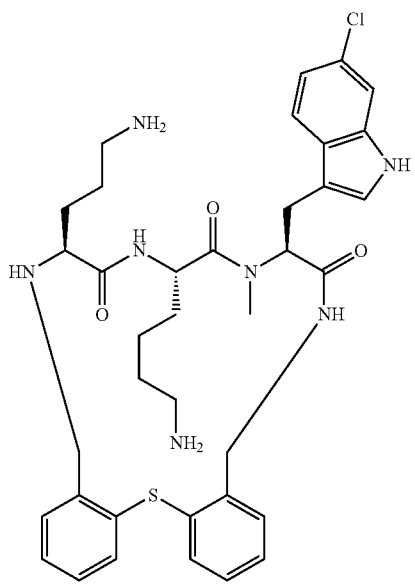 [SMILES: CN1C(=O)[C@H](CCCCN)NC(=O)[C@H](CCCN)NCc2ccccc2Sc2ccccc2CNC(=O)[C@@H]1Cc1c[nH]c2cc(Cl)ccc12]

Example 5 was prepared according to the General Procedure for Peptide Macrocycle Synthesis using the following starting materials:
Amino acids:
1. Fmoc-L-6-Cl-Trp-OH, followed by on-bead N-methylation of the Trp alpha-N,
2. Fmoc-L-Lys(BOC)-OH,
3. Fmoc-L-Orn(BOC)-OH.
Tether: Intermediate 4
MS (M+H)$^+$: expected 703.3; observed 704.3

Example 6

(12S,15S,18S)-15-(4-Amino-butyl)-18-(3-amino-propyl)-6-chloro-13-methyl-12-(1-methyl-1H-indol-3-ylmethyl)-2-thia-10,13,16,19-tetraaza-tricyclo[19.4.0.0*3,8*]pentacosa-1(21),3,5,7,22,24-hexaene-11,14,17-trione

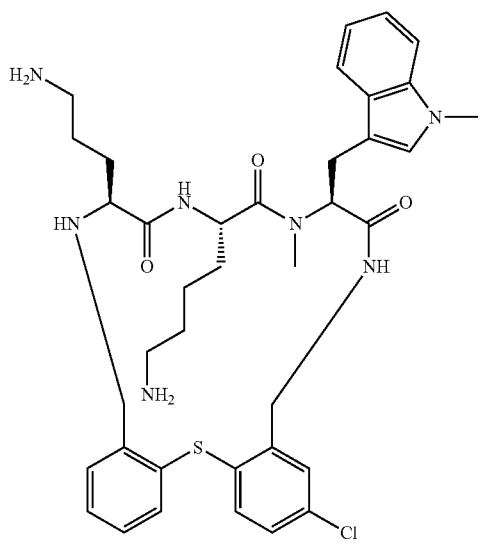 [SMILES: CN1C(=O)[C@H](CCCCN)NC(=O)[C@H](CCCN)NCc2ccccc2Sc2ccc(Cl)cc2CNC(=O)[C@@H]1Cc1cn(C)c2ccccc12]

Example 6 was prepared according to the General Procedure for Peptide Macrocycle Synthesis using the following starting materials:
Amino acids:
1. Fmoc-L-Trp(NMe)-OH, followed by on-bead N-methylation of the Trp alpha-N,
2. Fmoc-L-Lys(BOC)-OH,
3. Fmoc-L-Orn(BOC)-OH.
Tether: Intermediate 3
MS (M+H)$^+$: expected 717.3; observed 718.3

Example 7

(12S,15S,18S)-15-(4-Amino-butyl)-18-(3-amino-propyl)-6-chloro-12-(6-chloro-1H-indol-3-ylmethyl)-13-methyl-2-thia-10,13,16,19-tetraaza-tricyclo[19.4.0.0*3,8*]pentacosa-1(21),3,5,7,22,24-hexaene-11,14,17-trione

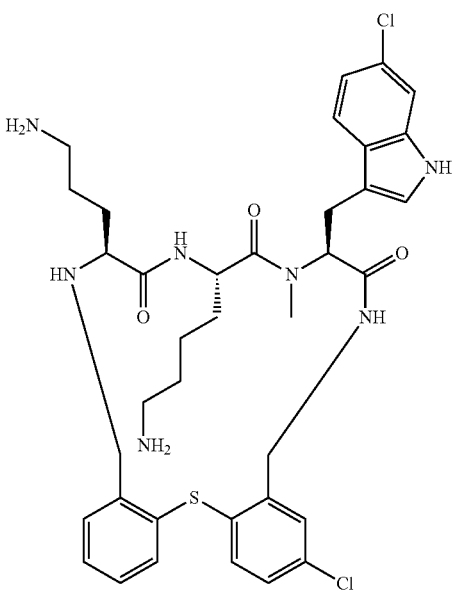 [SMILES: CN1C(=O)[C@H](CCCCN)NC(=O)[C@H](CCCN)NCc2ccccc2Sc2ccc(Cl)cc2CNC(=O)[C@@H]1Cc1c[nH]c2cc(Cl)ccc12]

Example 7 was prepared according to the General Procedure for Peptide Macrocycle Synthesis using the following starting materials:
Amino acids:
1. Fmoc-L-6-Cl-Trp-OH, followed by on-bead N-methylation of the Trp alpha-N,
2. Fmoc-L-Lys(BOC)-OH,
3. Fmoc-L-Orn(BOC)-OH.
Tether: Intermediate 3
MS (M+H)+: expected 737.3; observed 738.3

Example 8

(12S,15S,18S)-15-(4-Amino-butyl)-18-(3-amino-propyl)-6-chloro-12-(6-chloro-1-methyl-1H-indol-3-ylmethyl)-13-methyl-2-thia-10,13,16,19-tetraaza-tricyclo[19.4.0.0*3,8*]pentacosa-1(21),3,5,7,22,24-hexaene-11,14,17-trione

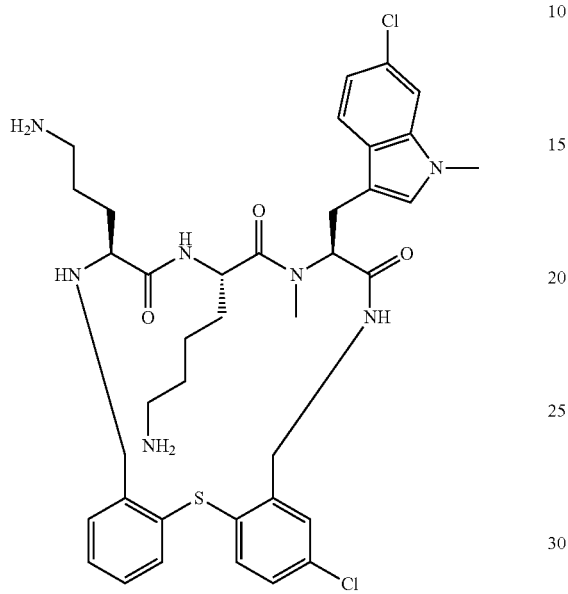

N-Methylation at Indole nitrogen occurred upon N-alkylation of activated Trp alpha-N. Example 8 was isolated from crude mixture of Example 18 using standard HPLC purification conditions.

MS (M+H)+: expected 751.3; observed 752.3

Example 9

(12S,15S,18S)-15-(4-Amino-butyl)-18-(3-amino-propyl)-6,7-dichloro-12-(1H-indol-3-ylmethyl)-13-methyl-2-thia-10,13,16,19-tetraaza-tricyclo[19.4.0.0*3,8*]pentacosa-1(25),3,5,7,21,23-hexaene-11,14,17-trione

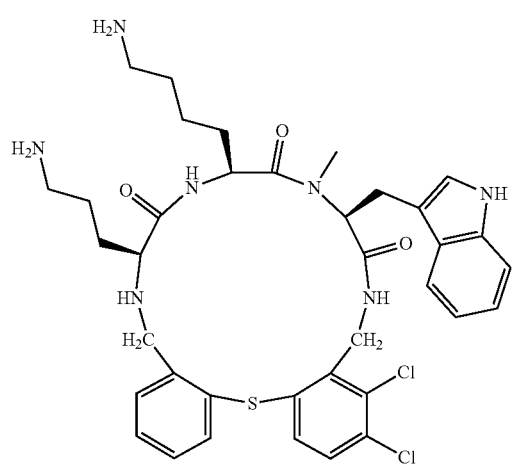 [SMILES: CN1C(=O)[C@H](CCCCN)NC(=O)[C@H](CCCN)NCc2ccccc2Sc2ccc(Cl)c(Cl)c2CNC(=O)[C@@H]1Cc1c[nH]c2ccccc12]

Example 9 was prepared according to the General Procedure for Peptide Macrocycle Synthesis using the following starting materials:

Amino acids:
1. Fmoc-NMe-L-Trp(BOC)-OH,
2. Fmoc-L-Lys(BOC)-OH,
3. Fmoc-L-Orn(BOC)-OH.

Tether: Intermediate 7

MS (M+H)+: expected 737.3; observed 738.3

Example 10

(12S,15S,18S)-15-(4-Amino-butyl)-18-(3-amino-propyl)-4-chloro-12-(1H-indol-3-ylmethyl)-13-methyl-7-trifluoromethyl-2-thia-10,13,16,19-tetraaza-tricyclo[19.4.0.0*3,8*]pentacosa-1(25),3,5,7,21,23-hexaene-11,14,17-trione

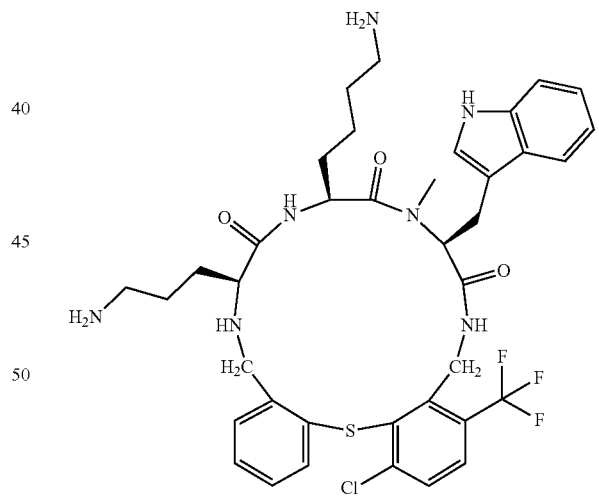

Example 10 was prepared according to the General Procedure for Peptide Macrocycle Synthesis using the following starting materials:

Amino acids:
1. Fmoc-NMe-L-Trp(BOC)-OH,
2. Fmoc-L-Lys(BOC)-OH,
3. Fmoc-L-Orn(BOC)-OH.

Tether: Intermediate 8

MS (M+H)+: expected 771.3; observed 772.2

Example 11

(12S,15S,18S)-15-(4-Amino-butyl)-18-(3-amino-propyl)-4-chloro-12-(1H-indol-3-ylmethyl)-13-methyl-6-trifluoromethyl-2-thia-10,13,16,19-tetraaza-tricyclo[19.4.0.0*3,8*]pentacosa-1(25),3,5,7,21,23-hexaene-11,14,17-trione

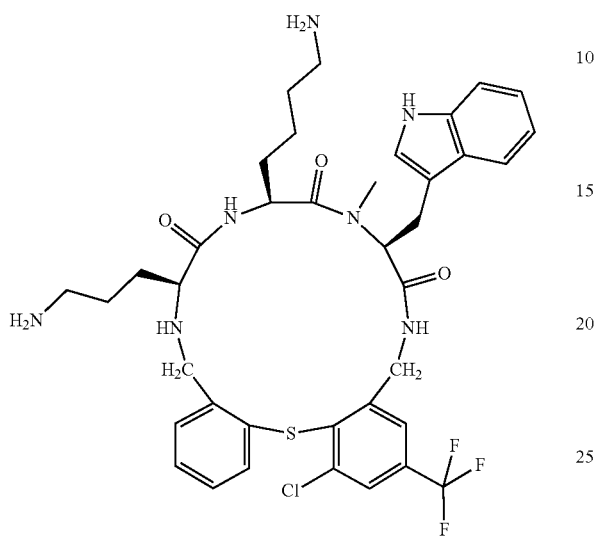

Example 11 was prepared according to the General Procedure for Peptide Macrocycle Synthesis using the following starting materials:
Amino acids:
1. Fmoc-NMe-L-Trp(BOC)-OH,
2. Fmoc-L-Lys(BOC)-OH,
3. Fmoc-L-Orn(BOC)-OH.
Tether: Intermediate 10
MS (M+H)$^+$: expected 771.2; observed 772.3

Example 12

(12S,15S,18S)-15-(4-Amino-butyl)-18-(3-amino-propyl)-4,6-dichloro-23-fluoro-12-(1H-indol-3-ylmethyl)-13-methyl-2-thia-10,13,16,19-tetraaza-tricyclo[19.4.0.0*3,8*]pentacosa-1(25),3,5,7,21,23-hexaene-11,14,17-trione

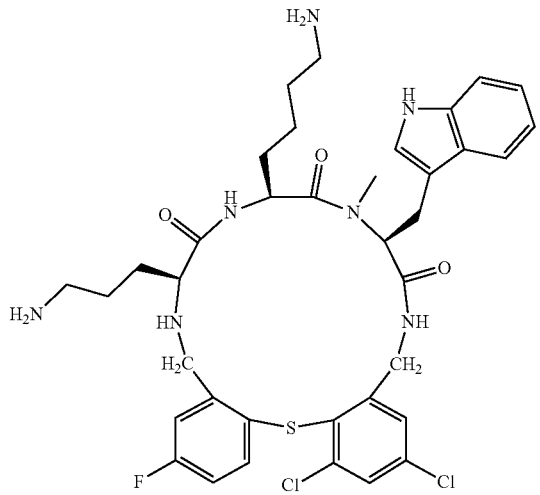 [SMILES: CN1C(=O)[C@H](CCCCN)NC(=O)[C@H](CCCN)NCc2cc(F)ccc2Sc2c(Cl)cc(Cl)cc2CNC(=O)[C@@H]1Cc1c[nH]c2ccccc12]

Example 12 was prepared according to the General Procedure for Peptide Macrocycle Synthesis using the following starting materials:
Amino acids:
1. Fmoc-NMe-L-Trp(BOC)-OH,
2. Fmoc-L-Lys(BOC)-OH,
3. Fmoc-L-Orn(BOC)-OH.
Tether: Intermediate 11
MS (M+H)+: expected 755.3; observed 756.3

Example 13

(12S,15S,18S)-15-(4-Amino-butyl)-18-(3-amino-propyl)-6-chloro-12-(1H-indol-3-ylmethyl)-13-methyl-4-trifluoromethyl-2-thia-10,13,16,19-tetraaza-tricyclo[19.4.0.0*3,8*]pentacosa-1(25),3,5,7,21,23-hexaene-11,14,17-trione

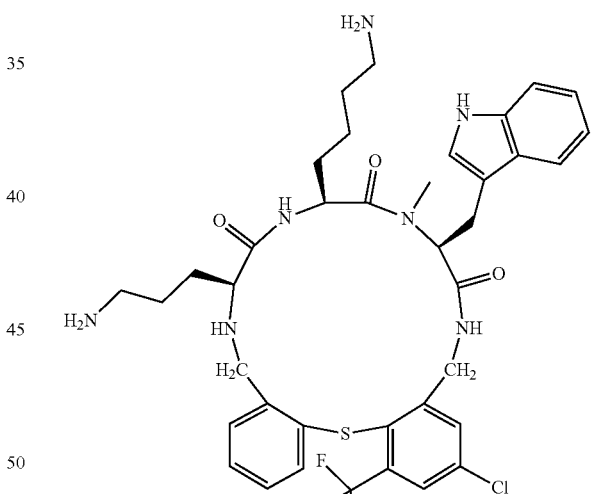

Example 13 was prepared according to the General Procedure for Peptide Macrocycle Synthesis using the following starting materials:
Amino acids:
1. Fmoc-NMe-L-Trp(BOC)-OH,
2. Fmoc-L-Lys(BOC)-OH,
3. Fmoc-L-Orn(BOC)-OH.
Tether: Intermediate 9
MS (M+H)$^+$: expected 771.3; observed 772.3

Example 14

(12S,15S,18S)-15-(4-Amino-butyl)-18-(3-amino-propyl)-6-chloro-12-(1H-indol-3-ylmethyl)-4,13-dimethyl-2-thia-10,13,16,19-tetraaza-tricyclo[19.4.0.0*3,8*]pentacosa-1(25),3,5,7,21,23-hexaene-11,14,17-trione

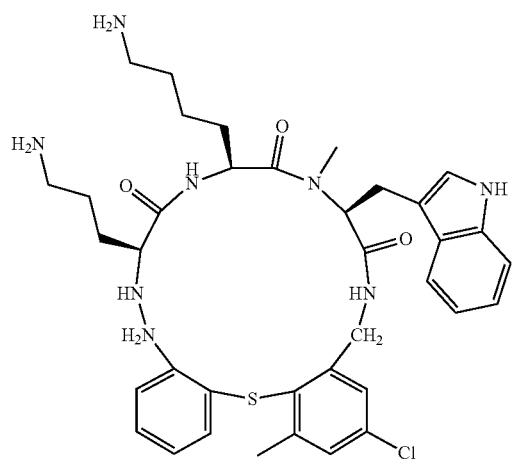 [SMILES: Cc1cc(Cl)cc2c1Sc1ccccc1NN[C@@H](CCCN)C(=O)N[C@@H](CCCCN)C(=O)N(C)[C@@H](Cc1c[nH]c3ccccc13)C(=O)NC2]

Example 14 was prepared according to the General Procedure for Peptide Macrocycle Synthesis using the following starting materials:

Amino acids:
1. Fmoc-NMe-L-Trp(BOC)-OH,
2. Fmoc-L-Lys(BOC)-OH,
3. Fmoc-L-Orn(BOC)-OH.

Tether: Intermediate 14

MS (M+H)$^+$: expected 717.3; observed 718.3

Example 15

(12S,15S,18S)-15-(4-Amino-butyl)-18-(3-amino-propyl)-6-chloro-13-methyl-12-(2-methyl-1H-indol-3-ylmethyl)-2-thia-10,13,16,19-tetraaza-tricyclo[19.4.0.0*3,8*]pentacosa-1(21),3,5,7,22,24-hexaene-1,14,17-trione

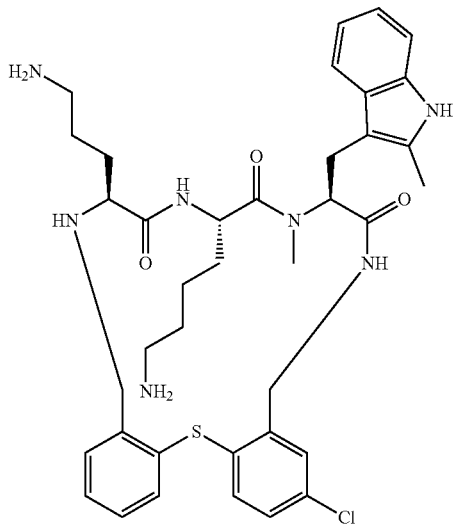 [SMILES: Cc1[nH]c2ccccc2c1C[C@H]1C(=O)NCc2cc(Cl)ccc2Sc2ccccc2CN[C@@H](CCCN)C(=O)N[C@@H](CCCCN)C(=O)N1C]

Example 15 was prepared according to the General Procedure for Peptide Macrocycle Synthesis using the following starting materials:

Amino acids:
1. Fmoc-2-Methyl-L-Trp-OH, followed by on-bead N-methylation of the Trp alpha-N,
2. Fmoc-L-Lys(BOC)-OH,
3. Fmoc-L-Orn(BOC)-OH.

Tether: Intermediate 3

MS (M+H)+: expected 717.3; observed 718.3

Example 16

(12S,15S,18S)-15-(4-Amino-butyl)-18-(3-amino-propyl)-4,13-dimethyl-12-(2-methyl-1H-indol-3-ylmethyl)-2-thia-10,13,16,19-tetraaza-tricyclo[19.4.0.0*3,8*]pentacosa-1(21),3,5,7,22,24-hexaene-11,14,17-trione

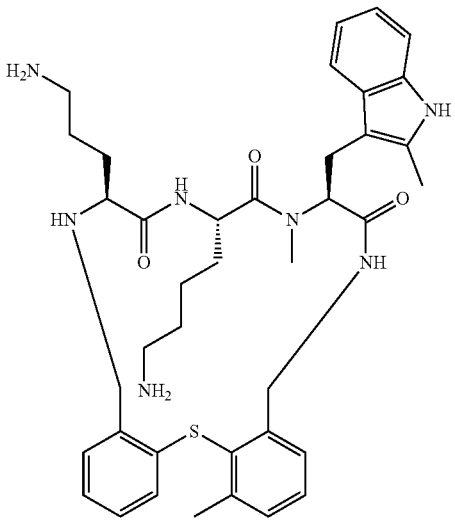 [SMILES: Cc1cccc2c1Sc1ccccc1CN[C@@H](CCCN)C(=O)N[C@@H](CCCCN)C(=O)N(C)[C@@H](Cc1c(C)[nH]c3ccccc13)C(=O)NC2]

Example 16 was prepared according to the General Procedure for Peptide Macrocycle Synthesis using the following starting materials:

Amino acids:
1. Fmoc-2-Methyl-L-Trp-OH, followed by on-bead N-methylation of the Trp alpha-N,
2. Fmoc-L-Lys(BOC)-OH,
3. Fmoc-L-Orn(BOC)-OH.

Tether: Intermediate 5

MS (M+H)$^+$: expected 697.7; observed 698.4

Example 17

(12S,15S,18S)-15-(4-Amino-butyl)-18-(3-amino-propyl)-4,6-dichloro-13-methyl-12-(2-methyl-1H-indol-3-ylmethyl)-2-thia-10,13,16,19-tetraaza-tricyclo[19.4.0.0*3,8*]pentacosa-1(21),3,5,7,22,24-hexaene-1,14,17-trione

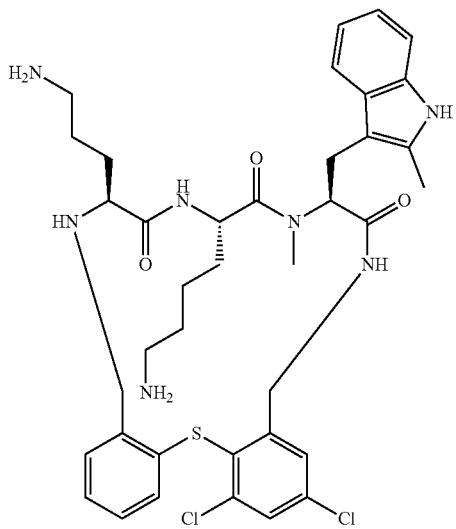 [SMILES: Cc1[nH]c2ccccc2c1C[C@H]1C(=O)NCc2cc(Cl)cc(Cl)c2Sc2ccccc2CN[C@@H](CCCN)C(=O)N[C@@H](CCCCN)C(=O)N1C]

Example 17 was prepared according to the General Procedure for Peptide Macrocycle Synthesis using the following starting materials:
Amino acids:
1. Fmoc-2-Methyl-L-Trp-OH, followed by on-bead N-methylation of the Trp alpha-N,
2. Fmoc-L-Lys(BOC)-OH,
3. Fmoc-L-Orn(BOC)-OH.
Tether: Intermediate 13
MS (M+H)$^+$: expected 751.3; observed 752.3

Example 18

(12S,15S,18S)-15-(4-Amino-butyl)-18-(3-amino-propyl)-6-ethyl-12-(1H-indol-3-ylmethyl)-13-methyl-2-thia-10,13,16,19-tetraaza-tricyclo[19.4.0.0*3,8*]pentacosa-1(25),3,5,7,21,23-hexaene-11,14,17-trione

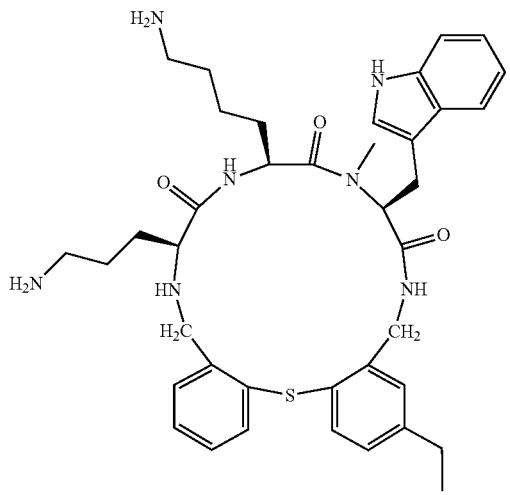 [SMILES: CCc1ccc2c(c1)CNC(=O)[C@H](Cc1c[nH]c3ccccc13)N(C)C(=O)[C@H](CCCCN)NC(=O)[C@H](CCCN)NCc1ccccc1S2]

Example 18 was prepared according to the General Procedure for Peptide Macrocycle Synthesis using the following starting materials:
Amino acids:
1. Fmoc-NMe-L-Trp(BOC)-OH,
2. Fmoc-L-Lys(BOC)-OH,
3. Fmoc-L-Orn(BOC)-OH.
Tether: Intermediate 16
MS (M+H)$^+$: expected 997.4; observed 998.4

Example 19

(12S,15S,18S)-15-(4-Amino-butyl)-18-(3-amino-propyl)-12-(1H-indol-3-ylmethyl)-13-methyl-6-phenyl-2-thia-10,13,16,19-tetraaza-tricyclo[19.4.0.0*3,8*]pentacosa-1(25),3,5,7,21,23-hexaene-11,14,17-trione

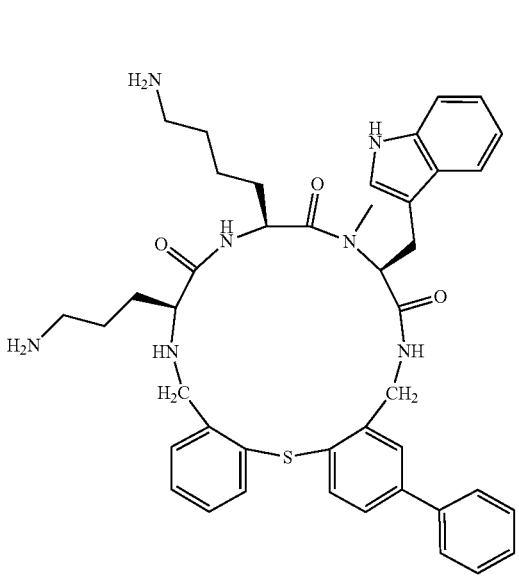 [SMILES: CN1C(=O)[C@H](CCCCN)NC(=O)[C@H](CCCN)NCc2ccccc2Sc2ccc(-c3ccccc3)cc2CNC(=O)[C@@H]1Cc1c[nH]c2ccccc12]

Example 19 was prepared according to the General Procedure for Peptide Macrocycle Synthesis using the following starting materials:
Amino acids:
1. Fmoc-NMe-L-Trp(BOC)-OH,
2. Fmoc-L-Lys(BOC)-OH,
3. Fmoc-L-Orn(BOC)-OH.
Tether: Intermediate 17
MS (M+H)+: expected 745.4; observed 746.4

Example 20

(12S,15S,18S)-15-(4-Amino-butyl)-18-(3-amino-propyl)-6-tert-butyl-12-(1H-indol-3-ylmethyl)-13-methyl-2-thia-10,13,16,19-tetraaza-tricyclo
[19.4.0.0*3,8*]pentacosa-1(25),3,5,7,21,23-hexaene-11,14,17-trione

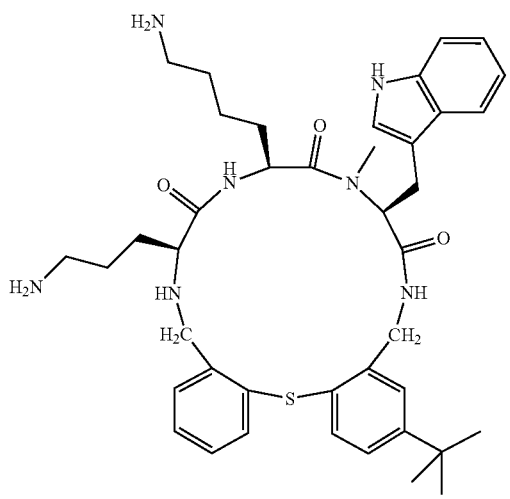 [SMILES: CN1C(=O)[C@H](CCCCN)NC(=O)[C@H](CCCN)NCc2ccccc2Sc2ccc(C(C)(C)C)cc2CNC(=O)[C@@H]1Cc1c[nH]c2ccccc12]

Example 20 was prepared according to the General Procedure for Peptide Macrocycle Synthesis using the following starting materials:
Amino acids:
1. Fmoc-NMe-L-Trp(BOC)-OH,
2. Fmoc-L-Lys(BOC)-OH,
3. Fmoc-L-Orn(BOC)-OH.
Tether: Intermediate 18
MS (M+H)$^+$: expected 725.4; observed 726.4

Example 21

(12S,15S,18S)-15-(4-Amino-butyl)-18-(3-amino-propyl)-12-(1H-indol-3-ylmethyl)-6-isopropyl-13-methyl-2-thia-10,13,16,19-tetraaza-tricyclo
[19.4.0.0*3,8*]pentacosa-1(25),3,5,7,21,23-hexaene-11,14,17-trione

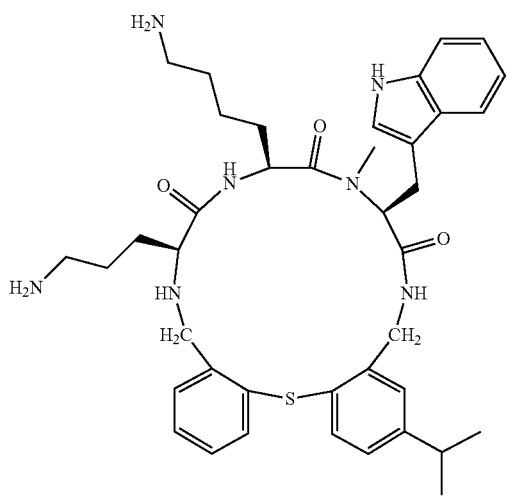 [SMILES: CC(C)c1ccc2c(c1)CNC(=O)[C@H](Cc1c[nH]c3ccccc13)N(C)C(=O)[C@H](CCCCN)NC(=O)[C@H](CCCN)NCc1ccccc1S2]

Example 21 was prepared according to the General Procedure for Peptide Macrocycle Synthesis using the following starting materials:
Amino acids:
1. Fmoc-NMe-L-Trp(BOC)-OH,
2. Fmoc-L-Lys(BOC)-OH,
3. Fmoc-L-Orn(BOC)-OH.
Tether: Intermediate 19
MS (M+H)+: expected 711.4; observed 712.4

Example 22

(11S,14S,17S)-14-(4-Amino-butyl)-11-(3-amino-propyl)-17-(1H-indol-3-ylmethyl)-16-methyl-23-phenyl-25-trifluoromethyl-2-thia-4,10,13,16,19-pentaaza-tricyclo[19.4.0.0*3,8*]pentacosa-1(25),3,5,7,21,23-hexaene-12,15,18-trione

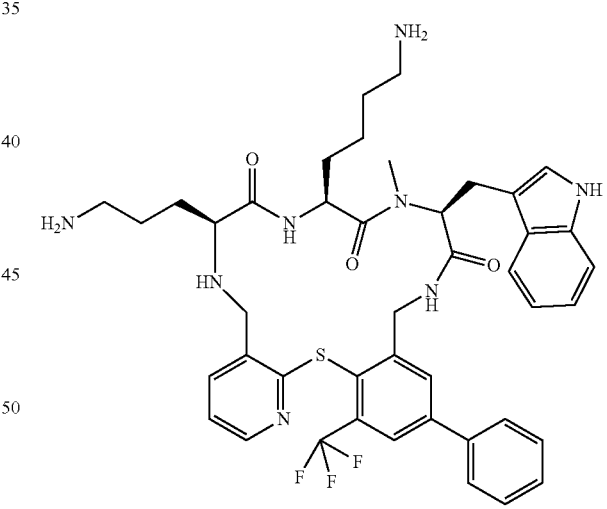

Example 22 was prepared according to the General Procedure for Peptide Macrocycle Synthesis using the following starting materials:
Amino acids:
1. Fmoc-NMe-L-Trp(BOC)-OH,
2. Fmoc-L-Lys(BOC)-OH,
3. Fmoc-L-Orn(BOC)-OH.
Tether: Intermediate 20
MS (M+H$^+$): expected 806.3; observed 807.3

Example 23

(11S,14S,17S)-14-(4-Amino-butyl)-11-(3-amino-propyl)-17-(1H-indol-3-ylmethyl)-16-methyl-23,25-bis-trifluoromethyl-2-thia-4,10,13,16,19-pentaaza-tricyclo[19.4.0.0*3,8*]pentacosa-1(25),3,5,7,21,23-hexaene-12,15,18-trione

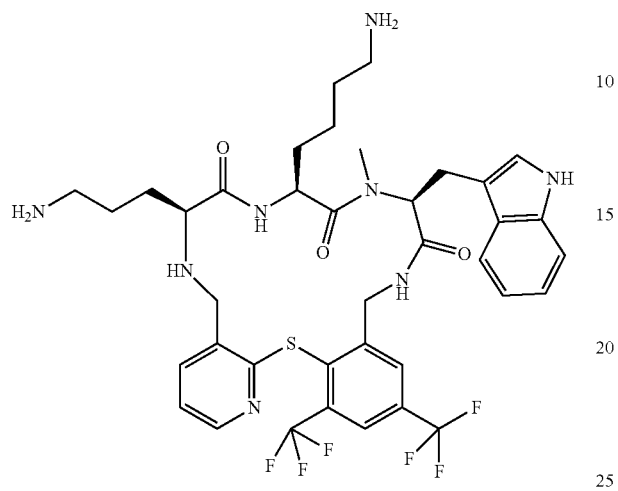

Example 23 was prepared according to the General Procedure for Peptide Macrocycle Synthesis using the following starting materials:
Amino acids:
1. Fmoc-NMe-L-Trp(BOC)-OH,
2. Fmoc-L-Lys(BOC)-OH,
3. Fmoc-L-Orn(BOC)-OH.
Tether: Intermediate 21
MS (M+H$^+$): expected 805.9; observed 807.3

Example 24

(11S,14S,17S)-14-(4-Amino-butyl)-11-(3-amino-propyl)-25-chloro-17-(1H-indol-3-ylmethyl)-16-methyl-23-trifluoromethyl-2-thia-7,10,13,16,19-pentaaza-tricyclo[19.4.0.0*3,8*]pentacosa-1(25),3,5,7,21,23-hexaene-12,15,18-trione

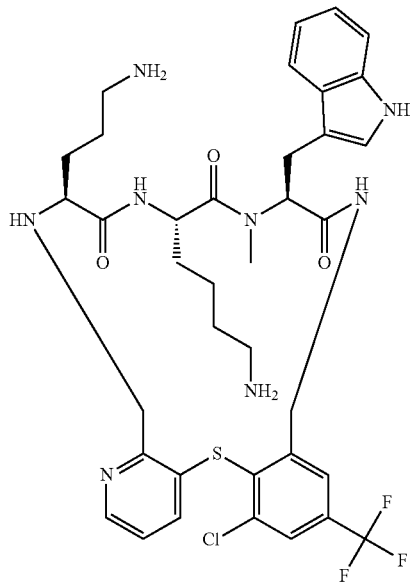 [SMILES: CN1C(=O)[C@H](CCCCN)NC(=O)[C@H](CCCN)NCc2ncccc2Sc2c(Cl)cc(C(F)(F)F)cc2CNC(=O)[C@@H]1Cc1c[nH]c2ccccc12]

Example 24 was prepared according to the General Procedure for Peptide Macrocycle Synthesis using the following starting materials:
Amino acids:
1. Fmoc-NMe-L-Trp(BOC)-OH,
2. Fmoc-L-Lys(BOC)-OH,
3. Fmoc-L-Orn(BOC)-OH.
Tether: Intermediate 22
MS (M+H$^+$): expected 772.3; observed 773.3 [(M+H)$^+$]

Example 25

(11R,14S,17S)-14-(4-Amino-butyl)-11-(3-amino-propyl)-25-chloro-17-(1H-indol-3-ylmethyl)-24-phenyl-2-thia-4,10,13,16,19-pentaaza-tricyclo[9.4.0.0*3,8*]pentacosa-1(25),3,5,7,21,23-hexaene-12,15,18-trione Example 25 was prepared according to the General Procedure for Peptide Macrocycle Synthesis using the following starting materials:
Amino acids:
1. Fmoc-L-Trp(BOC)-OH,
2. Fmoc-L-Lys(BOC)-OH,
3. Fmoc-D-Orn(BOC)-OH.
Tether: Intermediate 23
MS (M+H)$^+$: expected 767.32; observed 767.33

Example 26

(11S,14S,17S)-14-(4-Amino-butyl)-11-(3-amino-propyl)-25-chloro-17-(1H-indol-3-ylmethyl)-24-phenyl-2-thia-4,10,13,16,19-pentaaza-tricyclo[9.4.0.0*3,8*]pentacosa-1(25),3,5,7,21,23-hexaene-12,15,18-trione

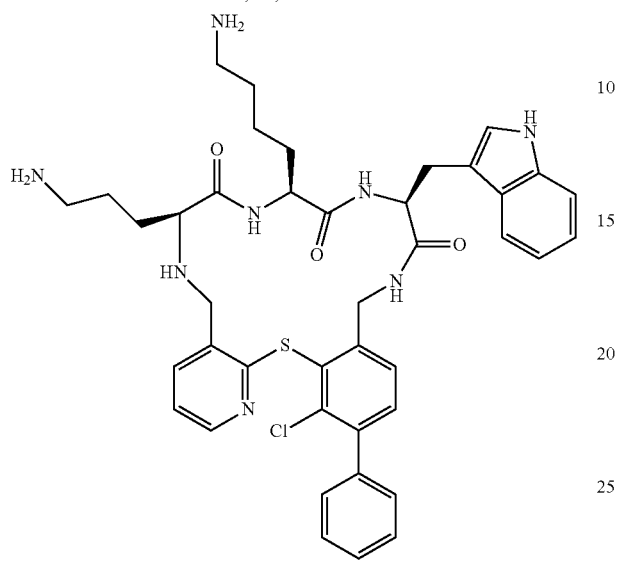

Example 26 was prepared according to the General Procedure for Peptide Macrocycle Synthesis using the following starting materials:
Amino acids:
1. Fmoc-L-Trp(BOC)-OH,
2. Fmoc-L-Lys(BOC)-OH,
3. Fmoc-L-Orn(BOC)-OH.
Tether: Intermediate 23
MS (M+H)$^+$: expected 767.32; observed 767.32

Example 27

(11R,14S,17S)-14-(4-Amino-butyl)-11-(3-amino-propyl)-25-chloro-17-(1H-indol-3-ylmethyl)-16-methyl-24-phenyl-2-thia-4,10,13,16,19-pentaaza-tricyclo[19.4.0.0*3,8*]pentacosa-1(25),3,5,7,21,23-hexaene-12,15,18-trione

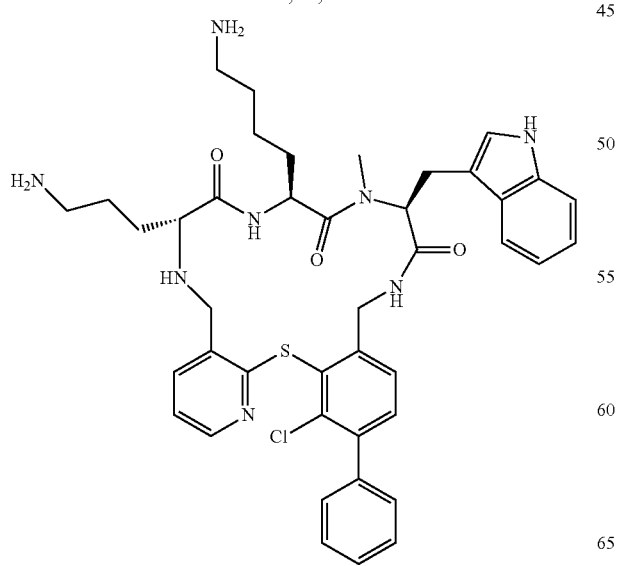

Example 27 was prepared according to the General Procedure for Peptide Macrocycle Synthesis using the following starting materials:
Amino acids:
1. Fmoc-L-NMe-Trp(BOC)-OH,
2. Fmoc-L-Lys(BOC)-OH,
3. Fmoc-D-Orn(BOC)-OH.
Tether: Intermediate 23
MS (M+H)$^+$: expected 781.33; observed 781.34

Example 28

(12S,15S,18S)-15-(4-Amino-butyl)-18-(3-amino-propyl)-12-(1H-indol-3-ylmethyl)-13-methyl-6-phenyl-4-trifluoromethyl-2-thia-10,13,16,19-tetraaza-tricyclo[19.4.0.0*3,8*]pentacosa-1(25),3,5,7,21,23-hexaene-11,14,17-trione Example 28 was prepared according to the General Procedure for Peptide Macrocycle Synthesis using the following starting materials:
Amino acids:
1. Fmoc-L-NMe-Trp(BOC)-OH,
2. Fmoc-L-Lys(BOC)-OH,
3. Fmoc-L-Orn(BOC)-OH.
Tether: Intermediate 24
MS (M+H)$^+$: expected 814.36; observed 814.37

Example 29

(11S,14S,17S)-14-(4-Amino-butyl)-11-(3-amino-propyl)-25-chloro-17-(1H-indol-3-ylmethyl)-16-methyl-22-phenyl-2-thia-4,10,13,16,19-pentaaza-tricyclo[19.4.0.0*3,8*]pentacosa-1(25),3(8),4,6,21,23-hexaene-12,15,18-trione

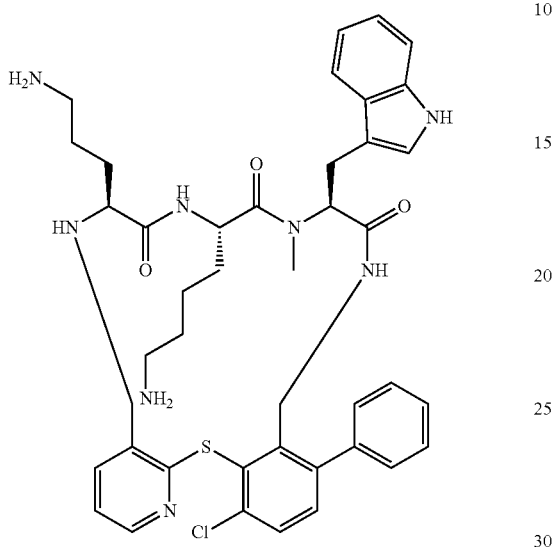

Example 29 was prepared according to the General Procedure for Peptide Macrocycle Synthesis using the following starting materials:
Amino acids:
1. Fmoc-NMe-L-Trp(BOC)-OH,
2. Fmoc-L-Lys(BOC)-OH,
3. Fmoc-L-Orn(BOC)-OH.
Tether: Intermediate 25
MS (M+H$^+$): expected 780.4; observed 781.3

Example 30

(12S,15S,18S)-15,18-Bis-(3-amino-propyl)-4,6-dichloro-12-(1H-indol-3-ylmethyl)-13-methyl-2-thia-10,13,16,19-tetraaza-tricyclo[19.4.0.0*3,8*]pentacosa-1(25),3,5,7,21,23-hexaene-11,14,17-trione

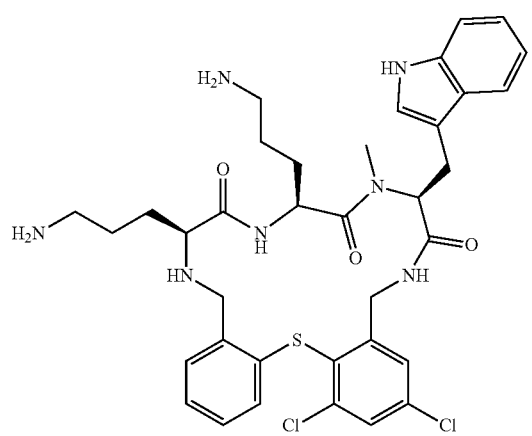 [SMILES: CN1C(=O)[C@H](CCCN)NC(=O)[C@H](CCCN)NCc2ccccc2Sc2c(Cl)cc(Cl)cc2CNC(=O)[C@@H]1Cc1c[nH]c2ccccc12]

Example 30 was prepared according to the General Procedure for Peptide Macrocycle Synthesis using the following starting materials:
Amino acids:
1. Fmoc-NMe-L-Trp(BOC)-OH,
2. Fmoc-L-Orn(BOC)-OH.
3. Fmoc-L-Orn(BOC)-OH.
Tether: Intermediate 15
MS (M+H)$^+$: expected 724.25; observed 724.20

Example 31

(11S,14S,17S)-14-(4-Amino-butyl)-11-(3-amino-propyl)-25-chloro-17-(5-chloro-1H-indol-3-ylmethyl)-16-methyl-22-trifluoromethyl-2-thia-4,10,13,16,19-pentaaza-tricyclo[19.4.0.0*3,8*]pentacosa-1(25),3,5,7,21,23-hexaene-12,15,18-trione

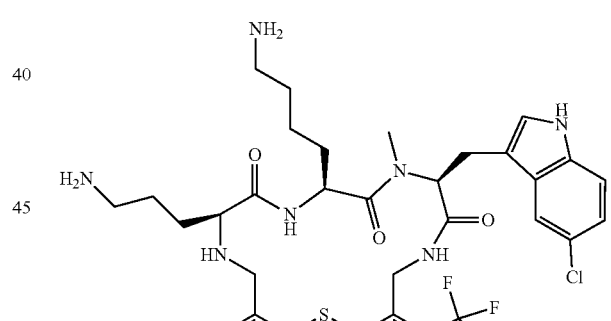

Example 31 was prepared according to the General Procedure for Peptide Macrocycle Synthesis using the following starting materials:
Amino acids:
1. Fmoc-L-NMe-5-Cl-Trp-OH,
2. Fmoc-L-Lys(BOC)-OH,
3. Fmoc-L-Orn(BOC)-OH.
Tether: Intermediate 12
MS (M+H)$^+$: expected 807.25; observed 807.39

Example 32

(12S,15S,18S)-15-(4-Amino-butyl)-18-(3-amino-propyl)-4-chloro-12-(1H-indol-3-ylmethyl)-13-methyl-6-phenyl-2-thia-111,13,16,19-tetraaza-tricyclo[19.4.0.0*3,8*]pentacosa-1(25),3,5,7,21,23-hexaene-11,14,17-trione

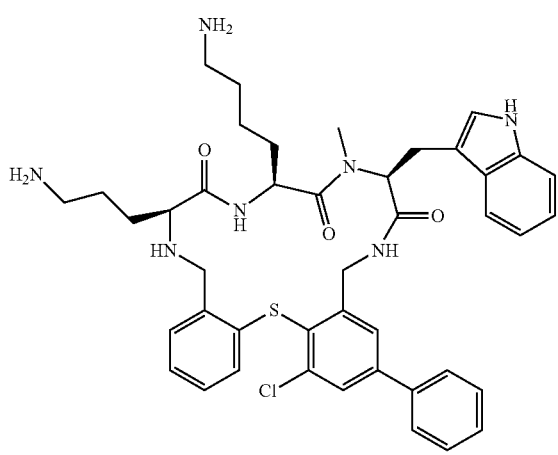 [SMILES: CN1C(=O)[C@H](CCCCN)NC(=O)[C@H](CCCN)NCc2ccccc2Sc2c(Cl)cc(-c3ccccc3)cc2CNC(=O)[C@@H]1Cc1c[nH]c2ccccc12]

Example 32 was prepared according to the General Procedure for Suzuki Coupling of boronic acid derivatives to Peptide Macrocycle Intermediates using the following starting materials:
Macrocycle Intermediate: Intermediate 31
Boronic Acid Derivative: Phenylboronic acid
MS (M+H)$^+$: expected 780.34; observed 780.5

Example 33

(12S,15S,18S)-15-(4-Amino-butyl)-18-(3-amino-propyl)-4-chloro-6-(2-chloro-phenyl)-12-(1H-indol-3-ylmethyl)-13-methyl-2-thia-10,13,16,19-tetraaza-tricyclo[19.4.0.0*3,8*]pentacosa-1(25),3,5,7,21,23-hexaene-11,14,17-trione

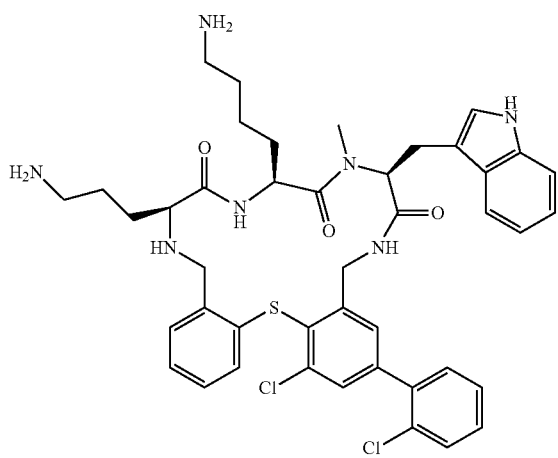 [SMILES: CN1C(=O)[C@H](CCCCN)NC(=O)[C@H](CCCN)NCc2ccccc2Sc2c(Cl)cc(-c3ccccc3Cl)cc2CNC(=O)[C@@H]1Cc1c[nH]c2ccccc12]

Example 33 was prepared according to the General Procedure for Suzuki Coupling of boronic acid derivatives to Peptide Macrocycle Intermediates using the following starting materials:
Macrocycle Intermediate: Intermediate 31
Boronic Acid Derivative: (2-chlorophenyl)boronic acid
MS (M+H)$^+$: expected 814.30; observed 814.5

Example 34

(12S,15S,18S)-15-(4-Amino-butyl)-18-(3-amino-propyl)-4-chloro-12-(1H-indol-3-ylmethyl)-13-methyl-6-pyridin-3-yl-2-thia-10,13,16,19-tetraaza-tricyclo[19.4.0.0*3,8*]pentacosa-1(25),3,5,7,21,23-hexaene-11,14,17-trione

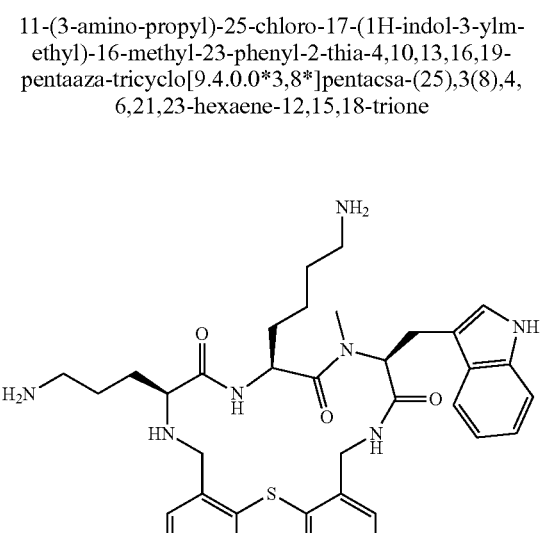

Example 34 was prepared according to the General Procedure for Suzuki Coupling of boronic acid derivatives to Peptide Macrocycle Intermediates using the following starting materials:
Macrocycle Intermediate: Intermediate 31
Boronic Acid Derivative: Pyridin-3-yl boronic acid
MS (M+H)$^+$: expected 781.33; observed 781.6

Example 35

11-(3-amino-propyl)-25-chloro-17-(1H-indol-3-ylmethyl)-16-methyl-23-phenyl-2-thia-4,10,13,16,19-pentaaza-tricyclo[9.4.0.0*3,8*]pentacsa-(25),3(8),4,6,21,23-hexaene-12,15,18-trione Example 35 was prepared according to the General Procedure for Peptide Macrocycle Synthesis using the following starting materials:
1. Fmoc-NMe-L-Trp(BOC)-OH,
2. Fmoc-L-Lys(BOC)-OH,
3. Fmoc-L-Orn(BOC)-OH.
Tether: Intermediate 26
MS (M+H)+: expected 780.4; observed 781.5

Example 36

(12S,15S,18S)-15-(4-Amino-butyl)-18-(3-aminopropyl)-6-bromo-4-chloro-12-(1H-indol-3-ylmethyl)-13-methyl-2-thia-10,13,16,19-tetraaza-tricyclo[19.4.0.0*3,8*]pentacosa-1(25),3,5,7,21,23-hexaene-11,14,17-trione

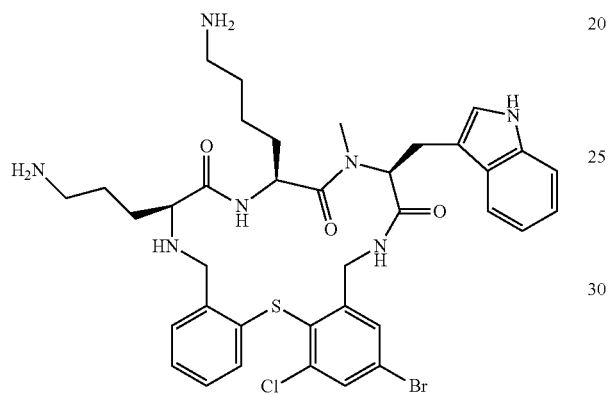

Example 36 was prepared by BOC-deprotection of intermediate 31.
MS (M+H)+: expected 782.22; observed 782.3

Example 37

(12S,15S,18S)-15-(4-Amino-butyl)-18-(3-aminopropyl)-4-chloro-12-(1H-indol-3-ylmethyl)-13-methyl-6-(1-methyl-1H-imidazol-4-yl)-2-thia-10,13,16,19-tetraaza-tricyclo[19.4.0.0*3,8*]pentacosa-1(25),3,5,7,21,23-hexaene-11,14,17-trione

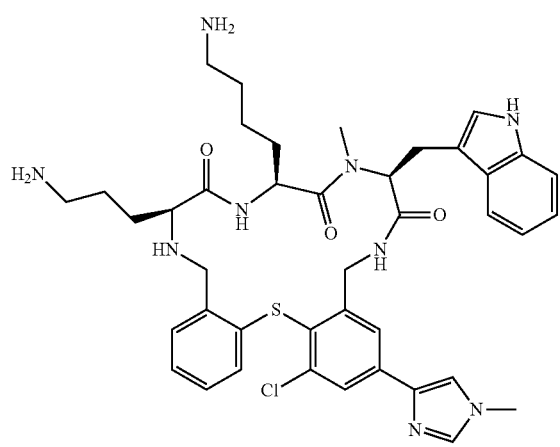 [SMILES: CN1C(=O)[C@H](CCCCN)NC(=O)[C@H](CCCN)NCc2ccccc2Sc2c(Cl)cc(-c3cn(C)cn3)cc2CNC(=O)[C@@H]1Cc1c[nH]c2ccccc12]

Example 37 was prepared according to the General Procedure for Suzuki Coupling of boronic acid derivatives to Peptide Macrocycle Intermediates using the following starting materials:

Macrocycle Intermediate: Intermediate 31
Boronic Acid Derivative: 1-methyl-4-(4,4,5,5-tetramethyl-1,3,2-dioxaborolan-2-yl)-1H-imidazole
MS (M+H)+: expected 784.34; observed 784.4

Example 38

3-[(11S,14S,17S)-14-(4-Amino-butyl)-17-(1H-indol-3-ylmethyl)-16-methyl-12,15,18-trioxo-23-phenyl-25-trifluoromethyl-2-thia-10,13,16,19-tetraaza-tricyclo[19.4.0.0*3,8*]pentacosa-1(25),3,5,7,21,23-hexaen-11-yl]-propionamide

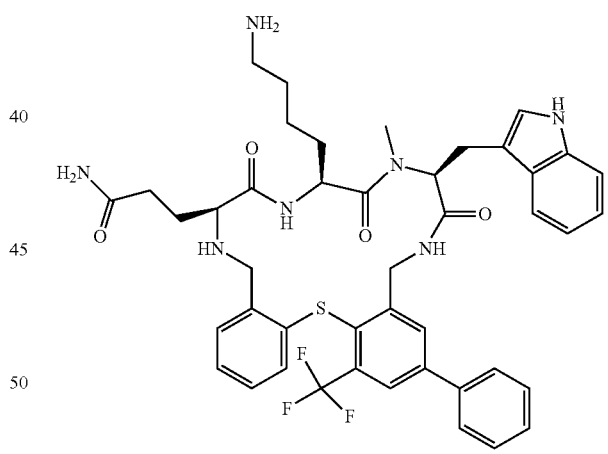

Example 38 was prepared according to the General Procedure for Peptide Macrocycle Synthesis using the following starting materials:
Amino acids:
1. Fmoc-L-NMe-Trp(BOC)-OH,
2. Fmoc-L-Lys(BOC)-OH,
3. Fmoc-L-Gln(TRT)-OH.
Tether: Intermediate 24
MS (M+H)+: expected 828.34; observed 828.6

Example 39

3-[(11S,14S,17S)-11-(3-Amino-propyl)-17-(1H-indol-3-ylmethyl)-16-methyl-12,15,18-trioxo-23-phenyl-25-trifluoromethyl-2-thia-10,13,16,19-tetraaza-tricyclo[19.4.0.0*3,8*]pentacosa-1(25),3,5,7,21,23-hexaen-14-yl]-propionamide

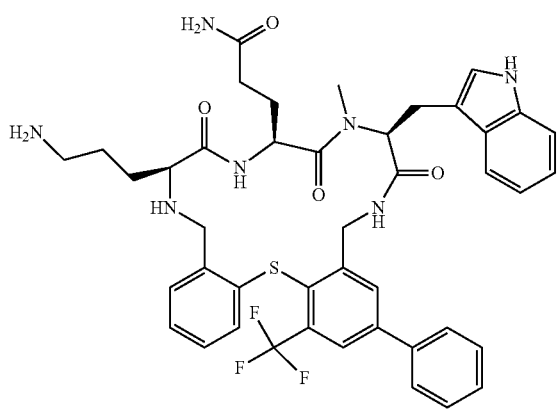 [SMILES: CN1C(=O)[C@H](CCC(N)=O)NC(=O)[C@H](CCCN)NCc2ccccc2Sc2c(cc(-c3ccccc3)cc2C(F)(F)F)CNC(=O)[C@@H]1Cc1c[nH]c2ccccc12]

Example 39 was prepared according to the General Procedure for Peptide Macrocycle Synthesis using the following starting materials:
Amino acids:
1. Fmoc-L-NMe-Trp(BOC)-OH,
2. Fmoc-L-Gln(TRT)-OH,
3. Fmoc-L-Orn(BOC)-OH.
Tether: Intermediate 24
MS (M+H)$^+$: expected 814.33; observed 814.4

Example 40

(11S,14S,17S)-14-(4-Amino-butyl)-11-(3-amino-propyl)-25-chloro-23-(2-chloro-pyridin-4-yl)-17-(1H-indol-3-ylmethyl)-16-methyl-2-thia-4,10,13,16,19-pentaaza-tricyclo[19.4.0.0*3,8*]pentacosa-1(21),3,5,7,22,24-hexaene-12,15,18-trione

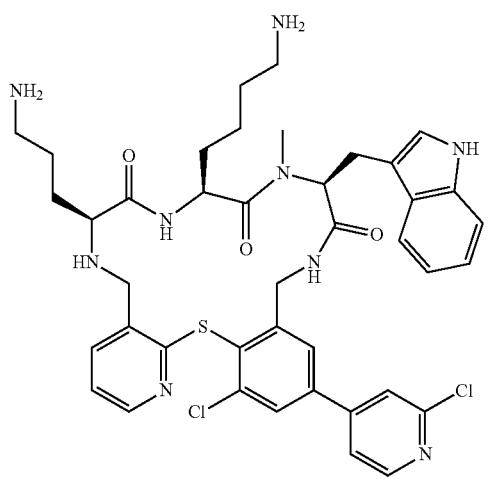 [SMILES: CN1C(=O)[C@H](CCCCN)NC(=O)[C@H](CCCN)NCc2cccnc2Sc2c(Cl)cc(-c3ccnc(Cl)c3)cc2CNC(=O)[C@@H]1Cc1c[nH]c2ccccc12]

Example 40 was prepared according to the General Procedure for Peptide Macrocycle Synthesis using the following starting materials:

1. Fmoc-NMe-L-Trp(BOC)-OH,
2. Fmoc-L-Lys(BOC)-OH,
3. Fmoc-L-Orn(BOC)-OH.
Tether: Intermediate 27
MS (M+H$^+$): expected 815.8; observed 816.6

Example 41

(12S,15S,18S)-15-(4-Amino-butyl)-18-(3-amino-propyl)-5-bromo-4-chloro-12-(1H-indol-3-ylmethyl)-13-methyl-2-thia-10,13,16,19-tetraaza-tricyclo[19.4.0.0*3,8*]pentacosa-1(25),3,5,7,21,23-hexaene-11,14,17-trione

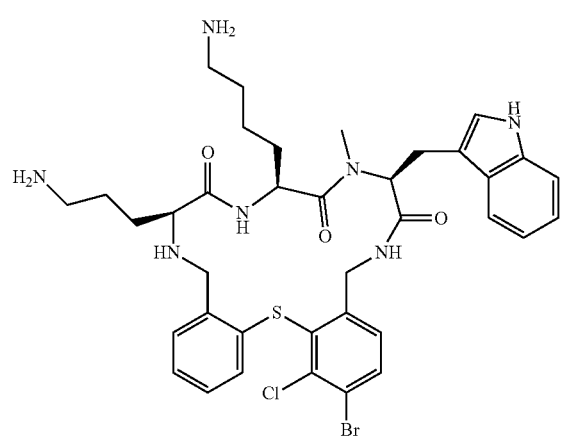 [SMILES: CN1C(=O)[C@H](CCCCN)NC(=O)[C@H](CCCN)NCc2ccccc2Sc2c(ccc(Br)c2Cl)CNC(=O)[C@@H]1Cc1c[nH]c2ccccc12]

Example 41 was prepared by BOC-deprotection of intermediate 32.
MS (M+H)$^+$: expected 782.22; observed 782.5

Example 42

(12S,15S,18S)-15-(4-Amino-butyl)-18-(3-amino-propyl)-4-chloro-12-(1H-indol-3-ylmethyl)-13-methyl-5-phenyl-2-thia-10,13,16,19-tetraaza-tricyclo[19.4.0.0*3,8*]pentacosa-1(25),3,5,7,21,23-hexaene-11,14,17-trione

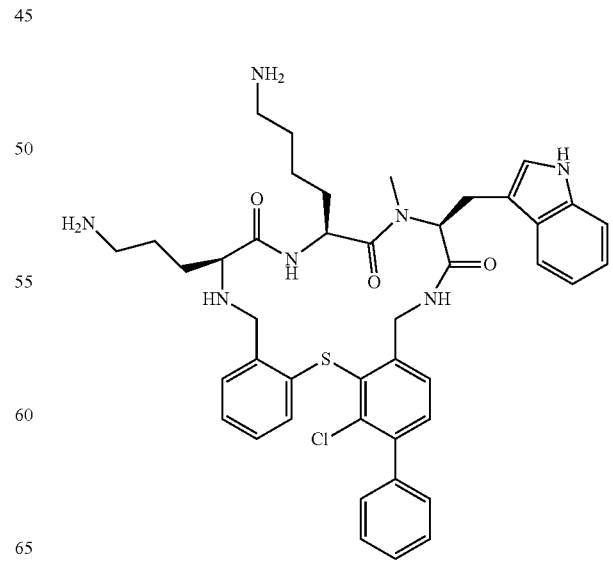

Example 42 was prepared according to the General Procedure for Suzuki Coupling of boronic acid derivatives to Peptide Macrocycle Intermediates using the following starting materials:

Macrocycle Intermediate: Intermediate 32
Boronic Acid Derivative: Phenylboronic acid
MS (M+H)⁺: expected 780.34; observed 780.5

Example 43

(8S,11S,14S)-8-((1H-Indol-3-yl)methyl)-11-(4-aminobutyl)-14-(3-aminopropyl)-3-chloro-9-methyl-5,6,8,9,11,12,15,16-octahydrobenzo[b]pyrido[3,2-p][1,5,8,11,14]thiatetraazacycloheptadecine-7,10,13(14H)-trione

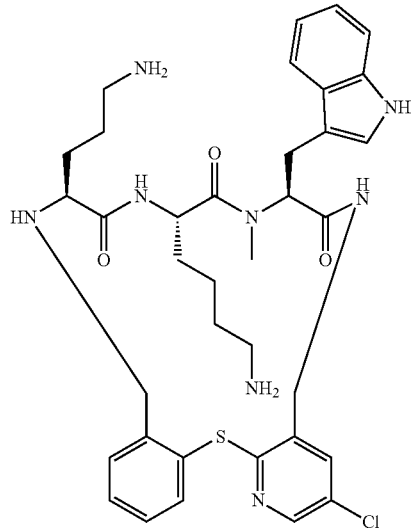 [SMILES: CN1C(=O)[C@H](CCCCN)NC(=O)[C@H](CCCN)NCc2ccccc2Sc2ncc(Cl)cc2CNC(=O)[C@@H]1Cc1c[nH]c2ccccc12]

The material was prepared in analogy to the General Procedure for Peptide Macrocycle Synthesis using the following reagents/conditions: Amino Acids: Fmoc-NMe-L-Trp(Boc)-OH, Fmoc-L-Lys(Boc)-OH, Fmoc-L-Orn(Boc)-OH. Reductive Amination: 1.2 eq Intermediate 106 in NMP/MeOH/AcOH 1:1:0.012 as solvent mixture. Macrocyclization: 1.2 eq HATU, 4 eq DIPEA, in DCM at rt 1 h. Deprotection: DCM/TFA 1:1, then concentrating in vacuo and stirring with acetonitrile/water 1:1. The title compound was obtained as light yellow foam (46 mg). MS ESI (m/z): 705.5 [(M+H)⁺]

Example 44

(11S,14S,17S)-14-(4-Amino-butyl)-11-(3-aminopropyl)-25-chloro-23-(2-chloro-pyridin-4-yl)-16-methyl-17-(2-methyl-1H-indol-3-ylmethyl)-2-thia-4,10,13,16,19-pentaaza-tricyclo[19.4.0.0*3,8*]pentacosa-1(25),3(8),4,6,21,23-hexaene-12,15,18-trione

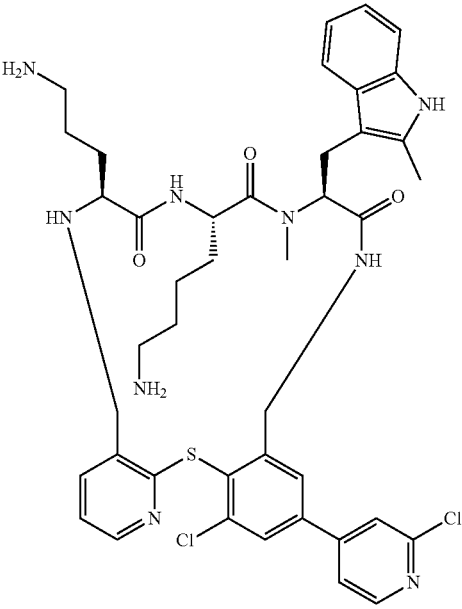 [SMILES: Cc1[nH]c2ccccc2c1C[C@H]1C(=O)NCc2cc(-c3ccnc(Cl)c3)cc(Cl)c2Sc2ncccc2CN[C@@H](CCCN)C(=O)N[C@@H](CCCCN)C(=O)N1C]

Example 44 was prepared according to the General Procedure for Peptide Macrocycle Synthesis using the following starting materials:

1. (S)-2-(9H-Fluoren-9-ylmethoxycarbonylamino)-3-(2-methyl-1H-indol-3-yl)-propionic acid,
2. Fmoc-L-Lys(BOC)-OH,
3. Fmoc-L-Orn(BOC)-OH.

Tether: Intermediate 27
MS (M+H⁺): expected 829.9; observed 830.3

Example 45

(11S,14S,17S)-14-(4-Amino-butyl)-11-(3-amino-propyl)-23-(3-benzyloxy-prop-1-ynyl)-25-chloro-17-(1H-indol-3-ylmethyl)-16-methyl-2-thia-4,10,13,16,19-pentaaza-tricyclo[19.4.0.0*3,8*]pentacosa-1(25),3(8),4,6,21,23-hexaene-12,15,18-trione

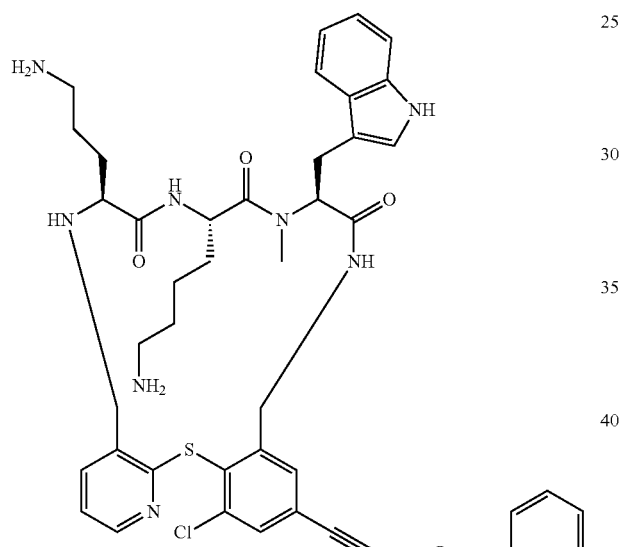

Example 45 was prepared according to the General Procedure for Peptide Macrocycle Synthesis using the following starting materials:

1. Fmoc-NMe-L-Trp(BOC)-OH,
2. Fmoc-L-Lys(BOC)-OH,
3. Fmoc-L-Orn(BOC)-OH.

Tether: Intermediate 28

MS (M+H$^+$): expected 848.5; observed 849.4

Example 46

(8S,11S,14S)-8-((1H-Indol-3-yl)methyl)-11-(4-aminobutyl)-14-(3-aminopropyl)-9-methyl-2-morpholino-5,6,8,9,11,12,15,16-octahydrobenzo[b]pyrido[3,2-p][1,5,8,11,14]thiatetraazacycloheptadecine-7,10,13(14H)-trione

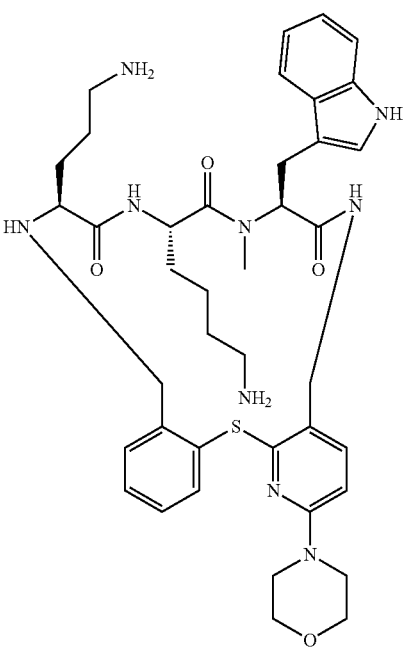 [SMILES: CN1C(=O)[C@H](CCCCN)NC(=O)[C@H](CCCN)NCc2ccccc2Sc2nc(N3CCOCC3)ccc2CNC(=O)[C@@H]1Cc1c[nH]c2ccccc12]

The material was prepared in analogy to the General Procedure for Peptide Macrocycle Synthesis using the following reagents/conditions: Amino Acids: Fmoc-NMe-L-Trp(Boc)-OH, Fmoc-L-Lys(Boc)-OH, Fmoc-L-Orn(Boc)-OH. Reductive Amination: 0.9 eq Intermediate 112 in NMP/MeOH/AcOH 1:1:0.012 as solvent mixture. Macrocyclization: 1.2 eq HATU, 4 eq DIPEA, in DCM at rt 1 h. Deprotection: DCM/TFA 1:1. The title compound was obtained as white powder (16 mg). MS ESI (m/z): 756.6 [(M+H)$^+$]

Example 47

(11S,14S,17S)-14-(4-Amino-butyl)-11-(3-aminopropyl)-25-chloro-16-methyl-17-(2-methyl-1H-indol-3-ylmethyl)-22-pyridin-4-yl-2-thia-4,10,13,16,19-pentaaza-tricyclo[19.4.0.0*3,8*]pentacosa-1(25),3(8),4,6,21,23-hexaene-12,15,18-trione

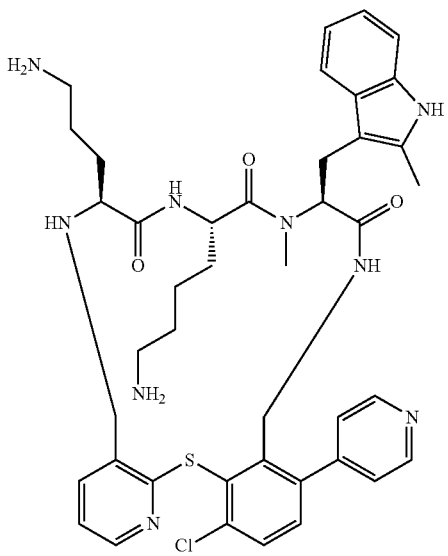 [SMILES: Cc1[nH]c2ccccc2c1C[C@H]1C(=O)NCc2c(-c3ccncc3)ccc(Cl)c2Sc2ncccc2CN[C@@H](CCCN)C(=O)N[C@@H](CCCCN)C(=O)N1C]

Example 47 was prepared according to the General Procedure for Peptide Macrocycle Synthesis using the following starting materials:
1. (S)-2-(9H-Fluoren-9-ylmethoxycarbonylamino)-3-(2-methyl-1H-indol-3-yl)-propionic acid,
2. Fmoc-L-Lys(BOC)-OH,
3. Fmoc-L-Orn(BOC)-OH.

Tether: Intermediate 29

MS (M+H)$^+$: expected 795.4; observed 796.4

Example 48

(12S,15S,18S)-15-(4-Amino-butyl)-18-(3-aminopropyl)-23-bromo-4-chloro-12-(1H-indol-3-ylmethyl)-13-methyl-2-thia-10,13,16,19-tetraaza-tricyclo[19.4.0.0*3,8*]pentacosa-1(25),3,5,7,21,23-hexaene-11,14,17-trione

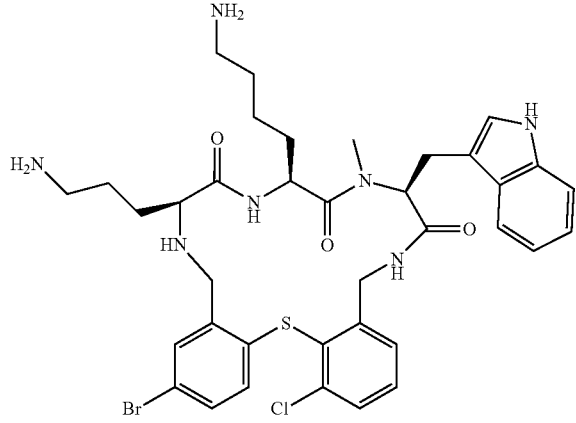 [SMILES: CN1C(=O)[C@H](CCCCN)NC(=O)[C@H](CCCN)NCc2cc(Br)ccc2Sc2c(Cl)cccc2CNC(=O)[C@@H]1Cc1c[nH]c2ccccc12]

Example 48 was prepared by BOC-deprotection of intermediate 33.

MS (M+H)$^+$: expected 782.22; observed 782.2

Example 49

(12S,15S,18S)-15-(4-Amino-butyl)-18-(3-aminopropyl)-4-chloro-12-(1H-indol-3-ylmethyl)-13-methyl-23-phenyl-2-thia-10,13,16,19-tetraaza-tricyclo[19.4.0.0*3,8*]pentacosa-1(25),3,5,7,21,23-hexaene-11,14,17-trione

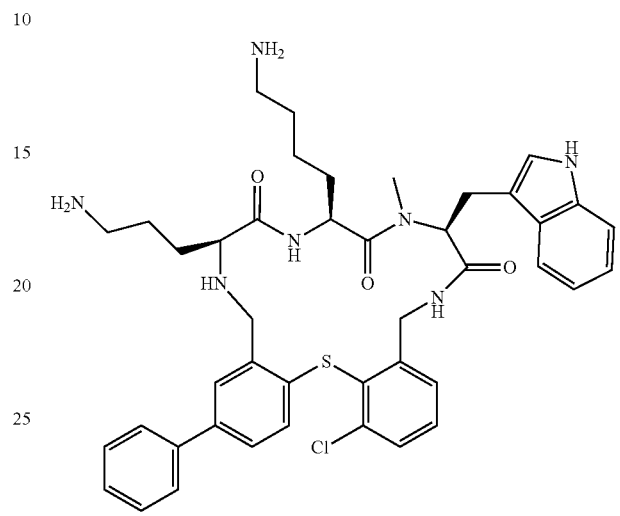

Example 49 was prepared according to the General Procedure for Suzuki Coupling of boronic acid derivatives to Peptide Macrocycle Intermediates using the following starting materials:

Macrocycle Intermediate: Intermediate 33
Boronic Acid Derivative: Phenylboronic acid MS (M+H)$^+$: expected 780.34; observed 780.5

Example 50

(12S,15S,18S)-15-(4-Amino-butyl)-23-(4-aminomethyl-phenyl)-18-(3-amino-propyl)-4-chloro-12-(1H-indol-3-ylmethyl)-13-methyl-2-thia-10,13,16,19-tetraaza-tricyclo[19.4.0.0*3,8*]pentacosa-1(25),3,5,7,21,23-hexaene-11,14,17-trione

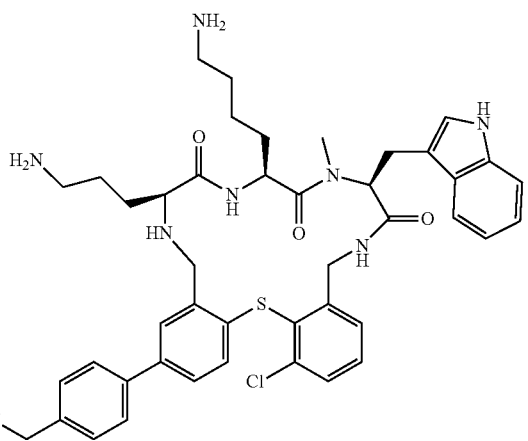

Example 50 was prepared according to the General Procedure for Suzuki Coupling of boronic acid derivatives to Peptide Macrocycle Intermediates using the following starting materials:
Macrocycle Intermediate: Intermediate 33
Boronic Acid Derivative: (4-(((tert-butoxycarbonyl)amino)methyl)phenyl)boronic acid
MS (M+H)+: expected 809.36; observed 809.7

Example 51

(12S,15S,18S)-15-(4-Amino-butyl)-18-(3-aminopropyl)-24-bromo-4-chloro-12-(1H-indol-3-ylmethyl)-13-methyl-2-thia-10,13,16,19-tetraaza-tricyclo[19.4.0.0*3,8*]pentacosa-1(25),3,5,7,21,23-hexaene-11,14,17-trione

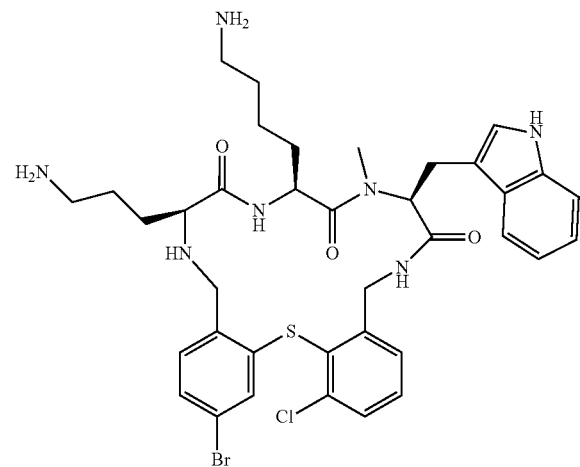 [SMILES: CN1C(=O)[C@H](CCCCN)NC(=O)[C@H](CCCN)NCc2ccc(Br)cc2Sc2c(Cl)cccc2CNC(=O)[C@@H]1Cc1c[nH]c2ccccc12]

Example 51 was prepared by BOC-deprotection of intermediate 34.
MS (M+H)+: expected 782.22; observed 782.3

Example 52

(12S,15S,18S)-15-(4-Amino-butyl)-18-(3-aminopropyl)-4-chloro-12-(1H-indol-3-ylmethyl)-13-methyl-24-phenyl-2-thia-10,13,16,19-tetraaza-tricyclo[19.4.0.0*3,8*]pentacosa-1(25),3,5,7,21,23-hexaene-11,14,17-trione

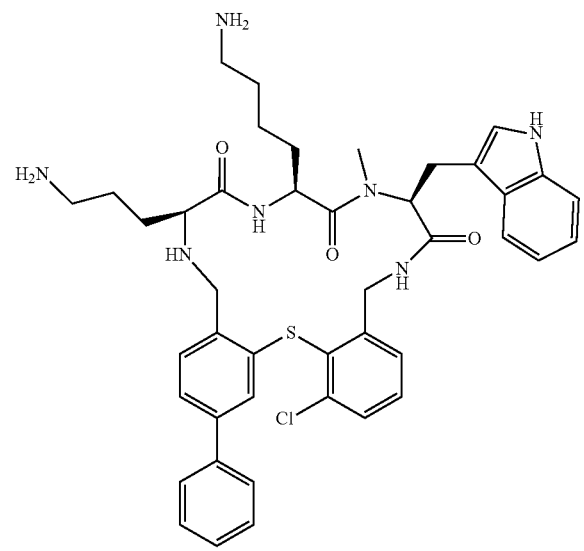 [SMILES: CN1C(=O)[C@H](CCCCN)NC(=O)[C@H](CCCN)NCc2ccc(-c3ccccc3)cc2Sc2c(Cl)cccc2CNC(=O)[C@@H]1Cc1c[nH]c2ccccc12]

Example 52 was prepared according to the General Procedure for Suzuki Coupling of boronic acid derivatives to Peptide Macrocycle Intermediates using the following starting materials:
Macrocycle Intermediate: Intermediate 34
Boronic Acid Derivative: Phenylboronic acid
MS (M+H)+: expected 780.34; observed 780.5

Example 53

4-[(11S,14S,17S)-14-(4-Amino-butyl)-11-(3-aminopropyl)-25-chloro-6-methyl-17-(2-methyl-1H-indol-3-ylmethyl)-12,15,18-trioxo-2-thia-4,10,13,16,19-pentaaza-tricyclo[19.4.0.0*3,8*]pentacosa-1(25),3(8),4,6,21,23-hexaen-23-yl]-benzenesulfonamide

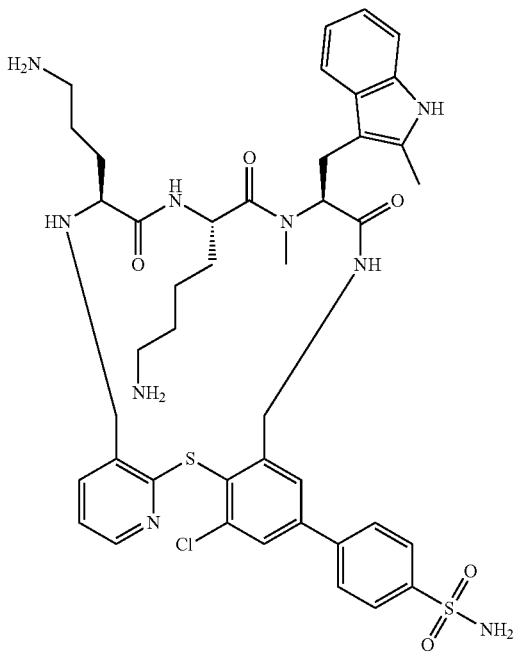 [SMILES: Cc1[nH]c2ccccc2c1C[C@H]1C(=O)NCc2cc(-c3ccc(S(N)(=O)=O)cc3)cc(Cl)c2Sc2ncccc2CN[C@@H](CCCN)C(=O)N[C@@H](CCCCN)C(=O)N1C]

Example 53 was prepared according to the General Procedure for Peptide Macrocycle Synthesis using the following starting materials:
1. (S)-2-(9H-Fluoren-9-ylmethoxycarbonylamino)-3-(2-methyl-1H-indol-3-yl)-propionic acid,
2. Fmoc-L-Lys(BOC)-OH,
3. Fmoc-L-Orn(BOC)-OH.
Tether: Intermediate 30
MS (M+H+): expected 873.5; observed 874.3

Example 54

(11S,14S,17S)-14-(4-Amino-butyl)-22-[3-(2-amino-ethyl)-phenyl]-11-(3-amino-propyl)-25-chloro-17-(1H-indol-3-ylmethyl)-16-methyl-2-thia-4,10,13,16,19-pentaaza-tricyclo[19.4.0.0*3,8*]pentacosa-1(25),3(8),4,6,21,23-hexaene-12,15,18-trione

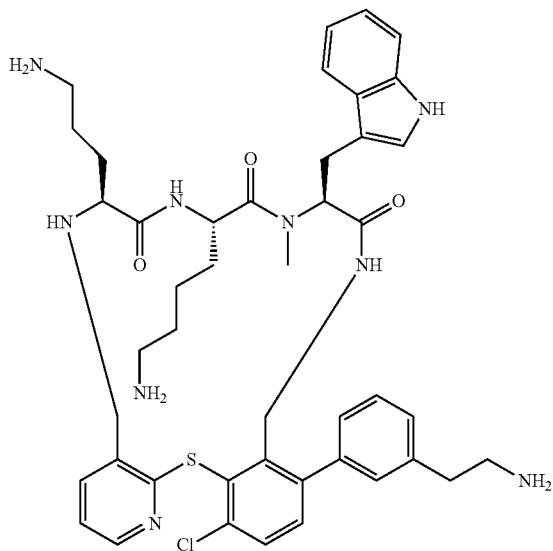 [SMILES: CN1C(=O)[C@H](CCCCN)NC(=O)[C@H](CCCN)NCc2cccnc2Sc2c(Cl)ccc(-c3cccc(CCN)c3)c2CNC(=O)[C@@H]1Cc1c[nH]c2ccccc12]

Example 54 was prepared according to the General Procedure for Suzuki Coupling of boronic acid derivatives to Peptide Macrocycle Intermediates using the following starting materials:
Macrocycle Intermediate: Intermediate 35
Boronic Acid Derivative: (3-(2-((tert-butoxycarbonyl)amino)ethyl)phenyl)boronic acid
MS (M+H$^+$): expected 823.4; observed 824.3

Example 55

(11S,14S,17S)-14-(4-Amino-butyl)-11-(3-amino-propyl)-25-chloro-17-(1H-indol-3-ylmethyl)-16-methyl-22-(4-piperazin-1-yl-phenyl)-2-thia-4,10,13,16,19-pentaaza-tricyclo[19.4.0.0*3,8*]pentacosa-1(25),3(8),4,6,21,2-hexaene-12,15,18-trione

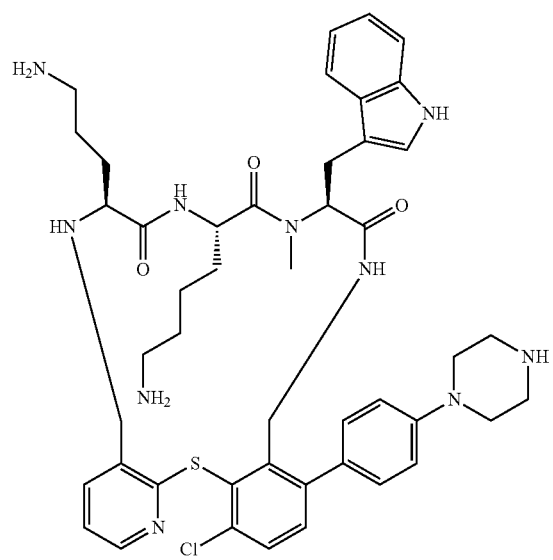 [SMILES: CN1C(=O)[C@H](CCCCN)NC(=O)[C@H](CCCN)NCc2cccnc2Sc2c(Cl)ccc(-c3ccc(N4CCNCC4)cc3)c2CNC(=O)[C@@H]1Cc1c[nH]c2ccccc12]

Example 55 was prepared according to the General Procedure for Suzuki Coupling of boronic acid derivatives to Peptide Macrocycle Intermediates using the following starting materials:
Macrocycle Intermediate: Intermediate 35
Boronic Acid Derivative: [4-(4-tert-butoxycarbonylpiperazin-1-yl)phenyl]boronic acid
MS (M+H$^+$): expected 864.4; observed 865.4

Example 56

Antimicrobial Susceptibility Testing: Minimum Inhibitory Concentration (MIC) Determination The in vitro antimicrobial activity of the compounds was determined through microbroth minimum inhibitory concentration (MIC) methodology performed according to the Clinical and Laboratory Standard Institute guidelines (CLSI—M07-A9 Jan. 2012. *Methods for Dilution Antimicrobial Susceptibility Tests for Bacteria That Grow Aerobically; Approved Standard—Ninth Edition*, Clinical and Laboratory Standards Institue, Wayne/PA, US and the CLSI—M100-S24 Jan. 2014. *Performance Standards for Antimicrobial Susceptibility Testing; Approved Standard—Fourth Informational Supplement*, Clinical and Laboratory Standards Institue, Wayne/PA, US).

The compound stock solution was freshly prepared at 10× the required top concentration for the MIC determination, i.e. at 1280 mg/L, by reconstitution of the dry compound in 50:50 water:DMSO.

Polystyrene non-treated 96 wells microtiter plates were used for preparing panel containing compound serial twofold diluted at two times the final testing concentration (e.g. range from 64 to 0.06 µg/ml) in cation adjusted Mueller Hinton broth medium (CAMHB).

Inoculum was prepared by the "direct colony suspension method". Colonies of *P. aeruginosa* ATCC27853 or clinical isolates were suspended in saline solution and adjusted to 0.5 McFarland, diluted 100 times in CAMHB broth and 50 µl added to each well (final concentration of cells ~5×10$^{(5)}$ CFU/ml and Final volume/well of 100 µl). Microtiter plates were sealed and incubated at 35±2° C.

MICs values were read after 20 hours of incubation and recorded as the lowest concentration of the antimicrobial that inhibits more or equal to 80% of growth of the organism as detected by the unaided eye and using a microtiter plate optical density reader (OD 600 nm).

Table 1 provides the minimum inhibitory concentration (MIC) in microgram per milliliter of the compounds of present invention obtained against the *P. aeruginosa* ATCC27853 (Table 1).

Example 57

Antimicrobial Susceptibility Testing: 50% Growth Inhibitory Concentration (IC50) Determination The in vitro antimicrobial activity of the compounds was alternatively determined according to the following procedure:

The assay used a 10-points Iso-Sensitest broth medium to measure quantitatively the in vitro activity of the compounds against *P. aeruginosa* NCTC11454.

Stock compounds in DMSO were serially twofold diluted (e.g. range from 50 to 0.097 µM final concentration) in 384 wells microtiter plates and inoculated with 49 µl the bacterial suspension in Iso-Sensitest medium to have a final cell concentration of ~5×10$^{(5)}$ CFU/ml in a final volume/well of 50 ul/well. Microtiter plates were incubated at 35±2° C.

Bacterial cell growth was determined with the measurement of optical density at λ=600 nm each 20 minutes over a time course of 16h.

Growth inhibition was calculated during the logarithmic growth of the bacterial cells with determination of the concentration inhibiting 50% (IC50) and 90% (IC90) of the growth.

Table 2 provides the 50% growth inhibitory concentrations (IC50) in micromoles per liter of the compounds of present invention obtained against *P. aeruginosa* NCTC11454.

Particular compounds of the present invention exhibit an IC50 (*P. aeruginosa* NCTC11454) ≤25 μmol/l.

More particular compounds of the present invention exhibit an IC50 (*P. aeruginosa* NCTC11454) ≤10 μmol/l.

Most particular compounds of the present invention exhibit an IC50 (*P. aeruginosa* NCTC11454) ≤5 μmol/l.

TABLE 1

Minimum inhibitory concentration (MIC) in microgram per milliliter of the compounds of present invention obtained against *P. aeruginosa* ATCC27853.

| Example | MIC ATCC27853 [μg/ml] |
|---|---|
| 1 | — |
| 2 | 32 |
| 3 | >64 |
| 4 | — |
| 5 | — |
| 6 | — |
| 7 | — |
| 8 | — |
| 9 | — |
| 10 | — |
| 11 | 16 |
| 12 | 32 |
| 13 | 16 |
| 14 | — |
| 15 | 32 |
| 16 | 32 |
| 17 | 32 |
| 18 | 32 |
| 19 | 32 |
| 20 | 32 |
| 21 | 32 |
| 22 | — |
| 23 | 32 |
| 24 | — |
| 25 | — |
| 26 | — |
| 27 | — |
| 28 | 8 |
| 29 | 32 |
| 30 | — |
| 31 | — |
| 32 | — |
| 33 | — |
| 34 | — |
| 35 | — |
| 36 | — |
| 37 | 32 |
| 38 | — |
| 39 | — |
| 40 | — |
| 41 | — |
| 42 | — |
| 43 | — |
| 44 | — |
| 45 | — |
| 46 | — |
| 47 | — |
| 48 | — |
| 49 | — |
| 50 | — |
| 51 | — |
| 52 | — |
| 53 | — |
| 54 | — |
| 55 | — |

TABLE 2

50% growth inhibition concentrations (IC50) in micromoles per liter of the compounds of present invention obtained against *P. aeruginosa* NCTC11454.

| Example | IC50 NCTC11454 [μmol/l] |
|---|---|
| 1 | 31.98 |
| 2 | >50.00 |
| 3 | — |
| 4 | 12.56 |
| 5 | 24.37 |
| 6 | 22.66 |
| 7 | 7.62 |
| 8 | 13.21 |
| 9 | 24.52 |
| 10 | 10.68 |
| 11 | — |
| 12 | — |
| 13 | — |
| 14 | 24.34 |
| 15 | 31.98 |
| 16 | — |
| 17 | — |
| 18 | — |
| 19 | — |
| 20 | — |
| 21 | — |
| 22 | 10.11 |
| 23 | — |
| 24 | 22.43 |
| 25 | 25.27 |
| 26 | 23.71 |
| 27 | 11.35 |
| 28 | 8.8 |
| 29 | — |
| 30 | 11.12 |
| 31 | 25.36 |
| 32 | 7.15 |
| 33 | 9.02 |
| 34 | 27.81 |
| 35 | 8.1 |
| 36 | 12.53 |
| 37 | 95.7 |
| 38 | 14.52 |
| 39 | 23.5 |
| 40 | 25.08 |
| 41 | 6.5 |
| 42 | 3.47 |
| 43 | 22.92 |
| 44 | 27 |
| 45 | 6.07 |
| 46 | 20.32 |
| 47 | 2.75 |
| 48 | 14.16 |
| 49 | 10.76 |
| 50 | 8.47 |
| 51 | 12.31 |
| 52 | 11.64 |
| 53 | 30.08 |

TABLE 2-continued

50% growth inhibition concentrations (IC50) in micromoles per liter of the compounds of present invention obtained against *P. aeruginosa* NCTC11454.

| Example | IC50 NCTC11454 [µmol/l] |
|---------|-------------------------|
| 54 | 29.14 |
| 55 | 26.62 |

The invention claimed is:

1. A method for the treatment of infections and resulting diseases caused by *Pseudomonas aeruginosa*, comprising the step of administering to a human being or animal in need thereof a compound of formula (I):

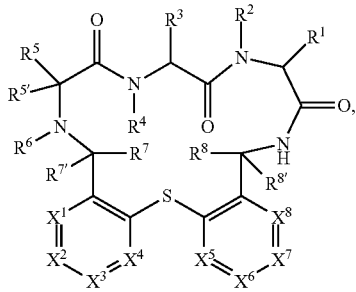

(I)

wherein:
$X^1$ is C—$R^{11}$;
$X^2$ is C—$R^{12}$;
$X^3$ is C—$R^{13}$;
$X^4$ is N;
$X^5$ is C—$R^{15}$;
$X^6$ is C—$R^{16}$;
$X^7$ is C—$R^{17}$;
$X^8$ is C—$R^{18}$;
$R^1$ is —(CH$_2$)m-heteroaryl optionally substituted with one or more halo or $C_{1-7}$-alkyl;
$R^2$, $R^4$ and $R^6$ are each individually selected from hydrogen or $C_{1-7}$-alkyl;
$R^3$ and $R^5$ are each independently selected from hydrogen, —$C_{1-7}$-alkyl, hydroxy-$C_{1-7}$-alkyl, —(CH$_2$)$_m$—NR$^{20}$R$^{21}$, —(CH$_2$)$_m$—C(O)NR$^{20}$R$^{21}$, —(CH$_2$)$_m$—CF$_2$—(CH$_2$)$_m$—NR$^{20}$R$^{21}$, —(CH$_2$)$_m$—NH—C(O)—(CH$_2$)$_m$—NR$^{20}$R$^{21}$ or —(CH$_2$)$_m$—O—(CH$_2$)$_n$—NR$^{20}$R$^{21}$, —(CH$_2$)$_m$—NH—C(NH)—NR$^{20}$R$^{21}$, —(CH$_2$)$_m$—NH—C(O)—OR$^{21}$, —(CH$_2$)$_o$—C$_{3-7}$-cycloalkyl, —(CH$_2$)$_o$-heterocycloalkyl, —(CH$_2$)$_o$-heteroaryl, —(CH$_2$)o-aryl, wherein cycloalkyl, heterocycloalkyl, heteroaryl and aryl are optionally substituted by halo, cyano, $C_{1-7}$-alkyl, $C_{1-7}$-haloalkyl, $C_{1-7}$-hydroxyalkyl, $C_{1-7}$-alkoxy or aryl;
$R^{5'}$ is hydrogen or $C_{1-7}$-alkyl;
$R^7$, $R^{7'}$ and $R^8$, $R^{8'}$ are each individually selected from hydrogen or $C_{1-7}$-alkyl;
$R^{11}$, $R^{12}$, $R^{13}$, $R^{14}$, $R^{15}$, $R^{16}$, $R^{17}$ and $R^{18}$ are each individually selected from hydrogen, halogen, $C_{1-7}$-alkyl, $C_{1-7}$-haloalkyl, hydroxy, $C_{1-7}$-hydroxyalkyl, $C_{1-7}$-alkoxy, $C_{1-7}$-haloalkoxy, —NR$^{24}$R$^{25}$, $C_{1-7}$-alkyl-NR$^{24}$R$^{25}$, aryl-$C_{1-7}$-alkyl-O—$C_{1-7}$-alkinyl-, aryl and heteroaryl, wherein aryl and heteroaryl are optionally substituted with one, two or three substituents selected from the list of halogen, cyano, $C_{1-7}$-alkyl $C_{1-7}$-haloalkyl, hydroxy, $C_{1-7}$-alkoxy, —NR$^{24}$R$^{25}$, $C_{1-7}$-alkyl-NR$^{24}$R$^{25}$, —CO—NH—(CH$_2$)$_n$—NR$^{24}$R$^{25}$, —CO—NH—(CH$_2$)$_r$—OH, —CO—NH—(CH$_2$)$_o$-heterocycloalkyl, —CO—OH, —O—$C_{1-7}$-hydroxyalkyl, —O—(CH$_2$)$_o$—CO—OH, —SO$_2$—$C_{1-7}$-alkyl, —SO$_2$—NR$^{24}$R$^{25}$, heterocycloalkyl, —O—heterocycloalkyl and heterocycloalkyl substituted with $C_{1-7}$-alkyl or oxo;
$R^{20}$ and $R^{22}$ are each individually selected from hydrogen, $C_{1-7}$-alkyl and benzyl;
$R^{21}$ and $R^{23}$ are each individually selected from hydrogen and $C_{1-7}$-alkyl;
$R^{24}$ and $R^{25}$ are each individually selected from hydrogen, $C_{1-7}$-alkyl, $C_{1-7}$-haloalkyl, $C_{1-7}$-hydroxyalkyl, and $C_{3-7}$-cycloalkyl;
m is 1, 2, 3, 4, 5 or 6;
n is 2, 3, 4, 5 or 6; and
o is 0, 1, 2, 3, 4, 5, 6, 7 or 8;
or a pharmaceutically acceptable salt thereof.

2. The method according to claim 1, wherein the compound has a structure of formula (Ia)

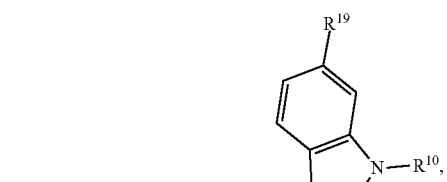
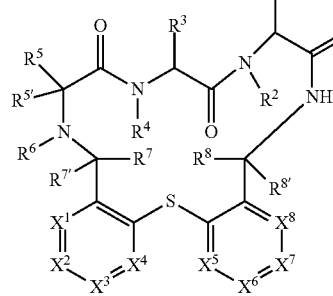

(Ia)

wherein:
$X^1$ is CR$^{11}$,
$X^2$ is CR$^{12}$,
$X^3$ is CR$^{13}$,
$X^4$ is N;
$X^5$ is CR$^{15}$,
$X^6$ is CR$^{16}$,
$X^7$ is CR$^{17}$,
$X^8$ is CR$^{18}$;
$R^2$, $R^4$ and $R^6$ are each individually selected from hydrogen or $C_{1-7}$-alkyl;
$R^3$ is —(CH$_2$)$_m$—NR$^{20}$R$^{21}$;
$R^5$ is —(CH$_2$)$_m$—NR$^{22}$R$^{23}$ or —(CH$_2$)$_o$-heterocycloalkyl, wherein heterocycloalkyl is optionally substituted by halo or $C_{1-7}$-alkyl;
R 7 and $R^8$ are hydrogen;
R 9 is hydrogen, halo or $C_{1-7}$-alkyl;
R 10 is hydrogen or $C_{1-7}$-alkyl;
$R^{11}$, $R^{12}$, $R^{13}$, $R^{14}$, $R^{15}$, $R^{16}$, $R^{17}$ and $R^{18}$ are each individually selected from hydrogen, halogen, $C_{1-7}$-alkyl, $C_{1-7}$-haloalkyl, hydroxy, $C_{1-7}$-hydroxyalkyl, $C_{1-7}$-alkoxy, $C_{1-7}$-haloalkoxy, —NR$^{24}$R$^{25}$, $C_{1-7}$-alkyl- NR$^{24}$R$^{25}$, aryl-C$_{1-7}$-alkyl-O—C$_{1-7}$-alkinyl-, aryl and heteroaryl, wherein aryl and heteroaryl are optionally substituted with one, two or three substituents selected from the list of halogen, cyano, C$_{1-7}$-alkyl C$_{1-7}$-haloalkyl, hydroxy, C$_{1-7}$-alkoxy, —NR$^{24}$R$^{25}$, C$_{1-7}$-alkyl-NR$^{24}$R$^{25}$, —CO—NH—(CH$_2$)$_n$—NR$^{24}$R$^{25}$, —CO—NH—(CH$_2$)$_r$—OH, —CO—NH—(CH$_2$)$_o$-heterocycloalkyl, —CO—OH, —O—C$_{1-7}$-hydroxyalkyl, —O—(CH$_2$)$_o$—CO—OH, —SO$_2$—C$_{1-7}$-alkyl, —SO$_2$—NR$^{24}$R$^{25}$, heterocycloalkyl, —O—heterocycloalkyl and heterocycloalkyl substituted with C$_{1-7}$-alkyl or oxo;

R 19 is hydrogen, halo, C$_{1-7}$-alkyl;

R$_{20}$, R$_{21}$, R$_{22}$ and R$^{23}$ are hydrogen; and

R 24 and R 25 are each individually selected from hydrogen and C$_{1-7}$-alkyl;

or a pharmaceutically acceptable salt thereof.

3. The method according to claim 1, wherein the compound has a structure of formula (Ib)

(Ib)

wherein:

X$^1$ is CR$^{11}$;

X$^4$ is N;

R$^2$ is selected from hydrogen and C$_{1-7}$-alkyl;

R$^9$ is hydrogen, halo or C$_{1-7}$-alkyl;

R$^{15}$ is hydrogen, halogen, C$_{1-7}$-alkyl, C$_{1-7}$-haloalkyl, —NR$^{24}$R$^{25}$, C$_{1-7}$-alkyl-NR$^{24}$R$^{25}$, hydroxy, C$_{1-7}$-alkoxy, haloC$_{1-7}$-alkoxy, benzyloxy-propynyl (—C≡C—CH$_2$—O-benzyl), heterocycloalkyl, aryl and heteroaryl,
  wherein aryl is optionally substituted with one —NR$^{20}$R$^{21}$ or heterocycloalkyl substituted with C$_{1-7}$-alkyl;

R$^{17}$ is hydrogen, halogen, C$_{1-7}$-alkyl, C$_{1-7}$-haloalkyl, —NR$^{24}$R$^{25}$, C$_{1-7}$-alkyl-NR$^{24}$R$^{25}$, hydroxy, C$_{1-7}$-alkoxy, haloC$_{1-7}$-alkoxy, benzyloxy-prop-1-ynyl, heterocycloalkyl, aryl and heteroaryl,
  wherein heterocycloalkyl is optionally substituted with one —NR$^{24}$R$^{25}$,
  wherein aryl and heteroaryl are optionally substituted with one, two or three substituents selected from the list of halogen, C$_{1-7}$-alkyl, C$_{1-7}$-haloalkyl, C$_{1-7}$-hydroxyalkyl, hydroxy, C$_{1-7}$-alkoxy, —NR$^{24}$R$^{25}$, SO$_2$—C$_{1-7}$-alkyl, —SO$_2$—NR$^{24}$R$^{25}$, heterocycloalkyl and heterocycloalkyl substituted with C$_{1-7}$-alkyl;

R$^{18}$ is hydrogen, halogen, C$_{1-7}$-alkyl, C$_{1-7}$-haloalkyl, hydroxy, C$_{1-7}$-hydroxyalkyl, C$_{1-7}$-alkoxy, C$_{1-7}$-haloalkoxy, —NR$^{24}$R$^{25}$, C$_{1-7}$-alkyl-NR$^{24}$R$^{25}$, aryl and heteroaryl,
  wherein aryl and heteroaryl are optionally substituted with one, two or three substituents selected from the list of halogen, cyano, C$_{1-7}$-alkyl C$_{1-7}$-haloalkyl, hydroxy, C$_{1-7}$-alkoxy, —NR$^{24}$R$^{25}$, C$_{1-7}$-alkyl-NR$^{24}$R$^{25}$, —CO—NH—(CH$_2$)$_r$—NR$_{24}$R$_{25}$, —CO—NH—(CH$_2$)$_o$—OH, —CO—NH—(CH$_2$)$_o$-heterocycloalkyl, —CO—OH, —O—C$_{1-7}$-hydroxyalkyl, —O—(CH$_2$)$_r$—CO—OH, —SO$_2$—C$_{1-7}$-alkyl, —SO$_2$—N$^{24}$R$^{25}$, heterocycloalkyl, —O—heterocycloalkyl and heterocycloalkyl substituted with C$_{1-7}$-alkyl or oxo;

R$^{19}$ is hydrogen, halo, C$_{1-7}$-alkyl;

R$^{20}$, R$^{21}$, R$^{22}$ and R$^{23}$ are hydrogen;

R$^{24}$ and R$^{25}$ are each individually selected from hydrogen and C$_{1-7}$-alkyl; and and Y is —CH$_2$— or —CO—;

or a pharmaceutically acceptable salt thereof.

4. The method according to claim 1, wherein said compound is selected from the group consisting of:

(12S,15S,18S)-15-(4-Amino-butyl)-18-(3-amino-propyl)-6-chloro-12-(1H-indol-3-ylmethyl)-13-methyl-2-thia-10,13,16,19-tetraaza-tricyclo[19.4.0.0*3,8*]pentacosa-1(21),3,5,7,22,24-hexaene-11,14,17-trione;

(12S,15S,18S)-15-(4-Amino-butyl)-18-(3-amino-propyl)-5-chloro-12-(1H-indol-3-ylmethyl)-13-methyl-2-thia-10,13,16,19-tetraaza-tricyclo[19.4.0.0*3,8*]pentacosa-1(21),3,5,7,22,24-hexaene-11,14,17-trione;

(12S,15S,18S)-15-(4-Amino-butyl)-18-(3-amino-propyl)-4-chloro-12-(1H-indol-3-ylmethyl)-13-methyl-2-thia-10,13,16,19-tetraaza-tricyclo[19.4.0.0*3,8*]pentacosa-1(21),3,5,7,22,24-hexaene-11,14,17-trione;

(12S,15S,18S)-15-(4-Amino-butyl)-18-(3-amino-propyl)-12-(1H-indol-3-ylmethyl)-13-methyl-5-trifluoromethyl-2-thia-10,13,16,19-tetraaza-tricyclo[19.4.0.0*3,8*]pentacosa-1(21),3,5,7,22,24-hexaene-11,14,17-trione;

(12S,15S,18S)-15-(4-Amino-butyl)-18-(3-amino-propyl)-12-(6-chloro-1H-indol-3-ylmethyl)-13-methyl-2-thia-10,13,16,19-tetraaza-tricyclo[19.4.0.0*3,8*]pentacosa-1(21),3,5,7,22,24-hexaene-11,14,17-trione;

(12S,15S,18S)-15-(4-Amino-butyl)-18-(3-amino-propyl)-6-chloro-13-methyl-12-(1-methyl-1H-indol-3-ylmethyl)-2-thia-10,13,16,19-tetraaza-tricyclo[19.4.0.0*3,8*]pentacosa-1(21),3,5,7,22,24-hexaene-11,14,17-trione;

(12S,15S,18S)-15-(4-Amino-butyl)-18-(3-amino-propyl)-6-chloro-12-(6-chloro-1H-indol-3-ylmethyl)-13-methyl-2-thia-10,13,16,19-tetraaza-tricyclo[19.4.0.0*3,8]pentacosa-1(21),3,5,7,22,24-hexaene-11,14,17-trione;

(12S,15S,18S)-15-(4-Amino-butyl)-18-(3-amino-propyl)-6-chloro-12-(6-chloro-1-methyl-1H-indol-3-ylmethyl)-13-methyl-2-thia-10,13,16,19-tetraaza-tricyclo[19.4.0.0*3,8*]pentacosa-1(21),3,5,7,22,24-hexaene-11,14,17-trione;

(12S,15S,18S)-15-(4-Amino-butyl)-18-(3-amino-propyl)-6,7-dichloro-12-(1H-indol-3-ylmethyl)-13-methyl-2-thia-10,13,16,19-tetraaza-tricyclo[19.4.0.0*3,8*]pentacosa-1(25),3,5,7,21,23-hexaene-11,14,17-trione;

(12S,15S,18S)-15-(4-Amino-butyl)-18-(3-amino-propyl)-4-chloro-12-(1H-indol-3-ylmethyl)-13-methyl-7- trifluoromethyl-2-thia-10,13,16,19-tetraaza-tricyclo[19.4.0.0*3,8*]pentacosa-1(25),3,5,7,21,23-hexaene-11,14,17-trione;
(12S,15S,18S)-15-(4-Amino-butyl)-18-(3-amino-propyl)-4-chloro-12-(1H-indol-3-ylmethyl)-13-methyl-6-trifluoromethyl-2-thia-10,13,16,19-tetraaza-tricyclo[19.4.0.0*3,8*]pentacosa-1(25),3,5,7,21,23-hexaene-11,14,17-trione;
(12S,15S,18S)-15-(4-Amino-butyl)-18-(3-amino-propyl)-4,6-dichloro-23-fluoro-12-(1H-indol-3-ylmethyl)-13-methyl-2-thia-10,13,16,19-tetraaza-tricyclo[19.4.0.0*3,8*]pentacosa-1(25),3,5,7,21,23-hexaene-11,14,17-trione;
(12S,15S,18S)-15-(4-Amino-butyl)-18-(3-amino-propyl)-6-chloro-12-(1H-indol-3-ylmethyl)-13-methyl-4-trifluoromethyl-2-thia-10,13,16,19-tetraaza-tricyclo[19.4.0.0*3,8*]pentacosa-1(25),3,5,7,21,23-hexaene-11,14,17-trione;
(12S,15S,18S)-15-(4-Amino-butyl)-18-(3-amino-propyl)-6-chloro-12-(1H-indol-3-ylmethyl)-4,13-dimethyl-2-thia-10,13,16,19-tetraaza-tricyclo[19.4.0.0*3,8*]pentacosa-1(25),3,5,7,21,23-hexaene-11,14,17-trione;
(12S,15S,18S)-15-(4-Amino-butyl)-18-(3-amino-propyl)-6-chloro-13-methyl-12-(2-methyl-1H-indol-3-ylmethyl)-2-thia-10,13,16,19-tetraaza-tricyclo[19.4.0.0*3,8*]pentacosa-1(21),3,5,7,22,24-hexaene-11,14,17-trione;
(12S,15S,18S)-15-(4-Amino-butyl)-18-(3-amino-propyl)-4,13-dimethyl-12-(2-methyl-1H-indol-3-ylmethyl)-2-thia-10,13,16,19-tetraaza-tricyclo[19.4.0.0*3,8*]pentacosa-1(21),3,5,7,22,24-hexaene-11,14,17-trione;
(12S,15S,18S)-15-(4-Amino-butyl)-18-(3-amino-propyl)-4,6-dichloro-13-methyl-12-(2-methyl-1H-indol-3-ylmethyl)-2-thia-10,13,16,19-tetraaza-tricyclo[19.4.0.0*3,8*]pentacosa-1(21),3,5,7,22,24-hexaene-11,14,17-trione;
(12S,15S,18S)-15-(4-Amino-butyl)-18-(3-amino-propyl)-6-ethyl-12-(1H-indol-3-ylmethyl)-13-methyl-2-thia-10,13,16,19-tetraaza-tricyclo[19.4.0.0*3,8*]pentacosa-1(25),3,5,7,21,23-hexaene-11,14,17-trione;
(12S,15S,18S)-15-(4-Amino-butyl)-18-(3-amino-propyl)-12-(1H-indol-3-ylmethyl)-13-methyl-6-phenyl-2-thia-10,13,16,19-tetraaza-tricyclo[19.4.0.0*3,8*]pentacosa-1(25),3,5,7,21,23-hexaene-11,14,17-trione;
(12S,15S,18S)-15-(4-Amino-butyl)-18-(3-amino-propyl)-6-tert-butyl-12-(1H-indol-3-ylmethyl)-13-methyl-2-thia-10,13,16,19-tetraaza-tricyclo[19.4.0.0*3,8*]pentacosa-1(25),3,5,7,21,23-hexaene-11,14,17-trione;
(12S,15S,18S)-15-(4-Amino-butyl)-18-(3-amino-propyl)-12-(1H-indol-3-ylmethyl)-6-isopropyl-13-methyl-2-thia-10,13,16,19-tetraaza-tricyclo[19.4.0.0*3,8*]pentacosa-1(25),3,5,7,21,23-hexaene-11,14,17-trione;
(11S,14S,17S)-14-(4-Amino-butyl)-11-(3-amino-propyl)-17-(1H-indol-3-ylmethyl)-16-methyl-23-phenyl-25-trifluoromethyl-2-thia-4,10,13,16,19-pentaaza-tricyclo[19.4.0.0*3,8*]pentacosa-1(25),3,5,7,21,23-hexaene-12,15,18-trione;
(11S,14S,17S)-14-(4-Amino-butyl)-11-(3-amino-propyl)-17-(1H-indol-3-ylmethyl)-16-methyl-23,25-bis-trifluoromethyl-2-thia-4,10,13,16,19-pentaaza-tricyclo[19.4.0.0*3,8*]pentacosa-1(25),3,5,7,21,23-hexaene-12,15,18-trione;
(11S,14S,17S)-14-(4-Amino-butyl)-11-(3-amino-propyl)-25-chloro-17-(1H-indol-3-ylmethyl)-16-methyl-23-trifluoromethyl-2-thia-7,10,13,16,19-pentaaza-tricyclo[19.4.0.0*3,8*]pentacosa-1(25),3,5,7,21,23-hexaene-12,15,18-trione;
(11R,14S,17S)-14-(4-Amino-butyl)-11-(3-amino-propyl)-25-chloro-17-(1H-indol-3-ylmethyl)-24-phenyl-2-thia-4,10,13,16,19-pentaaza-tricyclo[19.4.0.0*3,8*]pentacosa-1(25),3,5,7,21,23-hexaene-12,15,18-trione;
(11S,14S,17S)-14-(4-Amino-butyl)-11-(3-amino-propyl)-25-chloro-17-(1H-indol-3-ylmethyl)-24-phenyl-2-thia-4,10,13,16,19-pentaaza-tricyclo[19.4.0.0*3,8*]pentacosa-1(25),3,5,7,21,23-hexaene-12,15,18-trione;
(11R,14S,17S)-14-(4-Amino-butyl)-11-(3-amino-propyl)-25-chloro-17-(1H-indol-3-ylmethyl)-16-methyl-24-phenyl-2-thia-4,10,13,16,19-pentaaza-tricyclo[19.4.0.0*3,8*]pentacosa-1(25),3,5,7,21,23-hexaene-12,15,18-trione;
(12S,15S,18S)-15-(4-Amino-butyl)-18-(3-amino-propyl)-12-(1H-indol-3-ylmethyl)-13-methyl-6-phenyl-4-trifluoromethyl-2-thia-10,13,16,19-tetraaza-tricyclo[19.4.0.0*3,8*]pentacosa-1(25),3,5,7,21,23-hexaene-11,14,17-trione;
(11S,14S,17S)-14-(4-Amino-butyl)-11-(3-amino-propyl)-25-chloro-17-(1H-indol-3-ylmethyl)-16-methyl-22-phenyl-2-thia-4,10,13,16,19-pentaaza-tricyclo[19.4.0.0*3,8*]pentacosa-1(25),3(8),4,6,21,23-hexaene-12,15,18-trione;
(12S,15S,18S)-15,18-Bis-(3-amino-propyl)-4,6-dichloro-12-(1H-indol-3-ylmethyl)-13-methyl-2-thia-10,13,16,19-tetraaza-tricyclo[19.4.0.0*3,8*]pentacosa-1(25),3,5,7,21,23-hexaene-11,14,17-trione;
(11S,14S,17S)-14-(4-Amino-butyl)-11-(3-amino-propyl)-25-chloro-17-(5-chloro-1H-indol-3-ylmethyl)-16-methyl-22-trifluoromethyl-2-thia-4,10,13,16,19-pentaaza-tricyclo[19.4.0.0*3,8*]pentacosa-1(25),3,5,7,21,23-hexaene-12,15,18-trione;
(12S,15S,18S)-15-(4-Amino-butyl)-18-(3-amino-propyl)-4-chloro-12-(1H-indol-3-ylmethyl)-13-methyl-6-phenyl-2-thia-10,13,16,19-tetraaza-tricyclo[19.4.0.0*3,8*]pentacosa-1(25),3,5,7,21,23-hexaene-11,14,17-trione;
(12S,15S,18S)-15-(4-Amino-butyl)-18-(3-amino-propyl)-4-chloro-6-(2-chloro-phenyl)-12-(1H-indol-3-ylmethyl)-13-methyl-2-thia-10,13,16,19-tetraaza-tricyclo[19.4.0.0*3,8*]pentacosa-1(25),3,5,7,21,23-hexaene-11,14,17-trione;
(12S,15S,18S)-15-(4-Amino-butyl)-18-(3-amino-propyl)-4-chloro-12-(1H-indol-3-ylmethyl)-13-methyl-6-pyridin-3-yl-2-thia-10,13,16,19-tetraaza-tricyclo[19.4.0.0*3,8*]pentacosa-1(25),3,5,7,21,23-hexaene-11,14,17-trione;
11-(3-amino-propyl)-25-chloro-17-(1H-indol-3-ylmethyl)-16-methyl-23-phenyl-2-thia-4,10,13,16,19-pentaaza-tricyclo[19.4.0.0*3,8*]pentacosa-1(25),3(8),4,6,21,23-hexaene-12,15,18-trione;
(12S,15S,18S)-15-(4-Amino-butyl)-18-(3-amino-propyl)-6-bromo-4-chloro-12-(1H-indol-3-ylmethyl)-13-methyl-2-thia-10,13,16,19-tetraaza-tricyclo[19.4.0.0*3,8*]pentacosa-1(25),3,5,7,21,23-hexaene-11,14,17-trione;
(12S,15S,18S)-15-(4-Amino-butyl)-18-(3-amino-propyl)-4-chloro-12-(1H-indol-3-ylmethyl)-13-methyl-6-(1-methyl-1H-imidazol-4-yl)-2-thia-10,13,16,19-tetraaza-tricyclo[19.4.0.0*3,8*]pentacosa-1(25),3,5,7,21,23-hexaene-11,14,17-trione;
3-[(11S,14S,17S)-14-(4-Amino-butyl)-17-(1H-indol-3-ylmethyl)-16-methyl-12,15,18-trioxo-23-phenyl-25- trifluoromethyl-2-thia-10,13,16,19-tetraaza-tricyclo [19.4.0.0*3,8*]pentacosa-1(25),3,5,7,21,23-hexaen-11-yl]-propionamide;
3-[(11S,14S,17S)-11-(3-Amino-propyl)-17-(1H-indol-3-ylmethyl)-16-methyl-12,15,18-trioxo-23-phenyl-25-trifluoromethyl-2-thia-10,13,16,19-tetraaza-tricyclo [19.4.0.0*3,8*]pentacosa-1(25),3,5,7,21,23-hexaen-14-yl]-propionamide;
(11S,14S,17S)-14-(4-Amino-butyl)-11-(3-amino-propyl)-25-chloro-23-(2-chloro-pyridin-4-yl)-17-(1H-indol-3-ylmethyl)-16-methyl-2-thia-4,10,13,16,19-pentaaza-tricyclo[19.4.0.0*3,8*]pentacosa-1(21),3,5,7,22,24-hexaene-12,15,18-trione;
(12S,15S,18S)-15-(4-Amino-butyl)-18-(3-amino-propyl)-5-bromo-4-chloro-12-(1H-indol-3-ylmethyl)-13-methyl-2-thia-10,13,16,19-tetraaza-tricyclo [19.4.0.0*3,8*]pentacosa-1(25),3,5,7,21,23-hexaene-11,14,17-trione;
(12S,15S,18S)-15-(4-Amino-butyl)-18-(3-amino-propyl)-4-chloro-12-(1H-indol-3-ylmethyl)-13-methyl-5-phenyl-2-thia-10,13,16,19-tetraaza-tricyclo [19.4.0.0*3,8*]pentacosa-1(25),3,5,7,21,23-hexaene-11,14,17-trione;
(8S,11S,14S)-8-((1H-Indol-3-yl)methyl)-11-(4-aminobutyl)-14-(3-aminopropyl)-3-chloro-9-methyl-5,6,8,9,11,12,15,16-octahydrobenzo[b]pyrido[3,2-p][1,5,8,11,14]thiatetraazacycloheptadecine-7,10,13(14H)-trione;
(11S,14S,17S)-14-(4-Amino-butyl)-11-(3-amino-propyl)-25-chloro-23-(2-chloro-pyridin-4-yl)-16-methyl-17-(2-methyl-1H-indol-3-ylmethyl)-2-thia-4,10,13,16,19-pentaaza-tricyclo[19.4.0.0*3,8*]pentacosa-1(25),3(8),4,6,21,23-hexaene-12,15,18-trione;
(11S,14S,17S)-14-(4-Amino-butyl)-11-(3-amino-propyl)-23-(3-benzyloxy-prop-1-ynyl)-25-chloro-17-(1H-indol-3-ylmethyl)-16-methyl-2-thia-4,10,13,16,19-pentaaza-tricyclo[19.4.0.0*3,8*]pentacosa-1(25),3(8),4,6,21,23-hexaene-12,15,18-trione;
(8S,11S,14S)-8-((1H-Indol-3-yl)methyl)-11-(4-aminobutyl)-14-(3-aminopropyl)-9-methyl-2-morpholino-5,6,8,9,11,12,15,16-octahydrobenzo[b]pyrido[3,2-p][1,5,8,11,14]thiatetraazacycloheptadecine-7,10,13(14H)-trione;
(11S,14S,17S)-14-(4-Amino-butyl)-11-(3-amino-propyl)-25-chloro-16-methyl-17-(2-methyl-1H-indol-3-ylmethyl)-22-pyridin-4-yl-2-thia-4,10,13,16,19-pentaaza-tricyclo[19.4.0.0*3,8*]pentacosa-1(25),3(8),4,6,21,23-hexaene-12,15,18-trione;
(12S,15S,18S)-15-(4-Amino-butyl)-18-(3-amino-propyl)-23-bromo-4-chloro-12-(1H-indol-3-ylmethyl)-13-methyl-2-thia-10,13,16,19-tetraaza-tricyclo [19.4.0.0*3,8*]pentacosa-1(25),3,5,7,21,23-hexaene-11,14,17-trione;
(12S,15S,18S)-15-(4-Amino-butyl)-18-(3-amino-propyl)-4-chloro-12-(1H-indol-3-ylmethyl)-13-methyl-23-phenyl-2-thia-10,13,16,19-tetraaza-tricyclo [19.4.0.0*3,8*]pentacosa-1(25),3,5,7,21,23-hexaene-11,14,17-trione;
(12S,15S,18S)-15-(4-Amino-butyl)-23-(4-aminomethyl-phenyl)-18-(3-amino-propyl)-4-chloro-12-(1H-indol-3-ylmethyl)-13-methyl-2-thia-10,13,16,19-tetraaza-tricyclo[19.4.0.0*3,8*]pentacosa-1(25),3,5,7,21,23-hexaene-11,14,17-trione;
(12S,15S,18S)-15-(4-Amino-butyl)-18-(3-amino-propyl)-24-bromo-4-chloro-12-(1H-indol-3-ylmethyl)-13-methyl-2-thia-10,13,16,19-tetraaza-tricyclo [19.4.0.0*3,8*]pentacosa-1(25),3,5,7,21,23-hexaene-11,14,17-trione;
(12S,15S,18S)-15-(4-Amino-butyl)-18-(3-amino-propyl)-4-chloro-12-(1H-indol-3-ylmethyl)-13-methyl-24-phenyl-2-thia-10,13,16,19-tetraaza-tricyclo [19.4.0.0*3,8*]pentacosa-1(25),3,5,7,21,23-hexaene-11,14,17-trione;
4-[(11S,14S,17S)-14-(4-Amino-butyl)-11-(3-amino-propyl)-25-chloro-16-methyl-17-(2-methyl-1H-indol-3-ylmethyl)-12,15,18-trioxo-2-thia-4,10,13,16,19-pentaaza-tricyclo[19.4.0.0*3,8*]pentacosa-1(25),3(8),4,6,21,23-hexaen-23-yl]-benzenesulfonamide;
(11S,14S,17S)-14-(4-Amino-butyl)-22-[3-(2-amino-ethyl)-phenyl]-11-(3-amino-propyl)-25-chloro-17-(1H-indol-3-ylmethyl)-16-methyl-2-thia-4,10,13,16,19-pentaaza-tricyclo[19.4.0.0*3,8*]pentacosa-1(25),3(8),4,6,21,23-hexaene-12,15,18-trione; and
(11S,14S,17S)-14-(4-Amino-butyl)-11-(3-amino-propyl)-25-chloro-17-(1H-indol-3-ylmethyl)-16-methyl-22-(4-piperazin-1-yl-phenyl)-2-thia-4,10,13,16,19-pentaaza-tricyclo[19.4.0.0*3,8*]pentacosa-1(25),3(8),4,6,21,2-hexaene-12,15,18-trione;
or a pharmaceutically acceptable salt thereof.

5. The method according to claim 1, wherein said compound is 4-[(11S,14S,17S)-14-(4-Aminobutyl)-11-(3-aminopropyl)-17-(1H-indol-3-ylmethyl)-16-methyl-12,15,18-trioxo-2-thia-4,10,13,16,19-pentazatricyclo[19.4.0.03,8] pentacosa-1(25),3(8),4,6,21,23-hexaen-22-yl]benzoic acid, or a pharmaceutically acceptable salt thereof.

* * * * *